(12) United States Patent
Willand et al.

(10) Patent No.: US 11,364,381 B2
(45) Date of Patent: *Jun. 21, 2022

(54) METHODS FOR DELIVERING NEUROREGENERATIVE THERAPY AND REDUCING POST-OPERATIVE AND CHRONIC PAIN

(71) Applicant: Epineuron Technologies Inc., Mississauga (CA)

(72) Inventors: Michael Patrick Willand, Oakville (CA); Sergio David Aguirre, Bolton (CA)

(73) Assignee: Epineuron Technologies Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/335,056

(22) Filed: May 31, 2021

(65) Prior Publication Data
US 2021/0283399 A1  Sep. 16, 2021

Related U.S. Application Data

(63) Continuation-in-part of application No. PCT/US2020/053630, filed on Sep. 30, 2020.
(Continued)

(51) Int. Cl.
*A61N 1/36* (2006.01)
*A61N 1/05* (2006.01)

(52) U.S. Cl.
CPC ....... *A61N 1/0502* (2013.01); *A61N 1/36071* (2013.01); *A61N 1/36103* (2013.01);
(Continued)

(58) Field of Classification Search
CPC ........... A61N 1/36103; A61N 1/36071; A61N 1/36171; A61N 1/0551
See application file for complete search history.

(56) References Cited

U.S. PATENT DOCUMENTS

| 3,664,329 A | 5/1972 | Naylor |
| 3,830,226 A | 8/1974 | Staub et al. |

(Continued)

FOREIGN PATENT DOCUMENTS

| CN | 111511435 A | 8/2020 |
| DE | 102007036862 | 2/2009 |

(Continued)

OTHER PUBLICATIONS

U.S. Appl. No. 16/553,043 (U.S. Pat. No. 10,589,089), filed Aug. 27, 2019, Systems and Methods for Delivering Neuroregenerative Therapy.
(Continued)

*Primary Examiner* — Alyssa M Alter
(74) *Attorney, Agent, or Firm* — Knobbe, Martens, Olson & Bear, LLP

(57) ABSTRACT

A method of managing pain related to a peripheral nerve injury of a subject comprises delivering stimulation energy of a first frequency to the target nerve via at least one electrode assembly during a regenerative phase and delivering stimulation energy of a second frequency for a predetermined period via the at least one electrode assembly during at least one neuropathic pain management phase.

21 Claims, 99 Drawing Sheets

Related U.S. Application Data

(60) Provisional application No. 63/172,054, filed on Apr. 7, 2021, provisional application No. 63/044,208, filed on Jun. 25, 2020, provisional application No. 62/909,048, filed on Oct. 1, 2019.

(52) U.S. Cl.
CPC ........ *A61N 1/36171* (2013.01); *A61N 1/0551* (2013.01); *A61N 1/36128* (2013.01)

(56) References Cited

U.S. PATENT DOCUMENTS

| | | |
|---|---|---|
| 4,423,732 A | 1/1984 | Tarjan et al. |
| 4,662,884 A | 5/1987 | Stensaas et al. |
| 4,715,381 A | 12/1987 | Moberg |
| 4,774,967 A | 10/1988 | Zanakis et al. |
| 4,919,140 A | 4/1990 | Borgen et al. |
| 4,940,065 A | 7/1990 | Tanagho et al. |
| 4,979,511 A | 12/1990 | Terry, Jr. |
| 5,314,457 A | 5/1994 | Jeutter et al. |
| 5,344,438 A | 9/1994 | Testerman et al. |
| 5,433,735 A | 7/1995 | Zanakis et al. |
| 5,487,756 A | 1/1996 | Kallesoe et al. |
| 5,702,429 A | 12/1997 | King |
| 5,814,092 A | 9/1998 | King |
| 5,913,882 A | 6/1999 | King |
| 5,951,539 A | 9/1999 | Nita |
| 5,964,702 A | 10/1999 | Grill et al. |
| 6,188,931 B1 | 2/2001 | Holmström et al. |
| 6,270,460 B1 | 8/2001 | McCartan et al. |
| 6,292,697 B1 | 9/2001 | Roberts |
| 6,292,701 B1 | 9/2001 | Prass et al. |
| 6,312,392 B1 | 11/2001 | Herzen |
| 6,436,129 B1 | 8/2002 | Sharkey et al. |
| 6,600,956 B2 | 7/2003 | Maschino et al. |
| 6,937,904 B2 * | 8/2005 | Richmond ......... A61N 1/36103 607/46 |
| 6,941,171 B2 | 9/2005 | Mann et al. |
| 7,120,499 B2 | 10/2006 | Thrope et al. |
| 7,160,241 B1 | 1/2007 | Herbst |
| 7,239,918 B2 | 7/2007 | Strother et al. |
| 7,277,759 B2 | 10/2007 | Overstreet et al. |
| 7,283,867 B2 | 10/2007 | Strother et al. |
| D559,987 S | 1/2008 | Strother et al. |
| 7,326,181 B2 | 2/2008 | Katims |
| 7,343,202 B2 | 3/2008 | Mrva et al. |
| 7,349,743 B2 | 3/2008 | Tadlock |
| 7,376,467 B2 | 5/2008 | Thrope et al. |
| 7,392,093 B2 | 6/2008 | Khan |
| D581,530 S | 11/2008 | Thierfelder et al. |
| 7,450,992 B1 | 11/2008 | Cameron |
| 7,483,734 B2 | 1/2009 | Colthurst |
| 7,544,171 B2 | 6/2009 | Schaden et al. |
| 7,571,002 B2 | 8/2009 | Thrope et al. |
| 7,676,271 B2 | 3/2010 | Wahlstrand et al. |
| 7,797,058 B2 | 9/2010 | Mrva et al. |
| 7,822,486 B2 | 10/2010 | Foster et al. |
| 7,848,812 B2 | 12/2010 | Crowley et al. |
| 7,878,981 B2 | 2/2011 | Strother et al. |
| 7,896,815 B2 | 3/2011 | Thrope et al. |
| 7,917,230 B2 | 3/2011 | Bly |
| 7,957,796 B2 | 6/2011 | Maschino |
| 7,957,817 B1 | 6/2011 | Gillespie et al. |
| 7,996,092 B2 | 8/2011 | Mrva et al. |
| 8,065,014 B2 | 11/2011 | Zealear |
| 8,079,865 B1 | 12/2011 | Rundle |
| 8,086,318 B2 | 12/2011 | Strother et al. |
| 8,116,882 B2 | 2/2012 | Kowalczewski |
| D658,304 S | 4/2012 | Rundle et al. |
| 8,172,768 B2 | 5/2012 | Strother et al. |
| 8,231,402 B2 | 7/2012 | Rundle |
| D665,085 S | 8/2012 | Strother et al. |
| D674,105 S | 1/2013 | Rundle et al. |
| 8,357,006 B2 | 1/2013 | Rundle |
| D683,320 S | 5/2013 | Strother et al. |
| 8,463,383 B2 | 6/2013 | Sakai et al. |
| 8,478,428 B2 | 7/2013 | Cowley |
| 8,494,625 B2 | 7/2013 | Hargrove |
| 8,500,652 B2 | 8/2013 | Strother et al. |
| 8,515,520 B2 | 8/2013 | Brunnett et al. |
| 8,606,368 B2 | 12/2013 | Udo |
| 8,612,025 B2 | 12/2013 | Neisz et al. |
| 8,616,913 B2 | 12/2013 | Rundle |
| 8,626,302 B2 | 1/2014 | Bennett et al. |
| 8,660,646 B2 | 2/2014 | Laing et al. |
| 8,676,334 B2 | 3/2014 | Youn et al. |
| 8,700,177 B2 | 4/2014 | Strother et al. |
| 8,818,520 B2 | 8/2014 | Laing et al. |
| 8,880,189 B2 | 11/2014 | Lipani |
| 8,886,337 B2 | 11/2014 | Bennett et al. |
| 8,929,998 B2 | 1/2015 | Burgher et al. |
| 8,954,153 B2 | 2/2015 | Boggs, II |
| 8,965,499 B2 | 2/2015 | Cowley et al. |
| 8,965,516 B2 | 2/2015 | Bennett et al. |
| 8,989,855 B2 | 3/2015 | Murphy et al. |
| 8,989,859 B2 | 3/2015 | Deem et al. |
| 9,076,187 B1 | 7/2015 | Laing et al. |
| 9,084,551 B2 | 7/2015 | Brunnett et al. |
| 9,089,708 B2 | 7/2015 | Grill et al. |
| 9,114,250 B2 | 8/2015 | True et al. |
| 9,138,579 B2 | 9/2015 | Wolpaw et al. |
| 9,227,053 B2 | 1/2016 | Bonde et al. |
| 9,245,265 B2 | 1/2016 | Laing et al. |
| 9,283,031 B2 | 3/2016 | Janssen et al. |
| 9,283,379 B2 | 3/2016 | True et al. |
| 9,339,643 B1 | 5/2016 | Moffitt et al. |
| 9,339,647 B2 | 5/2016 | Strother et al. |
| 9,345,538 B2 | 5/2016 | Deem et al. |
| 9,352,146 B2 | 5/2016 | Langhals et al. |
| 9,381,343 B2 | 7/2016 | Bennett et al. |
| 9,399,134 B2 | 7/2016 | Simon et al. |
| 9,486,630 B2 | 11/2016 | Litvak et al. |
| 9,486,632 B2 | 11/2016 | Saab |
| 9,498,633 B2 | 11/2016 | Laing et al. |
| 9,550,061 B2 | 1/2017 | Litvak et al. |
| 9,555,245 B2 | 1/2017 | Boggs, II et al. |
| 9,630,011 B2 | 4/2017 | Lipani |
| 9,693,817 B2 | 7/2017 | Mehta et al. |
| 9,770,280 B2 | 9/2017 | Diederich et al. |
| 9,776,000 B2 | 10/2017 | Litvak et al. |
| 9,789,313 B2 | 10/2017 | Lipani |
| 9,802,051 B2 | 10/2017 | Mathur et al. |
| 9,821,163 B2 | 11/2017 | Fraga Da Silva et al. |
| 9,827,412 B2 | 11/2017 | Bennett et al. |
| 9,827,419 B2 | 11/2017 | Boggs, II et al. |
| 9,861,810 B2 | 1/2018 | Anikeeva et al. |
| 9,950,164 B2 | 4/2018 | Lipani |
| 9,956,393 B2 | 5/2018 | Perez et al. |
| 10,029,101 B2 | 7/2018 | Bennet et al. |
| 10,118,035 B2 | 11/2018 | Perez et al. |
| 10,143,840 B2 | 12/2018 | Perez et al. |
| 10,154,792 B2 | 12/2018 | Sakai et al. |
| 10,166,384 B2 | 1/2019 | Bennett et al. |
| 10,335,302 B2 | 7/2019 | Perez et al. |
| 10,376,145 B2 | 8/2019 | Perez et al. |
| 10,376,704 B2 | 8/2019 | Mathur et al. |
| 10,433,785 B2 | 10/2019 | Hausman et al. |
| 10,470,678 B2 | 11/2019 | Strother et al. |
| 10,589,089 B2 * | 3/2020 | Willand ............ A61N 1/36017 |
| 11,247,043 B2 | 2/2022 | Willand et al. |
| 11,247,044 B2 | 2/2022 | Willand et al. |
| 11,247,045 B2 | 2/2022 | Willand et al. |
| 2002/0065544 A1 | 5/2002 | Smits |
| 2002/0120309 A1 | 8/2002 | Richmond et al. |
| 2003/0088274 A1 | 5/2003 | Gliner et al. |
| 2003/0225331 A1 | 12/2003 | Diederich et al. |
| 2003/0233137 A1 | 12/2003 | Edward |
| 2005/0182455 A1 | 8/2005 | Thrope et al. |
| 2005/0182457 A1 | 8/2005 | Thrope et al. |
| 2005/0277844 A1 | 12/2005 | Strother et al. |
| 2005/0277999 A1 | 12/2005 | Strother et al. |
| 2006/0004429 A1 | 1/2006 | Mrva et al. |
| 2006/0025702 A1 | 2/2006 | Sterrantino et al. |

(56) References Cited

U.S. PATENT DOCUMENTS

| | | |
|---|---|---|
| 2006/0030919 A1 | 2/2006 | Mrva et al. |
| 2006/0149345 A1 | 7/2006 | Boggs, II et al. |
| 2006/0173507 A1 | 8/2006 | Mrva et al. |
| 2006/0194724 A1 | 8/2006 | Whitehurst et al. |
| 2006/0200207 A1 | 9/2006 | Thrope et al. |
| 2006/0200219 A1 | 9/2006 | Thrope et al. |
| 2007/0032836 A1 | 2/2007 | Thrope et al. |
| 2007/0032837 A1 | 2/2007 | Thrope et al. |
| 2007/0060955 A1 | 3/2007 | Strother et al. |
| 2007/0060967 A1 | 3/2007 | Strother et al. |
| 2007/0060968 A1 | 3/2007 | Strother et al. |
| 2007/0060979 A1 | 3/2007 | Strother et al. |
| 2007/0060980 A1 | 3/2007 | Strother et al. |
| 2007/0066995 A1 | 3/2007 | Strother et al. |
| 2007/0067000 A1 | 3/2007 | Strother et al. |
| 2007/0088406 A1 | 4/2007 | Bennett et al. |
| 2007/0123952 A1 | 5/2007 | Strother et al. |
| 2007/0191915 A1 | 8/2007 | Strother et al. |
| 2007/0239224 A1 | 10/2007 | Bennett et al. |
| 2007/0270921 A1 | 11/2007 | Strother et al. |
| 2007/0293910 A1 | 12/2007 | Strother et al. |
| 2007/0299483 A1 | 12/2007 | Strother et al. |
| 2008/0033500 A1 | 2/2008 | Strother et al. |
| 2008/0051647 A1 | 2/2008 | Wu et al. |
| 2008/0065167 A1 | 3/2008 | Boggs, II et al. |
| 2008/0065182 A1 | 3/2008 | Strother et al. |
| 2008/0071321 A1 | 3/2008 | Boggs, II et al. |
| 2008/0071322 A1 | 3/2008 | Mrva et al. |
| 2008/0132969 A1 | 6/2008 | Bennett et al. |
| 2008/0132974 A1 | 6/2008 | Strother et al. |
| 2008/0154335 A1 | 6/2008 | Thrope et al. |
| 2008/0161874 A1 | 7/2008 | Bennett et al. |
| 2008/0172116 A1 | 7/2008 | Mrva et al. |
| 2008/0249595 A1 | 10/2008 | McDaniel |
| 2008/0300654 A1 | 12/2008 | Lambert et al. |
| 2009/0062896 A1 | 3/2009 | Overstreet et al. |
| 2009/0132003 A1 | 5/2009 | Borgens et al. |
| 2010/0036445 A1 | 2/2010 | Sakai et al. |
| 2010/0036454 A1 | 2/2010 | Bennett et al. |
| 2010/0100158 A1 | 4/2010 | Thrope et al. |
| 2010/0152808 A1 | 6/2010 | Boggs, II |
| 2010/0152809 A1 | 6/2010 | Boggs, II |
| 2010/0152811 A1 | 6/2010 | Flaherty |
| 2010/0152812 A1 | 6/2010 | Flaherty et al. |
| 2010/0222844 A1 | 9/2010 | Troosters et al. |
| 2010/0274310 A1 | 10/2010 | Boggs, II et al. |
| 2010/0280584 A1 | 11/2010 | Johnson et al. |
| 2010/0298920 A1 | 11/2010 | Mrva et al. |
| 2011/0054346 A1 | 3/2011 | Hausman et al. |
| 2011/0060238 A1 | 3/2011 | Hausman et al. |
| 2011/0060242 A1 | 3/2011 | Hausman et al. |
| 2011/0060243 A1 | 3/2011 | Hausman et al. |
| 2011/0093032 A1 | 4/2011 | Boggs, II et al. |
| 2011/0125051 A1 | 5/2011 | Strother et al. |
| 2011/0257701 A1 | 10/2011 | Strother et al. |
| 2012/0142228 A1 | 6/2012 | Rundle |
| 2012/0238902 A1 | 9/2012 | Strother et al. |
| 2012/0291271 A1 | 11/2012 | Rundle |
| 2012/0296442 A1 | 11/2012 | Hausman |
| 2012/0323294 A1 | 12/2012 | Laing et al. |
| 2013/0018445 A1 | 1/2013 | Sakai et al. |
| 2013/0096641 A1 | 4/2013 | Strother et al. |
| 2013/0131753 A1 | 5/2013 | Simon et al. |
| 2013/0137288 A1 | 5/2013 | Rundle |
| 2013/0197615 A1 | 8/2013 | Rundle et al. |
| 2013/0204315 A1 | 8/2013 | Wongsarnpigoon et al. |
| 2013/0231715 A1 | 9/2013 | Grill, Jr. et al. |
| 2013/0245490 A1 | 9/2013 | Strother et al. |
| 2013/0296733 A1 | 11/2013 | Strother et al. |
| 2013/0303876 A1 | 11/2013 | Gelfand et al. |
| 2013/0338749 A1 | 12/2013 | Brunnett et al. |
| 2014/0058495 A1 | 2/2014 | Sakai et al. |
| 2014/0073985 A1 | 3/2014 | Sakai et al. |
| 2014/0081244 A1 | 3/2014 | Voeller et al. |
| 2014/0081353 A1 | 3/2014 | Cook et al. |
| 2014/0121741 A1 | 5/2014 | Bennett et al. |
| 2014/0194771 A1 | 7/2014 | Parker et al. |
| 2014/0194772 A1 | 7/2014 | Single et al. |
| 2014/0194948 A1 | 7/2014 | Strother et al. |
| 2014/0214129 A1 | 7/2014 | Waataja et al. |
| 2014/0214135 A1 | 7/2014 | Ben-David et al. |
| 2014/0236257 A1 | 8/2014 | Parker et al. |
| 2014/0243931 A1 | 8/2014 | Parker et al. |
| 2014/0277315 A1 | 9/2014 | Hanson et al. |
| 2014/0288613 A1 | 9/2014 | Laing et al. |
| 2014/0371622 A1 | 12/2014 | Hausman et al. |
| 2015/0032022 A1 | 1/2015 | Stone et al. |
| 2015/0313512 A1 | 11/2015 | Hausman et al. |
| 2015/0335887 A1 | 11/2015 | Riddle et al. |
| 2016/0038072 A1 | 2/2016 | Brown et al. |
| 2016/0038074 A1 | 2/2016 | Brown et al. |
| 2016/0045745 A1 | 2/2016 | Mathur et al. |
| 2016/0250466 A1 | 9/2016 | Boggs, II et al. |
| 2017/0239483 A1 | 8/2017 | Mathur et al. |
| 2017/0281945 A1 | 10/2017 | Gill et al. |
| 2017/0312499 A1 | 11/2017 | Linker et al. |
| 2018/0064484 A1 | 3/2018 | Diederich et al. |
| 2018/0078754 A1 | 3/2018 | Perez et al. |
| 2018/0078763 A1 | 3/2018 | Boggs, II et al. |
| 2018/0085580 A1 | 3/2018 | Perez et al. |
| 2018/0117344 A1 | 5/2018 | Mathur et al. |
| 2018/0338765 A1 | 11/2018 | Judy et al. |
| 2019/0110705 A1 | 4/2019 | Sakai et al. |
| 2019/0151660 A1 | 5/2019 | Boggs, II et al. |
| 2019/0217089 A1 | 7/2019 | Bayat et al. |
| 2019/0247652 A1 | 8/2019 | Boggs, II et al. |
| 2019/0255339 A1 | 8/2019 | Lee et al. |
| 2019/0275325 A1 | 9/2019 | Walter et al. |
| 2019/0381310 A1 | 12/2019 | Willand et al. |
| 2020/0086114 A1 | 3/2020 | Willand et al. |
| 2020/0155798 A1 | 5/2020 | Yang et al. |
| 2020/0338338 A1 | 10/2020 | Willand et al. |
| 2021/0001128 A1 | 1/2021 | Patnala et al. |
| 2021/0101011 A1 | 4/2021 | Scanlan et al. |
| 2021/0146121 A1 | 5/2021 | Scanlan et al. |
| 2021/0283393 A1 | 9/2021 | Willand et al. |
| 2021/0283399 A1 | 9/2021 | Willand et al. |

FOREIGN PATENT DOCUMENTS

| | | |
|---|---|---|
| EP | 3700617 | 9/2020 |
| GB | 2423020 | 8/2006 |
| GB | 2423022 | 8/2006 |
| JP | 2021/501027 | 1/2021 |
| WO | WO 2008/002917 | 1/2008 |
| WO | WO 2008/005843 | 1/2008 |
| WO | WO 2009/130515 | 10/2009 |
| WO | WO 2010/077494 | 7/2010 |
| WO | WO 2011/139779 | 11/2011 |
| WO | WO 2013/036630 | 3/2013 |
| WO | WO 2013/067018 | 5/2013 |
| WO | WO 2013/106884 | 7/2013 |
| WO | WO 2013/138786 | 9/2013 |
| WO | WO 2014/113813 | 7/2014 |
| WO | WO 2016/025909 | 2/2016 |
| WO | WO 2016/025910 | 2/2016 |
| WO | WO 2016/025912 | 2/2016 |
| WO | WO 2016/025913 | 2/2016 |
| WO | WO 2016/025915 | 2/2016 |
| WO | WO 2016/112398 | 7/2016 |
| WO | WO 2016/112400 | 7/2016 |
| WO | WO 2016/112401 | 7/2016 |
| WO | WO2016/125250 | 8/2016 |
| WO | WO 2016/183689 | 11/2016 |
| WO | WO 2017/011305 | 1/2017 |
| WO | WO 2017/064500 | 4/2017 |
| WO | WO 2017/139784 | 8/2017 |
| WO | WO 2018/048954 | 3/2018 |
| WO | WO 2018/237278 | 12/2018 |
| WO | WO 2019/084182 | 5/2019 |
| WO | WO 2019/103917 | 5/2019 |

(56) References Cited

FOREIGN PATENT DOCUMENTS

| | | |
|---|---|---|
| WO | WO 2019/165108 | 8/2019 |
| WO | WO 2020/097500 | 5/2020 |
| WO | WO 2021/067498 | 4/2021 |

OTHER PUBLICATIONS

U.S. Appl. No. 16/687,576, filed Nov. 18, 2019, Devices for Delivering Neuroregenerative Therapy.
U.S. Appl. No. 16/759,257, filed Aug. 24, 2020, Systems and Methods for Delivering Neuroregenerative Therapy.
U.S. Appl. No. 17/335,045, filed May 31, 2021, Electrode Interface Devices for Delivery of Neuroregenerative Therapy.
International Search Report and Written Opinion for PCT appl. PCT/US2018/057375 dated Jan. 11, 2019.
International Search Report and Written Opinion for PCT appl. PCT/US20/53630 dated Feb. 19, 2021.
Adams et al., "Computational modeling of neurons: intensity-duration relationship of extracellular electrical stimulation for changes in intracellular calcium," Journal of Neurophysiology, vol. 115(1), pp. 602-616 (2016).
Ahlborn et al., "One hour electrical stimulation accelerates functional recovery after femoral nerve repair," Exp. Neurol., vol. 208, pp. 137-144 (2007).
Al-Majed et al., "Brief electrical stimulation promotes the speed and accuracy of motor axonal regeneration," J. Neurosci., vol. 20, pp. 2602-2608 (2000).
Al-Majed et al., "Electrical stimulation accelerates and enhances expression of regeneration-associated genes in regenerating rat femoral motoneurons," Cell. Mol. Neurobiol., vol. 24(3), pp. 379-402 (Jun. 2004).
Al-Majed et al., "Electrical stimulation accelerates and increases expression of BDNF and trkB mRNA in regenerating rat femoral motoneurons," Eur. J. Neurosci., vol. 12, pp. 4381-4390 (2000).
Alrashdan et al., "Thirty minutes of low intensity electrical stimulation promotes nerve regeneration after sciatic nerve crush injury in a rat model," Acta. Neurol. Belg., vol. 110(2), pp. 168-179 (Jun. 2010).
Asensio-Pinilla et al., "Electrical stimulation combined with exercise increase axonal regeneration after peripheral nerve injury," Exp. Neurol., vol. 219(1), pp. 258-265 (Sep. 2009).
Balog et al., "Electrical stimulation for neuroregeneration in urology: a new therapeutic paradigm," Current Opinion in Urology, vol. 29(4), pp. 458-465 (Jul. 2019).
Baptista et al., "High- and low-frequency transcutaneous electrical nerve stimulation delay sciatic nerve regeneration after crush lesion in the mouse," Journal of the Peripheral Nervous System, vol. 13(1), pp. 71-80 (Mar. 1, 2008).
Barber et al., "Intraoperative Brief Electrical Stimulation of the Spinal Accessory Nerve (BEST SPIN) for prevention of shoulder dysfunction after oncologic neck dissection: a double-blinded, randomized controlled trial," Journal of Otolaryngology—Head & Neck Surgery, vol. 47, p. 7 (Jan. 23, 2018).
Brushart et al., "Electrical Stimulation Promotes Motoneuron Regeneration without Increasing its Speed or Conditioning the Neuron," J. Neurosci., vol. 22(15), pp. 6631-6638 (Aug. 1, 2002).
Brushart et al., "Electrical stimulation restores the specificity of sensory axon regeneration," Exp. Neurol., vol. 194(1), pp. 221-229 (Jul. 2005).
Calvey et al., "Short-Term Electrical Stimulation to Promote Nerve Repair and Functional Recovery in a Rat Model," The Journal of Hand Surgery, vol. 40(2), pp. 314-322 (Feb. 2015).
Cavalcante Miranda De Assis et al., "The Parameters of Transcutaneous Electrical Nerve Stimulation are Critical to its Regenerative Effects When Applied Just after a Sciatic Crush Lesion in Mice," BioMed Research International, vol. 2014, pp. 1-8 (2014).
Chen et al., "Effects of percutaneous electrical stimulation on peripheral nerve regeneration using silicone rubber chambers," J. Biomed. Mater. Res., vol. 57(4), pp. 541-549 (Dec. 15, 2001).
Cheng et al., "The Effects of Different Electrical Stimulation Protocols on Nerve Regeneration Through Silicone Conduits," Journal of Trauma-Injury Infection, vol. 56(6), pp. 1241-1246 (2004).
Cobianchi et al., "Differential effects of activity dependent treatments on axonal regeneration and neuropathic pain after peripheral nerve injury," Experimental Neurology, vol. 240, pp. 157-167 (Feb. 2013).
Deng et al., "Daily bilateral pudendal nerve electrical stimulation improves recovery from stress urinary incontinence," Interface Focus, vol. 9(4), p. 20190020 (Aug. 6, 2019).
Eberhardt et al., "BDNF/TrkB signaling regulates HNK-1 carbohydrate expression in regenerating motor nerves and promotes functional recovery after peripheral nerve repair," Exp. Neurol., vol. 198, pp. 500-510 (2006).
Elzinga et al., "Brief electrical stimulation improves nerve regeneration after delayed repair in Sprague Dawley rats," Experimental Neurology, vol. 269, pp. 142-153 (Jul. 2015).
English et al., "Electrical stimulation promotes peripheral axon regeneration by enhanced neuronal neurotrophin signaling," Devel. Neurobio., vol. 67(2), pp. 158-172 (Feb. 1, 2007).
English, A., "Enhancing axon regeneration in peripheral nerves also increases functionally inappropriate reinnervation of targets," The Journal of Comparative Neurology, vol. 490(4), pp. 427-441 (2005).
Foecking et al., "Single session of brief electrical stimulation immediately following crush injury enhances functional recovery of rat facial nerve," J. Rehabil. Res. Dev., vol. 49(3), pp. 451-458 (2012).
Geremia et al., "Electrical stimulation promotes sensory neuron regeneration and growth-associated gene expression," Exp. Neurol., vol. 205, pp. 347-359 (2007).
Gordon et al., "Augmenting nerve regeneration with electrical stimulation," Neurol. Res., vol. 30, pp. 1012-1022 (2008).
Gordon et al., "Brief electrical stimulation accelerates axon regeneration in the peripheral nervous system and promotes sensory axon regeneration in the central nervous system," Motor Control, vol. 13(4), pp. 412-441 (Oct. 2009).
Gordon et al., "Brief post-surgical electrical stimulation accelerates axon regeneration and muscle reinnervation without affecting the functional measures in carpal tunnel syndrome patients," Exp. Neurol., vol. 223(1), pp. 192-202 (May 2010).
Gordon et al., "Chapter 24 Electrical Stimulation for Improving Nerve Regeneration: Where do we Stand?" International Review of Neurobiology, vol. 87, pp. 433-444 (2009).
Gordon et al., "Experimental strategies to promote functional recovery after peripheral nerve injuries," J. Peripher. Nerv. Syst., vol. 8, pp. 236-250 (2003).
Gordon, T., "Electrical Stimulation to Enhance Axon Regeneration After Peripheral Nerve Injuries in Animal Models and Humans," Neurotherapeutics, vol. 13(2), pp. 295-310 (Jan. 11, 2016).
Haastert-Talini et al., "Electrical stimulation accelerates axonal and functional peripheral nerve regeneration across long gaps," J. Neurotrauma, vol. 28(4), pp. 661-674 (Apr. 2011).
Haastert-Talini et al., "Electrical Stimulation for Promoting Peripheral Nerve Regeneration," International Review of Neurobiology, vol. 109(), pp. 111-124 (2013).
Hamilton et al., "Misdirection of regenerating axons and functional recovery following sciatic nerve injury in rats," The Journal of Comparative Neurology, vol. 519(1), pp. 21-33 (2011).
Huang et al., "Electrical stimulation accelerates motor functional recovery in the rat model of 15-mm sciatic nerve gap bridged by scaffolds with longitudinally oriented microchannels," Neurorehabil. Neural Repair, vol. 24(8), pp. 736-745 (Oct. 2010).
Huang et al., "Electrical stimulation accelerates motor functional recovery in autograft-repaired 10 mm femoral nerve gap in rats," J. Neurotrauma, vol. 26(10), pp. 1805-1813 (Oct. 2009).
Huang et al., "Electrical stimulation accelerates nerve regeneration and functional recovery in delayed peripheral nerve injury in rats," Eur. J. Neurosci., vol. 38(12), pp. 3691-3701 (Dec. 1, 2013).
Huang et al., "Electrical stimulation induces calcium-dependent release of NGF from cultured Schwann cells," Glia, vol. 58(5), pp. 622-631 (2010).

(56) References Cited

OTHER PUBLICATIONS

Huang et al., "Electrical Stimulation to Conductive Scaffold Promotes Axonal Regeneration and Remyelination in a Rat Model of Large Nerve Defect," PLoS ONE, vol. 7(6), p. e39526 (Jun. 21, 2012).

Jo et al., "Comparing electrical stimulation and tacrolimus (FK506) to enhance treating nerve injuries," Muscle & Nerve, vol. 60(5), pp. 629-636 (Nov. 1, 2019).

Kerns et al., "Electrical field effects on crushed nerve regeneration," Exp. Neurol., vol. 117(1), pp. 71-80 (Jul. 1992).

Kim et al., "Subthreshold continuous electrical stimulation facilitates functional recovery of facial nerve after crush injury in rabbit," Muscle Nerve, vol. 43(2), pp. 251-258 (Feb. 1, 2011).

Kim et al., "The effect of subthreshold continuous electrical stimulation on the facial function of patients with Bell's palsy," Acta Oto-Laryngologica, vol. 136(1), pp. 100-105 (Jan. 2, 2016).

Koo et al., "Wireless bioresorbable electronic system enables sustained nonpharmacological neuroregenerative therapy," Nature Medicine, p. 1 (Oct. 8, 2018).

Lal et al., "Electrical stimulation facilitates rat facial nerve recovery from a crush injury," Otolaryngol. Head Neck Surg., vol. 139(1), pp. 68-73 (Jul. 2008).

Lee et al., "Functional regeneration of a severed peripheral nerve with a 7-mm gap in rats through the use of an implantable electrical stimulator and a conduit electrode with collagen coating," Neuromodulation, vol. 13(4), pp. 299-304 (Oct. 2010).

Lee et al., "Functional regeneration of severed peripheral nerve using an implantable electrical stimulator," Conf. Proc. IEEE Eng. Med Biol. Soc. 2010, pp. 1511-1514 (2010).

Liss et al., "Electric stimulation of a transsected nerve does not seem to prevent loss of sensory neurons: an experimental study in cats," Scand. J. Plast. Reconstr. Surg. Hand. Surg., vol. 33(4), pp. 403-409 (Dec. 1999).

Longo et al., "Electromagnetic fields influence NGF activity and levels following sciatic nerve transection," J. Neurosci. Res., vol. 55(2), pp. 230-237 (Jan. 15, 1999).

López-Álvarez et al, "Chronic electrical stimulation reduces hyperalgesia and associated spinal changes induced by peripheral nerve injury," Neuromodulation (Feb. 20, 2019).

Lu et al., "Effects of electrical stimulation at different frequencies on regeneration of transected peripheral nerve," Neurorehabil. Neural Repair, vol. 22(4), pp. 367-373 (Aug. 2008).

Lu et al., "Use of Electrical Stimulation at Different Current Levels to Promote Recovery After Peripheral Nerve Injury in Rats," The Journal of Trauma: Injury, Infection, and Critical Care, vol. 67(5), pp. 1066-1072 (Nov. 1, 2009).

MacEwan et al., "Therapeutic electrical stimulation of injured peripheral nerve tissue using implantable thin-film wireless nerve stimulators," Journal of Neurosurgery, pp. 1-10 (Feb. 9, 2018).

McCaig et al., "Electrical fields, nerve growth and nerve regeneration," Exp. Physiol., vol. 76(4), pp. 473-494 (Jul. 1, 1991).

McLean et al., "Delayed Nerve Stimulation Promotes Axon-Protective Neurofilament Phosphorylation, Accelerates Immune Cell Clearance and Enhances Remyelination In Vivo in Focally Demyelinated Nerves," PLOS ONE, vol. 9(10), p. e110174 (Oct. 13, 2014).

Mendez et al., "Brief electrical stimulation after facial nerve transection and neurorrhaphy: a randomized prospective animal study," Journal of Otolaryngology—Head & Neck Surgery, vol. 45, p. 7 (Feb. 1, 2016).

Nix et al., "Electrical stimulation of regenerating nerve and its effect on motor recovery," Brain Res., vol. 272(1), pp. 21-25 (Aug. 1, 1983).

Park et al., "Effects of Repeated 20-Hz Electrical Stimulation on Functional Recovery Following Peripheral Nerve Injury," Neurorehabil. Neural Repair (Jul. 2019).

Pockett et al., "Acceleration of peripheral nerve regeneration after crush injury in rat," Neurosci. Lett., vol. 59(2), pp. 221-224 (Aug. 30, 1985).

Power et al, "Postsurgical Electrical Stimulation Enhances Recovery Following Surgery for Severe Cubital Tunnel Syndrome: A Double-Blind Randomized Controlled Trial," Neurosurgery (Aug. 20, 2019).

Rui, B., "An implantable electrical stimulator used for peripheral nerve rehabilitation in rats," Experimental and Therapeutic Medicine, vol. 6(1), pp. 22-28 (May 13, 2013).

Senger et al., "Conditioning electrical stimulation promotes functional nerve regeneration," Exp. Neurol., vol. 315, pp. 60-71 (May 2019).

Senger et al., "Electrical stimulation as a conditioning strategy for promoting and accelerating peripheral nerve regeneration," Experimental Neurology, vol. 302, pp. 75-84 (Apr. 1, 2018).

Shapira et al., "Brief Electrical Stimulation Promotes Nerve Regeneration Following Experimental In-Continuity Nerve Injury," Neurosurgery, vol. 85(1), pp. 156-163 (Jun. 11, 2018).

Singh et al., "Accelerated axon outgrowth, guidance, and target reinnervation across nerve transection gaps following a brief electrical stimulation paradigm," J. Neurosurg., vol. 116(3), pp. 498-512 (Mar. 2012).

Sobotka et al., "Intraoperative 1-Hour Electrical Nerve Stimulation Enhances Outcomes of Nerve-Muscle-Endplate Band Grafting Technique for Muscle Reinnervation," Journal of Reconstructive Microsurgery, vol. 33(8), pp. 533-543 (Oct. 2017).

Su et al., "Late administration of high-frequency electrical stimulation increases nerve regeneration without aggravating neuropathic pain in a nerve crush injury," BMC Neuroscience, vol. 19, p. 37 (Jun. 25, 2018).

Tang et al., "Direct electrical stimulation on the injured ulnar nerve using acupuncture needles combined with rehabilitation accelerates nerve regeneration and functional recovery—A case report," Complementary Therapies in Medicine, vol. 24, pp. 103-107 (Feb. 2016).

Udina et al., "Electrical stimulation of intact peripheral sensory axons in rats promotes outgrowth of their central projections," Experimental Neurology, vol. 210(1), pp. 238-247 (Mar. 2008).

Udina et al., "Rolipram-induced elevation of cAMP or chondroitinase ABC breakdown of inhibitory proteoglycans in the extracellular matrix promotes peripheral nerve regeneration," Exp. Neurol., vol. 223(1), pp. 143-152 (May 2010).

Vivó et al., "Immediate electrical stimulation enhances regeneration and reinnervation and modulates spinal plastic changes after sciatic nerve injury and repair," Experimental Neurology, vol. 211(1), pp. 180-193 (May 2008).

Wang et al., "Electrical stimulation promotes motor nerve regeneration selectivity regardless of end-organ connection," J. Neurotrauma, vol. 26(4), pp. 641-649 (Apr. 2009).

Ward et al., "Optogenetically-enhanced Axon Regeneration: Motor-versus Sensory-Neuron Specific Stimulation," Eur. J. Neurosci., vol. 47(4), pp. 294-304 (Feb. 2018).

Wenjin et al., "Electrical Stimulation Promotes BDNF Expression in Spinal Cord Neurons Through Ca2+- and Erk-Dependent Signaling Pathways," Cell. Mol. Neurobiol., vol. 31 (3), pp. 459-467 (Jan. 23, 2011).

Willand et al., "Electrical Stimulation to Promote Peripheral Nerve Regeneration," Neurorehabil. Neural Repair, vol. 30(5), pp. 490-496 (Jun. 1, 2016).

Witzel et al., "Electrical Nerve Stimulation Enhances Perilesional Branching after Nerve Grafting but Fails to Increase Regeneration Speed in a Murine Model," J. Reconstr. Microsurg., vol. 32(6), pp. 491-497 (Jul. 2016).

Wong et al., "Electrical stimulation enhances sensory recovery: A randomized controlled trial," Ann. Neurol., vol. 77(6), pp. 996-1006 (Jun. 1, 2015).

Xu et al. "Electrical Stimulation Promotes Regeneration of Defective Peripheral Nerves after Delayed Repair Intervals Lasting under One Month," PLoS ONE, vol. 9(9), p. e105045 (Sep. 2, 2014).

Yeh et al., "Timing of applying electrical stimulation is an important factor deciding the success rate and maturity of regenerating rat sciatic nerves," Neurorehabil. Neural Repair, vol. 24(8), pp. 730-735 (Oct. 2010).

Zhang et al., "Electrical stimulation enhances peripheral nerve regeneration after crush injury in rats," Mol. Med. Rep., vol. 7(5), pp. 1523-1527 (May 2013).

(56) References Cited

OTHER PUBLICATIONS

Zuo et al., "A single session of brief electrical stimulation enhances axon regeneration through nerve autografts," Experimental Neurology, vol. 323, p. 113074 (to be published Jan. 2020).

* cited by examiner

METHODS FOR DELIVERING NEUROREGENERATIVE THERAPY AND REDUCING POST-OPERATIVE AND CHRONIC PAIN

CROSS-REFERENCE TO RELATED APPLICATIONS

This application is a continuation-in-part (CIP) of PCT Application PCT/US2020/053630 filed Sep. 30, 2020, which claims priority to U.S. Provisional Application Nos. 62/909,048 filed Oct. 1, 2019 and 63/044,208 filed Jun. 25, 2020. This application claims priority to U.S. Provisional Application Nos. 63/044,208 filed Jun. 25, 2020 and 63/172,054 filed Apr. 7, 2021. The contents of each of the aforementioned applications are incorporated by reference herein in their entireties.

FIELD

This application relates generally to devices, systems and methods for locating and/or treating (e.g., regenerating, facilitating the treatment of, etc.) injured tissue, and more specifically, to devices, systems and methods that facilitate the regeneration of injured nerves (e.g., neuroregeneration) and/or the pain that accompanies nerve injury.

BACKGROUND

Peripheral nerve injuries are severely debilitating, affecting otherwise healthy patients by limiting their ability to perform activities of daily living. Peripheral nerve injuries may result from various etiologies, from complex trauma to iatrogenic and compressive neuropathies. However, despite various etiologies the mainstay to repair peripheral nerve damage is surgical repair of transected nerve ends or surgical release of compressed nerves. Unfortunately, even the best surgical procedures usually leave patients with marked deficits. In addition, patients often have neuropathic pain associated with a nerve injury. Pain may be present at the site of injury or radiate along the injured nerve, or in cases of compression, pain may radiate downstream from the site of injury. Given the disability associated with nerve injuries, a need clearly exists to improve outcomes.

Currently, clinical treatment of injured peripheral nerves is primarily surgical, either releasing the source of nerve compression or reattaching the transected nerve directly or with grafting materials. Surgery permits nerve regrowth by re-establishing nerve continuity but functional recovery remains inadequate. Generally, nerves regenerate slowly (~1 mm/day at their fastest) requiring long periods of time before reconnecting with denervated target muscle or sensory end-organs. The window of opportunity for nerve regeneration is short with the regenerative capacity of the injured neurons and the regenerative support of the distal nerve stump declining with time and distance. These factors together with the misdirection of regenerating nerves account for the frequent poor recovery. In addition to poor recovery, patients are often faced with pain resulting from the nerve injury. This pain may present clinically in the form of allodynia or hyperalgesia. This pain may be transient in nature, resolving when tissue becomes reinnervated or may become chronic if nerve regeneration results in a neuroma formation. Poor regeneration can lead to not only diminished functional motor outcomes, but chronic pain and an increase in residual sensory abnormalities. Enhancing nerve regeneration can result in better tissue reinnervation which not only improves functional outcomes but reduces the potential for developing chronic or other long-term pain. Chronic or long-term pain can also include pain that persists past a normal healing time (e.g., a normal time vis-à-vis a particular type of injury or other source of pain). As used herein, "chronic pain" or "long-term pain" can include, but is not limited to, pain that lasts twelve weeks or longer.

SUMMARY

According to some embodiments, an electrical lead assembly configured to be inserted at least partially within an anatomy of a subject comprises at least one electrode (e.g., one, two, three, four, more than 4 electrodes) configured to be placed adjacent to targeted tissue of the subject to perform a desired procedure, a first insert located along a first portion of the lead assembly, wherein the first insert comprises plastic deformation properties to facilitate a shaping of the lead assembly along the first portion, wherein the first portion is configured to substantially maintain a shape following the shaping of the lead assembly, wherein the first portion extends to a distal end of the lead assembly, and wherein the first portion is configured to be shaped in order to maintain a desired shape and position relative to the targeted tissue of the subject. The assembly further includes a second insert located along a second portion of the lead assembly, wherein a rigidity of the second insert is greater than a rigidity of the first insert, wherein the second portion extends to a proximal end of the lead assembly, and at least one outer covering configured to extend from the proximal end to the distal end of the lead assembly, wherein the at least one electrode is located along the first portion of the lead assembly, wherein the proximal end is configured to be inserted into a port of an electrical stimulation device, and wherein the first portion of the lead assembly is configured to be shaped following percutaneous insertion into the anatomy of the subject by selectively exerting forces or moment along at least one portion of the first portion.

According to some embodiments, an outer diameter or other cross-sectional dimension of the lead assembly is constant or substantially constant along a length of the lead assembly (e.g., within a 5% deviation, except for a possible rounded distal end), the rigidity of the second insert is at least 100 times (e.g., at least 100, 1000, 2000, 10000, 15000, 20000, 25000, 30000, etc.) greater than the rigidity of the first insert (e.g., as determined by Young's modules and/or coefficient of stiffness), and plastic deformation properties of the first insert are greater than elastic deformation properties of the at least one covering.

According to some embodiments, an outer diameter or other cross-sectional dimension of the lead assembly is constant or substantially constant along a length of the lead assembly. In some embodiments, a maximum variation in the outer diameter or other cross-sectional dimension is 5% (e.g., 0 to 1, 1 to 2, 2 to 3, 3 to 4, 4 to 5%, values between the foregoing values or ranges, etc.) along the length of the lead assembly.

According to some embodiments, the rigidity of the second insert is at least 100 times (e.g., at least 100, 1000, 2000, 10000, 15000, 20000, 25000, 30000, etc.) greater than the rigidity of the first insert.

According to some embodiments, the proximal end comprises at least one electrical contact that extends to an exterior of the lead assembly, wherein the at least one electrical contact is electrically coupled to the at least one electrode along the first portion of the lead assembly. In some embodiments, the proximal end is configured to be inserted (e.g., directly inserted) into a port of an electrical stimulation device without the need for an additional connector or component.

According to some embodiments, plastic deformation properties of the first insert are greater than elastic deformation properties of the at least one covering. In some embodiments, the first insert extends to or near a distal end of the second insert. In some embodiments, the first insert does not extend to or near a distal end of the second insert.

According to some embodiments, the at least one electrode comprises a proximal electrode and a distal electrode, wherein the proximal and distal electrodes are located along the first portion of the lead assembly (e.g., located along a distal one-half, one-third or one-quarter of the lead assembly).

According to some embodiments, the at least one outer covering comprises a single member that extends from the proximal end to the distal end of the lead assembly. In some embodiments, the at least one outer covering comprises at least two separate members that form a substantially seamless surface along an exterior of the lead assembly. In some embodiments, the at least one outer covering along the proximal end of the lead assembly comprises a color that is different than a distal portion of the at least one outer covering.

According to some embodiments, the first portion of the lead assembly is configured to be shaped using forceps.

According to some embodiments, a distal aspect or portion of the outer covering comprises a lower durometer or hardness than a proximal aspect of the outer covering. In some embodiments, a Shore D durometer of the distal aspect of the outer covering is between 20D and 50D, wherein a Shore D durometer of proximal aspect of the outer covering is between 50D and 80D, and wherein a thickness of the outer covering is between 100 and 400 µm.

According to some embodiments, the first insert comprises an annealed metal or alloy. In some embodiments, the first insert is electrically coupled to a wire. In some embodiments, the second insert is physically coupled to an insulative material. In some embodiments, the second insert comprises a non-annealed metal. In some embodiments, the second insert provides a backbone for a connector set. In one embodiment, the connector set is operatively coupled to a stimulator.

According to some embodiments, a diameter or other cross-sectional dimension of the insert is 100% to 500% of the thickness of the outer covering. In some embodiments, the outer diameter through the length of the electrical lead assembly is uniform to facilitate removal of shafts or tools.

According to some embodiments, a Shore D durometer of the outer covering is between 20D and 80D, a thickness of the outer covering is between 100 and 400 µm, the first insert comprises an annealed metal or alloy, and a diameter or other cross-sectional dimension of the insert is 100% to 500% of the thickness of the outer covering. In some embodiments, the annealed metal or alloy comprises copper.

According to some embodiments, a diameter or other cross-sectional dimension of the insert is 100% to 500% of the thickness of the outer covering.

According to some embodiments, the outer covering comprises a uniform or continuous (e.g., or substantially uniform or continuous) thickness through a length of the electrical lead assembly.

According to some embodiments, a distal aspect of the outer covering comprises a lower durometer or hardness than a proximal aspect of the outer covering. In some embodiments, a Shore D durometer of the distal aspect of the outer covering is between 20D and 50D. In some embodiments, a Shore D durometer of proximal aspect of the outer covering is between 50D and 80D. In some embodiments, a Shore D durometer of the outer covering is between 20D and 80D. In some embodiments, a thickness of the outer covering is between 100 and 400 µm.

According to some embodiments, the first insert comprises an annealed metal or alloy. In some embodiments, the annealed meal or alloy comprises copper. In some embodiments, a diameter or other cross-sectional dimension of the insert is 100% to 500% of a thickness of the outer covering.

According to some embodiments, the lead assembly is configured to at least partially surround a targeted nerve or nerve bundle. In some embodiments, the lead assembly is configured to be used during a neuroregenerative procedure. In some embodiments, the lead assembly is configured to be used during a pain management procedure. In some embodiments, the lead assembly is configured to be used during a both a neuroregenerative procedure and a pain management procedure.

According to some embodiments, an electrical lead assembly configured to be inserted at least partially within an anatomy of a subject includes at least one electrode, an insert (e.g., a distal insert) located along a distal portion of the lead assembly, wherein the insert comprises plastic deformation properties to facilitate a shaping of the lead assembly along the distal portion, wherein the distal portion is configured to substantially maintain a shape following the shaping of the lead assembly, wherein the distal portion extends to a distal end of the lead assembly, and at least one outer covering configured to extend from a proximal end to the distal end of the lead assembly, wherein plastic deformation properties of the insert are greater than elastic deformation properties of the at least one covering, wherein the at least one electrode is located along the distal portion of the lead assembly, wherein the distal portion of the lead assembly is configured to be shaped following percutaneous insertion into the anatomy of the subject by selectively exerting forces or moment along at least one portion of the first portion, and wherein an outer diameter or other cross-sectional dimension of the lead assembly is constant or substantially constant along a length of the lead assembly.

According to some embodiments, a maximum variation in the outer diameter or other cross-sectional dimension is 5% along the length of the lead assembly.

According to some embodiments, the proximal end of the lead assembly comprises a proximal insert, the proximal insert being more rigid than the insert (e.g., distal insert). In some embodiments, the rigidity of the proximal insert is at least 100 times greater than the rigidity of the insert. In some embodiments, the proximal end is configured to be inserted into a port of an electrical stimulation device. In some embodiments, the proximal end is configured to be inserted into a port of an electrical stimulation device without the need for an additional connector or component.

According to some embodiments, the at least one electrode comprises a proximal electrode and a distal electrode, wherein the proximal and distal electrodes are located along a distal one-third of the lead assembly.

According to some embodiments, the at least one outer covering comprises a single member that extends from the proximal end to the distal end of the lead assembly. In some embodiments, the at least one outer covering comprises at least two separate members that form a substantially seamless surface along an exterior of the lead assembly.

According to some embodiments, a method of managing pain related to a peripheral nerve injury of a subject comprises delivering stimulation energy of a first frequency to the target nerve via at least one electrode assembly during a regenerative phase, wherein delivering said stimulation energy creates a neuroregenerative effect to the target nerve resulting in enhanced tissue reinnervation, wherein the enhanced tissue reinnervation is configured to result in a reduced potential for developing long-term pain, and delivering stimulation energy of a second frequency for a predetermined period via the at least one electrode assembly during at least one neuropathic pain management phase, wherein delivering stimulation energy during the at least one neuropathic pain management phase alleviates neuropathic pain of the subject caused by the peripheral nerve injury.

According to some embodiments, the method additionally comprising accessing a target nerve using a para-incisional approach, wherein the target nerve is a peripheral nerve that has sustained injury, wherein the frequency of the neuropathic pain management phase is greater than the frequency of the neuroregenerative phase.

According to some embodiments, the method further comprises accessing a target nerve using a para-incisional approach, wherein the target nerve is a peripheral nerve that has sustained injury.

According to some embodiments, the frequency of the neuropathic pain management phase is greater than the frequency of the neuroregenerative phase. In some embodiments, pain management therapy comprises stimulation in the 50 to 200 Hz range (e.g., 50-60, 50-55, 55-60, 52-58 Hz, values between the foregoing ranges, etc.). In some embodiments, the frequency of the neuropathic pain management phase is 20 KHz to 500 KHz. In some embodiments, the frequency of the neuropathic pain management phase is 1 KHz to 10 KHz.

According to some embodiments, accessing the target nerve is performed percutaneously.

According to some embodiments, delivering stimulation energy during the regenerative phase is sufficient to elicit a response. In some embodiments, the response relates to an action potential or an evoked response in the subject. In some arrangements, the elicited response during the regenerative phase is configured to, at least in part, confirm validation of therapeutic efficacy of neuroregenerative therapy in the subject.

According to some embodiments, delivering stimulation energy during the neuropathic pain management phase is sufficient to elicit a response. In some arrangements, the response relates to an action potential or an evoked response in the subject. In some embodiments, the elicited response during the neuropathic pain management phase is configured to, at least in part, confirm relief from neuropathic pain in the subject.

According to some embodiments, a system comprises one or more components configured to deliver stimulation energy of the first frequency and the second frequency to accomplish any one of the methods described above.

According to some embodiments, the systems and methods disclosed herein are configured to provide a targeted approach to both treating injured tissue and reducing neuropathic pain with electrical stimulation by enhancing tissue reinnervation.

In some embodiments, the systems described herein may deliver one or more bouts of neuroregenerative therapy and separate pain management therapy. In other arrangements, multiple bouts of neuroregenerative therapy may be delivered that lead to enhanced tissue reinnervation. In such embodiments, a diminished potential for developing chronic pain or other long-term pain can result for a patient or other subject while applying pain management waveforms may reduce short-term acute pain.

According to some embodiments, a system (and corresponding method) configured to deliver targeted electrical stimulation therapy to injured nerves is amenable to fit the needs of different injuries and clinical workflows, including different anatomical areas, injured nerves, nerve diameters, and types of nerve injury. The system can advantageously provide users with the ability to seamlessly interchange nerve interfaces to connect with and deliver neuroregenerative therapy (e.g., for neuroregeneration). The embodiments disclosed herein provide flexibility to users to apply neuroregenerative therapy prior to surgery, at the time of surgery, post-surgery, or a combination thereof, as desired or required.

According to some embodiments, additionally, the systems and methods allow for confirmation that the stimulating electrodes are functioning correctly by providing a means to verify the integrity of the electrode and/or system either through a physical self-verification or automatic verification steps. This becomes advantageous in situations where motor nerves are transected and no physical response (e.g., no muscle contraction) is present or in situations where a pure sensory nerve is transected and there are no physical responses to begin with. This same verification method allows for safe and continuous delivery of neuroregenerative therapy by monitoring current flow through the electrodes.

According to some embodiments, the systems and methods disclosed herein further allow users to perform nerve location tasks using the same or different nerve interfaces prior to commencing neuroregenerative therapy. The system is also configured to incorporate a single button that controls stimulus parameters, system modes, and therapy time providing an easy to use interface for a clinician minimizing training and complexity.

According to some embodiments, a method of stimulating a target nerve of a subject comprises, during a first phase, delivering stimulation energy of a first frequency via at least one electrode assembly, and, during a second phase, delivering to the subject stimulation energy of a second frequency for a predetermined period via the at least one electrode assembly, wherein delivering stimulation energy to the subject during the second phase creates a regenerative effect (e.g., neuroregenerative effect) to the target nerve, and wherein delivering stimulation energy during the first phase is configured to confirm at least one validation condition. In some embodiments, the second frequency is greater than the first frequency.

According to some embodiments, a method of stimulating a target nerve of a subject comprises, during a first phase, delivering stimulation energy of a first frequency via at least one electrode assembly, and, during a second phase, delivering to the subject stimulation energy of a second frequency for a predetermined period via the at least one electrode assembly, wherein delivering stimulation energy to the subject during the second phase creates a neuroregenerative effect to the target nerve, and wherein the second frequency is greater than the first frequency.

According to some embodiments, the at least one validation condition is that the at least one electrode assembly is working. In some embodiments, delivering stimulation energy during the first phase is configured to activate an indicator that the at least one electrode assembly is working. In some embodiments, the indicator comprises a visual indicator (e.g., a LED or other light source). In other arrangements, the indicator comprises a non-visual indicator (e.g., an audible indicator, a haptic feedback indicator, etc.).

According to some embodiments, the at least one validation condition is that the at least one electrode is contacting the target nerve. In some embodiments, delivering stimulation energy during the first phase is configured to facilitate locating the target nerve. In some embodiments, delivering stimulation energy at a first frequency during the first phase creates a visible and/or verbal (e.g., oral) response from the subject. In several embodiments, the visible response comprises a twitch, reflex, muscle response or other involuntary bodily movement.

According to some embodiments, the predetermined period is at least 10 minutes. In some embodiments, the predetermined period is at least 20 minutes or 30 minutes. In some arrangements, the predetermined period is 10 minutes to 60 minutes.

According to some embodiments, the first frequency is 1 Hz to 40 Hz. In some embodiments, the first frequency is lower than 40 Hz. In some embodiments, the second frequency is 1 Hz to 100 Hz. In some embodiments, the first frequency is 1 Hz to 10 Hz, and wherein the second frequency is 10 Hz to 100 Hz.

According to some embodiments, the method further comprises positioning the at least one electrode assembly adjacent the target nerve of the subject.

The method additionally includes at least partially securing the at least one electrode assembly to the target nerve of the subject. In some embodiments, at least partially securing the at least one electrode assembly to the target nerve comprises using at least one of a suture, a barb, a tissue anchor, a flap and another type of mechanical connector. In one embodiment, at least partially securing the at least one electrode assembly to the target nerve comprises using an adhesive.

According to some embodiments, positioning the at least one electrode assembly adjacent the target nerve comprises not fastening the at least one electrode assembly to the subject. In some embodiments, wherein positioning the at least one electrode assembly adjacent the target nerve comprises aligning the at least one electrode assembly adjacent or near the target nerve (e.g., with or without the aid of an insertion tool).

According to some embodiments, wherein delivering stimulation energy to the subject during the first phase comprises delivering the stimulation energy in a repetitive burst sequence. In some embodiments, wherein repetitive burst sequence comprises at least two pulses. In some embodiments, wherein repetitive burst sequence comprises at least three pulses.

According to some embodiments, wherein the at least one electrode is included as part of a bipolar electrode assembly. In some embodiments, wherein positioning the at least one electrode assembly at or adjacent the target nerve comprises advancing the at least one electrode assembly and a lead secured to the at least one electrode through a cannula, sheath or other device with an internal opening. In some embodiments, in intraoperative settings, the at least one electrode assembly comprises a cuff electrode.

According to some embodiments, a device for stimulating a target nerve of a subject comprises at least one electrode assembly, and a lead physically coupled to the at least one electrode assembly, wherein, during a first phase, the at least one electrode is configured to deliver stimulation energy of a first frequency via at least one electrode assembly, wherein, during a second phase, the at least one electrode is configured to deliver to the subject stimulation energy of a second frequency for a predetermined period via the at least one electrode assembly, wherein delivery of stimulation energy to the subject during the second phase creates a neuroregenerative effect to the target nerve, and wherein delivery of stimulation energy to the subject during the first phase is configured to confirm at least one validation condition.

According to some embodiments, the at least one validation condition is that the at least one electrode assembly is working. In some embodiments, the device further comprises an indicator, wherein delivering stimulation energy during the first phase is configured to activate the indicator, the indicator being configured to provide confirmation that the at least one electrode assembly is working. In some embodiments, the indicator comprises a visual indicator (e.g., a LED or other light source). In some embodiments, the indicator comprises a non-visual indicator (e.g., an audible indicator, a haptic feedback indicator, etc.).

According to some embodiments, the at least one validation condition is that the at least one electrode is contacting the target nerve. In some embodiments, the delivery of stimulation energy during the first phase is configured to facilitate locating the target nerve. In some embodiments, the delivery of stimulation energy at a first frequency during the first phase creates a visible and/or verbal (e.g., oral) response from the subject. In some embodiments, the visible response comprises a twitch, reflex, muscle response or other involuntary bodily movement.

According to some embodiments, the first frequency is 1 Hz to 40 Hz. In some embodiments, the first frequency is lower than 40 Hz. In some embodiments, the second frequency is 1 Hz to 100 Hz. In some embodiments, the first frequency is 1 Hz to 10 Hz, and wherein the second frequency is 10 Hz to 100 Hz.

According to some embodiments, the delivery of stimulation energy to the subject during the first phase comprises delivering the stimulation energy in a repetitive burst sequence. In some embodiments, the repetitive burst sequence comprises at least two pulses. In some embodiments, the repetitive burst sequence comprises at least three pulses. In some embodiments, the least one electrode assembly comprises a cuff electrode.

According to some embodiments, a method of stimulating a target nerve of a subject comprises identifying the target nerve, positioning at least one electrode assembly relative to the subject to selectively stimulate the target nerve, and delivering therapeutic stimulation energy to the subject via the at least one electrode assembly for a predetermined time period to create a neuroregenerative effect to the target nerve, wherein the predetermined time period is at least 10 minutes (e.g., 10 minutes, 10-30 minutes, 10-60 minutes, etc.), and wherein the at least one electrode assembly comprises a first electrode positioned immediately adjacent the target nerve and a second electrode, the second electrode being positioned physically apart from the first electrode.

According to some embodiments, the second electrode comprises a patch electrode positioned on a skin surface of the subject. In one embodiment, the first and second electrodes are included as part of a bipolar electrode assembly. In some embodiments, identifying the target nerve comprises soliciting a response from the subject via delivery of a validation stimulus to the subject. In some embodiments, the validation stimulus comprises a frequency that is lower than a frequency of the therapeutic stimulation energy. In some embodiments, the validation stimulus comprises a repetitive burst sequence with at least two pulses. In some embodiments, the repetitive burst sequence comprises at least three pulses.

According to some embodiments, a method of stimulating a target nerve of a subject comprises identifying the target nerve, positioning at least one electrode assembly adjacent to the target nerve, prior to positioning the at least one electrode assembly adjacent to the target nerve, validating that the at least one electrode is electrically activated when subjected to a validation stimulus, wherein the validation stimulus originates from a validation stimulus source, and delivering therapeutic stimulus to the subject via the at least one electrode assembly for a predetermined time period to create a neuroregenerative effect to the target nerve, wherein the therapeutic stimulus originates from a therapeutic stimulus source, wherein the predetermined time period is at least 10 minutes.

According to some embodiments, the validation stimulus source is the same as the therapeutic stimulus source, such that the validation stimulus source and the therapeutic stimulus source comprise a single stimulus course. In some embodiments, the single stimulus source comprises a handheld device. In some embodiments, the validation stimulus source is different from the therapeutic stimulus source. In some embodiments, the validation stimulus comprises lower frequency than the therapeutic stimulus. In some embodiments, the validation stimulus comprises a repetitive burst sequence with at least two pulses. In some embodiments, the repetitive burst sequence comprises at least three pulses (e.g., 3, 4, 5 pulses, more than 5 pulses, etc.).

According to some embodiments, the present application discloses an electrical stimulation system comprising one or more electrodes that may be used for intra-operative or peri-operative nerve stimulation. In some embodiments, the system comprises a relatively small size, suitable to fit into the palm of an end-user. In some embodiments, one or more of the configurations disclosed herein provide the ability to interface the system with different electrodes. In some embodiments, the system is designed to be single use and disposable providing end-users, such as surgeons or other practitioners, the ability to use the system intraoperatively (e.g., provided the system is sterilized and packaged in appropriate packaging material).

In some embodiments, the various systems, devices and methods disclosed herein provide a practitioner with a way of locating a damaged nerve and treating it with electrical stimulation. The embodiments can be used intra-operatively or peri-operatively.

In some embodiments, the system can be used in peri-operative settings. The housing of the system can include controls (e.g., one or more sets of controls) to change the stimulus amplitude and/or other settings.

In some embodiments, the system comprises one or more controls to start, stop, pause, restart and/or otherwise alter the delivery of energy to heal injured tissue. In some embodiments, the system additionally comprises circuitry to enable power to the system and thus provide stimulation only when the appropriate interface has been connected. Visual indicators may be included on the housing or the connected interface. These indicators may provide end-users with signals relaying information regarding the status of the system, the active interface use, the mode it is operating in, the stimulus settings, and/or the time remaining on the delivery of the treatment. The indicators may comprise multiple light emitting diodes, graphical displays, or similar emissive elements. The housing also may contain an element used to secure the system to a surgical drape or other structure. This element may be but is not limited to an adhesive, strap, hook, or clip.

Additional aspects of the system include the ability to provide either monopolar or bipolar stimulation. In the case of intraoperative use, where the exposed injured tissue is preferably a nerve, the system may be deployed using a bipolar or monopolar electrode apparatus to interface with the injured nerve. The described electrode apparatus may allow the user to interface any diameter nerve by wrapping the electrode carrier body around the nerve and securing the wrapped portion in place using tabs. Lateral deflection of the tabs releases the wrapped nerve allowing easy removal of the electrode. One aspect of the electrode apparatus is that it is molded in a flat or open configuration allowing the electrode to spring back to this configuration when wrapped around a nerve. Molded tabs on the electrode allow the head portion of the electrode to be secured underneath them preventing the electrode to spring back to its flat configuration and maintaining a wrap around the interfaced nerve to deliver the appropriate stimulation treatment.

In some embodiments, for peri-operative use, an electrode is placed either during a surgical procedure or peri-operatively using a percutaneous method. In some embodiments, a monopolar electrode can be used where the electrode interface may not be in contact with the nerve directly. In such arrangements, the system can connect or otherwise couple to a return electrode (e.g., which can include a patch type electrode placed on the skin and connected to the system directly).

According to some embodiments, additional aspects of the system include a stimulation signal (e.g., that may comprise either constant voltage or constant current pulses). In some embodiments, a constant current pulse is used. In some embodiments, constant current stimulation amplitudes range from 0 to 20 milliamperes (e.g., 0-1, 1-2, 2-3, 3-4, 4-5, 5-6, 6-7, 7-8, 8-9, 9-10, 10-15, 15-20 milliamperes, values within the foregoing ranges, etc.).

According to some embodiments, for safe stimulation over a period a time, biphasic pulse outputs are used. This can help ensure that no net charge is being delivered at the electrode interface. In some embodiments, charge balancing is accomplished using a passive element (e.g., such as a capacitor coupled to the output of the stimulator). In some embodiments, active methods sample the output offset of the stimulator in a feedback loop and/or correct this either by generating additional pulses of the correct polarity or injecting a reverse offset to ensure that the net charge is zero. Other methods not specifically described herein may also be employed.

According to some embodiments, additional aspects of the system include a test mode (e.g., to allow the user to first deliver low-frequency stimulation (e.g., from 0.1 to 10 Hz) that permits the end-user to visualize if the injured tissue responds to stimulation). In some embodiments, the various configurations enable the user to adjust the stimulus output to a desired level and initiate the therapeutic delivery of electrical stimulation. Additional parameters can be adjusted.

According to some embodiments, additional aspects of the system include a modification of the first phase of stimulation and housing to accommodate a bipolar probe electrode to serve as a nerve locator. In some embodiments, the test mode can be modified to deliver electrical stimulation pulses sufficient to elicit a strong muscle contractile response following probe connection with a peripheral nerve. In several arrangements, the test mode provides stimulation doublet pulses (e.g., doublets) used to exploit the muscle catch-like property where successive stimuli lead to fused contractions. In certain embodiments, doublets allow for a greater muscle excursion and can be helpful in nerve location.

According to some embodiments, a method for treating injured tissue (e.g., nerve) comprises first interfacing tissue with an electrode suitable to the use-case (e.g., intra or peri-operative, other procedure, etc.). The method can also comprise securing or otherwise coupling an electrode to the system. In some embodiments, the system is then enabled to provide test stimulation to verify the responsiveness of the tissue to electrical stimulation. In some embodiments, the system is configured to permit the user to modify one or more operational parameters (e.g., amplitude). The method further includes the user initiating neuroregenerative therapy to treat the injured tissue (e.g., targeted nerve).

According to some embodiments, the methods disclosed herein are configured to provide a targeted approach to treating injured tissue with electrical stimulation. In some embodiments, unlike other stimulation systems, the systems, devices and methods disclosed herein can be configured to enable users to choose whether to apply the system intra-operatively using a pre-determined suitable electrode interface or peri-operatively using a suitable electrode interface. In some embodiments, the length of a surgical procedure will determine how the device is applied.

According to some embodiments, a method of placing an electrical lead assembly at least partially within an anatomy of a subject comprises percutaneously inserting the electrical lead assembly within the anatomy of the subject, the lead assembly comprising at least one electrode configured to contact targeted tissue of the subject to perform a desired procedure, wherein the electrical lead assembly further comprises an insert and outer covering, wherein the insert comprises elastic deformation properties to facilitate shaping or re-shaping of the electrical lead assembly, and wherein the outer covering comprises elastic deformation properties to permit the outer covering to undergo a temporary change in shape once a force is exerted on the electrical lead assembly. The method further comprises shaping the electrical lead assembly after percutaneous insertion into the anatomy of the subject by selectively exerting forces or moment along at least one portion of the electrical lead assembly, wherein the elastic deformation properties of the outer covering are not greater than (e.g., are equal to or less than) the plastic deformation properties of the insert, and wherein shaping the electrical lead assembly can place the at least one electrode of the electrical lead assembly along the targeted tissue.

According to some embodiments, the desired procedure comprises a neuroregenerative procedure and/or pain management procedure. In some embodiments, the targeted tissue comprises nerve tissue.

According to some embodiments, an electrical lead assembly configured to be inserted at least partially within an anatomy of a subject comprises at least one electrode configured to contact targeted tissue of the subject to perform a desired procedure, an insert, wherein the insert comprises elastic deformation properties to facilitate shaping or re-shaping of the electrical lead assembly, and an outer covering, wherein the outer covering comprises elastic deformation properties to permit the outer covering to undergo a temporary change in shape once a force is exerted on the electrical lead assembly, wherein the electrical lead assembly is configured to be shaped following percutaneous insertion into the anatomy of the subject by selectively exerting forces or moment along at least one portion of the electrical lead assembly.

According to some embodiments, a shapeable lead assembly is configured to be shaped in a desired manner before and/or during a procedure, such as, for example, after the lead assembly has been at least partially placed within the anatomy of a subject. The shapeable lead assembly can be shaped during a neuroregenerative procedure to contact and/or otherwise interface with a targeted nerve.

According to some embodiments, a shapeable lead assembly includes an insert or other member and an outer jacket or other outer covering. The insert can be configured to facilitate shaping or re-shaping of the assembly and can include plastic deformation properties (e.g., the insert can be configured for distortion that occurs when a material is subjected to certain forces and/or stresses that exceed its yield strength and cause it to elongate, bend, twist and/or the like. Such a distortion can be temporary, such that the insert or other member can maintain its shape when no external forces are exerted on it (e.g., as it sits on a table or other surface, until a user exerts another bending or other re-shaping force or moment, etc.). The outer jacket or other outer covering of the lead assembly can include elastic deformation properties (e.g., is configured to undergo a temporary change in shape once a force is exerted on the lead assembly, and thus the outer jacket or covering). Such members with elastic deformation properties are configured to reassume their original shape or orientation (e.g., are at least partially self-reversing) once the force or moment is removed or reduced.

BRIEF DESCRIPTION OF THE DRAWINGS

These and other features, aspects and advantages of the present application are described with reference to drawings of certain embodiments, which are intended to illustrate, but not to limit, the concepts disclosed herein. The attached drawings are provided for the purpose of illustrating concepts of at least some of the embodiments disclosed herein and may not be to scale.

DETAILED DESCRIPTION

Figure 1:
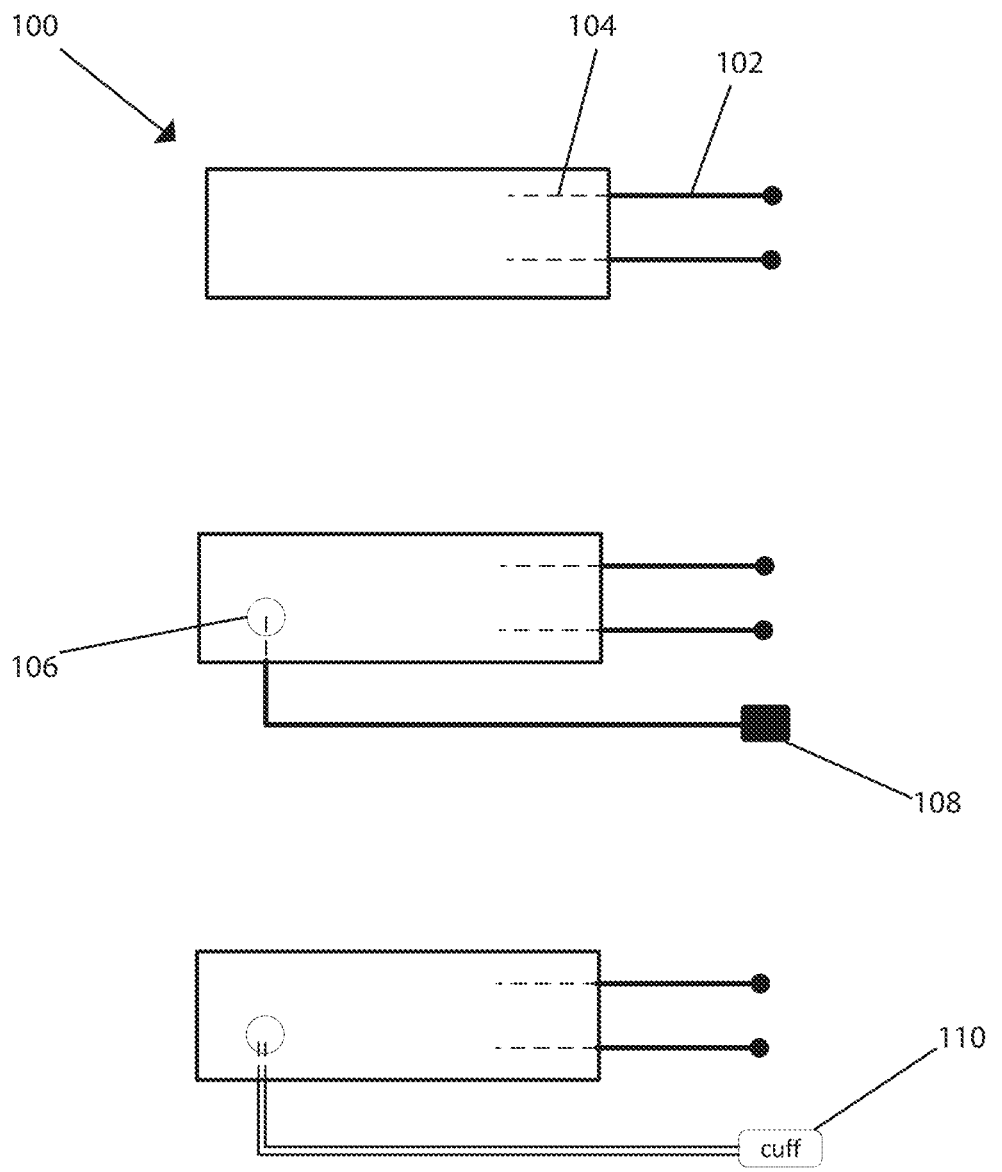
FIG. 1 illustrates a schematic of various configurations of the system according to one embodiment.

The devices, systems and associated methods described herein may be used during surgical procedures to locate nerve tissue, test nerve tissue excitability and/or provide neuroregenerative therapy (e.g., electrical stimulation) to treat targeted nerve tissue (e.g., injured nerve tissue). The embodiments disclosed herein can be used for peripheral nerves; however, other types of nerves can also be targeted, such as, for example, nerves in the autonomic system or nerves in the central nervous system. For example, peripheral nerves may include the median nerve in the upper limb, the sciatic nerve in the lower limb, smaller nerves (e.g., the intercostal branches in the thorax), etc. Autonomic nerves may include, without limitation, the vagus nerve. Nerves in the central nervous system may reside in the spinal cord or brain.

According to some embodiments, the systems and methods disclosed herein are configured to provide a targeted approach to both treating injured tissue and reducing neuropathic pain with electrical stimulation by enhancing tissue reinnervation.

In some embodiments, the systems described herein may deliver one or more bouts of neuroregenerative therapy and separate pain management therapy. In other arrangements, multiple bouts of neuroregenerative therapy may be delivered that lead to enhanced tissue reinnervation. In such embodiments, a diminished potential for developing chronic pain or other long-term pain can result for a patient or other subject while applying pain management waveforms may reduce short-term acute pain.

In some embodiments, a system (and corresponding method) configured to deliver targeted electrical stimulation therapy to injured nerves is amenable to fit the needs of different injuries and clinical workflows, including different anatomical areas, injured nerves, nerve diameters, and types of nerve injury. The system can advantageously provide users with the ability to seamlessly interchange nerve interfaces to connect with and deliver neuroregenerative therapy (e.g., for neuroregeneration). The embodiments disclosed herein provide flexibility to users to apply neuroregenerative therapy prior to surgery, at the time of surgery, post-surgery, or a combination thereof, as desired or required. The delivery of neuroregenerative therapy can occur before, during or after the delivery of pain management therapy, as desired or required.

Additionally, the systems and methods allow for confirmation that the stimulating electrodes are functioning correctly by providing a means to verify the integrity of the electrode and/or system either through a physical self-verification or automatic verification steps. This becomes advantageous in situations where motor nerves are transected and no physical response (e.g., no muscle contraction) is present or in situations where a pure sensory nerve is transected and there are no physical responses from the start. This same verification method allows for safe and continuous delivery of neuroregenerative therapy by monitoring current flow through the electrodes.

In some embodiments, the systems and methods disclosed herein further allow users to perform nerve location tasks using the same or different nerve interfaces prior to commencing neuroregenerative therapy. The system is also configured to incorporate a single button that controls stimulus parameters, system modes, and therapy time providing an easy to use interface for a clinician minimizing training and complexity.

There exists a need for a purposely designed system that can accommodate an appropriate nerve interface for prolonged stimulation and deliver electrical stimulation to injured nerves to accelerate nerve regeneration. Many medical disciplines can benefit from using the disclosed system and interface to accelerate nerve regeneration. These disciplines include but are not limited to: plastic surgery, orthopedic surgery, otolaryngology, oral surgery, and neurosurgery. In addition, clinical diagnoses that would be improved from using the disclosed device include but are not limited to: sharp lacerations, nerve transection, nerve compression, compressive neuropathy, cancer injury to nerve, peripheral neuropathy, iatrogenic nerve injury, obstetrical brachial plexus palsy, neonatal brachial plexus palsy, facial paralysis, and radiculopathy.

More specifically, the disclosed system and interface is designed for intra-operative use and/or peri-operative use, and may improve surgical outcomes in the following situations: nerve transection, nerve decompression, nerve transfer, nerve graft, neurolysis, nerve allograft, thoracic outlet decompression, carpal tunnel release, cubital tunnel release, and tarsal tunnel release. While these listed examples may benefit from the disclosed device, the list is not exhaustive and only provides an example of what medical conditions may be treated.

Additionally, following one or more of the above listed nerve injuries, patients may experience pain following incomplete or impaired nerve regeneration. Pain may present as allodynia or hyperalgesia along the injured nerves pathway and distally connected tissues. The disclosed system and methods may be used to provide pain management therapy to these injured nerves.

In some arrangements, during the course of certain surgical procedures (e.g., complex or complicated surgical procedures), nerves may not be visible and/or may be surrounded by connective tissue, scar tissue and/or other type of tissue. Devices such as nerve locators can be used to probe tissue using electrical stimuli to test and confirm if the tissue is a nerve. Furthermore, there are instances where a nerve locator is used to test for motor components of a nerve fascicle prior to a nerve transfer procedure.

In some embodiments, a nerve may be transected or cut (e.g., partially transected, mostly transected, fully transected, etc.), crushed and/or otherwise injured or damaged. In such instances, the injured nerve(s) may benefit from application of stimulation therapy. For example, in some embodiments, brief but continuous electrical stimulation applied to the proximal segments of the injured nerves can provide therapy and/or other benefits to the targeted nerve(s). In some embodiments, such a treatment can accelerate nerve regeneration of injured nerves. This treatment is referred to herein as neuroregenerative therapy.

In some embodiments, the application of a single bout of neuroregenerative therapy may lead to enhanced tissue reinnervation that ultimately results in, among other benefits and advantages, a diminished potential for developing chronic pain for a patient, a decrease in residual sensory abnormalities and an increase in fine motor skill.

In some arrangements, multiple bouts of neuroregenerative therapy may lead to enhanced tissue reinnervation, which ultimately can result in, among other benefits and advantages, a diminished potential for developing chronic pain for a patient, a decrease in residual sensory abnormalities, and an increase in fine motor skill.

The various embodiments disclosed herein offer one or more advantages. For example, the devices and systems described herein provide the ability to function as a handheld, dual-purpose technology that is designed and otherwise configured to deliver both nerve location/testing functionality, neuroregenerative therapy (e.g., continuous stimulation, intermittent stimulation, etc.) for the treatment of injured nerves (e.g., neuroregeneration), and pain management therapy. An additional advantage of the described embodiments is the ability to switch between bipolar and monopolar stimulation nerve probes as well as other probes or electrodes that can be interfaced with the system.

In some embodiments, the surgeon or other practitioner benefits by using the various devices, systems and/or methods disclosed hereon. For example, the various embodiments disclosed herein can be fully integrated, can replace multiple (e.g., two or more, separate, etc.) devices and/or systems, can be controlled using a single hand and/or can provide one or more benefits or advantages.

Another benefit provided by one or more of the embodiments discussed herein is that the disclosed devices/system may apply continuous stimulation for a pre-defined period of time allowing the system to be used hands free (e.g., without the need to manipulate or otherwise use a button or other controller to deliver stimulating energy) when used to treat injured tissue.

General System Overview

In one embodiment, the system comprises of a housing, a nerve probe, a port for additional electrodes, visual indicators, a power source, a stimulus pulse generator/controller, a central processing unit, and user controls. With specific reference to the schematic of FIG. 1, the system 100 can be configured to function in multiple configurations. Additional configurations of the system may also exist, even though not specifically illustrated in FIG. 1 and/or other figures of the present disclosure. For any of the embodiments disclosed herein, a device or system can include fewer components and/or features, as desired or required. For example, in some arrangements, a device or system does not include a visual indicator, a power source and/or the like.

In one configuration, the nerve probe 102 is bi-polar, that is, comprising two separate electrode conductors that are internally connected to a stimulus generator. In another configuration, as also illustrated in FIG. 1, the nerve probe may be bi-polar, that is comprising two separate electrode conductors. However, in the illustrated arrangement, the conductors 104 can be shorted together internally essentially producing a single probe. This connected probe may function in some embodiments as a monopolar probe if an appropriate return electrode is connected to the system's electrode port 106. As shown schematically in FIG. 1, the return electrode 108 can comprise a needle, surface pad and/or another conductive material so long as a return path is present. Additional details regarding such embodiments are provided herein.

In the configurations discussed above, the system 100 may be used to probe nerve tissue with a stimulus being delivered at or near the nerve probe. Thus, the system 100 can be used as a nerve locator or evaluator. The bi-polar or monopolar configurations may be advantageous to surgeons depending on the location of the nerve that is being probed or the type of surgical procedure being performed.

In yet another configuration, such as in the embodiment also shown in FIG. 1, a cuff-type electrode 110 that is configured to interface (e.g., directly, indirectly, etc.) with a nerve may be connected to the system's electrode port. Such an embodiment can be advantageous for delivering neuroregenerative therapy to an injured nerve. In such a configuration, the stimulus output may be driven (e.g., entirely) to the plugged-in electrode and not the nerve probe.

In some embodiments, the electrode that is plugged into the port may comprise of one or more electrode contacts, and through the electrode port, may be physically connected to the stimulus generator. Regardless of the exact configuration used, in some embodiments of the present application, the system can be configured to detect if and which electrode is plugged into the port and ensure the appropriate stimulation is output is being driven. Additional details about various system embodiments, components, portions, subsystems and/or the like are provided below.

Housing

Figure 2A:
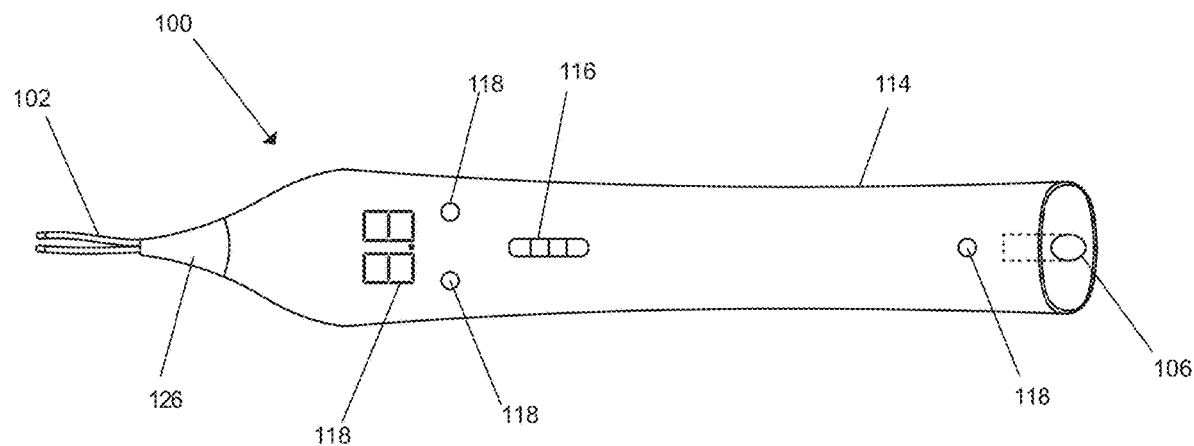
FIG. 2A illustrates a top view of a hand-held nerve locator according to one embodiment.

In some embodiments, as illustrated in FIG. 2A, the system can comprise a housing 114 that may include user controls 116, visual indicators 118, a power source, a stimulus pulse generator/controller, a central processing unit and/or any other component or portion, as desired or required. As shown, the housing can include one or more materials, such as, for example, thermoplastic type material (e.g., polyethylene, polypropylene, polyvinyl chloride, polystyrene, polyamides, polyesters, polyurethanes, etc.), thermoplastic elastomers (e.g., in some embodiments resulting in a soft grip-able texture), metals or alloys (e.g., stainless steel, aluminum, other brushed or polished metals or alloys, etc.), composite materials and/or the like, as desired or required.

In some embodiments, the housing and accompanying internal components can be configured to be reused. Thus, such components or portions can be designed and otherwise configured to be sterilized and/or otherwise cleaned. For example, the system can be sterilized via exposure to ethylene oxide, chlorine dioxide, vaporized hydrogen peroxide, gamma rays, electron beams and/or the like.

Figure 2B:
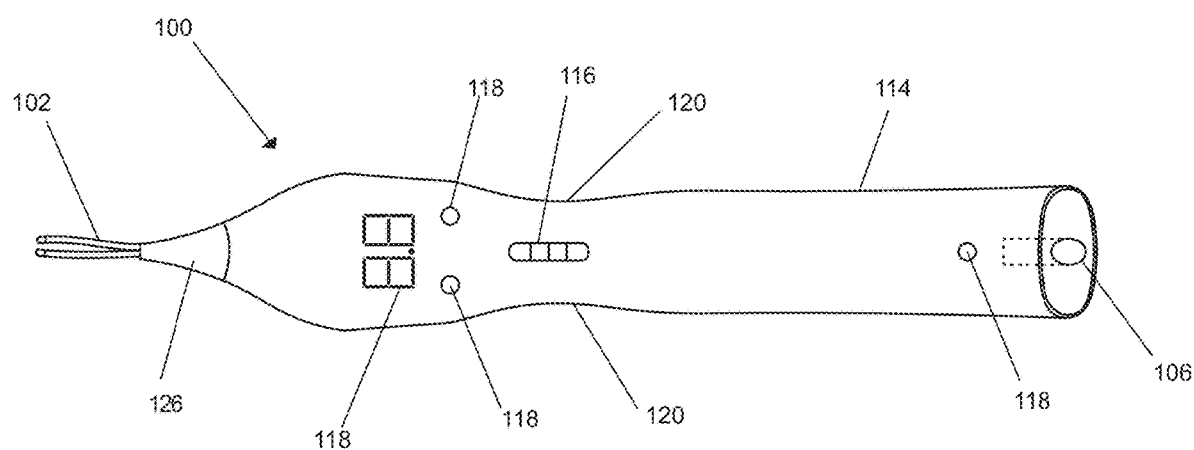
FIG. 2B illustrates a top view of a hand-held nerve locator according to one embodiment incorporating lateral grooves to facilitate holding using one hand.

According to some embodiments, the housing is designed to fit ergonomically into the hand of a surgeon, as illustrated in FIG. 2B. Thus, in some arrangements, the housing is shaped with grooves or scallops 120 and/or the housing includes an ergonomic shape to facilitate holding regardless of the handedness (e.g., right-handedness or left-handedness) of the user. In other embodiments, the housing is specifically designed for a single handedness of a user (e.g., right-handedness or left-handedness). Such grooves or scallops 120 can be symmetrical, non-symmetrical, aligned, offset and/or otherwise configured. As shown, in one embodiment, the deepest portion of the grooves 120 may be offset from the widest portion of the housing in range of 0.1 to 10 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10 mm, distances between the foregoing, etc.).

Figure 2C:
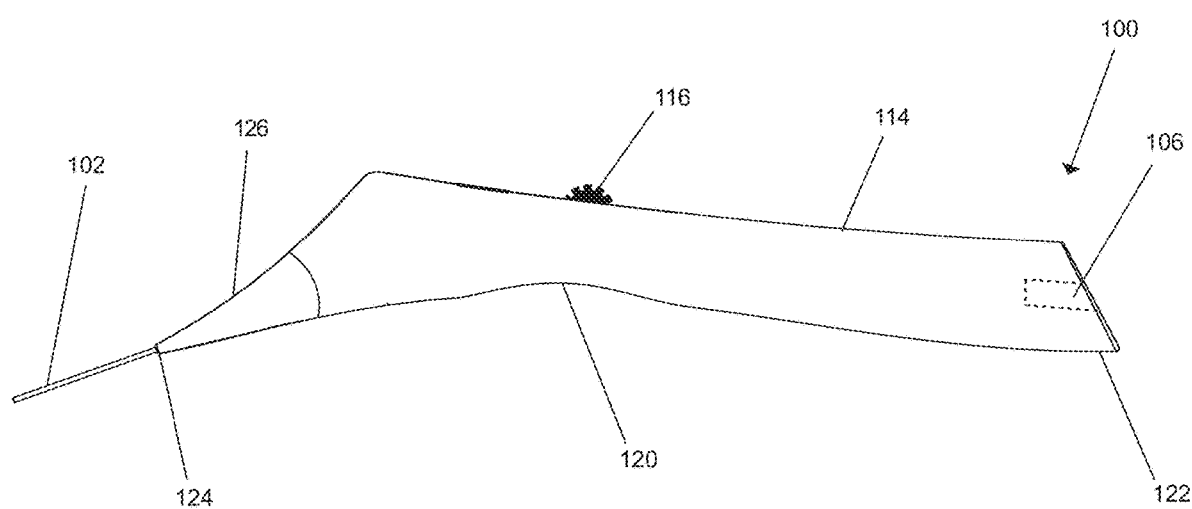
FIG. 2C illustrates a side view of a hand-held nerve locator according to one embodiment incorporating a vertical groove to facilitate rotation and access to controls using one hand.
Figure 2D:
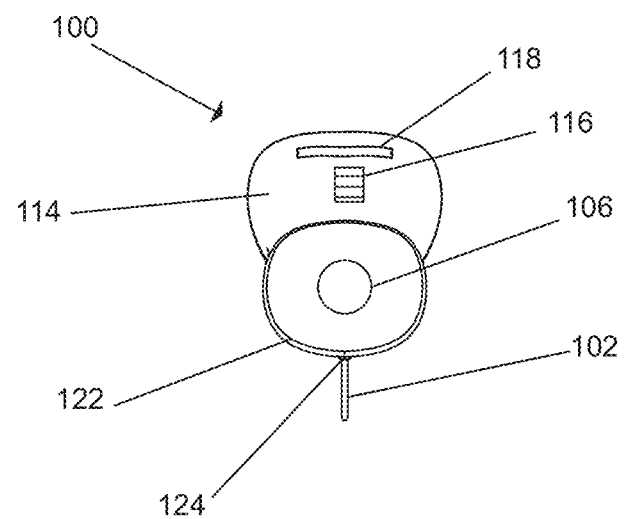
FIG. 2D illustrates a rear view of the hand-held nerve locator according to one embodiment showing access to the nerve port.

In some embodiments, the grooves 120 may be along the longitudinal axis, horizontal axis, the underside of the housing, or a combination of above. See, for example, FIG. 2C. In some embodiments, the housing comprises a proximal end 122 and distal end 124. The distal end 124 can include visual indicators 118 and a nerve probe 102 or a combination thereof. In some embodiments, the proximal end comprises a nerve port 106 that may include a nerve probe 102.

In some embodiments, the distal end and proximal end may be collinear or offset. For example, in some arrangements, the distal end and proximal end are offset by an angle ranging from 1° to 30° (e.g., 1-2, 2-3, 3-4, 4-5, 5-6, 6-7, 7-8, 7-8, 8-9, 9-10, 10-15, 15-20, 20-25, 25-30, 5-25, 10-20°, angles between the foregoing ranges, etc.), resulting in an angled distal end (e.g., relative to the proximal end). In some embodiments, such an angled distal end configuration can advantageously facilitate use of the device as shown, e.g., in FIG. 2C. Additionally, the angled offset can help prevent the housing from rolling (e.g., off a table, cart, other platform, etc.) if placed on a moderately inclined or uneven surface such as when a surgeon or other practitioner may set aside the housing to perform other operative tasks.

In some embodiments, the length of the housing, or the distance from proximal to distal ends, can be 10 to 40 cm (e.g., 10-15, 15-20, 20-25, 25-30, 30-35, 35-40, 15-25, 20-40 cm, lengths between the foregoing ranges, etc.). In other embodiments, the length of the housing can be less than 10 cm or greater than 40 cm, as desired or required by particular application or use. Further, the width (e.g., diameter or cross-section dimension) of the housing can be 0.5 to 3 cm (e.g., 0.5-1, 1-1.5, 1.5-2, 0.5-2, 2-2.5, 2.5-3 cm widths between the foregoing ranges, etc.).

In some embodiments, the proximal end of the housing comprises a hook-shaped or other curved or angled extension or an enclosed ring physically connected to the housing. In some arrangements, the extension may be used to hang the housing from an IV pole, another type of hook and/or the like.

In some embodiments, the housing may include a slot or opening to facilitate a pull-tab that interfaces with a battery. The pull-tab may allow for separation of the battery contacts preventing powering of the system. This is advantageous as it, among other things, prolongs the shelf life of the system. In some embodiments, the pull-tab slot or opening is located at, in or along the proximal end of the housing and the width of the slot may range from 5 mm to 30 mm (or the width of the housing). The height of the slot can range from 0.1 to 2 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-1.5, 1.5-2 mm, heights between the foregoing ranges, etc.).

As illustrated in FIGS. 2A to 2D, the system 100 can comprise a first set of user operable controls 116 for adjusting the parameters of the stimulus being delivered. In some embodiments, the system is configured to permit the user to discretely control the stimulus parameters, for example the stimulus amplitude or pulse width, to determine the threshold of nerve activation (e.g., threshold testing) and/or the like. This can be particularly relevant when a nerve is encompassed by scar tissue and/or other tissue (e.g., and requires a relatively large stimulus current to depolarize). Dissection of the scar and/or other obstructing tissue can result in a lower requirement for activation current.

In one embodiment, the controls may include two buttons. In another arrangement, the first set of controls may include a slider or similar feature or device. In yet another arrangement, the first set of controls may include a wheel control (e.g., a roller, a wheel, etc.). However, any other type of control (e.g., button, dial, etc.) can be incorporated into the device, either in lieu of or in addition a slider and/or a wheel control. In some arrangements, when using the wheel control, a discrete set of steps may allow for adjusting the stimulus amplitude. Thus, the wheel and/or any other control can be configured to be moved between discrete steps or positions. However, in other arrangements, the stimulus amplitude can be selected along a range of non-discrete levels (e.g., along a continuous spectrum of amplitudes). In some arrangements, the wheel may be coupled to a rotary encoder to discretize the movement of the wheel. In other arrangements, the rotary encoder may include detents to provide tactile feedback to the user when engaging the control.

According to some arrangements, the system may also include a secondary set of user operable controls. Such secondary controls can be configured to start, stop and/or pause the initiation or cessation of the treatment. In one embodiment, the secondary control may be used to power the system on and off. In some arrangements, the secondary set of controls may be placed near the first set of user operable controls. In one embodiment, the secondary control may be part of the primary user control. For example, the slider or wheel control may be coupled to a switch such that pressing the slider or wheel control results in activation of a momentary switch or similar. Any other type of control (e.g., button, switch, foot pedal, touchscreen, etc.) can be used.

In one embodiment, the system comprises a pull-tab control (e.g., as described herein) to control power to the system. In some arrangements, the system includes a switch or button used to control power to the system.

According to some embodiments, as discussed in greater detail herein, the system can also comprise a nerve port 106 coupled (e.g., physically coupled, operatively coupled, etc.) to the housing. This can allow users to connect (e.g., physically or operatively couple) a separate electrode to the system. As a control, the act of plugging in or physically connecting a separate electrode to the system may change the operating mode of the system as described earlier in system configurations.

In some embodiments, shown in FIGS. 2A to 2D, the nerve port may be included in the proximal aspect 122 of the housing. In some arrangements, the nerve port can allow for connections parallel to the longitudinal axis of the housing (see, e.g., FIG. 2D). In other arrangements, the nerve port may be included such that the connected component connector is perpendicular (e.g., exactly perpendicular, or generally or substantially perpendicular) to the longitudinal axis of the housing. In one embodiment, the act of plugging in or physically connecting a separate electrode to the system enables the system to power on.

Figure 3:
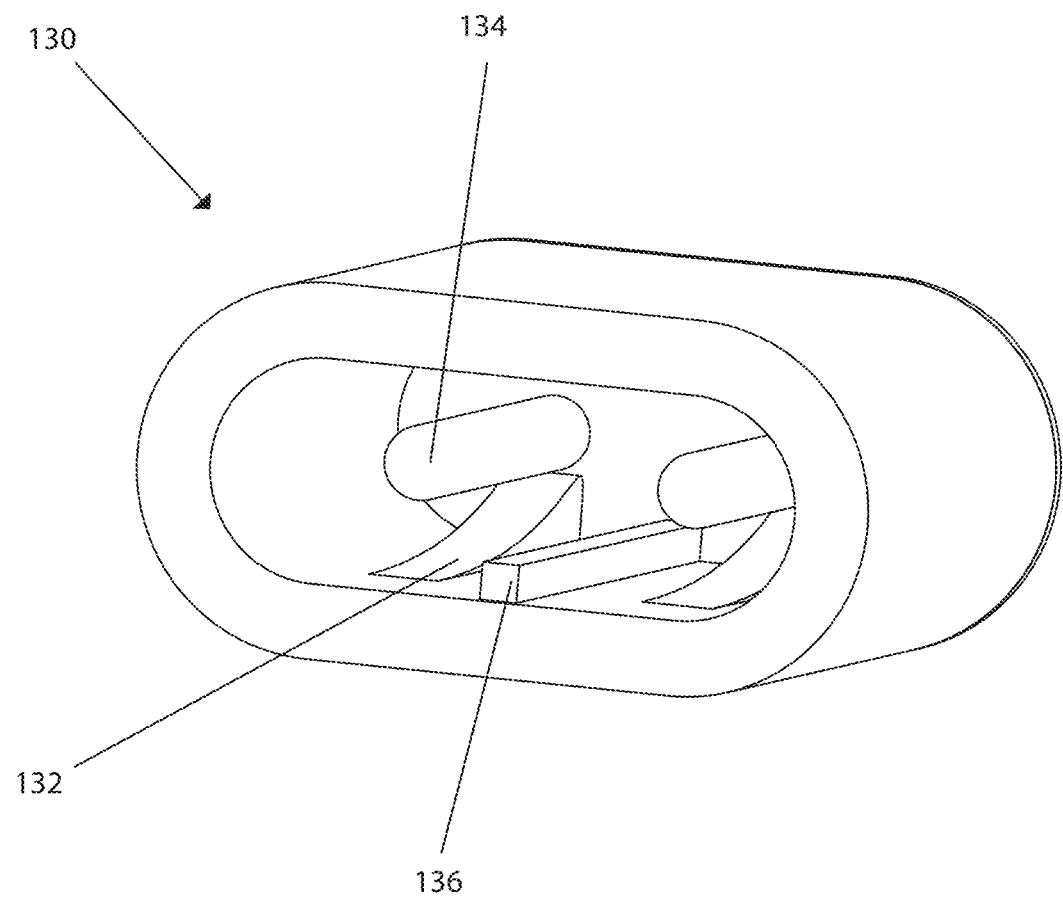
FIG. 3 illustrates an oblique view of a modified touch-proof jack according to one embodiment used to provide a contact for jack detection circuitry.

To detect if an electrode is present and physically connected to the system, a modified jack 130 may be included with the nerve port, as depicted in FIG. 3. For example, in some embodiments, the jack 130 can comprise a touch-proof jack (e.g., designed according to IEC 60601). The modified jack may include a flexible contact 132 that may be in physical contact with the main pin 134. However, in such an embodiment, upon introduction of an electrode lead connector, the physical connection between the flexible contact and main pin can be configured to be broken. In some arrangements, the jack can include one or more flexible contacts. In other arrangements, a polarity stand-off 136 may be included with the jack 130 to ensure the correct polarity of the plug being connected. In some embodiments, a standard touch-proof jack 130 with multiple pins/contacts or equivalent is used. In other embodiments, the jack or coupling 130 can be differently configured or designed (e.g., with another set of features or components), as desired or required.

Figure 4:
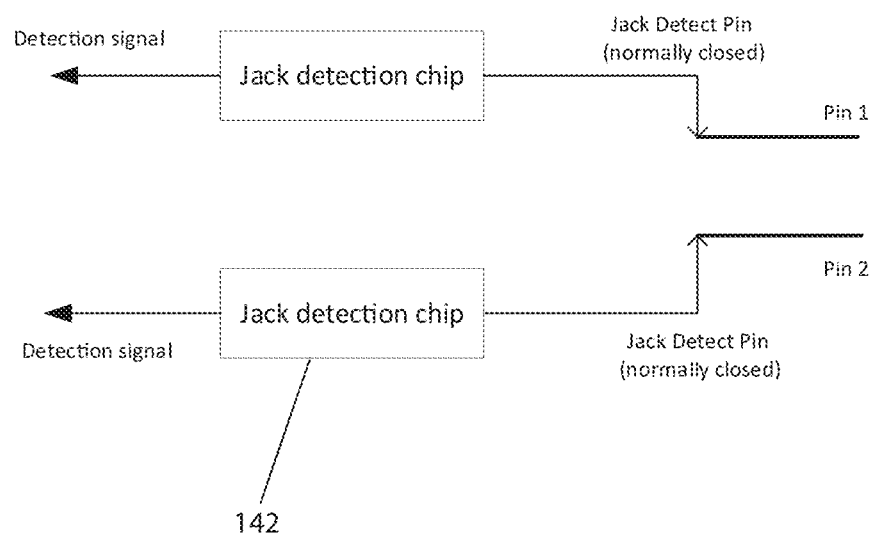
FIG. 4 illustrates a schematic of jack detection circuitry according to one embodiment configured to detect medical touchproof connections.

In some embodiments, the contacts on the jack may be wired to a jack detection circuit shown 142, such as the one illustrated in FIG. 4. This circuit 142 can include a microcontroller and passive components that may be used to detect the status of the connection.

In one embodiment, the circuit 142 includes standard jack detection chips 142 used in the mobile phone industry to detect headsets. These chips may include but are not limited to NCX8193 from NXP Semiconductors or MAX13330 from Maxim Semiconductor. In some arrangements, the chips can be configured to include the benefit of moisture detection, which allows the system to prevent enabling full power or other settings if moisture is detected in the jack housing. This may arise, for instance, when the system is used in an intraoperative setting.

Indicators

In several embodiments, the system comprises at least one set of indicators 118. In one embodiment, the first indicator may include a bar graph type display made by placing at least two visual emitting devices (e.g., LEDs) near one another. In some arrangements, the first indicator may include a multi-segment (e.g., 7-segment) display, as shown in FIG. 2A. The multi-segment (e.g., 7-segment) display may include more than one digit and decimal place, as desired or required. In some embodiments, the first indicator may comprise of a liquid crystal display (LCD), a plasma display, cathode ray tube display (CRT), organic light-emitting diode display (OLED), thin-film transistor display (TFT) and/or any other type of display.

In one embodiment, the purpose of such displays or indicators is to convey information regarding stimulus parameters, such as, for example and without limitation, amplitude, pulse width, frequency, duration, other time parameter and/or the like. In some arrangements, the display is configured to provide information related to time, such as, for example, a timer or countdown clock. Such information can be beneficial and advantageous in determining the time remaining or elapsed of a treatment application and can help guide the surgeon or other practitioner is conducting neuroregenerative therapy (e.g., such as brief electrical stimulation, other type of electrical stimulation, etc.) of injured or other targeted nerve tissue. In some arrangements, a combination of stimulus parameters, time-related parameters and/or any other data or information is displayed on the indicator. Such data and/or information, regardless of its exact nature, can be displayed in an alternating manner, via user controlled switch and/or the like. In some arrangements, the user can customize the type and/or manner in which the data and/or information is provided by the indicator (e.g., what data/information is provided, how it is provided to the user, etc.).

By way of example, according to some arrangements, the first set of indicators may be used to indicate power being delivered to the system. In one example, when the previously described pull-tab (or similar feature or component) is used to control power delivery to the system and a user pulls the tab, the first indicator may illuminate indicating that the system is powered.

In some embodiments, the system comprises additional indicators, as desired or required. For example, the system can include a second (or additional) set(s) of indicators 118 that can advantageously provide to the practitioner or other user additional data and/or information provided by a first indicator (e.g., time-related data or information, stimulus parameters, etc.). In some embodiments, the system may include a third set of indicators 118. In one embodiment, the third set of indicators 118 is located at or near the distal aspect of the housing. However, the indicator(s) of the system, regardless of how many are included, what data/information they are configured to provide, etc., can be included at any location, as desired or required. By way of example, the third set of indicators can comprise LEDs situated in a cap 126 that acts as a light pipe. Such a cap can be physically (e.g., directly or indirectly) coupled to the housing 114. In some arrangements, the cap and light pipe may can be designed and/or otherwise configured to permit visibility from any direction, such as, for example, when viewing the housing from above, below, beside, behind and/or the like (e.g., due to the angled distal aspect).

In some embodiments, an indicator (e.g., a first, a second, a third indicator, etc.) can be configured to display the status of the system. For example, a first solid color can indicate the state (e.g., active or inactive) of the output. In some arrangements, the output may be physically (e.g., directly or indirectly) connected or coupled to the nerve probe. Thus, for instance, in some arrangements, a first solid color may indicate if the nerve probe is active. In one specific example, referring to the previously described system configurations, a first solid color may indicate the nerve probe is active in either a bi-polar or monopolar configuration.

In some embodiments, a set of indicators (e.g., a third set of indicators) can be configured to flash (e.g., on/off) a first color to indicate output of a stimulus. In some arrangements, the flashing may be timed to coincide with the output of a stimulus pulse. In other arrangements, the flashing may be asynchronous with the output of a stimulus pulse. Any other type of configuration can be used to provide data and/or other information to the user via the indicators (e.g., different textual and/or graphical representation, different alert effects, etc.), as desired or required.

In some embodiments, the flashing is replaced with a pulsating output. In some arrangements, the pulsating output may include the ramping up of the light intensity from zero to a predetermined maximum and then a ramp down from the maximum to zero. In some arrangements, the pulsating output starts the ramping up from a non-zero intensity value and concludes the ramp down from the maximum to a non-zero intensity value.

In some embodiments, a visual indicator (e.g., the third set of visual indicators) can be configured to flash or pulsate to indicate an open circuit between the stimulating electrode and the return electrode. In one specific example, if there is no contact between the bi-polar tips of the nerve probe, an open circuit would be indicated that may trigger the flashing or pulsating of the visual indicator. In another specific example, when the system is operating in the previously described monopolar configuration, the lack of current flow between the stimulating electrode and the return electrode may trigger the flashing or pulsating of the visual indicator. In some embodiments, the flashing of an indicator (e.g., the third indicator) with a first color may occur at stimulus settings greater than zero.

In some embodiments, flashing or pulsating of an indicator (e.g., the third indicator) may occur with a second color. In some arrangements, the second color may be different from the first color. By way of example, the flashing or pulsating of the second color may indicate a closed circuit. In one embodiment, if there is current flow contact between the bi-polar tips of the nerve probe, an indication of a closed circuit would be provided, which trigger the flashing or pulsating of the visual indicator. In another specific example, when the system is operating in the previously described monopolar configuration, when current flow is present between the stimulating electrode and the return electrode, the flashing or pulsating of the visual indicator may be activated or triggered.

In some embodiments, the system may include a fourth (or additional) set(s) of indicators 118, as desired or required for a particular application or use. In some arrangements, the fourth set of indicators may be present next or near to the nerve port 106. In some embodiments, the fourth set of indicators may indicate the status of the nerve port 106. In some arrangements, the fourth set of indicators may function similarly to the third set (and/or other sets) of indicators and can comprise of multiple colored indicators and/or similar outputs.

The indicators described above can be incorporated into any of the device or system embodiments described herein and may be modified as desired or required.

Central Processing Unit

In some embodiments, any of the system configurations described herein can be part of a smart system with various electronic features, safety mechanisms and/or the like. Details about some of such features, mechanisms and/or other properties are provided herein.

Figure 5:
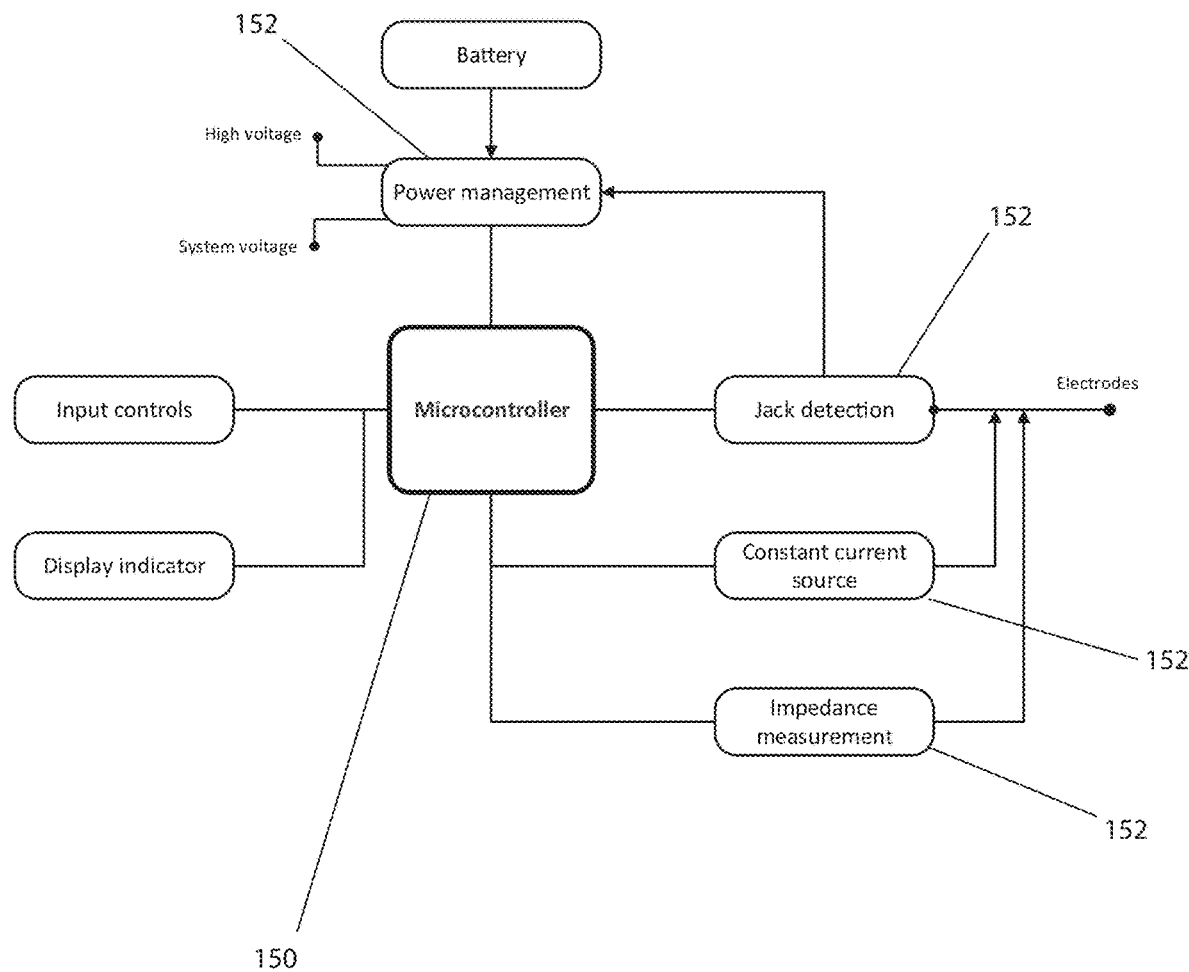
FIG. 5 illustrates a schematic view of the main microcontroller and sub-systems that interact with the microcontroller to create the system according to one embodiment.

In some embodiments, a control sub-system or central processing unit of the system can be built in association (e.g., around) a microcontroller 150. In some arrangements, the microcontroller is configured to be programmed, to store and execute code and/or otherwise carry out certain tasks to property and effectively operate the system. In some embodiments, the microcontroller contains timing features, e.g., enabling a timed stimulus output. In other embodiments, the microcontroller interfaces with at least one or more sub-systems 152 that are described herein (see, e.g., FIG. 5).

Power Source

In some embodiments, any of the systems disclosed herein can be designed to be relatively small, to be disposable, to include handheld operation and/or to include other desired or required features. In other arrangements, the system may be reusable.

In some embodiments, the system is powered or electrically energized using an energy source, such as a battery, an AC source and/or the like. In some arrangements, the power source comprises a battery with a standard lithium coin cell. In other arrangements, however, if a larger capacity is needed, type N batteries or other similar alkaline batteries may be substituted. In some arrangements, the battery may be rechargeable. Any other type of battery or other local power source can be used, as desired or required.

In some embodiments, the system may include a power management sub-system. In these embodiments, the power management sub-system may include one or more sub-components, such as, for example, a low-noise low-dropout switching type regulators to maintain stable operating voltages in the range of 3 to 5 V. For example, in some embodiments a Texas Instruments LP5912 can be used.

In some embodiments, the power-management sub-system comprises a second sub-component having a means to generate higher voltages required to stimulate tissue. In such embodiments, the power management sub-system can include a low-power step-up boost converter, such as, by way of example and without limitation, a Texas Instruments TPS61096A. In some embodiments, the higher voltage range may be between 10 and 50 V (e.g., 10-15-15-20, 20-25, 25-30, 30-35, 35-40, 40-45, 45-50, 20-40, 25-35 V, values between the foregoing, etc.).

In some embodiments, the sub-components of the power management sub-system are regulated (e.g., enabled and disabled) via a microcontroller 150. In other arrangements, the act of physically connecting or plugging in an electrode into the nerve port 106 may enable or disable the sub-components of the power management sub-system via the jack detection circuitry 142 that was described herein.

In some embodiments, the power management sub-system may include a tilt sensor. Such a tilt sensor can be configured to provide data and/or other information to the user. For example, data or information can relate to whether the system was placed on a flat surface or is being held in a non-horizontal position. In some arrangements, the output of the tilt sensor may engage a low power mode through the power management sub-system.

Output Stage

In some embodiments, the system comprises a stimulus output stage sub-system. In some arrangements, the electrical output of such a sub-system is configured to selectively stimulate tissue. The system microcontroller can be configured to generate a rectangular stimulus pulse that is conditioned by the stimulus output stage sub-system. The stimulus output stage sub-system can be configured to generate the stimulus pulse. In some embodiments, the stimulus pulse comprises of a biphasic constant current or voltage pulse.

In some embodiments, the stimulus output stage sub-system comprises a capacitively-coupled output, e.g., to help ensure that a net-zero charge is being delivered to the tissue. In some embodiments, the stimulus output stage sub-system comprises a H-bridge used to switch current polarity. The H-bridge can be coupled to a current source, as desired or required. In some embodiments, the current source comprises a Howland current pump.

According to some embodiments, the stimulus output stage sub-system is configured to generate stimulus pulses with pulse durations ranging from 1 to 500 microseconds (e.g., 1-5, 5-10, 10-20, 20-30, 30-40, 40-50, 50-60, 60-70-70-80, 80-90-100, 100-120-120-140, 140-160, 160-180, 180-200, 200-250, 250-300, 300-350, 350-400, 400-450, 450-500, 0-20, 1-30, 0-40, 0-50, 0-100, 50-150, 100-200, 100-300 microseconds, durations between the foregoing ranges, etc.). In some arrangements, the sub-system is configured to generate stimulus pulses amplitudes ranging from 0-20 mA (e.g., 0-1, 1-2, 2-3, 3-4, 4-5, 5-6, 6-7, 7-8, 8-9, 9-10, 10-15, 15-20 mA, values between the foregoing, etc.). In some arrangements, the sub-system is configured to generate pulse trains in the frequency range of 0.1-100 Hz (e.g., 0.1-0.5, 0.5-1, 1-2, 2-3, 3-4, 4-5, 5-10, 10-15, 15-20, 20-25, 25-30, 30-40, 40-50, 50-60, 60-70, 70-80, 80-90, 90-100, 20-80-40-60, 10-70 Hz, frequencies between the foregoing, etc.).

Figure 6A:
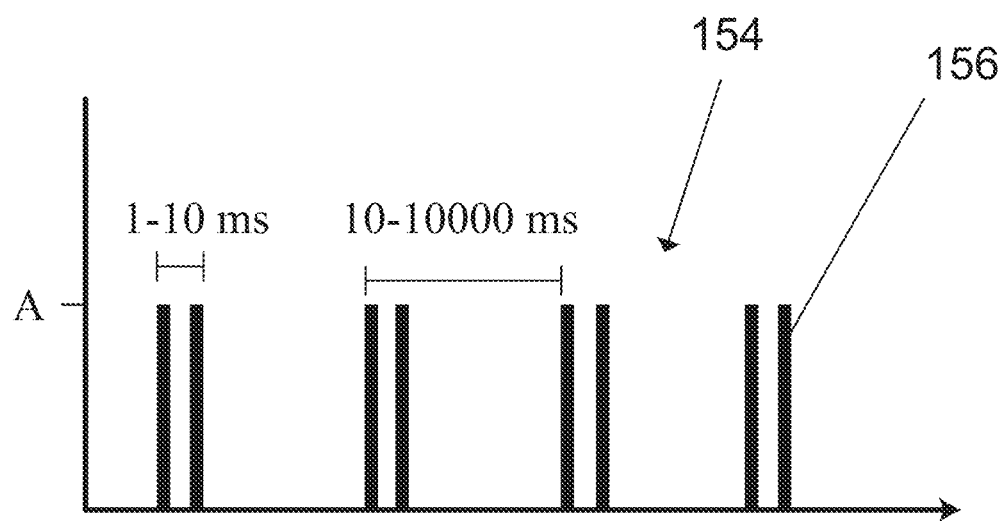
FIG. 6A illustrates a graph depicting doublet stimulus pulses at an arbitrary amplitude according to one embodiment.

According to some embodiments, the pulse train 154 comprises one or more pulses at an amplitude A separated by a short inter-pulse interval, called a doublet pulse 156, in the range of 1-10 ms (e.g., 1-2, 2-3, 3-4, 4-5, 5-6, 6-7, 7-8, 8-9, 9-10 ms, intervals between the foregoing, etc.). One embodiment of such a configuration is illustrated schematically in FIG. 6A. In some embodiments, use of doublet pulses allows exploitation of a muscle's natural catch like property resulting in greater muscle contraction or visible response.

Figure 6B:
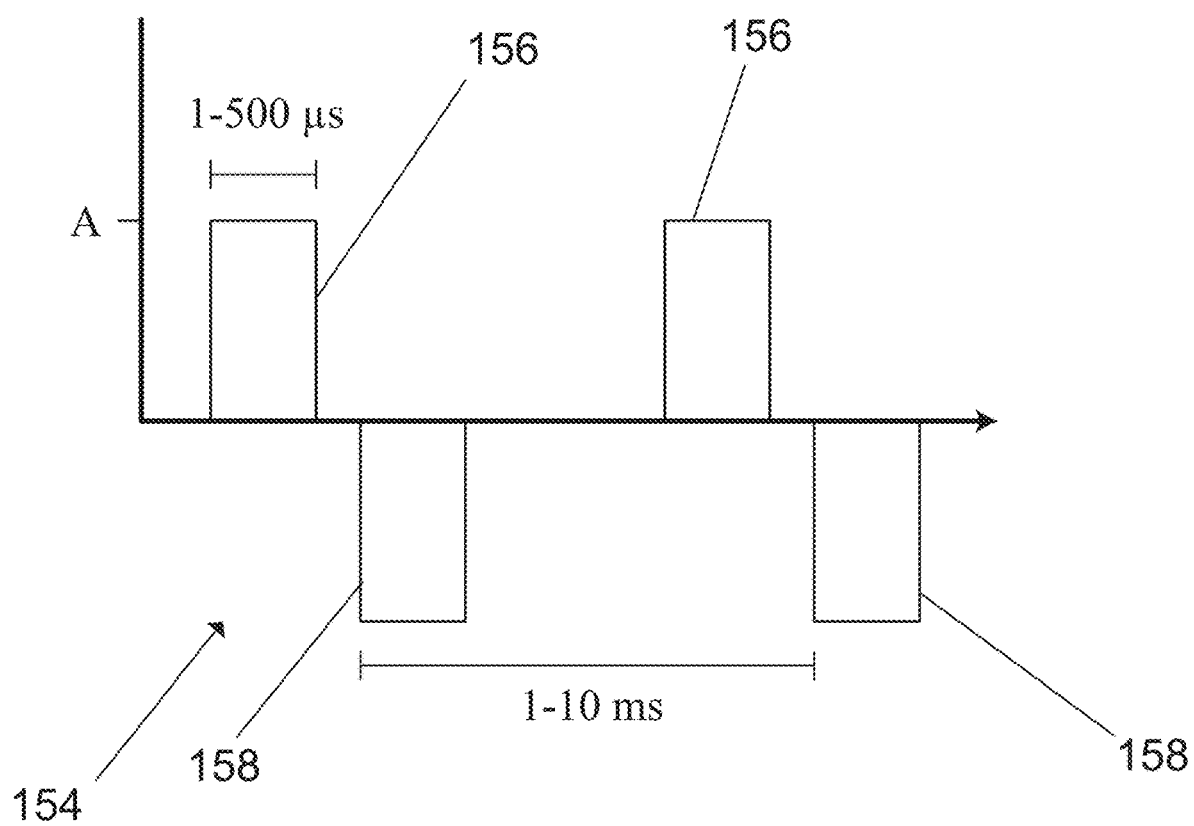
FIG. 6B illustrates a graph depicting bi-phasic doublet stimulus pulses at an arbitrary amplitude according to one embodiment.
Figure 6C:
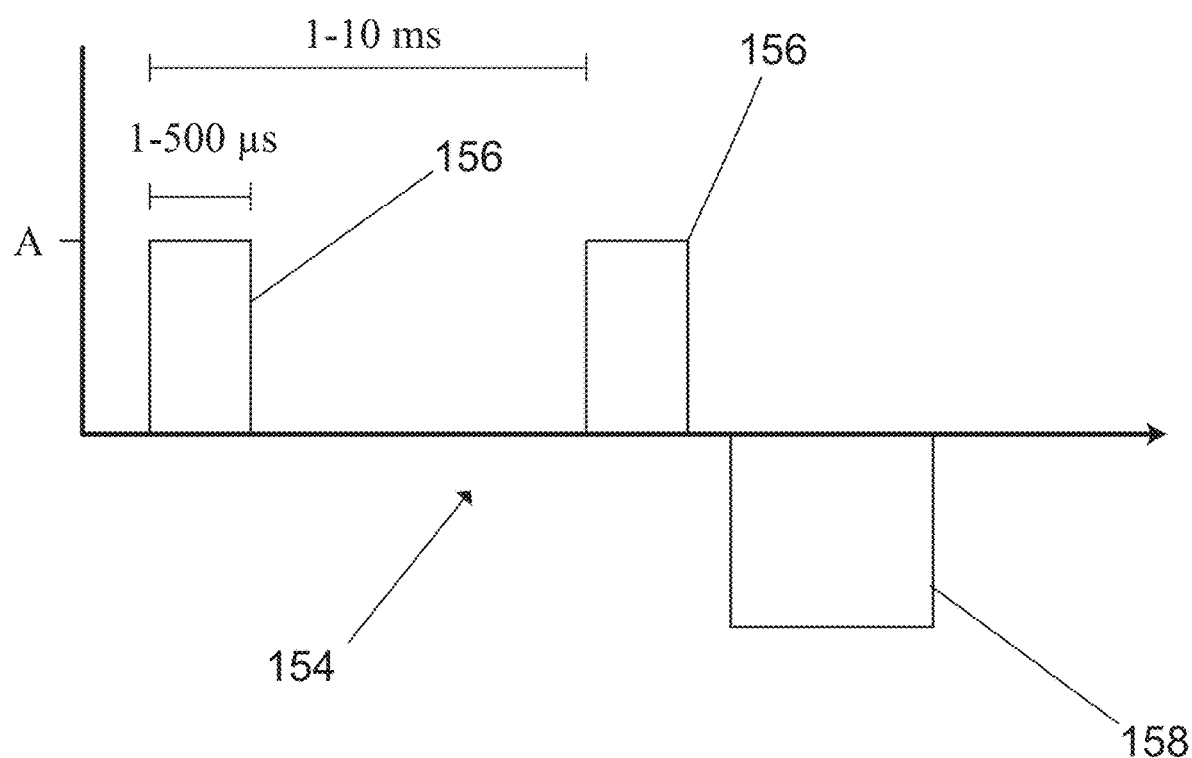
FIG. 6C illustrates a graph depicting using a single charge balancing pulse following a doublet stimulus pulse at an arbitrary amplitude according to one embodiment.
Figure 6D:
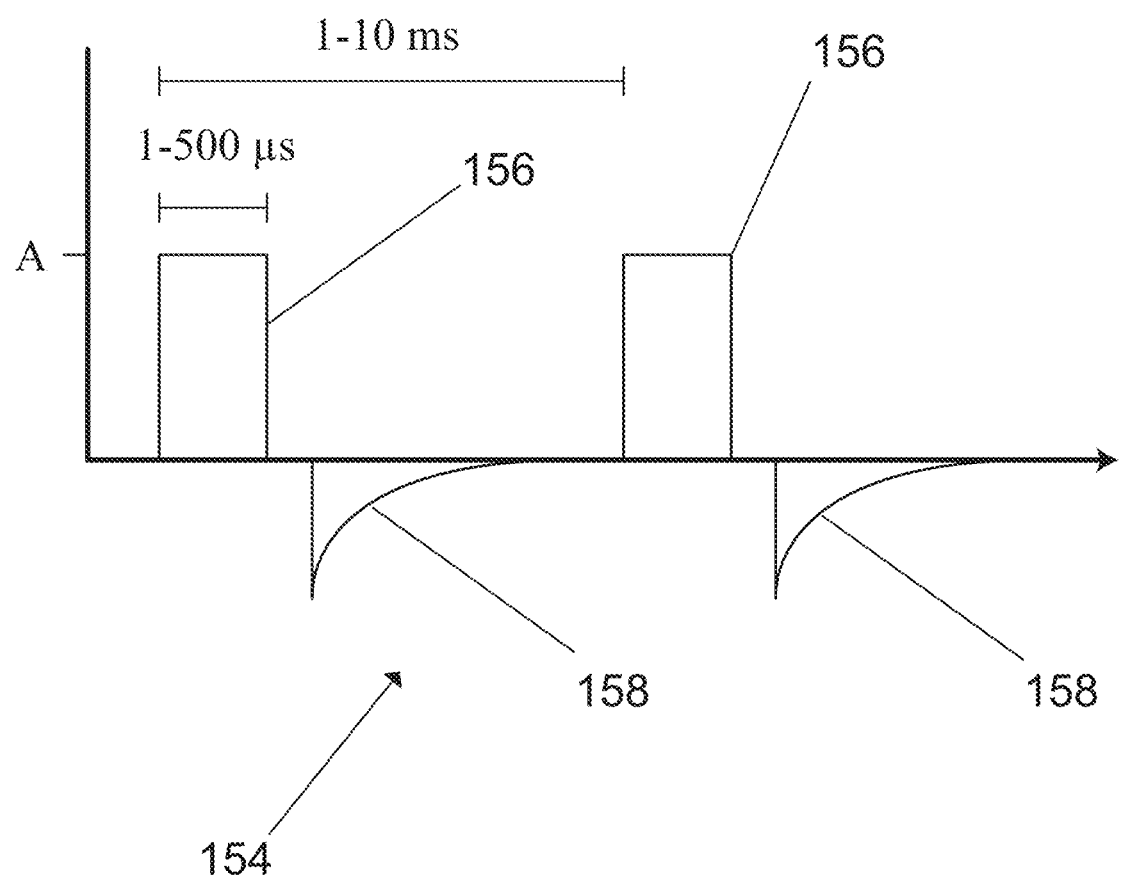
FIG. 6D illustrates a graph depicting exponentially rising charge balancing pulses following each pulse in a doublet pulse train at an arbitrary amplitude according to one embodiment.

In some embodiments, the doublet pulses 156 may be charge balanced individually, that is, each doublet pulse may be followed by a charge recovery pulse 158 that is equal duration but opposite polarity. See, e.g., FIG. 6B. In other arrangements, the doublet pulse may be charged balanced as a whole, such that a charge recovery pulse 158 that is equal in duration to the sum of the individual doublet pulse 156 durations. See, e.g., FIG. 6C. In other arrangements, the charge recovery pulse may be generated passively by AC coupling the stimulator output. Such an embodiment produces exponentially decaying charge recovery pulses 158 that are followed by each output pulse (e.g., each doublet pulse may include a passively generated charge recovery pulse), as shown in FIG. 6D. In some embodiments, the sub-system generates stimulus pulses, amplitudes, and/or trains sufficient to depolarize nerve fibers and elicit action potentials.

Safety Mechanisms

To ensure patient safety, in some embodiments, electrical energy is only delivered to the stimulating electrode or nerve probe 106 that is in contact with neural tissue when the impedance is less than 10 kOhm (e.g., less than 10 kOhm, less than 9 kOhm, less than 8 kOhm, less than 7 kOhm, less than 6 kOhm, less than 5 kOhm, less than 4 kOhm, less than 3 kOhm, less than 2 kOhm, less than 1 kOhm, etc.). In some embodiments, electrical energy is only delivered to the stimulating electrode or nerve probe 106 that is in contact with neural tissue when the impedance is between 0 and 10 kOhm (e.g., 0-1, 1-2, 2-3, 3-4, 4-5, 5-6, 6-7, 7-8, 8-9, 9-10 KOhm, impedances between the foregoing ranges, etc.).

In some embodiments, a system according to any of the configurations disclosed herein includes an impedance measurement sub-system. Such a sub-system can comprise a circuit that generates a sin-wave with said circuit coupled to a constant current source and further coupled to a set of electrodes. In some embodiments, the constant current source may comprise of a Howland current pump.

In some embodiments, the sin wave is generated using a microcontroller's digital to analog converter. In other arrangements, a microcontroller's pulse-width modulation output is used and coupled to a low-pass filter. In some arrangements, the low-pass filter comprises passive components, while in other arrangements the filter comprises active components (e.g., an active filter).

In some embodiments, the impedance measurement sub-system includes an instrumentation amplifier coupled to the electrode path used to measure impedance. Impedance measurement can be calculated within the sub-system and sent (e.g., digitally) to the microcontroller. In other arrangements, the microcontroller samples the analog impedance value and converts the value to a digital representation internally.

In some embodiments, when an electrode is properly placed in contact with neural tissue, the electrode-tissue impedance will be smaller than the impedance when the electrode is not in contact with tissue. In some arrangements, the impedance is such circumstance is typically less than 10 kOhm (e.g., 0-1, 1-2, 2-3, 3-4, 4-5, 5-6, 6-7, 7-8, 8-9, 9-10, 3-8, 1-10, 4-8 KOhm, impedances between the foregoing ranges, etc.). Such lower resistance can exist because healthy, internal human tissue provides a relatively low resistance electrical pathway through which electrical current may pass. In some embodiments, resistances exceeding a threshold value (e.g., 10 kOhm) can be an indication of improper placement of the electrode. In some arrangements, the system is configured of recognizing values exceeding such a threshold.

In some embodiments, the system is configured to periodically detect the impedance during the continuous application of electrical stimulation. In some arrangements, if relatively high impedance is detected (e.g., high compared to a threshold level or upper limit), the system can be designed and otherwise configured to pause the application of continuous electrical stimulation and enable an indicator 118 on the housing 114 to alert the operator. In other arrangements, the system is configured to terminate (e.g., automatically stop) the stimulus output and/or prompt the user. In some embodiments, the indicator comprises a visual indicator; however, in other embodiments, the indicator can include an auditory indicator and/or any other type of indicator, either in addition to or in lieu of visual indication.

As noted herein, to further enhance patient safety, in some embodiments, the output of the system is capacitively coupled to prevent net DC charge inflow into the electrode tissue interface.

Nerve Probe and Electrodes

A nerve probe 102 can be used to probe tissue to test for excitability. Bodily tissues such as nerves may conduct action potentials towards a muscle when probed using physical means, electrical stimulation and/or the like resulting in a muscle twitch, reflex or contraction. According to some embodiments, the devices and systems disclosed herein include a nerve probe physically coupled to the housing and electrically coupled to the stimulus output stage sub-system.

In some embodiments, the nerve probe comprises a single conductive element in the shape of a cylinder or rod that extends from the housing's distal end. In other embodiments, the shape of conductive element can vary. In some arrangements, the nerve probe is entirely (or nearly entirely) electrically insulated except for a small de-insulated component on the distal aspect of the nerve probe. For example, the majority of the nerve probe is electrically insulated (e.g., over 70%, 70-100%, 80-95%, etc.). The area of de-insulation can range from 0.1 mm$^2$ to 10 mm$^2$ (e.g., 0.1-0.5, 0.5-1, 1-2, 2-3, 3-4, 4-5, 5-6, 6-7, 7-8, 8-9, 9-10, 2-8, 1-9, 4-8 mm$^2$, areas within the foregoing ranges, etc.). In some embodiments, the insulation may be manually configured to de-insulate the probe by a varying percentage, such as, for example 1-30% (e.g., 1-2, 2-3, 3-4, 4-5, 5-10, 10-15, 15-20, 20-25, 25-30%, percentages within the foregoing ranges, etc.).

In some arrangements, the single conductive element functions as a cathode or stimulating electrode. In such an arrangement, an appropriate return path for current to flow is necessary. In some embodiments, the return path may be provided by connecting a return electrode to the nerve port 106. The return electrode can comprise a needle, a surface pad, another conductive element and/or the like.

In some embodiments, the nerve probe comprises a plurality of conductive elements. In some arrangements, one or more of the conductive elements can be designed and otherwise configured to function as a return electrode or anode, while one or more of the conductive elements can be designed and otherwise configured to function as cathodes or stimulating electrodes.

In some embodiments, the conductive elements comprise one or more metals or alloys (e.g., stainless steel, platinum, iridium, gold, etc.). In one arrangement, the conductive elements comprise platinum or 90/10 platinum iridium, gold. The conductive elements can comprise any other conductive metal, alloy and/or other material, as desired or required.

In some embodiments, the length of the conductive elements is 0.5 to 10 cm (e.g., 0.5-1, 1-2, 2-3, 3-4, 4-5, 5-6, 6-7, 7-8, 8-9, 9-10, 3-7, 5-10, 0-5 cm, lengths within the foregoing ranges, etc.). However, the length of the conductive elements can be greater than 10 cm to meet the requirements of a particular application or use. The diameter or other cross-sectional dimension of the conductive elements can be 0.1 to 5 mm (e.g., 0.1-0.2, 0.2-0.3, 0.3-0.4, 0.4-0.5, 0.5-1, 1-2, 2-3, 3-4, 4-5, 0.1-2, 1-2 mm, values within the foregoing ranges, etc.). However, the diameter (or other cross-sectional dimension) of the conductive elements can be greater than 5 mm and/or to meet the requirements of a particular application or use.

In some embodiments, the system does not include a nerve probe. Instead, for such configurations, the system can rely on an appropriate electrode apparatus to be connected to the nerve port. In some arrangements, the electrode apparatus comprises monopolar or bipolar catheter type apparatus. Such arrangements can be particularly advantageous in peri-operative scenarios where the lead may be placed intraoperatively and, due to its shape, may be easily removed from a closed incision or percutaneous access point.

In some embodiments, a nerve cuff electrode apparatus is connected to the nerve port. A cuff electrode can be particularly advantageous in intraoperative settings where a dissected nerve is easily accessible. However, as discussed herein, for any embodiments disclosed in this application, the electrode can include a configuration other than a cuff electrode.

Certain embodiments of a nerve cuff electrode apparatus 10 are illustrated in FIGS. 7 to 11. As shown, the nerve cuff electrode apparatus 10 can comprise a carrier body 12. In some embodiments, the carrier body 12 and/or other portions of the apparatus 10 comprise one or more insulative materials, such as, for example, silicone rubber, other elastomeric and/or polymeric materials and/or any other materials. One or more materials can be used, either in lieu of or in addition to rubber, such as, for example and without limitation, thermoplastic elastomers, elastomeric polyurethanes and/or the like. In some embodiments, the material(s) included in the apparatus are flexible so as to permit bending without breaking, fracturing and/or other damage brought about by movement during use.

In some embodiments, the electrode apparatus 10 is arranged in a longitudinal manner with the length being considerably longer than the width. For example, in some embodiments, the ratio of the length to width of the electrode apparatus 10 can be between 1:1 to 20:1 (e.g., 2:1, 3:1, 4:1, 5:1, 6:1, 7:1, 8:1, 9:1, 10:1, 15:1, 20:1, ratios within the foregoing ranges, etc.). In some embodiments, electrode apparatus 10 comprises two ends, a head portion 16 and a tail portion 26.

Figure 7A:
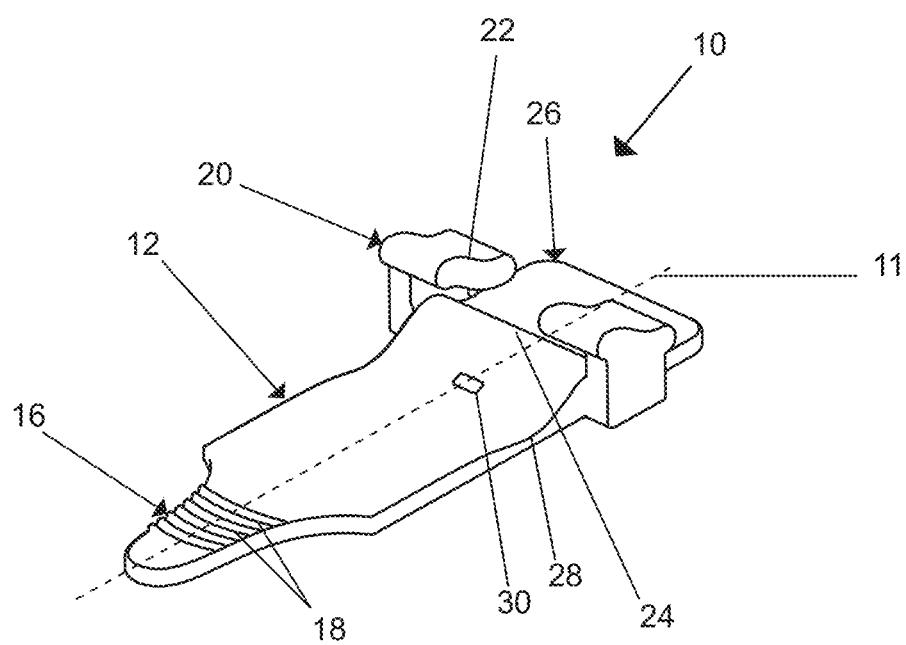
FIG. 7A illustrates a perspective view of an embodiment of the apparatus where the electrode configuration is monopolar with a single electrode pad being present in the thickest portion of the carrier according to one embodiment.

As shown in FIG. 7A, the apparatus 10 can include a longitudinal axis 11 that extends longitudinally or lengthwise along the apparatus 10. The length of the device can be 20 to 80 mm. The width of the apparatus 10 (e.g., the dimension perpendicular to the longitudinal axis 11) can be 5 to 30 mm. Thus, in some embodiments, the length of the apparatus 10 is 2 to 5 times the width of the apparatus. However, in other arrangements, the width can be equal or greater than the length. In some embodiments, the thickness of the head portion 16 can be 1.5 mm. In some arrangements, the thickness can range from 0.1 mm to 5 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5 mm, thicknesses within the foregoing ranges, etc.), as desired or required.

The head portion can contain a tapered end 16 that is rounded and contains gripping structures 18 that aid a surgeon in handling the electrode apparatus. In some embodiments, the gripping structures 18 are present on either side of the tapered end of the carrier. However, in other embodiments, gripping structures 18 are included only on one side. In some embodiments, the gripping structures 18 include ridges, recesses, protrusions and/or the like. In some embodiments, such structures 18 are formed into the surface or body of the apparatus, and thus, form a unitary structure with the portion in which they are included. For example, the ridges or other structures 18 can be molded (e.g., injected molded) together with the main portion of the apparatus. However, in other arrangements, the gripping structures 18 are separate from the main portion of the apparatus and/or are created after the main portion of the apparatus is formed (e.g., via one or more connections technologies or methods, by removal of material, etc.). In some embodiments, the gripping structures are replaced by a through-hole or multiple holes where one or more sutures can be threaded.

With continued reference to FIG. 7A, the tail portion 26 of the apparatus 10 can be non-tapered. However, in other configurations, at least a portion of the tail portion 26 is tapered, as desired or required. In some embodiments, the tail portion 26 comprises rounded or curved corners to facilitate handling of the apparatus. In some embodiments, the tail portion comprise one or more areas that are substantially thicker than the head portion to encompass a through-hole in the longitudinal axis 11 that allows for placement of electrode lead wires. In some embodiments, the thicker area can be greater than 1 times thicker than the head portion (e.g., 1 to 5, 1 to 10, 1 to 20 times thicker, etc.), but not thicker than the grooved body 24. In some embodiments, the thickening of the tail portion may be in the opposite direction from the thickening of the grooved body 24 and can also include a through-hole in a diagonal direction from the bottom face of the tail portion to the midbody to allow accommodation of an electrode lead wire.

As shown in FIG. 7A, the mid portion of the carrier can include two features: a grooved body 24 and a winged locking mechanism 20. The grooved body 24 can be structured and configured so that when a surgeon places a nerve on the electrode apparatus 10, the nerves longitudinal axis is perpendicular (e.g., substantially perpendicular) to the electrode's longitudinal axis 11, with the nerve itself naturally settling in the thinner mid-portion 28 of the grooved body, in some embodiments.

In some embodiments, the winged locking mechanism may be positioned in various locations longitudinally and may include more than one set (e.g., 2 wings) at each location. In some embodiments, the locking wings are positioned in a staggered arrangement.

The thinner mid-portion 28 of the grooved body 24 can be shaped to facilitate placement of a nerve and to wrap or bend the head portion 16 of the apparatus around (e.g., at least partially around) the nerve. In terms of nerve placement, in some embodiments, the thinner mid-portion 28 follows the shape of a semi-circle or other circular or curved shape. This can help prevent the nerve tissue from sliding off the electrode apparatus 10. The radius of curvature of the thinner mid-portion 28 can range from 1 to 10 mm (e.g., 1-2, 2-3, 3-4, 4-5, 5-6, 6-7, 7-8, 8-9, 9-10, 2-8, 4-8, 5-10 mm, radii within the foregoing ranges, etc.). In some arrangements, the radius of curvature is greater than 10 mm (e.g., 10-15, 15-20, 10-20, 10-50 mm, radii between the foregoing, greater than 50 mm, greater than 100 mm, etc.), as desired or required.

In some embodiments, the thinner mid-portion 28 of the grooved body 24 is flat and tangent to the head portion 16 of the electrode apparatus 10. The thickness of the mid-portion can range from 0.1 mm to 5 mm. In some arrangements, such as the desired curved shape described above, the thinnest section can be 0.1 mm (e.g., 0.05 mm to 2 mm). In some embodiments, the thinnest section can be 10% (e.g., 5-25%) of the thickest section of the head portion 16 of the electrode apparatus 10. The thickness of the mid-portion 28 can be designed and otherwise configured to adjust for how flexible the apparatus is when the head portion 16 is wrapped around a nerve.

In some embodiments, the grooved body 24 of the mid portion 28 comprises of a uniform or a generally uniform thickness. That is, the mid portion is of similar thickness as the connected head portion 16, providing a flat plane. In some arrangements, the carrier may include electrodes placed on the underside of the carrier 12. In some embodiments, the locking mechanisms may be engaged in a reverse orientation such that when carrier is folded, the head portion 16 engages the locking mechanism from the direction of the tail portion.

In some arrangements, the desired curved shape described herein follows the shape of a semi-circle or other partially rounded or curved shape with a uniform thickness to that of the head portion 16. In some arrangements, the base of the semi-circular groove can protrude, at least partially, below the plane of the head portion 16 to create a larger circumference for nerve placement.

In some embodiments, the groove also contains one or more conductive electrodes 30 that may be present in various configurations as outlined further below. In some arrangements, the purpose of the groove is to facilitate interfacing with a nerve while preventing or limiting slippage of the nerve. Such a configuration can also, in some embodiments, facilitate contact between the nerve and the conductive electrode(s) 30. Once the nerve is in place, the surgeon or other practitioner can grasp the tapered head portion 16 of the carrier (e.g., using either forceps, his/her fingers, other devices or methods, etc.) and can wrap (e.g., at least partially) the nerve. In some embodiments, to lock the cuff in place, the tapered head portion 16 is placed underneath the winged locking mechanism 20. Since the electrode apparatus can advantageously be configured to accommodate different diameter nerves or nerve bundles, the surgeon or other practitioner can apply as much or as little wrapping pressure to sufficiently cover the nerve. To securely lock the tapered head portion 16, the surgeon can laterally deflect the winged locking tabs 22 and place the tapered head portion 16 underneath them and then release the tabs.

In one embodiment, the carrier is molded in a flattened or opened position. For example, the carrier can be bent and placed underneath the locking tabs 22. In some embodiments, a natural bias force exists that presses or otherwise urges the tapered head portion 16 against the locking tabs 22 preventing the tapered portion from sliding further down the longitudinal axis 11 of the apparatus and potentially compressing the interfaced nerve.

In some arrangements, when a surgeon or other practitioner is finished using the electrode apparatus 10, he or she can laterally deflect the locking tabs 22, and the tapered head portion 16 of the carrier can be configured to spring back due to the bias force pushing back to its original flat or open conformation. Such a feature can allow for quick release of the interfaced nerve. Accordingly, the surgeon or other practitioner can then pull the nerve cuff from the tail end 26 and slide it from beneath the interfaced nerve without damaging it.

With continued reference to FIG. 7A, a single conductive electrode pad 30 is placed on the grooved portion of the carrier 24. In some arrangements, this is the thickest portion of the carrier and serves one or more purposes (e.g., to provide an insulative barrier to prevent current spread, to provide stiffness to reduce the probability of electrode pad delamination during the time it is flexed around the nerve and then released, etc.).

Figure 7B:
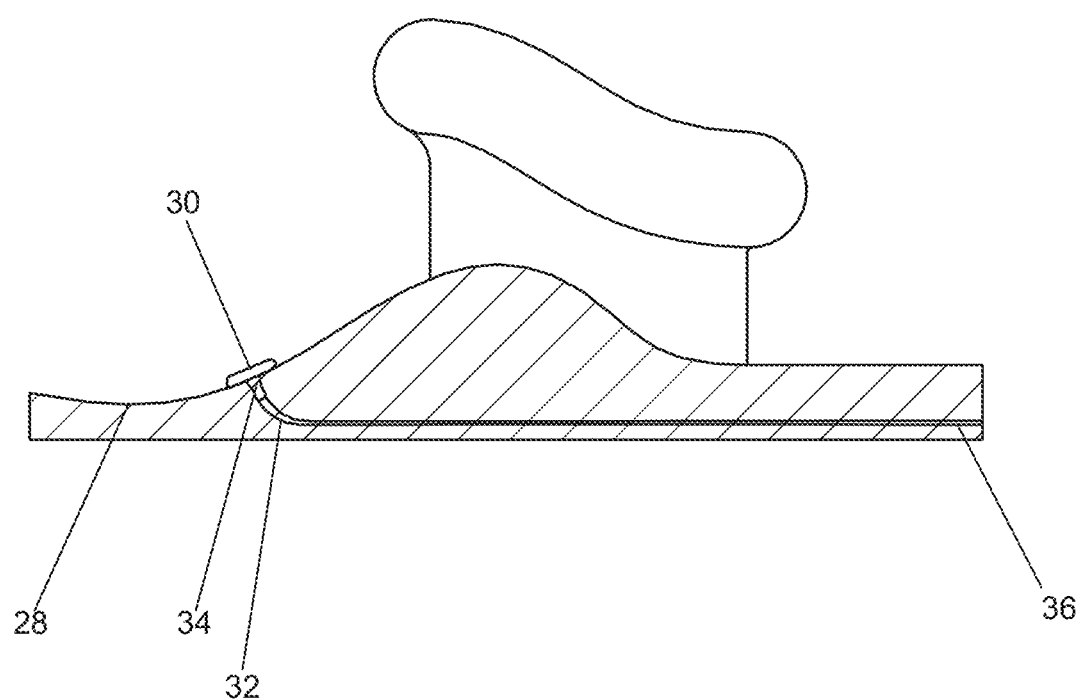
FIG. 7B illustrates a cross-sectional view of the carrier showing the attachment of the single electrode pad to a lead wire with the lead wire being externalized from the carrier at the tail portion according to one embodiment.

In some embodiments, the electrode pad 30 comprises a monopolar single contact configuration. A lead wire 32 can be coupled to the electrode pad 30 (e.g., via laser or resistance welding, crimping, using other technologies or techniques, etc.). In some embodiments, a physical conductive connection is made with the electrode pad. FIG. 7B illustrates a cross-sectional view through a midplane of the electrode apparatus 10. As shown, an electrode pad 30 is coupled to a lead wire 32. The tail end of the lead 36 can be externalized from the electrode apparatus.

Figure 8A:
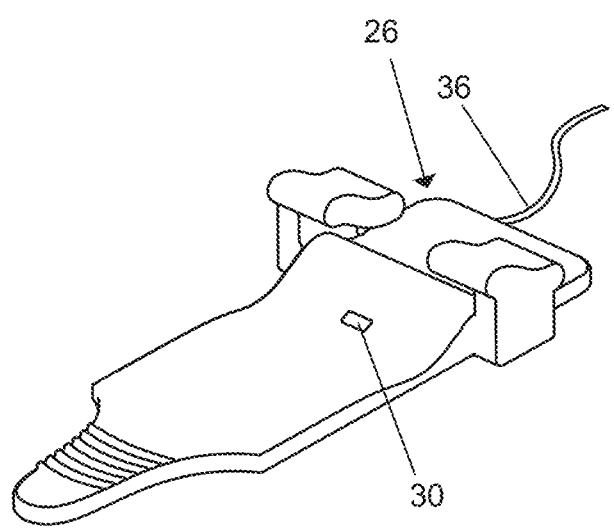
FIG. 8A illustrates a perspective view of the apparatus with lead cable exiting the carrier along the longitudinal axis from the tail end of the carrier according to one embodiment.
Figure 8B:
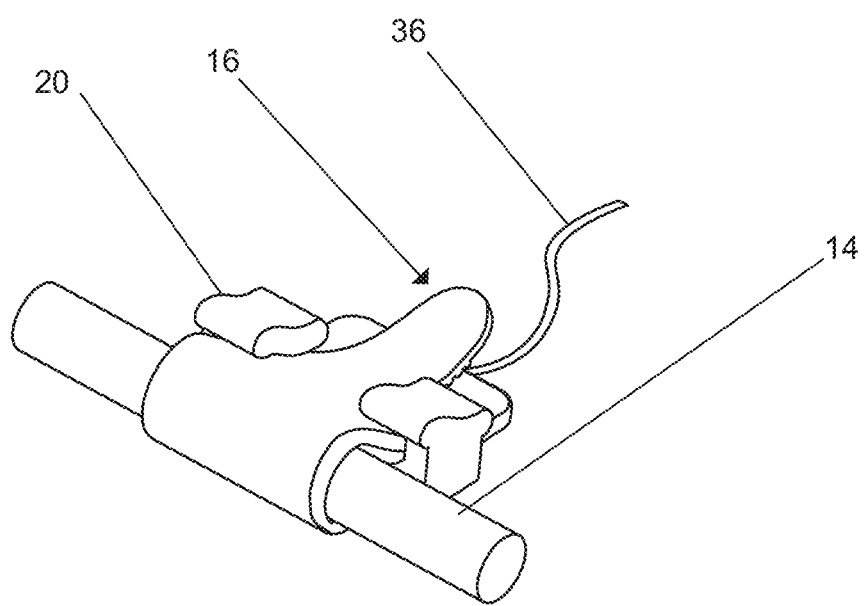
FIG. 8B illustrates a perspective view of the locking mechanism being engaged with the carrier being wrapped around a tubular structure according to one embodiment.
Figure 8C:
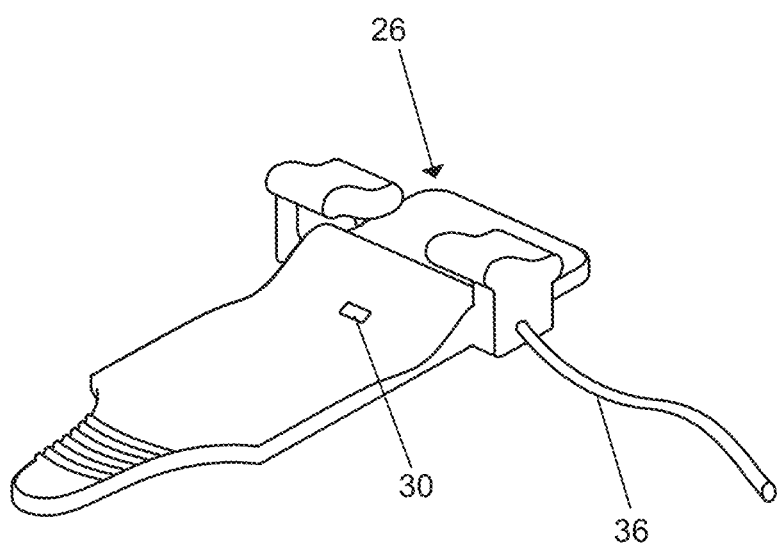
FIG. 8C illustrates a perspective view of the apparatus with lead cable exiting the carrier perpendicular to the longitudinal axis according to one embodiment.

According to some embodiments, as shown in FIG. 8A, the tail end of the lead 36 exits the apparatus from the tail end of the carrier 26, parallel or generally parallel to the longitudinal axis of the carrier. In some arrangements, when interfaced with a nerve 14 (see FIG. 8B), the apparatus 10 with secured head portion 16 using the winged locking mechanism 20 has the lead wire positioned conveniently away from the nerve. Accidental pulling or movement of the lead wire can move the interfaced nerve 14 in a direction close to perpendicular to its longitudinal axis. In another embodiment, as shown in FIG. 8C, the tail end of the lead wire 36 can exit perpendicular to the longitudinal axis 11 of the carrier 12.

Figure 9A:
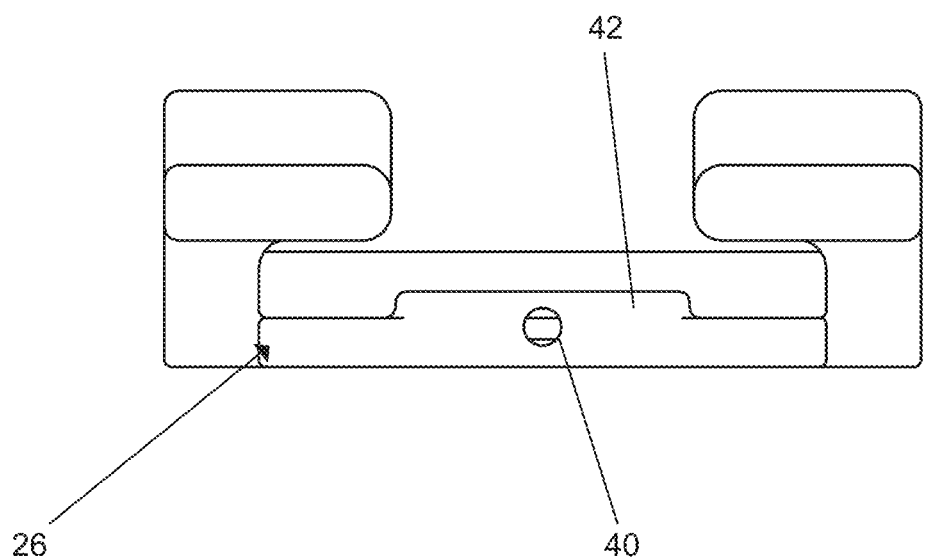
FIG. 9A illustrates a rear view of the apparatus showing a single through-hole starting at the tail portion of the apparatus and used to place an electrode according to one embodiment.
Figure 9B:
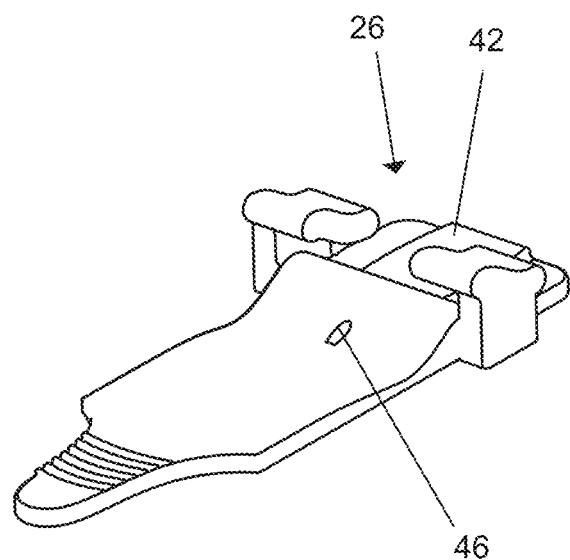
FIG. 9B illustrates a perspective view of the apparatus shown in FIG. 3A and highlights the exit portion of the through-hole.

In some arrangements, as shown in FIG. 9A, the electrode pad 30 and lead wire 32 are connected to the carrier via a through-hole 40. In some embodiments, the through-hole is cut or otherwise created in a thickened portion 42 of the tail end of the carrier 26. In some embodiments, as depicted in FIG. 9B, the through-hole can be a straight line from the tail end of the carrier 26 and can exit through a hole or other opening 46 of the grooved body 24.

In some embodiments, the through-hole containing lead wire 32 comprises one or more through-holes with the angle between their longitudinal axis varying. Such a configuration can result in a chamber where a lead wire 32 can be placed similar to what is shown in FIG. 7B. In some arrangements, the longitudinal axes of the through-holes are angled at 45 degrees (e.g., 30-60 degrees) to one another. In some arrangements, such an angle is between 0 and 90 degrees (0-10-10-20, 20-30, 30-40, 40-50, 50-60, 60-70, 70-80, 80-90, 45-90, 45-60, 15-45 degrees, angles within the foregoing ranges, etc.), as desired or required.

In some embodiments, the electrode pad 30 is secured to the apparatus via a secondary enlarged electrode area 34 that is substantially larger than the through-hole in which the lead wire is inserted. In some embodiments, the electrode pad 30 is protruding relative to the adjacent portions of the apparatus. In other arrangements, the electrode pad may be insert molded flush or recessed relative to the adjacent portions of the apparatus. In other arrangements, the electrode pad is secured by an enlarged secondary electrode area 34 and/or is flush or recessed relative to the adjacent portions of the apparatus, as desired or required.

Figure 10A:
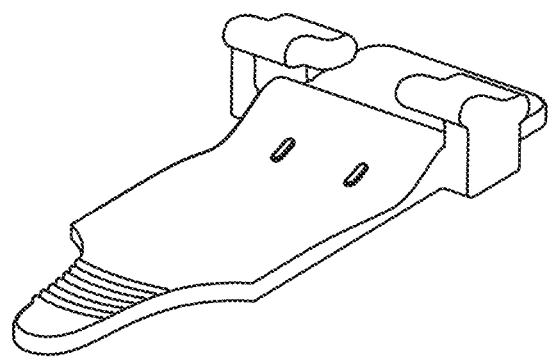
FIG. 10A illustrates a perspective view of one embodiment of the apparatus where the electrode configuration is bipolar with two electrode pads according to one embodiment.

According to some embodiments, as illustrated in FIG. 10A, the electrode contact pads of an electrode apparatus 10' are not limited to a single conductive pad. Instead, as shown, the apparatus can include two (or more) pads placed in a bipolar configuration (e.g., in a similar manner to the single electrode pad 30). The spacing between bipolar pads can be 5 mm. In some arrangements, the spacing can range from 0.1 mm to 5 mm or from 0.1 mm to the width of the electrode apparatus.

Figure 10B:
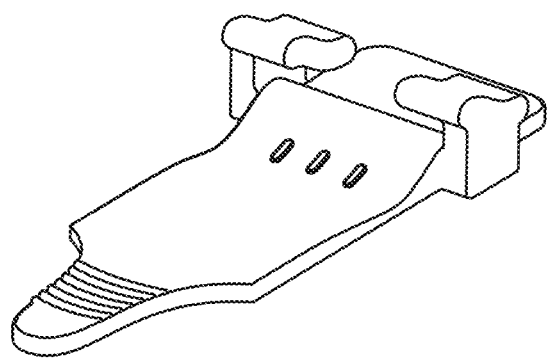
FIG. 10B illustrates a perspective view of one embodiment of the apparatus where the electrode configuration is tripolar with three electrode pads according to one embodiment.

For more precise or selective stimulation of axons within a nerve, a tripolar electrode pad configuration may be used, as shown in the electrode apparatus 10" of FIG. 10B. The spacing between adjacent electrode pads may range from 0.1 mm to 2 mm. In some arrangements, a plurality of more than three electrode pads can be introduced with contact spacing ranging from 0.1 mm so long as the electrode pads fit into the width of the apparatus.

Figure 11A:
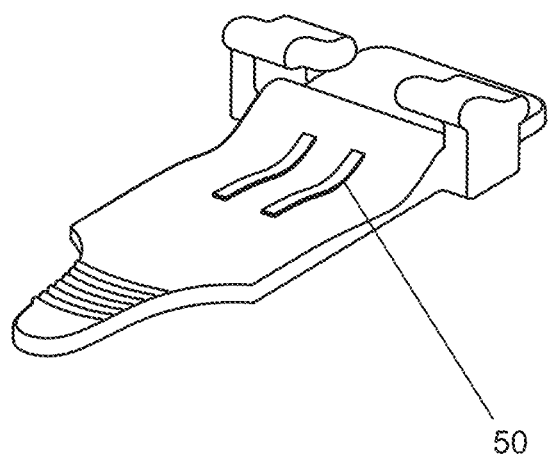
FIG. 11A illustrates a perspective view of one embodiment of the apparatus where the electrode configuration is bipolar with two electrode pads that are made from metallic foil and oriented in a longitudinal direction along the grooved portion of the carrier according to one embodiment.
Figure 11B:
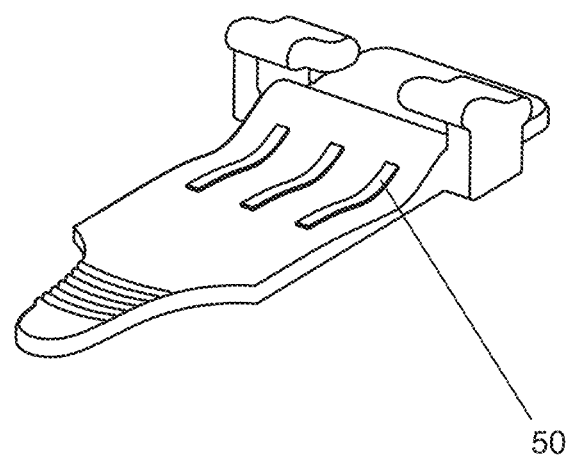
FIG. 11B illustrates a perspective view of one embodiment of the apparatus where the electrode configuration is tripolar with three electrode pads that are made from metallic foil and oriented in a longitudinal direction along the grooved portion of the carrier according to one embodiment.

In yet other embodiments, as illustrated in FIGS. 11A and 11B, electrode pads can be in the configuration of a conductive electrode strip 50 and either printed on the carrier, glued to the carrier using adhesive and/or disposed on the carrier using some other method or technology. In some embodiments, the electrode pads comprise metallic foil (e.g., platinum iridium 90/10) and arranged in a bipolar configuration (FIG. 11A). In some embodiments, the metallic foil can comprise gold and/or any other conductive material, either in addition to or in lieu of platinum iridium, as desired or required. In some embodiments, as depicted in FIG. 11B, a tripolar configuration of foil strips can be used.

The spacing between adjacent strips can be similar to the spacing between electrode pads described above.

Figure 11C:
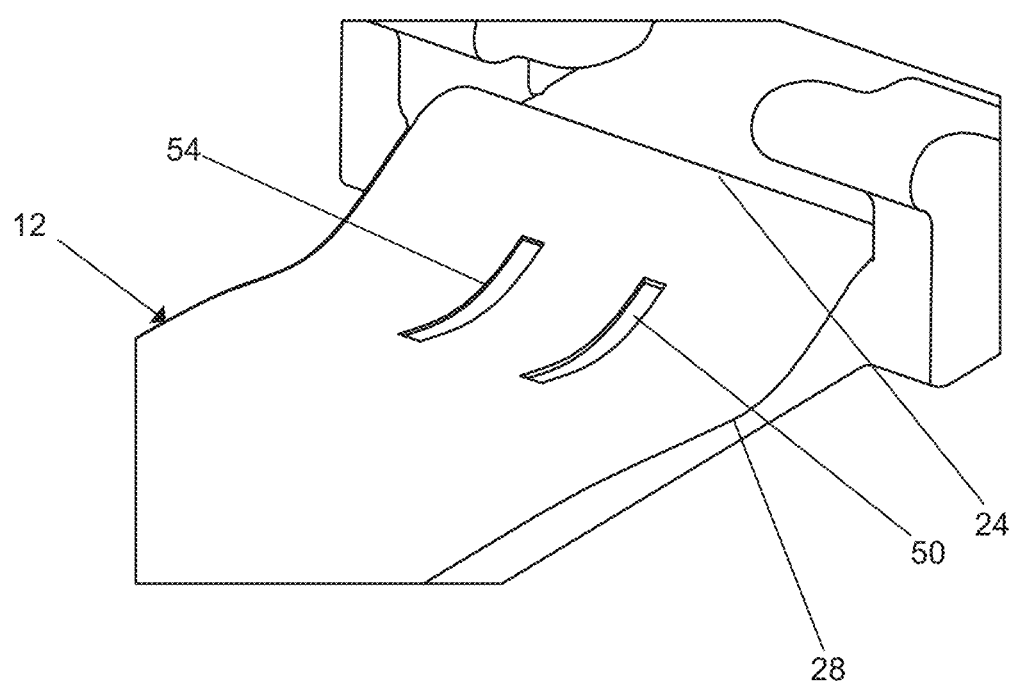
FIG. 11C illustrates a closer perspective view of one embodiment of the apparatus where the electrode configuration is bipolar with two electrode pads that are made from metallic foil and oriented in a longitudinal direction along the grooved portion of the carrier according to one embodiment.

The conductive electrode strip 50 can be embedded within the carrier body 12, as shown in FIG. 11C. In some embodiments, the carrier comprises laser cut windows or other openings 54 to at least partially expose the metal contacts and permit interfacing with tissue. According to some arrangements, the majority of the foil is placed within the thinner mid-portion of the grooved body 28 or grooved body 24 of the carrier 12. This can be particularly helpful with respect to conductive strip electrode placement, in some embodiments, to minimize or reduce potential delamination when the head portion 16 is wrapped around the nerve 14 and interfaced with the winged locking mechanism 20. The conductive electrode strips can be configured in a variety of ways including an array arrangement of a plurality of electrode strips (more than 3, e.g., 4, 5, 6, etc.), as desired or required for a particular application or use. In some embodiments, as discussed in greater detail herein, the electrode apparatus 10 can be used to record tissue or nerve activity as well deliver electrical stimulation.

Figure 12:
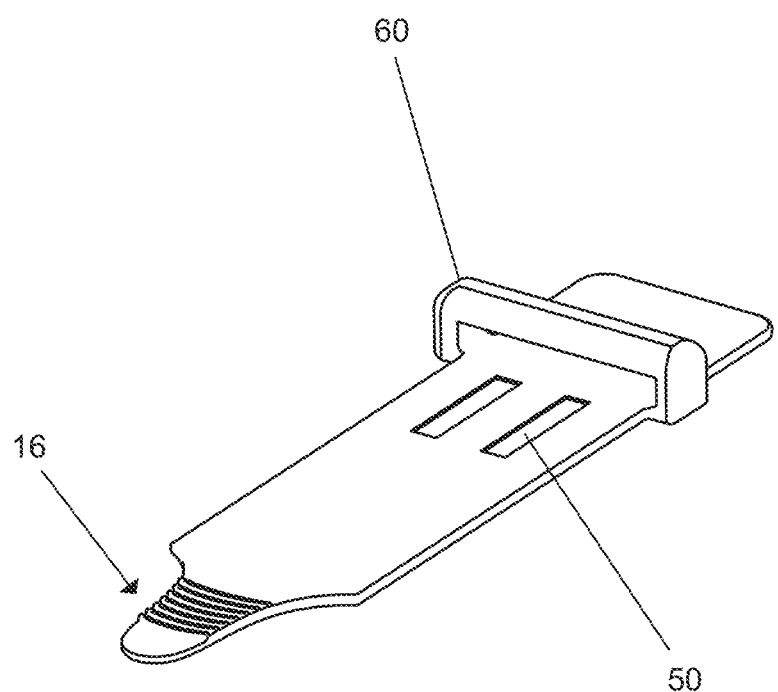
FIG. 12 illustrates a perspective view of an embodiment where the locking mechanism is a circular strap according to one embodiment.

FIG. 12 illustrates yet another embodiment of an electrode apparatus. As shown, the locking apparatus can include a strap 60 that allows a surgeon or other practitioner to pull the head portion 16 of the carrier body 12 under the strap 60 (e.g., using forceps or some other tool). Such movement can permit the surgeon or other practitioner to size the carrier body 12 to fit a nerve appropriately. As in previous embodiments, the molding of the electrode apparatus 10 in a flat configuration can create a biasing force (e.g., to press upwardly on the strap when the head portion 16 of the carrier is threaded under the strap). Such a biasing force can help prevent or reduce the likelihood of the head portion 16 from undesirable movement. Additionally, the friction of the elastomeric material can further prevent or reduce the likelihood of movement of the head portion 16 of the carrier body 12 while engaged with the strap 60. In some embodiments, in order to remove the electrode apparatus from the nerve, the surgeon or other practitioner may cut or otherwise compromise the strap 60. This can release the head portion 16, and the biasing force can allow the electrode apparatus 10 to return to a flat or generally flat conformation.

In some embodiments, a conductive electrode strip 50 can be included in any of the electrode configurations disclosed herein. The strips can extend to the location of the strap 60 in one direction and to the tapered portion of the head portion 16 of the apparatus. The conductive strips 50 can be attached or otherwise coupled to the electrode carrier body 12 (e.g., as previously described). The electrodes may not be limited to the described strips but may also include other electrode embodiments described previously.

Figure 13:
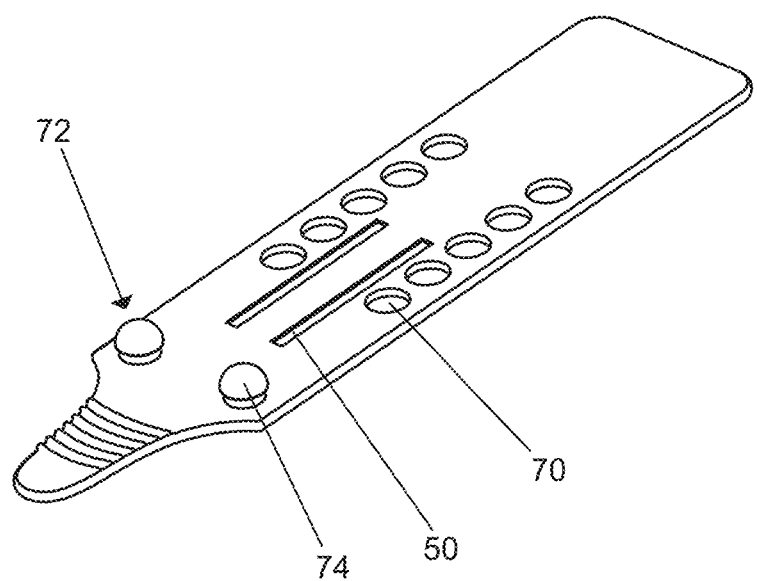
FIG. 13 illustrates a perspective view of an embodiment where the locking mechanism is a set of paired apertures arranged longitudinally along the carrier and one pair of protrusions or buttons that engage with the apertures according to one embodiment.

In some arrangements, as shown in FIG. 13, the locking apparatus includes one or more paired apertures 70 and one pair of corresponding protrusions 72 or buttons with a surface protrusion (e.g., with a diameter that is larger than the aperture). The apertures can range in diameters (or other cross-sectional dimensions) from 1 to 10 mm (e.g., 1-2, 2-3, 3-4, 4-5, 5-6, 6-7, 7-8, 8-9, 9-10, 2-8, 4-8, 1-5, 5-10 mm, dimensions within the foregoing ranges, etc.). However, the diameters or other cross-sectional dimensions can be greater than 10 mm or smaller than 1 mm, as desired or required for a particular application or use. The corresponding paired buttons or protrusions 72 can include a cap 74 (e.g., a hemi-spherical cap) with a diameter or other cross-sectional dimension that may be equal to or larger than the paired aperture 70. In some embodiments, the protrusions comprise a cylindrical (or generally cylindrical) section that is attached to the carrier body 12 and may be smaller than the hemi-spherical cap 74.

In some embodiments, one or more different locking mechanisms can be combined such that the head and tail ends are fastened more securely. In some embodiments, the head portion 16 is fastened with a winged mechanism at a given longitudinal position and additionally fastened with a secondary mechanism (e.g., of the same winged mechanism or other mechanism), to provide additional locking strength in securely holding the head portion. The surgeon or other practitioner can determine whether using additional locking mechanisms is necessary at the time of use.

In any of the embodiments disclosed herein, one or more conductive electrode strips 50 can be included. The strip(s) can extend to the last pair or locking apertures 70 in one direction and to the paired buttons 72 in the other direction. The conductive strips 50 can be attached to the electrode carrier body 12 as previously described. The electrodes may not be limited to the described strips, but may also include other electrode embodiments described herein, as desired or required for a particular application or use.

In some embodiments, the carrier body 12 includes two or more sets of winged locking mechanisms (e.g., placed on either side of a symmetrical groove within the carrier body). In some arrangements, the carrier body can comprise one or more electrodes within the groove. The carrier body and accompanying locking mechanisms can be configured to engage with a second carrier body containing one or more electrodes. In some embodiments, the second carrier body is equal to or longer than the first carrier body. The second carrier body can be placed on top of the first carrier body and engage the locking mechanisms in order to secure a nerve placed between both carrier bodies.

The distance between the locking mechanisms and the groove can be variable or can be symmetrical with respect to the grooves center line. In some arrangements, the locking mechanisms include a strap or locking apertures as described herein.

Figure 14:
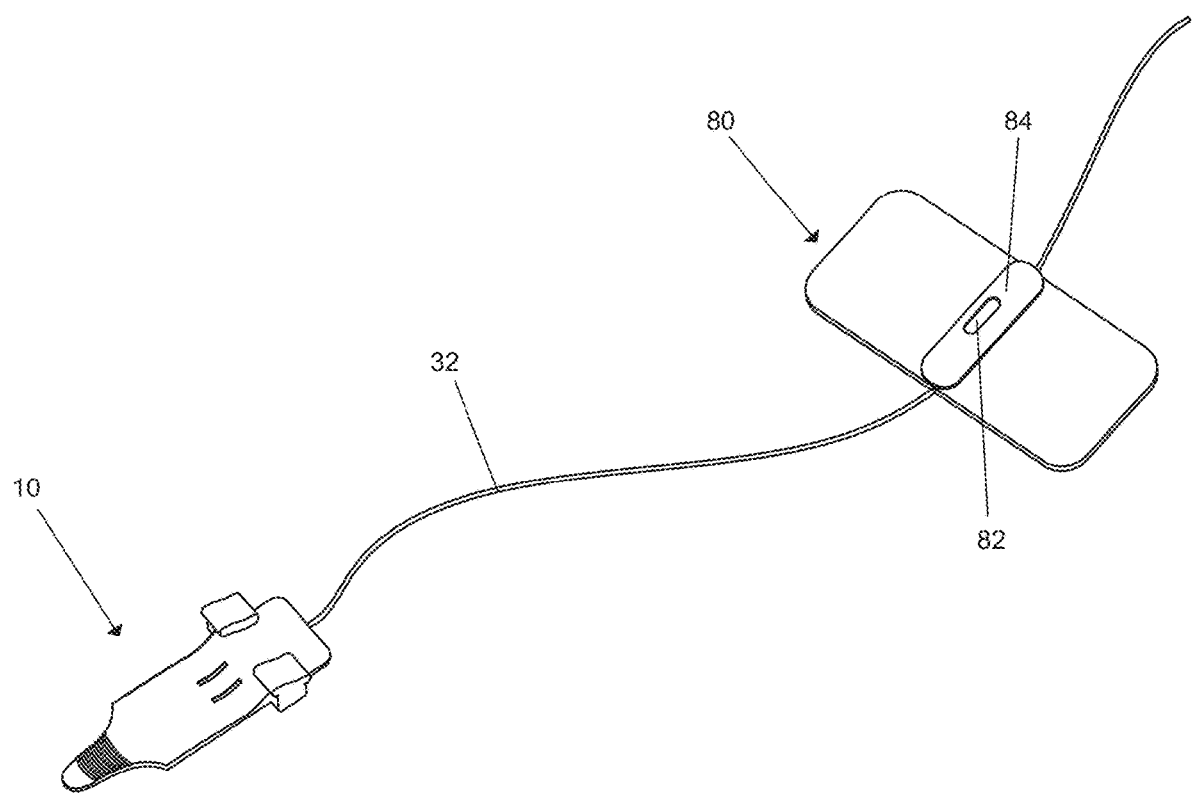
FIG. 14 illustrates a perspective view of an embodiment where an adhesive patch containing a visual indicator is coupled to the proximal end of the lead wire of the electrode apparatus according to one embodiment.

According to some embodiments, as shown in FIG. 14, an adhesive patch 80 is added to the lead wire 32. This can advantageously assist to stabilize the electrode apparatus 10 and prevent (or at least reduce the likelihood of) any inadvertent movement. By way of example, such movement can occur if a user accidentally pulls on the lead wire 32 or interacts with the wire during a surgical procedure. The adhesive patch 80 can be affixed (e.g., directly or indirectly) to a part of the anatomy that is close to an incision or other area being treated or targeted.

In one embodiment, the adhesive patch 80 comprises carbon impregnated rubber or similar elastomeric materials. The elastomeric materials used for the patch 80 can be impregnated with conductive elements, as desired or required. In one embodiment, the adhesive patch 80 (e.g., one side of patch) can include a conductive adhesive gel (e.g. Parker Labs Tensive Conductive Adhesive Gel).

The adhesive patch 80 can include a rectangular shape. For example, in some embodiments, the patch is rectangular and comprises a length of 10 mm to 100 mm and a width of 5 mm to 50 mm. Thus, in some embodiments, the length of the adhesive patch 80 is 1.5 to 5 times the width of the adhesive patch 80. In one embodiment, the distance of the adhesive patch 80 to the electrode apparatus 10 may range from 50 mm to 300 mm. The size, orientation, dimensions and/or other properties of the patch can be different than disclosed herein. For example, in some arrangements, the shape of the patch is circular, oval, triangular, other polygonal, irregular and/or the like.

With continued reference to FIG. 14, the adhesive patch 80 can comprise one or more visual indicators 82, such as LEDs, to provide a status indication to the user. The indicator can be powered by a connected device such as an electrical stimulator or biological amplifier.

In some embodiments, the indication is configured to confirm proper delivery of stimulus pulses or high impedance of the electrode. In some arrangements, the indicator is configured to display, in the case of neuroregenerative therapy, a timer or stimulation amplitude levels. Any other data, information, confirmation and/or the like can be configured to be provided to the user, as desired or required.

In some embodiments, the adhesive patch 80 comprising one or more indicator(s) 82 (e.g., visual indicator(s)), can include a molded section 84 to embed the indicator. In some arrangements, the molded section includes additional circuitry (e.g., to power the indicator, to control the indicator, to provide other non-visual cues to the end user, etc.), as needed or required.

In some embodiments, the electrode apparatus 10 that is connected to the adhesive patch 80 comprises a single electrode contact resulting in a monopolar stimulation field. In some arrangements, the adhesive patch 80 can function as a return electrode for the monopolar stimulation field.

Figure 15A:
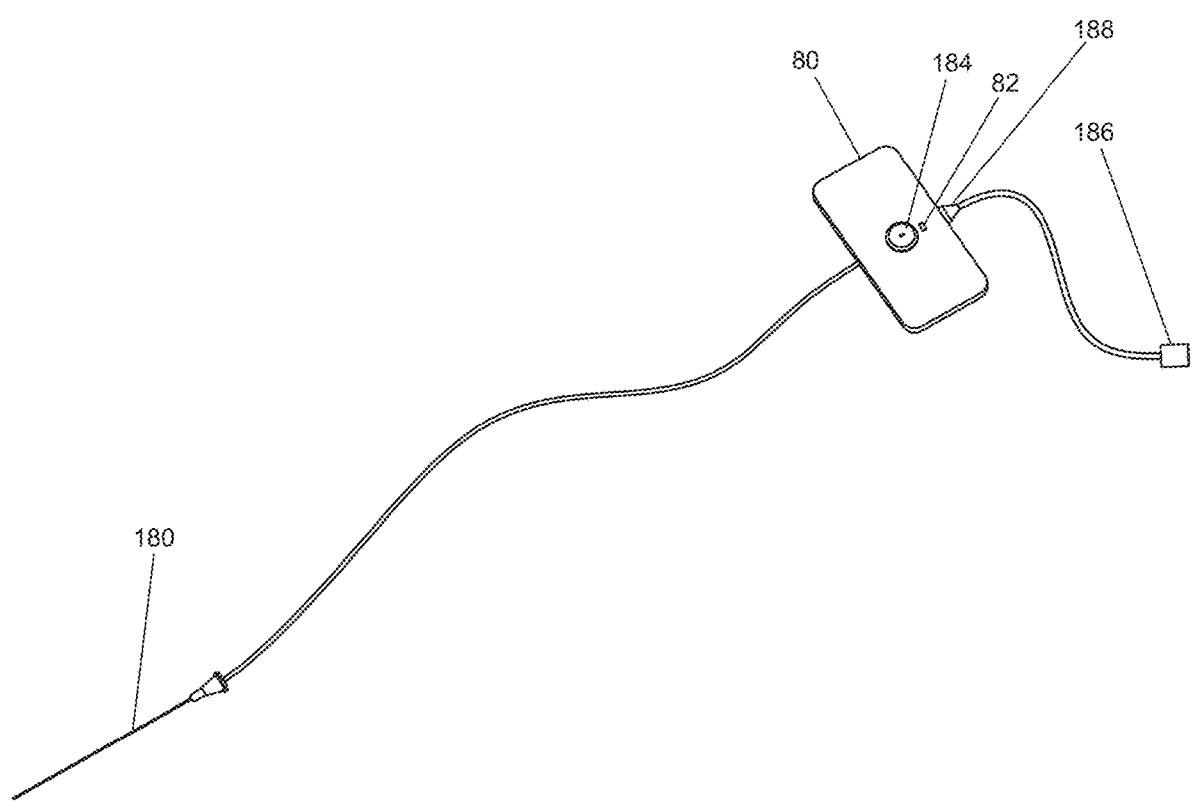
FIG. 15A illustrates a perspective view of an embodiment where an adhesive patch is coupled to a monopolar needle electrode with the patch serving as a return according to one embodiment.
Figure 15B:
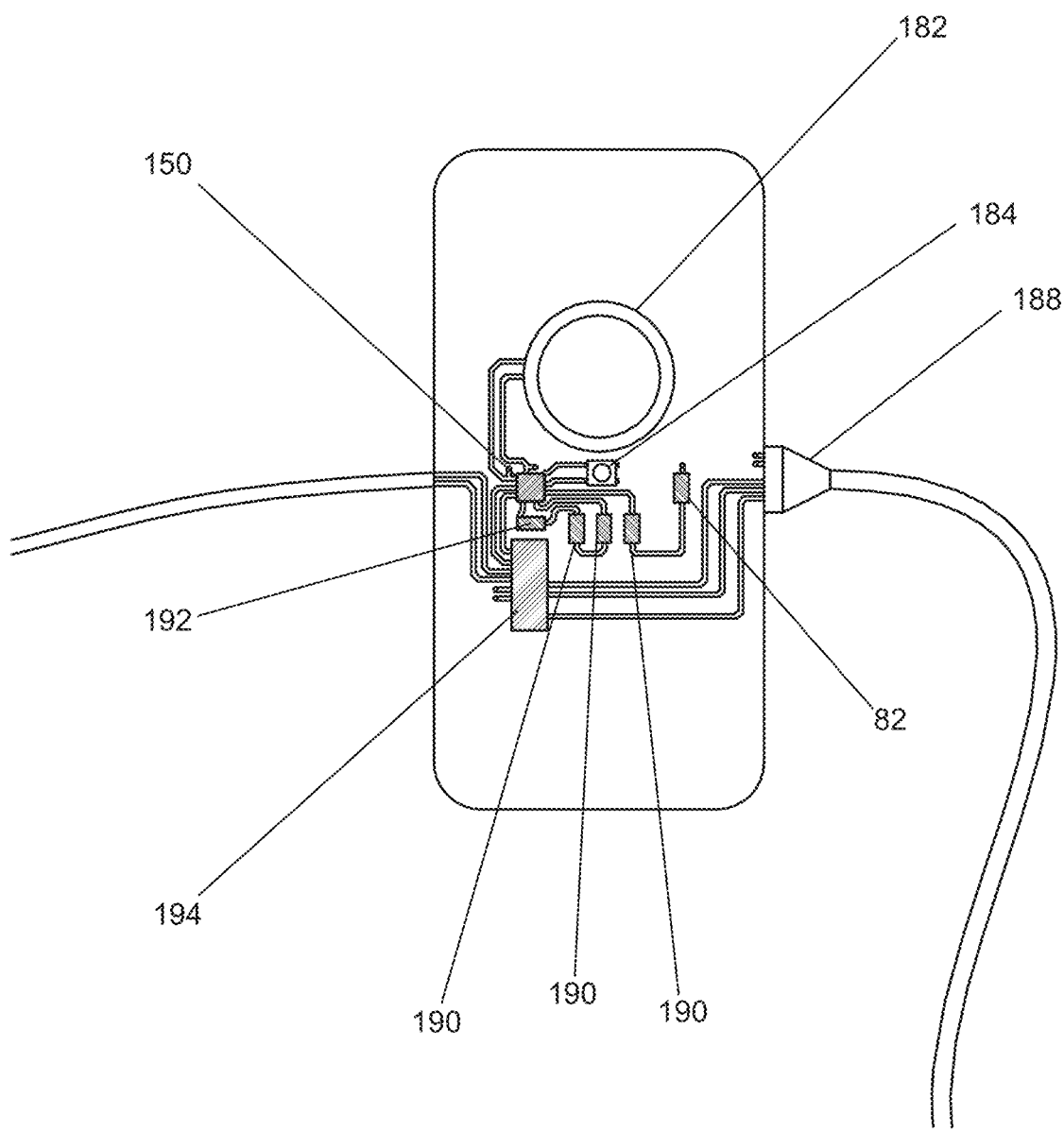
FIG. 15B illustrates a top view of the circuitry layer of the adhesive patch stimulator according to one embodiment.

In other arrangements, as illustrated in FIG. 15A, the adhesive patch 80 may connect to a monopolar electrode 180 that comprises a needle or needle-like apparatus. The adhesive patch 80 comprises circuitry to shape and deliver stimulus pulses to a connected electrode (see, e.g., FIG. 15B). In some arrangements, the patch and circuitry are powered by an included battery source 182. The circuitry can comprise elements similar to those described herein with reference to other embodiments for the electrical stimulation system, such as a microcontroller 150. In some embodiments, the circuitry comprises a time (e.g., 555 timer) or similar device, component or feature used to generate the stimulus pulses. In the embodiments discussed above, associative passive elements can also comprise the circuitry such as resistors 190 and capacitors 192, as needed or required.

In some embodiments, the adhesive patch 80 comprising circuitry used to shape and deliver stimulus pulses, may include one or more indicators 82 (e.g., visual indicators), as described in greater detail herein. In some embodiments, the function of the adhesive patch 80 and included circuitry is to test the connectivity and placement of the monopolar electrode.

In some embodiments, as illustrated in FIG. 15A, the adhesive patch 80 includes a push-button 184 used to initiate or deliver one or more stimulus pulses to the electrode 180. In some arrangements, such a push-button 184 can also be configured to change the stimulus amplitude and/or other stimulus parameters (e.g., frequency, pulse width and/or the like), as desired or required for a particular application or use.

In some embodiments, the adhesive patch 80 may include a multi-segment display (e.g., a 7-segment display). The 7-segment or other multi-segment display can comprise more than one digit and decimal place, as desired or required. The display can include a liquid crystal display (LCD), a plasma display, an organic light-emitting diode display (OLED), a thin-film transistor display (TFT) and/or any other type of display, as desired or required for a particular application or use. The display may provide information such as stimulus parameters, therapy time remaining, battery power levels, mode of operation, connectivity with other devices, etc.

In some arrangements, the adhesive patch 80 comprises a connector 186 used to interface with a second stimulation system. Such a connector can function similarly to the previously described nerve port embodiments. In some arrangements, the connector 186 comprises a molded component 188 that interfaces with the adhesive patch 80 (e.g., seamlessly or nearly seamlessly). In some embodiments, the second stimulation system includes a battery with greater capacity or any other type of system, device, component and/or the like, as desired or needed for a particular application or use. The second stimulation system can include elements similar to stimulation systems described with reference to other embodiments herein. In some embodiments, the second stimulation system may be incorporated into the adhesive patch.

Figure 15C:
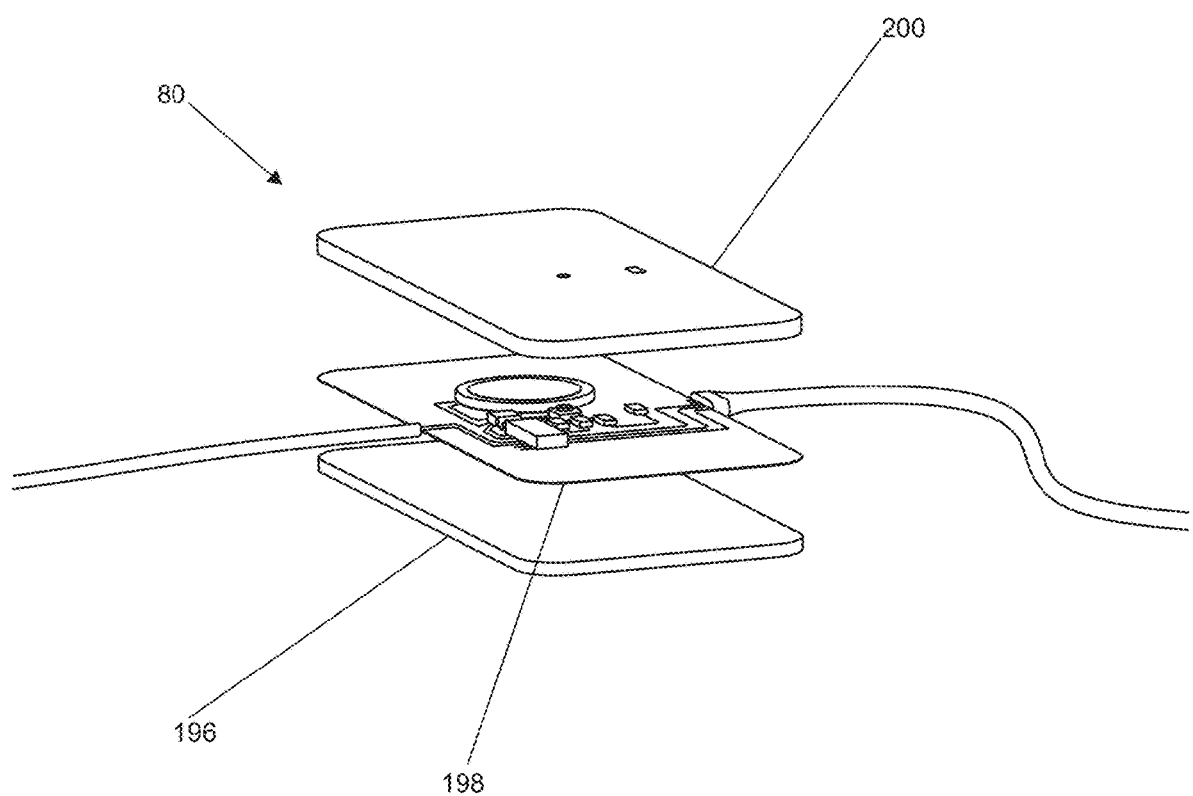
FIG. 15C illustrates an exploded view of the assembly of the adhesive patch stimulation system incorporating a conductive rubber skin interface, a circuitry layer and a elastomeric protective layer according to one embodiment.

According to some embodiments, the circuitry present on the adhesive patch may include elements such as switches 194 or other components or features to direct the stimulus output from the first or second stimulation system. In some embodiments, the adhesive patch comprises of multiple layers (see, e.g., FIG. 15C). Some of the layers in such a confirmation can include a gelled conductive rubber layer 196, a layer incorporating electrical circuitry and other electrical elements 198, an elastomeric protective layer 200 and/or any other layers or components.

Figure 16A:
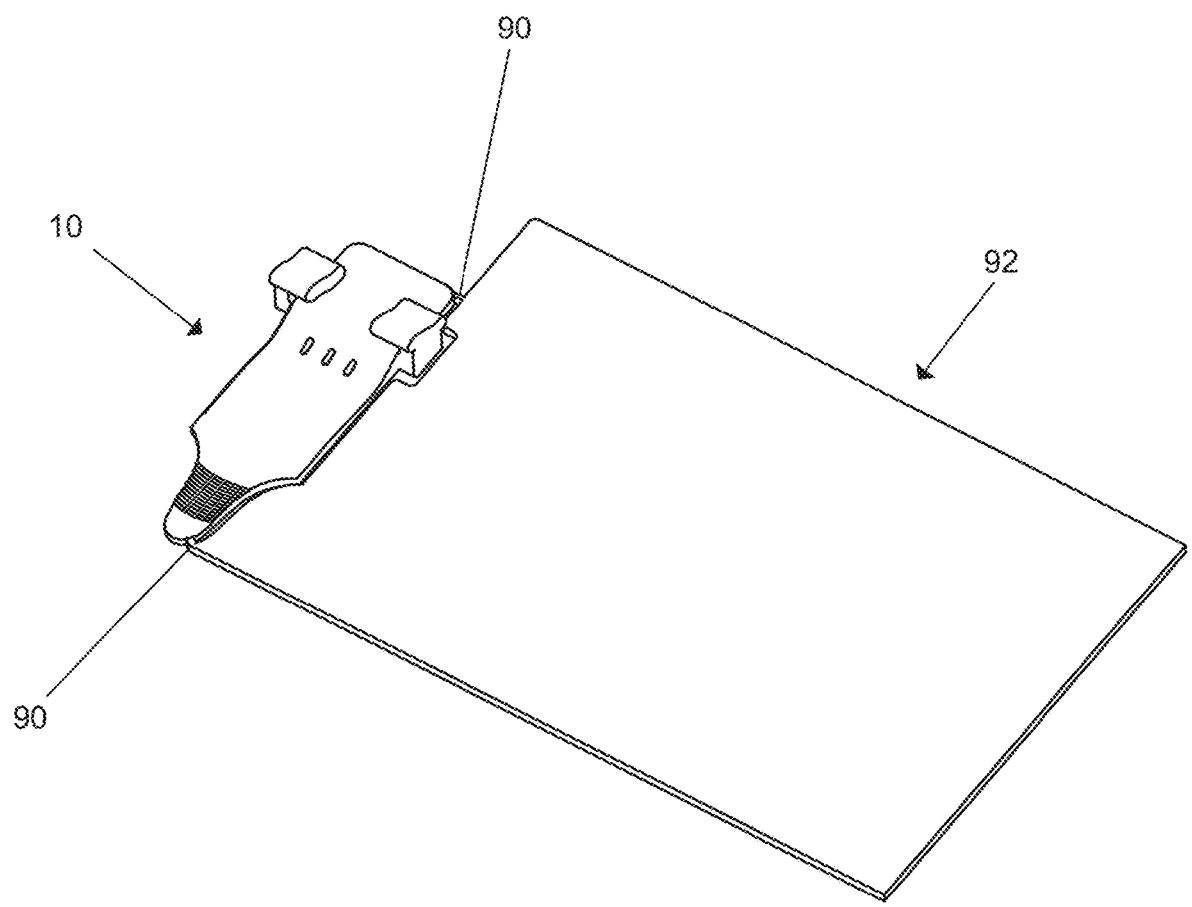
FIG. 16A illustrates a perspective view of an embodiment of the apparatus showing the carrier coupled to a polymer background material used for isolating a tissue of interest from surrounding tissue according to one embodiment.

In some embodiments, as depicted in FIG. 16A, the electrode carrier body 12 is coupled (e.g., directly or indirectly) via one or more small tabs 90 to a polymer or microsurgical background material 92. Such a material 92 can typically be used to separate or isolate a nerve or other tissue from surrounding tissue, allowing a surgeon or other practitioner to focus (e.g., solely or more exclusively) on repair or dissection of the isolated tissue.

Figure 16B:
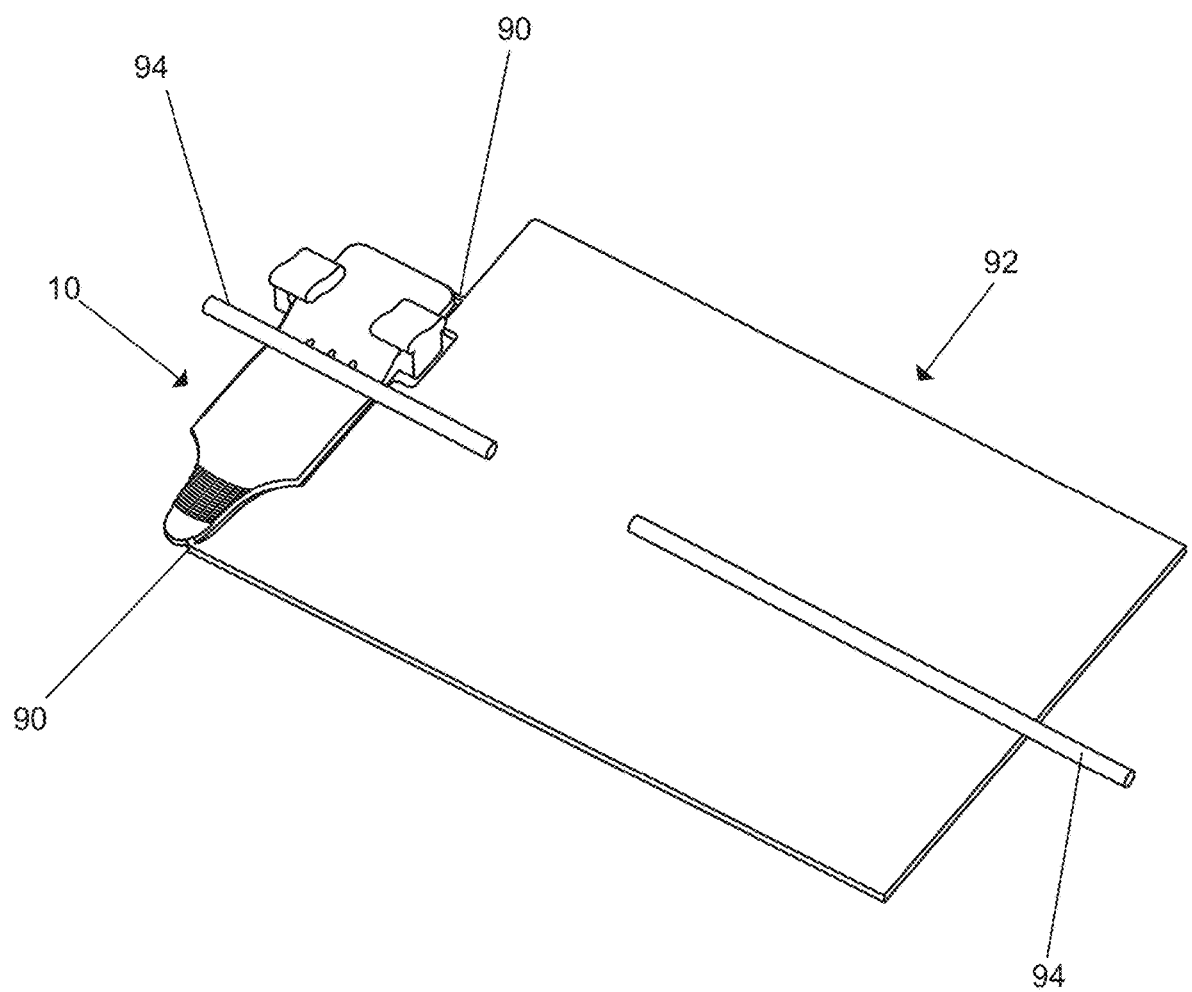
FIG. 16B illustrates a perspective view of an embodiment of the apparatus showing the carrier coupled to a polymer background material used for isolating a tissue of interest from surrounding tissue with a transected nerve situated on the background material according to one embodiment.

According to some embodiments, as illustrated in FIG. 16B, the carrier 12 and coupled background material are used to isolate an injured nerve 94 (e.g. a transected nerve) with the proximal end of the injured nerve placed on the electrode apparatus 10. The distal end of the injured nerve 94 can be placed on the background material. If, by way of example depicted in FIG. 16B, a transected nerve does not require a nerve graft to bridge the distance between proximal and distal ends, the coaptation of both nerve ends can be accomplished directly on top of the background material. If a nerve graft is to be used to bridge the gap between proximal and distal ends of a transected nerve, the insertion of the nerve graft can be accomplished on the background material.

Figure 16C:
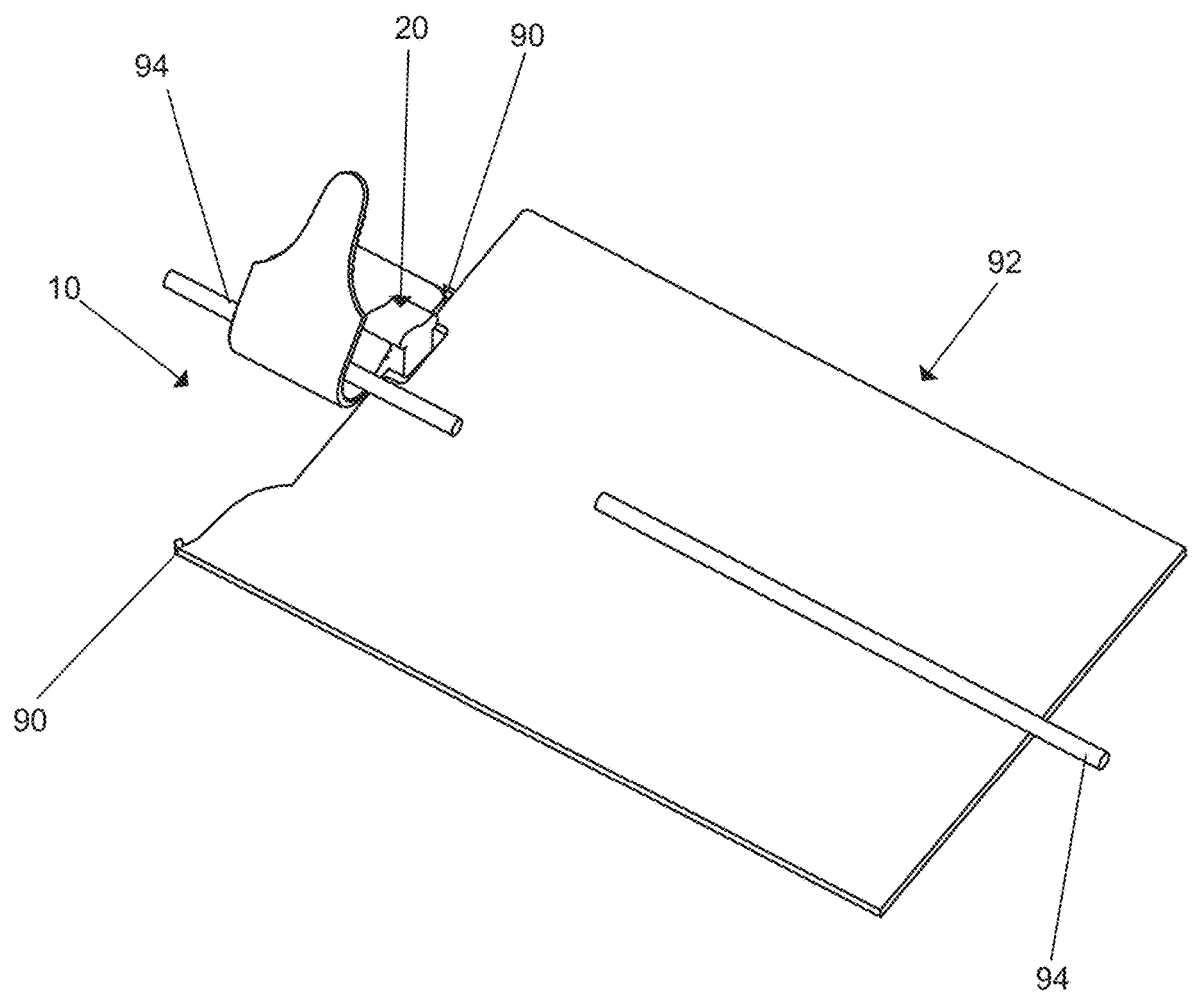
FIG. 16C illustrates a perspective view of an embodiment of the apparatus showing the carrier being folded to wrap the nerve while still partially coupled to a polymer background material used for isolating a tissue of interest from surrounding tissue with a transected nerve situated on the background material according to one embodiment.

In one embodiment, prior to repair of the injured nerve 94 (e.g., immediately prior to such repair), the electrode apparatus 10 can be disconnected from the background material by cutting (or otherwise compromising) the tabs 90. In some embodiments, the disconnected carrier body 12 can then wrap or surround the injured nerve 94, as shown in FIG. 16C, with wrapping of the proximal nerve stump prior to engaging the winged locking mechanism 20, and neuroregenerative therapy (e.g., relatively brief electrical stimulation) may be delivered to accelerate and facilitate nerve regeneration. During this time, a surgeon can perform a nerve repair or graft installment distally (e.g., immediately distally) to the electrode apparatus with the distal aspect of the proximal portion of the nerve and the distal transected nerve 94 being positioned on the background material 92.

For any of the embodiments disclosed herein, or equivalents thereof, a lead wire 32 connected to the conductive electrode pads 30 can be coupled (e.g., connected) to a stimulus output sub-system. This can help provide stimulation pulses to depolarize axons or electrically stimulate tissue. In other embodiments, the lead wire may be connected to a biological amplifier to record signals from a nerve or other tissue and/or to any other system, subsystem, device and/or the like, as desired or needed for a particular application, indication or use.

Figure 17A:
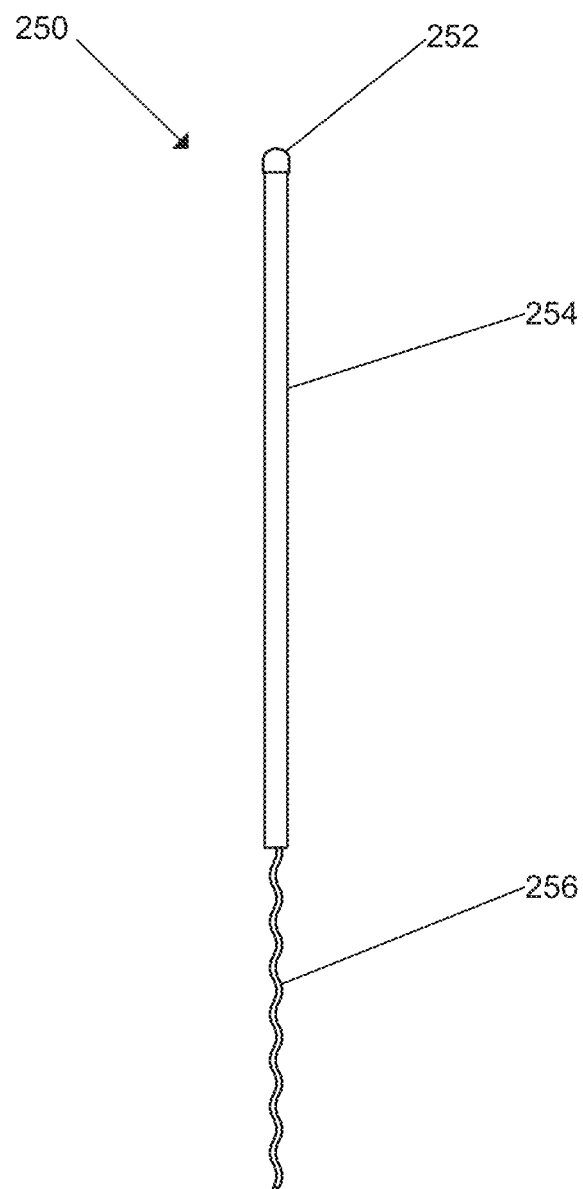
FIG. 17A illustrates one embodiment of an electrical lead.

According to some embodiments, a percutaneous electrode lead 250 may be coupled to the adhesive patch 80. The electrode lead, as illustrated in FIG. 17A, may comprise of one or more conductive elements 252. The conductive elements can be placed on or near the tip of the lead, as illustrated in one example in FIG. 17A. In other arrangements, the conductive elements 252 can be positioned along the length of the lead, either in lieu of or in addition to being at or near the tip of the lead, as desired or required.

In some embodiments, the electrode lead comprises a circular or curved shape (e.g., at least a partial circular or curved shape) and comprises an outer diameter (or other cross-sectional dimension) of 0.1 to 5 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 1-4, 0.5-4, 1-4 mm, ranges between the foregoing, etc.). In some arrangements, the diameter or other cross-sectional dimension is determined (at least in part, e.g., largely) by the lead housing 254 (e.g., the size, shape and/or other characteristics of the lead housing). In other embodiments, the electrode comprises a needle.

Figure 17B:
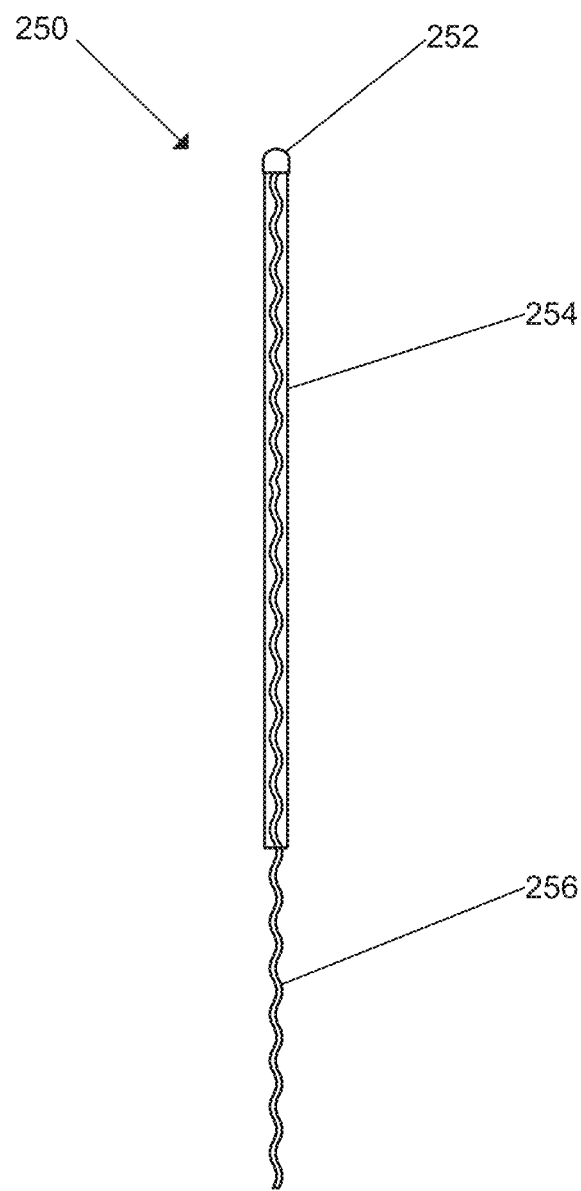
FIG. 17B illustrates one embodiment of an electrical lead.

The lead housing 254 can comprise one or more elastic or semi-elastic materials, such as, for example, silicone rubber (e.g., silicone rubber tube), polyurethane, other polymeric materials, other types of elastomeric or rubber materials, other flexible or semi-flexible materials, etc. The lead can be placed near a nerve through an existing incision or through a percutaneous approach (e.g., where a needle or other sharp object with a cannula are utilized to provide access to the nerve). The flexibility of its materials/construction and/or similar physical characteristics of the lead housing 254 can be selected to facilitate for easy removal of the percutaneous electrode lead 250. In some embodiments, the lead housing 254 comprises a lead wire 256 that is physically connected to a conductive element 252, as illustrated, e.g., in FIG. 17B.

In some embodiments, the lead housing can comprise of a uniform or continuous material thickness throughout the length of the lead. In other embodiments, the lead housing includes areas of different thickness that serve as bendable joints that can provide added flexibility for shaping the lead. In some arrangements, desired shapes are retained until other forces are applied that reshape the lead, for example manual manipulation or the act of lead removal. In other embodiments, these joint segments may comprise of materials different from the rest of the housing. In some embodiments, the joint segments may be more or less flexible than the remainder of the lead housing.

In some embodiments, the lead housing may include a coiled wire that is used to provide shape memory for the lead. This can be particularly advantageous in areas where the lead is required to bend and maintain its shape. In some arrangements, the coiled wire spans the length of the lead. In other arrangements, the coiled wire may only span a first length or portion (e.g., the first 10 cm or less, such as, for example, 0-10, 2-8, 1-5, 5-10 cm, lengths between the foregoing ranges, etc.) of the lead. However, the extent of the coiled wire need not be limited to these distances (e.g., can be greater than 10 cm, as desired or required). In some embodiments, the coiled wire is physically coupled (e.g., directly or indirectly) to an electrode. In other embodiments, the coiled wire is not electrically coupled to any stimulating electrodes. In some embodiments, the coiled wire serves as an electrical connector to other circuitry located at, along or near the distal end of the lead housing. Depending on the application, required flexibility and memory properties and/or other design considerations, the spacing between adjacent coils is zero (e.g., the coils are touching one another) or is a fixed distance. In some embodiments, the coiled wire is insulated or uninsulated. In some arrangements, the coiled wire is encased in flexible material such as various durometers of Pellethane® or Pebax® or similar thermoplastic polyurethanes or elastomers materials.

In some embodiments, the percutaneous electrode lead 250 can be connected to an extension wire that is then connected to the stimulation unit to provide more length in cases where the stimulation unit is placed further from the area where the electrode lead 250 is placed. The extension wire can comprise an additional length of 30 to 100 cm (30-40, 40-50, 50-60, 60-70, 70-80, 80-90, 90-100, 50-80 cm, distances between the foregoing ranges, etc.). The extension wire may be of similar or different material properties with at least one end that interfaces the electrode lead and makes electrical contact and at least one end that interfaces the stimulation unit and makes electrical contact. In some embodiments, when the stimulation unit, the extension wire and electrode lead are connected, they function as an integrated unit and perform similarly as described.

In some embodiments, the electrode lead housing 254 includes fiducial and/or other markers to help indicate distance from the tip of the lead. Other markers (e.g., fiducial markers) can include radiopaque markers or high echogenicity markers for image guided placement of the lead. Image guided placement of the electrode lead 250 may be advantageous in situations where direct visualization of the injured nerve and/or the electrode lead is not possible. Such situations, for example, may arise when a patient is undergoing a nerve repair or decompressive procedure under local anesthesia. Depolarization of axons is not possible within the region that is anaesthetized. In some embodiments, in order to provide neuroregenerative therapy to the injured nerve, it is advantageous to place the electrode lead 250 proximal to the region of anesthesia. In some embodiments, for the therapy to be effective (or more effective), the electrical field that is produced by the lead must depolarize the non-anesthetized proximal branches of the injured nerve. In one non-limiting example, a patient may undergo carpal tunnel release under local anesthesia, a procedure that anesthetizes the wrist. In some embodiments, proximal branches of the medial nerve, such as in the forearm, are not superficial, and image-guided placement of the electrode lead 250 would be advantageous to a surgeon in order to precisely target the proximal component of the injured median nerve. In some arrangements, image-guided placement also assures that blind insertion of the lead does not result in damage to surrounding vascular structures.

In another example, insertion of the electrode lead using image guidance may also be advantageous in situations where a nerve repair or other surgery may have been performed previously but the patient did not receive electrical stimulation therapy at time of the original repair procedure. In such situations, placement of the electrode lead using image guidance can take place hours, days, or weeks following a repair procedure. Placement of the electrode may also occur prior to a nerve repair procedure. Such placement may elicit an electrical stimulation conditioning effect of the cell body. Image guidance may be performed using ultrasound, fluoroscopy, x-ray, or other imaging modalities.

In some embodiments, the markers comprise one or more protrusions and/or recesses (e.g., dimples or reverse dimples). In such configurations, the protrusions, recesses and/or similar features can serve a dual or multi-faceted purpose or function. For example, not only could such features function as a fiducial marker, but they can also help restrict (or limit) movement of the lead when placed inside an object (e.g., cannula, sheath, another cylindrical object, another object with one or more openings, etc.).

Figure 17C:
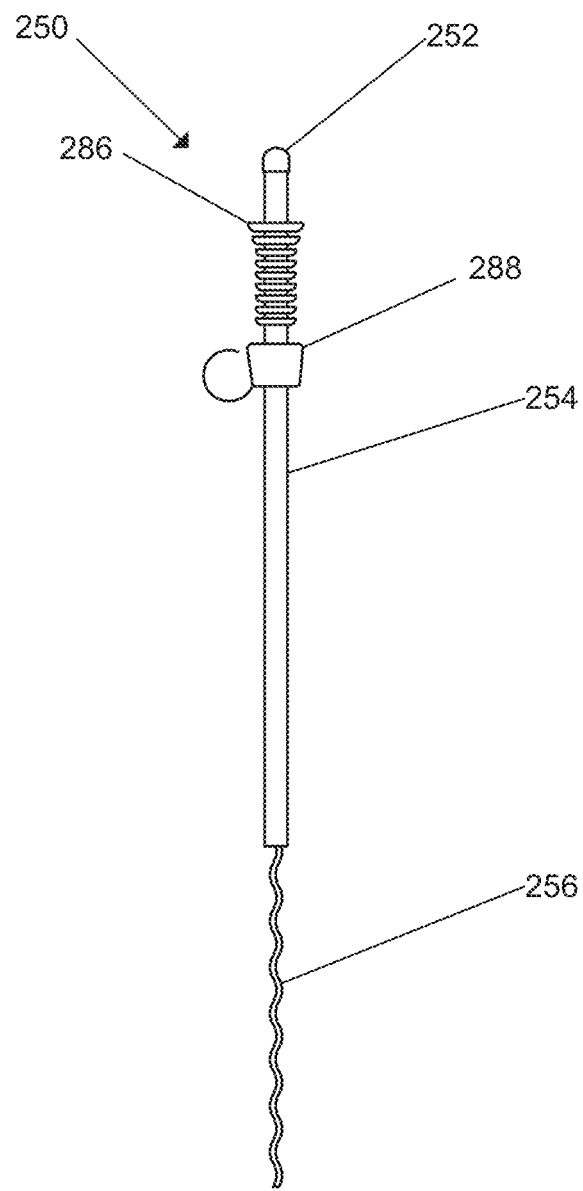
FIG. 17C illustrates one embodiment of an electrical lead.

In some embodiments, as illustrated, by way of example, in FIG. 17C, the lead housing 254 comprises a textured, ribbed and/or other non-smooth surface 286. Such a configuration can help increase the contact surface area and improve localized anchoring of lead in situ with neighboring tissue. For instance, circular or linear substructures can be included that protrude from the surface (e.g., in a winged-like manner). In addition, or in lieu of such embodiments, recessed features may be included. For example, such recessed features can be depressed within the surface of the material. In some embodiments, substructures may be shaped or differently sized as to limit or enhance prevention of movement in certain directions, while facilitating movement in others as to provide improved temporary immobilization of lead in situ. In yet another embodiment, substructures may include a single or multiple rings, hook-shaped structures and/or any other anchoring features or members 288 to improve or otherwise enhance anchoring of the electrode lead with suturing, or similar, to neighboring tissue. In other arrangements, fibrin glue or similar tissue adhesives may be used to temporarily anchor the electrode lead. Such designs can be advantageous to users in order to affix stimulating leads in close proximity to targeted nerve tissue, ensure minimal or reduced unintended movement, facilitate removal of the lead with minimal disturbance to tissues once stimulation is complete and/or provide one or more other advantages or benefits. By way of an example, a user can place the lead parallel or approximately parallel or tangential to a targeted nerve structure, and if desired, use standard medical sutures and/or other fixation technologies to engage flexible structures on the lead to anchor to tissue.

Figure 17D:
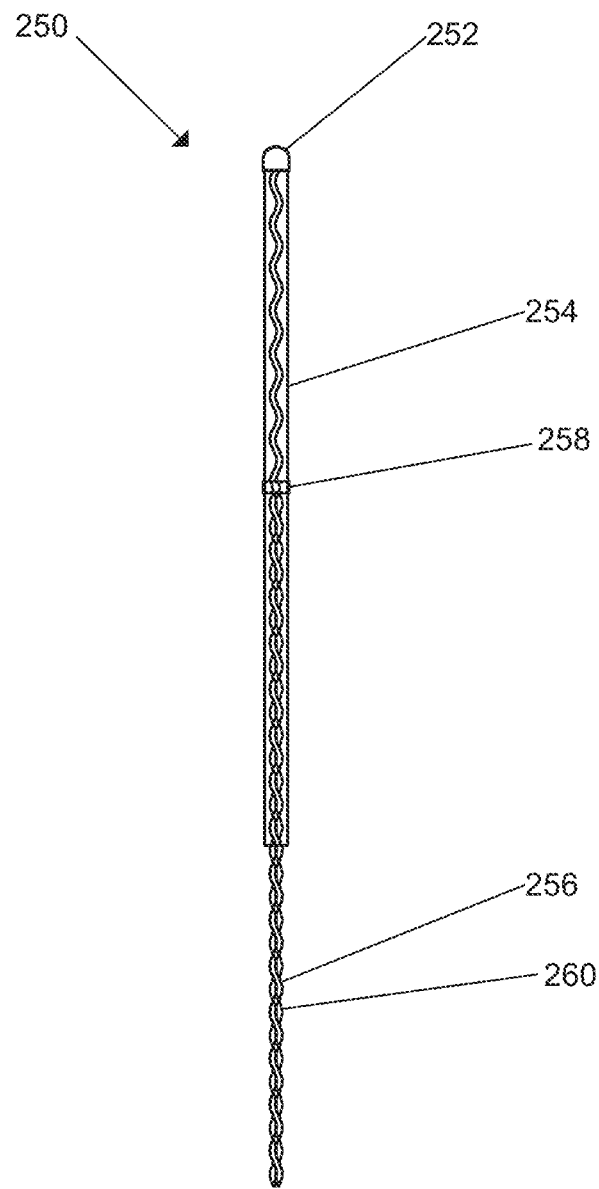
FIG. 17D illustrates one embodiment of an electrical lead.

In some embodiments, as illustrated in FIG. 17D, the percutaneous electrode lead 250 comprises multiple conductive elements, 252, 258. The conductive elements 252, 258 can include different shapes, sizes and/or other characteristics, as desired or required. For example, as illustrated in FIG. 17D, the conductive element at the tip 252 of the electrode lead can be shaped in a manner to cap the electrode lead housing 254 and also provide a larger surface area that may be used to provide stimulus current to tissue such as peripheral nerves. With continued reference to FIG. 17D, a second conductive element 258 can be shaped as a ring with said ring varying in thickness from 0.1-10 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 2-8, 3-6, 1-3, 3-5, 5-8 mm, ranges between the foregoing, etc.) and can be physically coupled to a conductive insulated wire 260. In some arrangements, a second conductive element 258 can be used as a return electrode for the first conductive element essentially creating a bipolar stimulating field. In other arrangements, the second conductive element is used as a signal path for other circuitry and is combined with additional conductive elements placed on the lead. The plurality of conductive elements can also form an electrical stimulation array allowing to shape or otherwise modify or impact the current field.

Figure 18A:
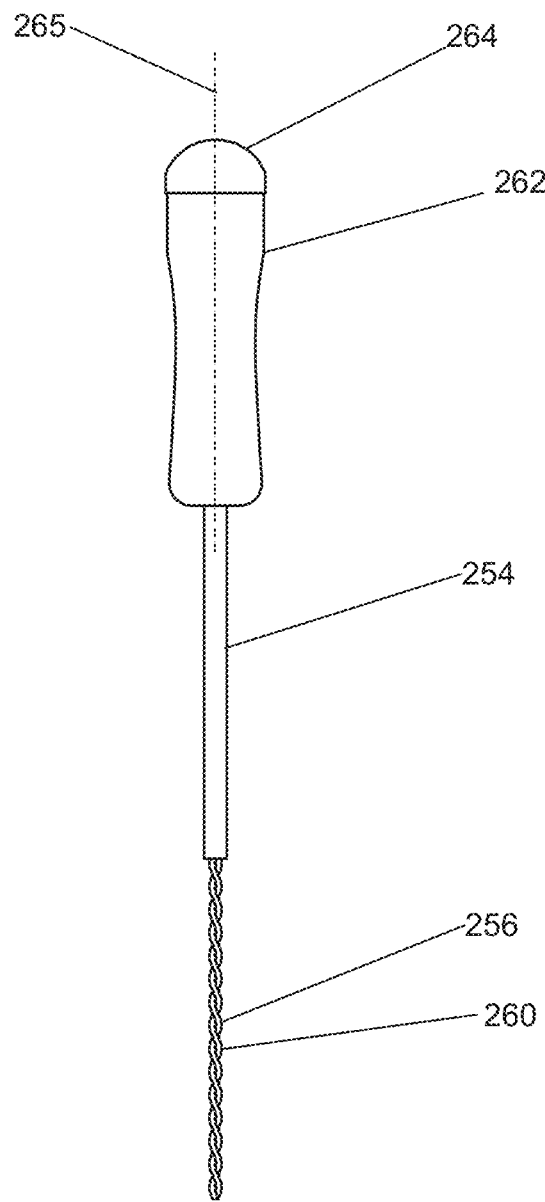
FIG. 18A illustrates one embodiment of an electrical lead coupled to a cap element.

In some embodiments, as illustrated in FIG. 18A, the percutaneous electrode lead 250 is coupled to a cap element that comprises an enclosure 262 (e.g., a shaped, plastic or other elastomeric or electrically non-conductive enclosure or member) and a conductive surface 264. In some arrangements, the conductive surface 264 is larger than the enclosure 262. The plastic enclosure 262 can be greater than one but less than twenty times the diameter of the electrode lead (e.g., 1 to 20 times, such as, 1-5, 2-4, 5-10, 10-20, 5-15, values between the foregoing, etc.), as desired or required. In some arrangements, the percutaneous electrode lead 250 that comprises a conductive element at the tip 252 (as previously described herein), may be in physical contact (e.g., at least partial physical contact) with the larger conductive surface 264 present on the cap, effectively creating a larger stimulating surface. As an example, if the electrode lead is coupled to a pulse generator, covered with the described cap, and said pulse generator outputs a long duration pulse (e.g., a pulse having a wavelength greater than 200 µs), the larger conductive surface of the cap may be used to stimulate muscle tissue. In the context of verifying stimulus output, this may be advantageous since a smaller conductive surface (e.g., as included on an electrode lead) may not create a sufficiently large electric field to elicit a visual muscle contraction. The use of the larger conductive surface on the cap to stimulate muscle can arise, for instance, in situations where an intact uninjured motor nerve is not readily accessible for stimulation. Using the cap to create a visual contraction in the muscle can provide enhanced confirmation to the user that stimulus is being output to the electrode.

In some arrangements, the cap may be shaped similarly to a pen-like structure to facilitate holding, grasping, manipulation, use and/or the like. In such an arrangement, the cap may function as a nerve locator. In some embodiments, the cap may include a monopolar probe or a bipolar probe. These probes can be configured to provide a smaller conductive surface for fine resolution of the stimulating field in order to map anatomical location of nerves. These arrangements can advantageously allow for a multi-function system providing both nerve location functionality and neuroregenerative functionality.

In some embodiments, the cap comprises two or more pieces or portions that snap-fit together around the electrode lead. In other embodiments, any other type of connection or attachment method or technology can be used, such as friction or press fit, couplings (e.g., standard or non-standard), mechanical fasteners or other mechanical connections, etc.

Figure 18B:
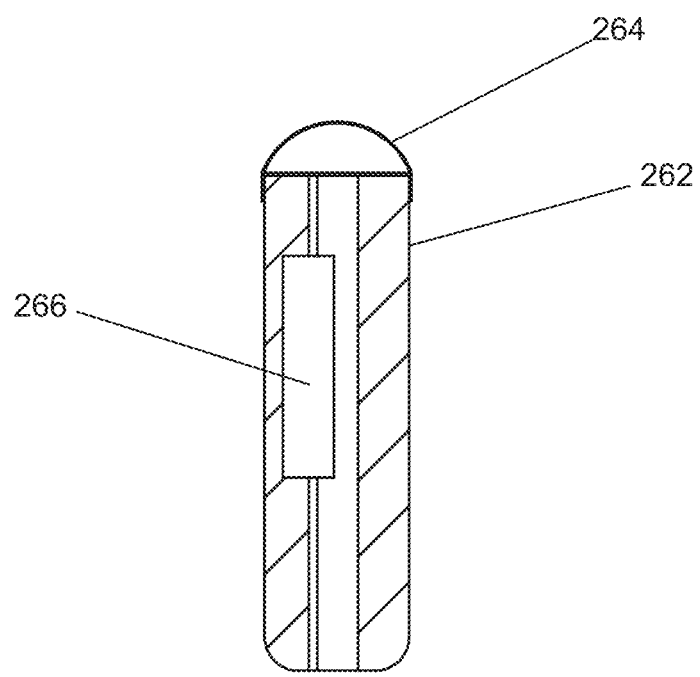
FIG. 18B illustrates one embodiment of a cap element comprising electrical circuitry.
Figure 18C:
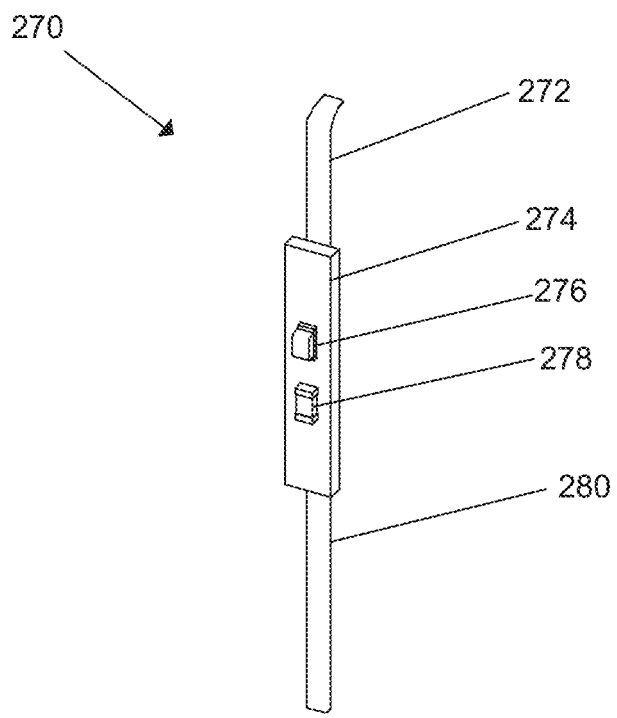
FIG. 18C illustrates one embodiment of an assembly configured to be secured to a cap element.

In some embodiments, the enclosure 262 (e.g., shaped enclosure) includes space for embedded circuitry. In some arrangements, the enclosure comprises a shaped plastic enclosure. FIG. 18B provides a cross-section view of the cap with reference to the plane 265 drawn in FIG. 18A and includes the potential space for circuitry 266. In some embodiments, such circuitry comprises one or more assemblies 270, such as illustrated in FIG. 18C. In one example, as shown, the assembly 270 comprises two conductive components, a distal component 272 and a proximal component 280 that interface with a printed circuit board 274. The printed circuit board can include passive and/or active components. In some embodiments, the printed circuit board 274 comprises a resistor 276 and a LED 278.

In yet other embodiments, the circuitry comprises a combination of indicators and controls, including, by way of example, one or more LEDs (and/or other indicators) and/or one or more buttons or other controls or controllers. Such a design can be advantageous to users in order to activate pulse generation, verify functional output at tip (e.g., by way of an illuminating LED) and/or in one or more other manners. By way of an example, a user can connect the electrode lead 250 to a pulse generator, activate pulse generation using the button on the electrode cap and verify function by observing LED on the electrode cap. Such a button, control or other controller can also be configured to change the stimulus amplitude and/or one or more other stimulus parameters (e.g., frequency, pulse width and/or the like), as desired or required for a particular application or use.

Figure 18D:
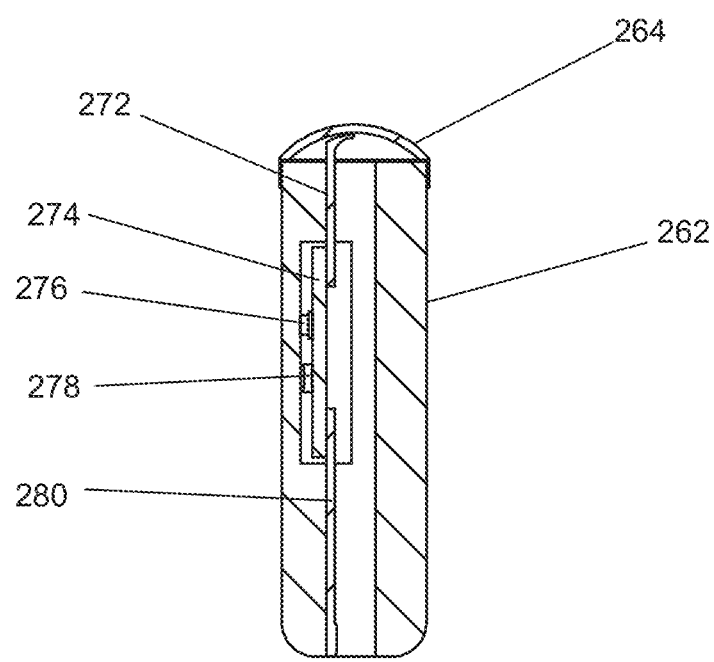
FIG. 18D illustrates the assembly of FIG. 18C secured to the cap element of FIG. 18B.
Figure 18E:
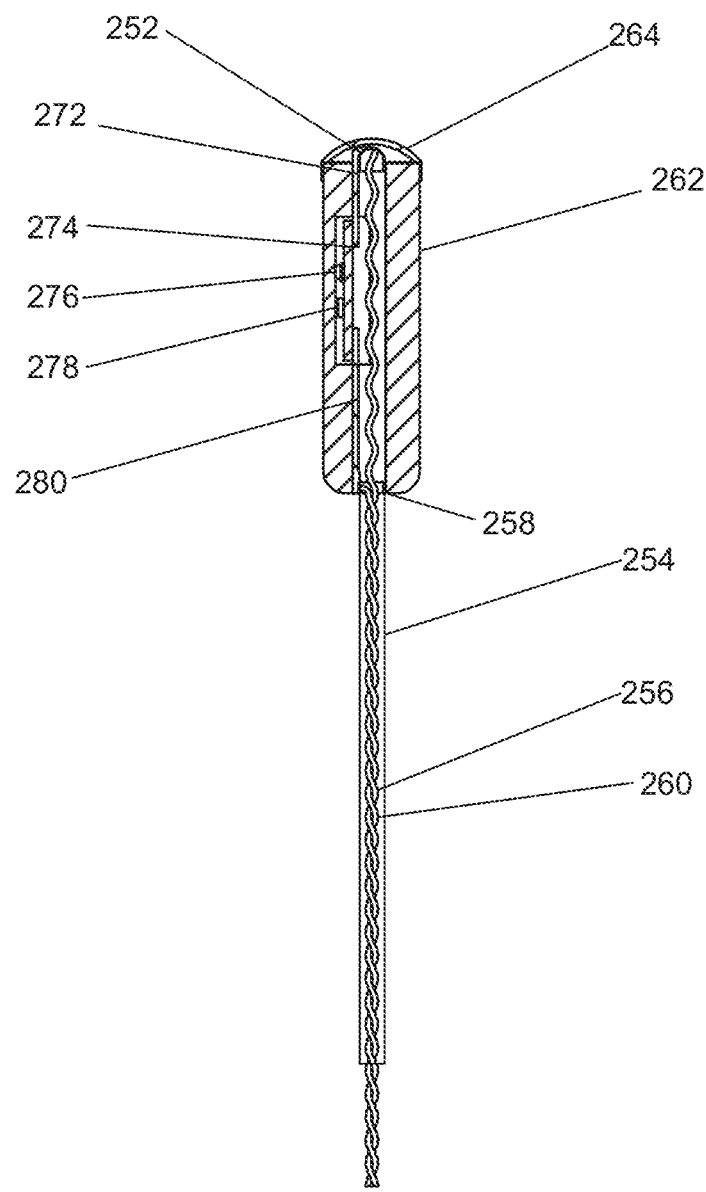
FIG. 18E illustrates one embodiment of an electrical lead comprising a cap element.

FIG. 18D illustrates the electrode cap 261 with the embedded assembly 270 of FIG. 18C. In some embodiments, the distal conductive component 272 is coupled (e.g., physically connected) to the conductive surface 264 on the cap. When the cap is fully assembled relative to the electrode lead 250, the proximal conductive component 280 of the cap can be in physical contact with a conductive element 258 on the electrode lead, as depicted, for example, in FIG. 18E.

In some arrangements, when the cap is appropriately shaped and otherwise configured, connection of the conductive tip 252 of the lead to the distal conductive component 272, along with connection of the secondary conductive element on the lead 258 to the proximal conductive component 280, can allow for current to flow from the lead tip, through the circuitry in the printer circuit board 274 and out to the secondary conductive element 258 on the lead. Such a design can be advantageous to permit users to test if the conductive tip is functional.

By way of an example, a user can connect the electrode lead 250 to a pulse generator. When a pulse is elicited from the generator, provided the conductive tip 252 is not damaged and the cap is interfaced appropriately with both the conductive tip 252 and the secondary conductive element on the lead 258, current may flow through the circuit board and activate the LED or other indicator. Thus, visual confirmation can be provided to the user that current is flowing through the conductive tip 252. In some embodiments, confirmation of current flow to conductive tip may be provided in one or more forms, including, without limitation, visually, audibly, haptically and/or in any other manner, including combinations of the foregoing. Such a configuration can be incorporated into any of the implementations disclosed herein or variations thereof.

Figure 19:
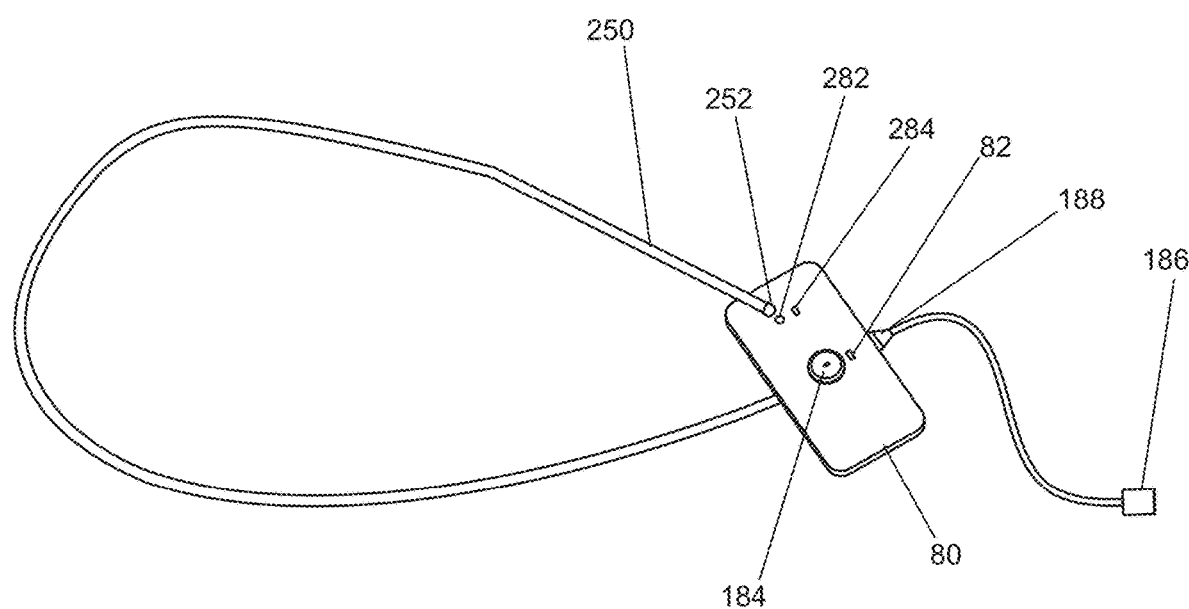
FIG. 19 illustrates one embodiment of an adhesive patch that includes an exposed conductive contact.

According to some embodiments, the adhesive patch 80 includes an exposed (e.g., at least partially) conductive contact 282 as shown in FIG. 19. Additionally, the adhesive patch 80 can include one or more LEDs (and/or other visual indicators) 284 that can be coupled (e.g., directly or indirectly) to the conductive contact through one or more resistive or other elements. By way of an example, as shown in FIG. 19, the adhesive patch 80 can comprise a percutaneous electrode lead 250 (e.g., in accordance with those described herein or equivalents thereof). In some arrangements, for a user to test if the conductive tip of the lead 252 is functional, practitioner or other user can place the tip 252 in physical contact (e.g., at least partial physical contact) with the exposed conductive contact 282 on the adhesive patch. In some embodiments, provided that the patch is outputting a stimulus pulse, a particular action by the user (e.g., depressing a switch 184), the LED or other visual or other indicator 284 can be activated (e.g., illuminated), thereby providing visual confirmation that the conductive tip is functional and is able to pass stimulus current. In some embodiments, confirmation that conductive element is functional may include visual, audible or haptic indication, or a combination thereof.

In some embodiments, the patch 80 comprises a microcontroller and a stimulus generator such that the stimulus generator outputs a low amplitude AC waveform that in some embodiments may be used as a verification signal. In some embodiments, by way of example, the amplitudes are 0.1 µA to 10 µA (e.g., 0.1-0.2, 0.2-0.3, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 0.1-1, 0.5-2, 1-5, 5-10 µA, values between the foregoing, etc.). In other embodiments, the amplitudes are less than 0.1 µA (e.g., 0.01-0.1, 0.005-0.001 µA, less than 0.005 µA, etc.) or greater than 10 µA (e.g., 10-15, 15-20, more than 20 µA, etc.), as desired or required. AC waveforms may include a square wave, sinusoidal wave, or other alternating current waveforms at frequencies greater than 1 Hz (e.g., 1-2, 2-3, 3-4, 4-5, 5-6, 6-7, 7-8, 8-9, 9-10 Hz, frequencies between the foregoing ranges, greater than 10 Hz, etc.) or frequencies smaller than 1 Hz (0.01-0.1, 0.1-0.2, 0.2-0.3, 0.3-0.4, 0.4-0.5, 0.5-1, 0.3-0.7 Hz, frequencies between the foregoing ranges, etc.).

In some embodiments, the stimulus generator is coupled (e.g., physically (e.g., directly or indirectly), operatively, etc.) to the electrode lead. In some embodiments, the microcontroller is programmed to prevent output of stimulus pulses (such as, for example, the pulses that have been described herein) until the verification signal has been applied to an exposed conductive contact 282, as shown, for example, in FIG. 19. Such a "verify to unlock" feature can be advantageous to users as it verifies (e.g., directly) the functionality and integrity of the electrode lead 250 and conductive tip 252.

Figure 20A:
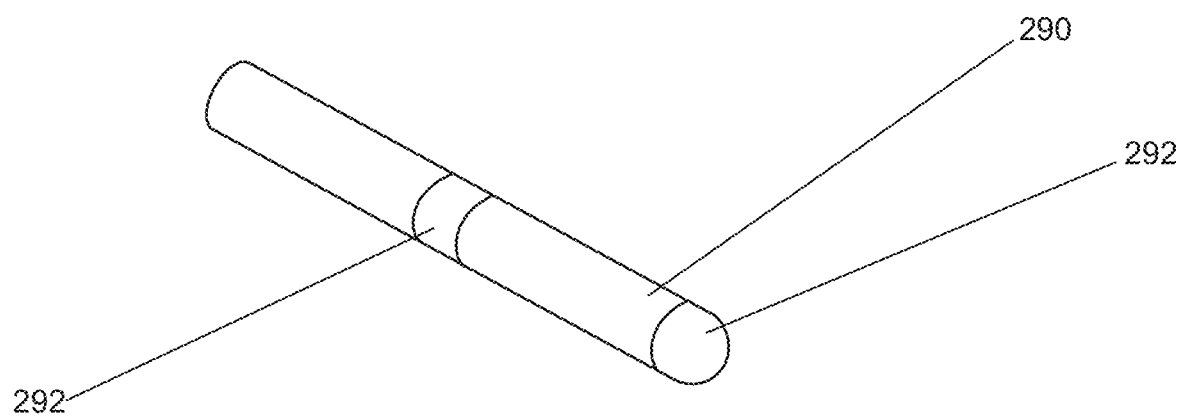
FIG. 20A illustrates one embodiment of a verification assembly that includes a conductive element.

In some embodiments, the electrode lead wire is coupled to cuff electrode apparatus 10 (e.g., such as those apparatuses described herein, variations thereof and/or any other type of cuff electrode). To verify output of the cuff electrode, a verification bar 290, such as the one illustrated in FIG. 20A, can include one or more conductive elements 292 and can be placed within a wrapped or unwrapped cuff electrode.

Figure 20B:
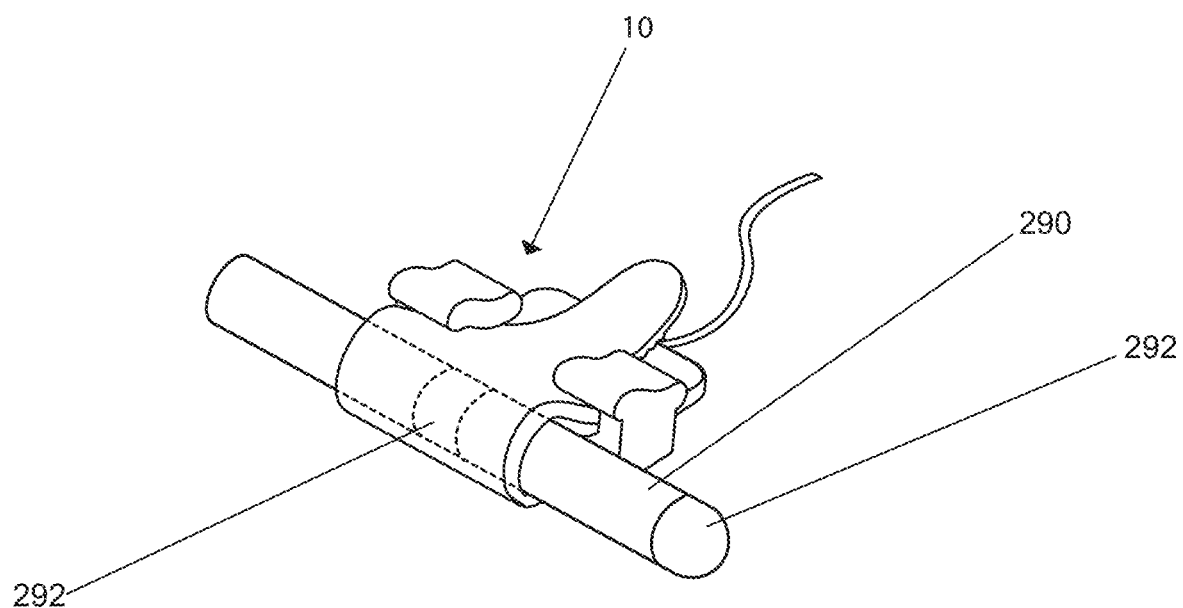
FIG. 20B illustrates one embodiment of a cuff electrode apparatus that is interfaced with the verification bar.

According to some arrangements, as illustrated in FIG. 20B, a cuff electrode apparatus 10 with a monopolar electrode configuration (e.g., such as any of the embodiments thereof described herein) is configured to interface with the verification bar 290 or similar features or portion. In some configurations, a conductive element within the verification bar is in physical contact (e.g., at least in partial physical contact) with the monopolar electrode within the cuff. Further, the conductive element can also be coupled to a conductive element that is at or near the tip of the bar and in an area that is not wrapped by the electrode. In some embodiments, a user can selectively verify stimulus output of the cuff electrode apparatus 10 by placing the exposed conductive tip on an exposed contact surface used for lead testing such as the previously described exposed contact on a patch used for lead testing 282. This process of verification is similar to those described herein when using a percutaneous lead wire with conductive tip and can be applied to any embodiments disclosed herein.

Figure 20C:
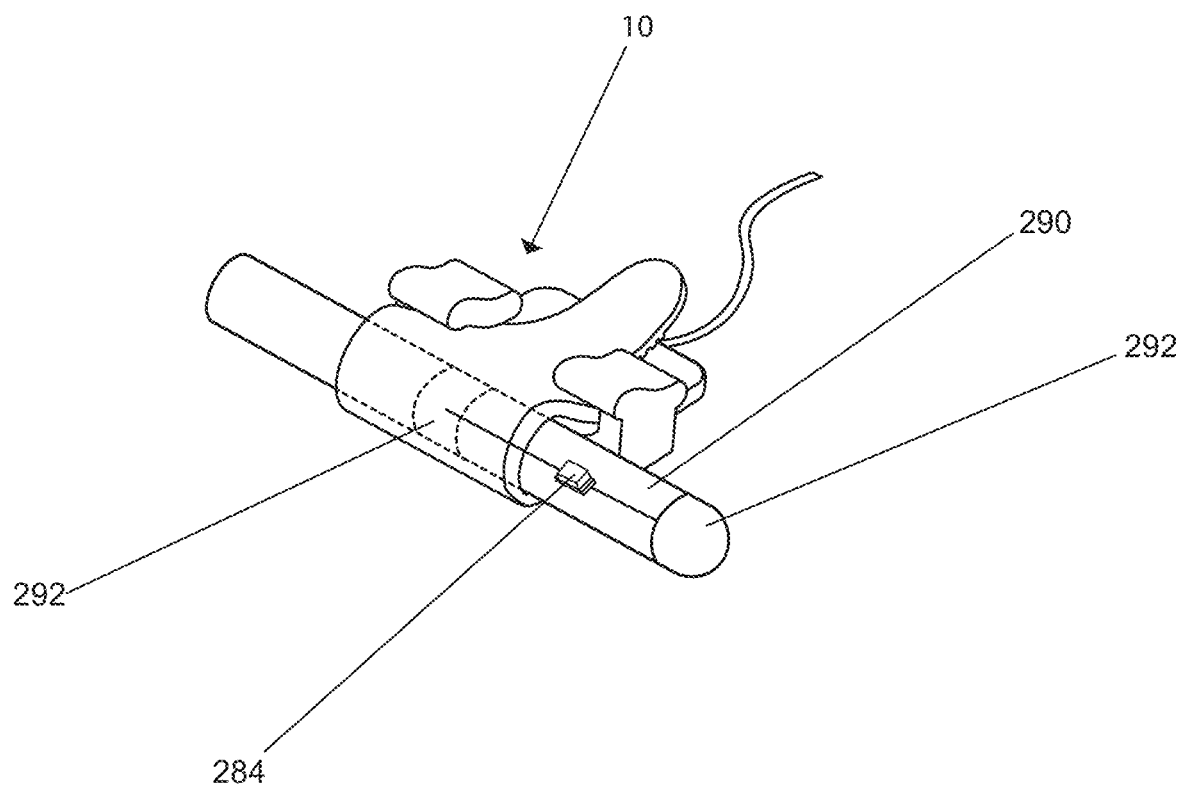
FIG. 20C illustrates one embodiment of a cuff electrode apparatus that is interfaced with the verification bar.

In certain embodiments, the verification bar 290 includes one or more LEDs and/or other visual indicators for testing verification 284. In one example, as illustrated in FIG. 20C, the verification bar 290 comprises a conductive element 292 that is in contact with an electrode of an electrode apparatus 10 (e.g., such as those described previously herein). The conductive element 292 of the verification bar 290 can be coupled to a LED or other visual indicator, which is coupled (e.g., operatively, electrically, etc.) to a second conductive element 292. A user can verify stimulus output of a cuff electrode apparatus 10 by placing the exposed conductive tip on an exposed contact surface used for lead testing (e.g., the previously described exposed contact on a patch used for lead testing 282). In some embodiments, activation of the LED or other indicator 284 within the verification bar can indicate proper current conduction from the electrode apparatus 10.

Figure 20D:
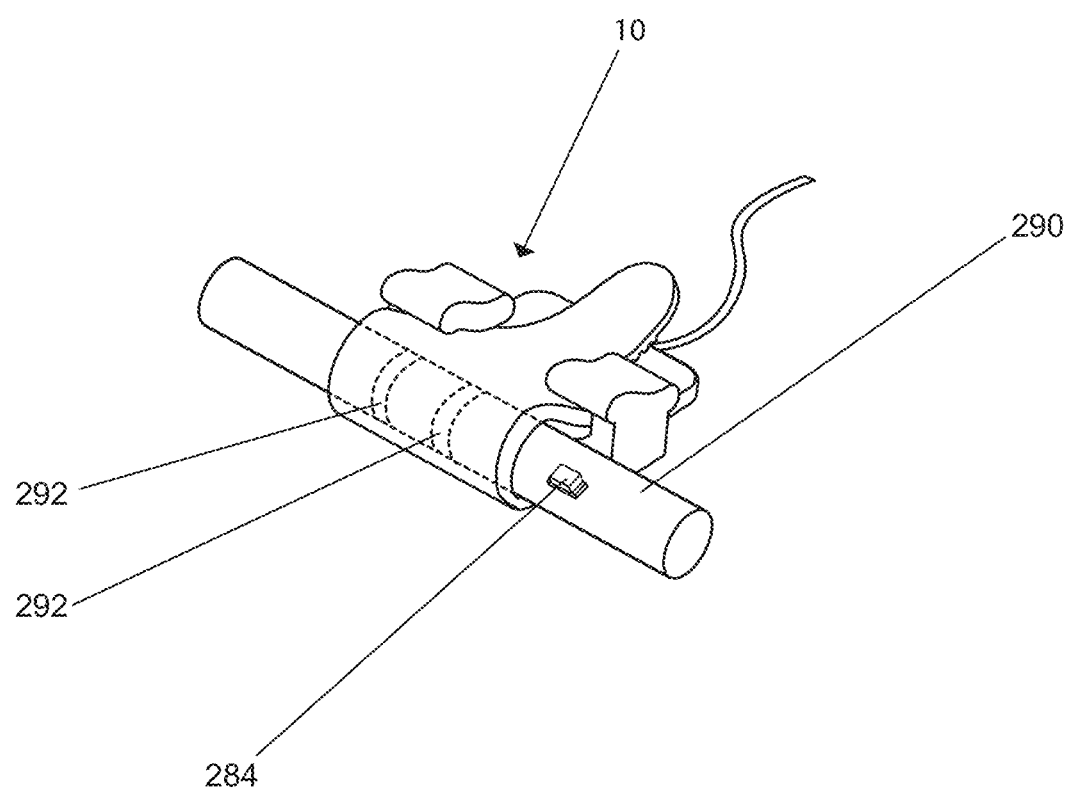
FIG. 20D illustrates one embodiment of a cuff electrode apparatus that is interfaced with the verification bar.

In some embodiments, the verification bar 290 is designed and otherwise configured to interface with a multi-contact electrode apparatus. In one example, as shown in FIG. 20D, the verification bar 290 comprises two conductive elements 292 such that each conductive element 290 of the verification bar is in physical contact (e.g., at least in partial physical contact) with a separate electrode of a cuff electrode apparatus 10. In some embodiments, the verification bar 290 that interfaces with multiple electrodes can include one or more LEDs and/or other visual or other indicators, as desired or required. With continued reference to the example depicted in FIG. 20D, verification of the stimulus output can be advantageously performed directly at the level of the electrode apparatus without use of a separate exposed contact surface for lead testing. In some embodiments, the verification bar 290 may be physically coupled to the adhesive patch 80.

Figure 21A:
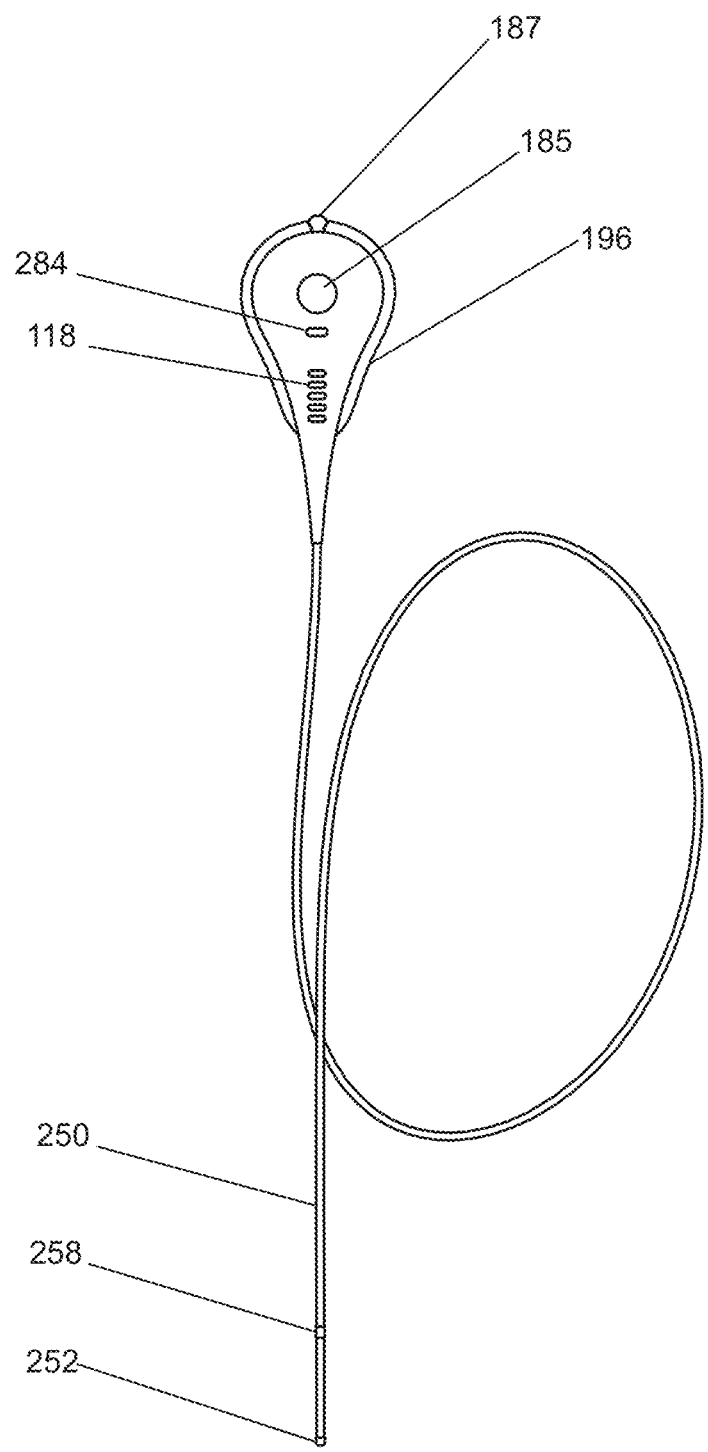
FIGS. 21A and 21B illustrate one embodiment of an electrode comprising of a percutaneous lead coupled to a housing including a stimulation source.
Figure 21B:
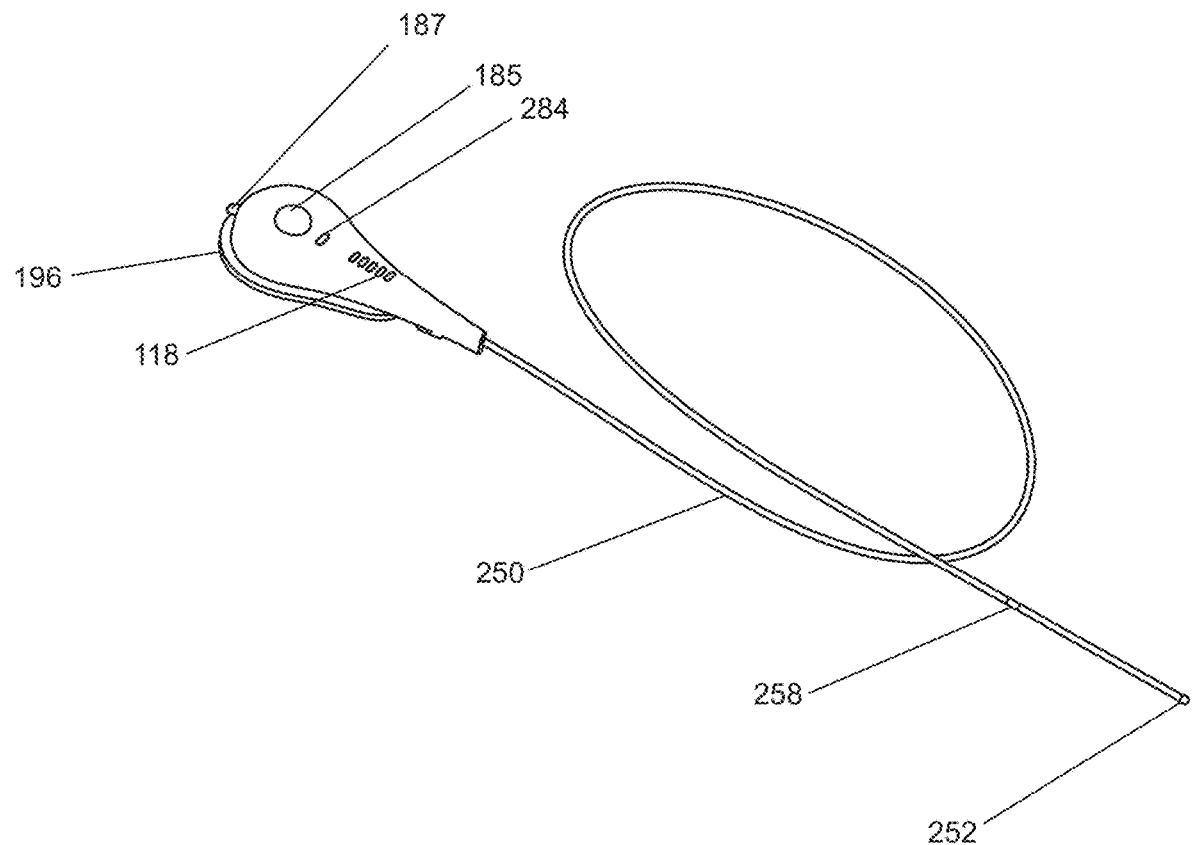

In some embodiments, the percutaneous electrode lead 250 with multiple conductive elements 258 (e.g., as described herein), is coupled (e.g., physically, electrically, operatively, etc.) to a stimulation source that can include circuitry to test the connectivity and placement of the electrode lead. In some arrangements, the stimulation source can also be configured to provide neuroregenerative therapy (e.g., via the delivery of stimulation energy). One such embodiment, which can be termed a functionalized electrode, is illustrated in FIGS. 21A and 21B. In some embodiments, such an electrode can comprise a percutaneous lead coupled to a housing that may include a stimulation source.

Figure 21C:
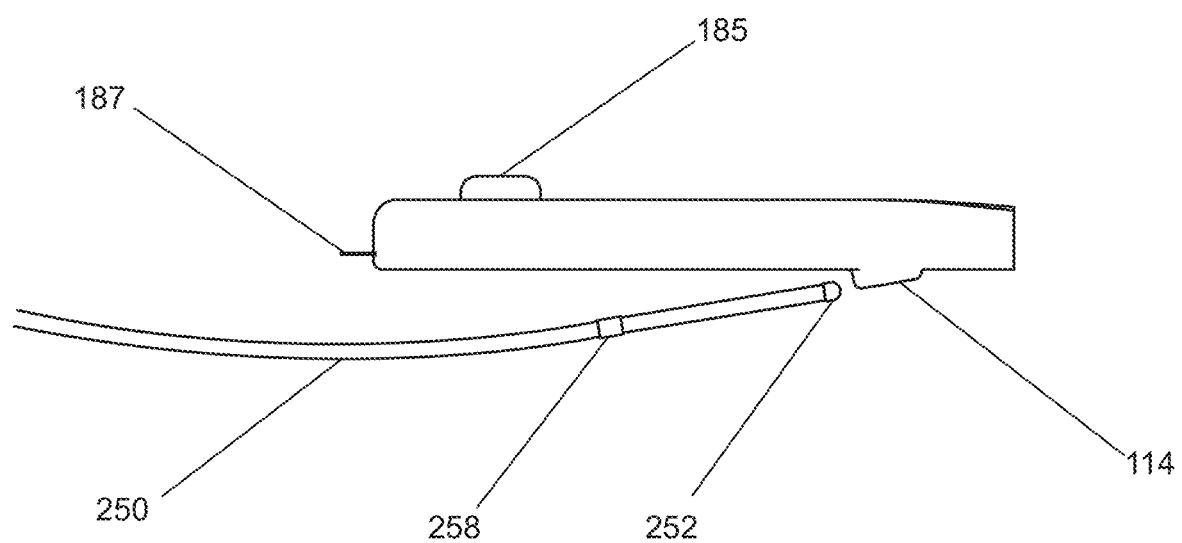
FIG. 21C illustrates one embodiment of an electrode comprising of a percutaneous lead coupled to a housing including a stimulation source.

In some embodiments, as illustrated in FIG. 21C, verification of the stimulus output can be performed by inserting one or more conductive elements of the lead into a housing 114 of an electrical stimulation apparatus that comprises of verification test elements, as described herein. In some embodiments, such a stimulation apparatus can include one or more visual elements 284 and/or can include another type of indication to the user (e.g., audible indication, haptic indication, etc.) to notify a user that the stimulus output is verified.

According to some embodiments, the housing of the electrical stimulation apparatus comprises a pull-tab 187 (e.g., as described herein with reference to other embodiments). In some arrangements, a stimulation apparatus includes one or more verification mechanisms or features to help place the system in an "unlock" mode (e.g., as also described herein). By way of example, a percutaneous electrode lead with multiple conductive elements can be packaged with one or more conductive elements inserted into the housing of a stimulation apparatus with a pull-tab or similar feature. When a user removes the pull-tab, the stimulation apparatus can notify (e.g., immediately notify, such as within less than one second) a user the status of the stimulus output using the indicator that is included in the corresponding device (e.g., visual indicator, audio indicator, haptic indicator, combination thereof, etc.). In other embodiments, notification to a user can take other forms (e.g., other types of indication, within other time frames, etc.), as desired or required. The status may be used to "unlock" or turn on stimulation circuitry or prevent the circuitry from being powered. This may be advantageous to a user in that the appropriate functionality of the pulse generator and the electrode lead integrity may be evaluated in a single step and without the need of placing the lead on or near excitable tissue and delivering stimulus pulses.

In some embodiments, the pull-tab may be replaced by a tactile switch 185 or other type of switch. In some arrangements, the stimulation apparatus includes multiple indicators (e.g., visual, audible, haptic, other indicators, etc.) that may be used to provide (e.g., display) information, including, without limitation, time, relative stimulus amplitude 118 and/or the like.

Figure 22:
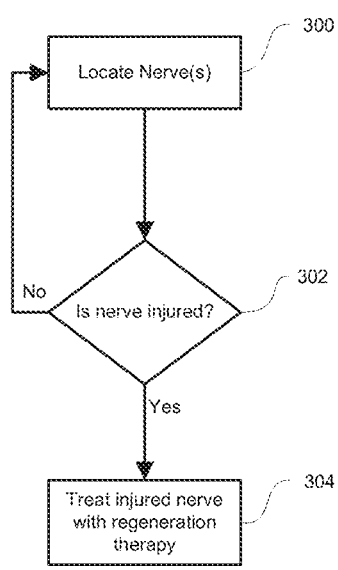
FIGS. 22 and 23 include flow diagrams illustrating two different embodiments of methods for using the systems and devices disclosed herein.
Figure 23:
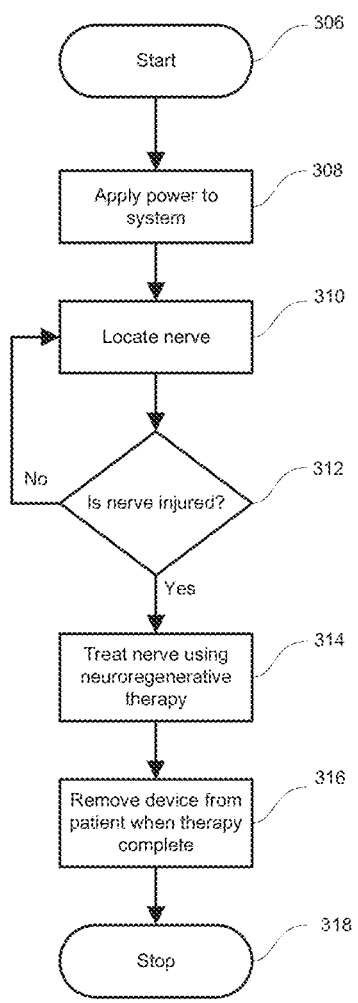

According to some arrangements, shown in FIGS. 22 and 23, the device or system is used to first locate a nerve 300, 310, and if an injured nerve is found or otherwise detected 302, 312, to provide neuroregenerative therapy to it 304, 314. In some embodiments, the device or system is used only as a nerve locator or only as a regenerative therapy system. However, in some configurations, it is advantageous for the device or system to be adapted to do both the detection and subsequent delivery of energy (e.g., for neuroregenerative therapy). Such features can be incorporated into any of the device or system embodiments disclosed herein.

In some embodiments, the device or system comprises a single control button or other control or controller (e.g., which can take the form of something other than a button) used to switch between a first phase of stimulation and a second phase of stimulation. Such a button or other control or controller can also be used to adjust stimulus output parameters and control visual indicators and/or conduct any other function, as desired or required.

Intraoperative Nerve Location and Therapy

According to some arrangements, one intended use of the system is in the operating room. Thus, the system can be designed, customized and otherwise configured with such intended use mind. The various systems disclosed herein can advantageously function and operate as a dual-purpose device serving the needs of both nerve location functionality and nerve (e.g., neuroregenerative) therapy.

In some embodiments, the housing of the system comprises a bipolar probe type electrode used for nerve location purposes with a port used to connect a cuff-type electrode that can be used to interface with an injured nerve to deliver neuroregenerative therapy to injured nerve tissue. The bipolar electrode apparatus may be similar to any of the ones described in greater detail herein. In one embodiment, the injured tissue is a peripheral nerve. However, in other arrangements, the injured tissue can include any other type of nerves, such as autonomic nerves. In other embodiments, a bipolar electrode may be one of various types that are common to those skilled in the art. In such configurations and uses, the surgeon or other practitioner can physically connect an electrode with lead wire and connector to a jack or other coupling location located on the housing unit. A flow diagram of one embodiment of usage of a dual-purpose device is schematically illustrated in FIG. 24 and described in greater detail below.

Figure 24:
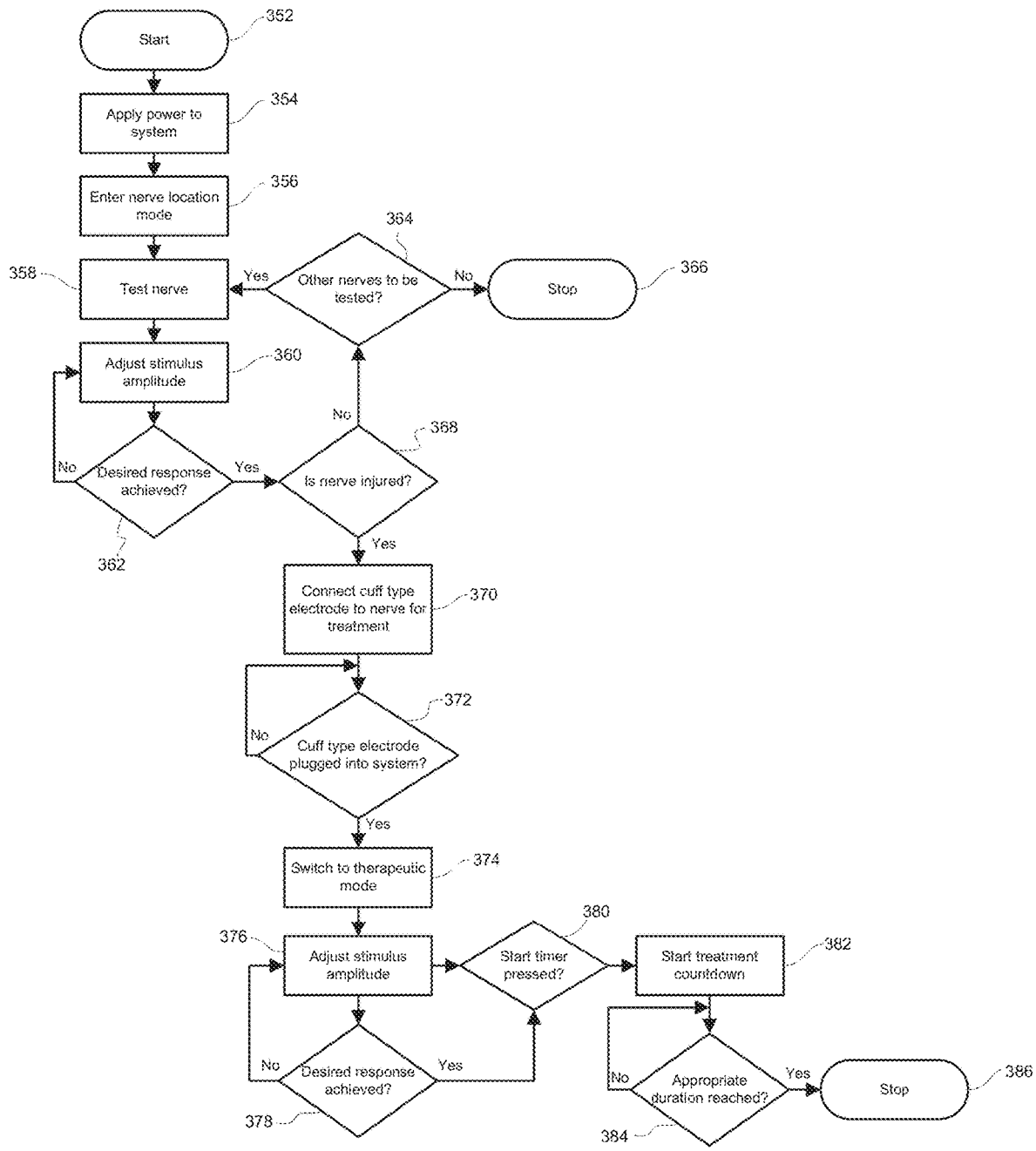
FIG. 24 is a flow diagram illustrating the process of locating and treating an injured nerve in an intraoperative setting using the described system according to one embodiment.

In one embodiment, as illustrated in the example of FIG. 24, when the system is first powered on 354, it is configured to enter a "test" mode. In one example, the test mode is adapted to assist in locating nerves 356. The test mode can comprise pulse trains, with each stimulus pulse comprising a doublet pulse (e.g., separated by a particular inter-pulse interval). For example, in some embodiments, the inter-pulse interval can be 5 ms, as described herein and shown in, for example, FIG. 6A. However, in other arrangements, the inter-pulse interval can be less than or greater than 5 ms, as desired or required (e.g., 0-5 ms, 5-10 ms, greater than 10 ms, etc.). The pulse trains can be applied to a targeted nerve to test the integrity and function of the connected muscle 358. The doublet pulses can be configured to increase (e.g., maximize) or otherwise enhance the torque time interval and reduce stimulus amplitude requirements.

In some embodiments, the pulses are output at a frequency of 10 Hz or lower to provide a tetanic like contraction. The frequency range may include 0.1-40 Hz (e.g., 0.1-0.2, 0.2-0.3, 0.3-0.4, 0.4-0.5, 0.5-1, 1-2, 2-3, 3-4, 4-5, 5-10, 10-15, 15-20, 20-30, 30-40 Hz, frequencies within the foregoing ranges, etc.).

In some embodiments, the amplitude of the stimulus can be configured to be adjusted 360 until a desired response is reached 362. If the user is satisfied with the testing of a targeted nerve, he/she can selectively choose to test other nerves 364, and the process of adjusting amplitudes can be repeated. In some embodiments, once the desired response for a nerve that was to be tested is reached, the user can be done using the system 366.

In some embodiments, with continued reference to FIG. 24, when a user is satisfied with locating nerves and/or when a determination is made that a nerve is injured 368 (e.g., the nerve is injured given a particular threshold level or response), the practitioner can connect an electrode (e.g., a cuff-type electrode, any other type of electrode, etc.) to a nerve port located on the housing 370. Any other type of electrode can be used, as desired or required. The system can be configured to detect the electrode 372 and appropriately direct the stimulus output from the probe to the electrode. When this occurs, the system mode can be switched to neuroregenerative treatment mode 374. The stimulus amplitude can be changed 376 until a desired response is reached 378. The user can then initiate treatment 380 of an injured nerve using neuroregenerative therapy. In some embodiments, the system comprises a timer that limits the duration of neuroregenerative therapy 382 and checks to ensure that the total time was not exceeded 384. In such embodiments, once the prescribed or required time requirement has been reached, the system can be configured to shut off 386 (e.g., automatically, according to a predetermined protocol or algorithm). Further, the system can be configured to provide the practitioner with an appropriate indication or cue (e.g., a visual cue, audio cue and/or any other indication).

In some embodiments, intraoperative use of the system can comprise hands-free usage (full or partial hands-free usage). For example, the system can operate in a mode so that it may be placed within the operative field and require minimal or reduced attention from operative staff during the period of stimulation. As previously discussed, the shape of the housing can be used to prevent the system from rolling off the operative table or sterile towels that are placed on a patient. Additionally, as also discussed herein, the inclusion of a specially-shaped (e.g., hook-shaped) extension element or other feature can assist the user to couple the system to an IV pole or other structure in relative proximity to the subject being treated. Advantageously, these features can permit and facilitate hands-free use with minimal or reduced intervention from operative staff. In some arrangements, the system is single use, and hence, once turned on or otherwise activated, the system can no longer be turned off. For example, in some arrangements, when the pull-tab is removed, engaging power the source, the device has a finite functional period dictated by the battery life. In some embodiments, the pull-tab may be replaced by an on/off switch or similar feature or component, thereby making the device reusable.

Peri-Operative Use

As noted herein and described in greater detail below, any system embodiments disclosed herein can be also be used in a peri-operative setting or application. For example, in some embodiments, a system in accordance with the various arrangements described herein can be configured to connect to a mono-polar electrode (e.g., serving as the active stimulating electrode or cathode). Such a monopolar electrode can comprise various forms including and without limitation, a needle electrode, a catheter or cylindrical type electrode and/or the like that may be placed close to an injured nerve percutaneously or be placed close to the nerve when the injured nerve is exposed. As disclosed herein, any other type of electrode can be incorporated into a device or system design or the execution of a treatment method.

In some embodiments, a monopolar lead is substituted as the nerve probe and a return electrode is connected to the nerve port. In some embodiments, a multi-conductor electrode lead is connected to the nerve port. One of the conductors of the system can connect to a monopolar lead placed within the patient while a second conductor may be connected to a return electrode such as a surface pad or needle. In some embodiments, the nerve probe is not present requiring only connection to the nerve port in order to output electrical stimulation pulses, as shown, for example, in FIG. 21A. Some embodiments of the system can be advantageous in certain indications and for certain uses, such as, for example, carpal tunnel release surgery.

In both use cases outlined above (e.g., both in the intraoperative and peri-operative contexts), the system is not necessarily limited to be used in the manner described for those use cases. For example, the peri-operative use case may also be applied intraoperatively if the end-user decides it more appropriate to stimulate using a monopolar electrode lead or similar lead.

Figure 25:
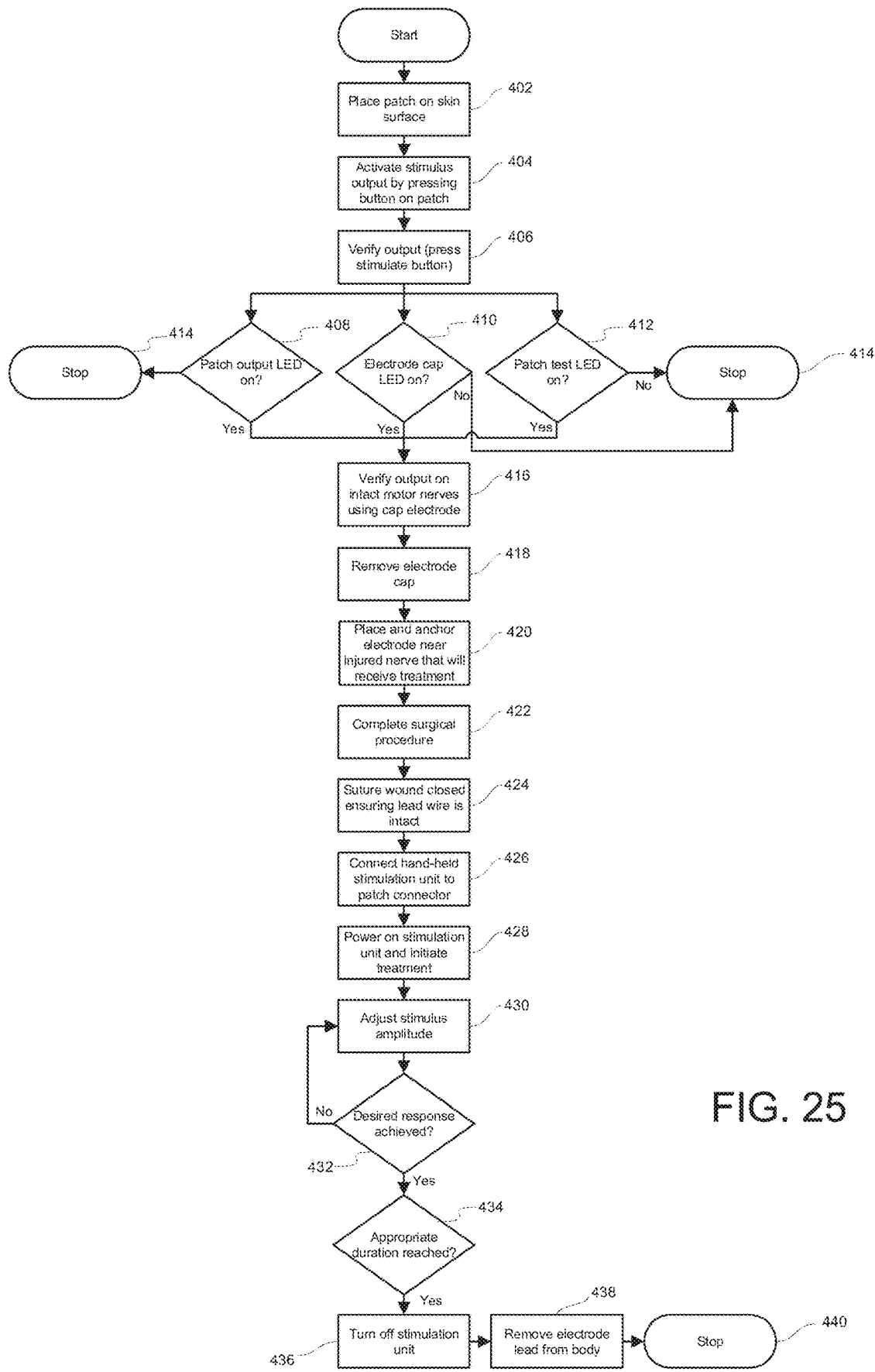
FIG. 25 is a flow diagram illustrating the process of locating and treating an injured nerve in an intraoperative setting using the systems and devices disclosed herein according to another embodiment.

FIG. 25 outlines a flow diagram of one embodiment of usage of a peri-operative system (e.g., such as a patch described herein). In one embodiment, a user places an adhesive patch 80 on the skin of a patient 402. The location of the patch is not specific, and in some embodiments, it is satisfactory as long as it is in at least partial physical contact with the skin of the patient or subject. In one embodiment, the built-in stimulus generator within the patch is activated by pressing a switch or other controller 404. The switch or other controller can be identical or similar to those described herein.

According to some embodiments, the output of the pulse generator comprises single pulses, pulse trains, doublet pulse trains or any other type of pulses. The pulses can be constant voltage or constant current pulses with amplitudes sufficient to depolarize a nerve or muscle provided the appropriate electrode contact and/or other operational parameters are used. In one arrangement, once the stimulus generator is activated, the user may want to verify the stimulus output 406. In some embodiments, such verification is accomplished in one or more steps, in accordance with one or more of the configurations described herein.

In some arrangements, the user may observe the stimulus output LED 82 on the patch itself 408 (and/or be alerted of stimulus output using another type of visual, audible, haptic and/or other indicator or output). If an electrode cap, similar to the embodiments described herein, is assembled with the electrode lead, the user can observe a LED (or other indicator) within the cap turn on when the stimulus is output 410.

According to some arrangements, where no cap is present, the user can touch the electrode lead to a conductive surface used for testing output on the patch itself 412, when connected a LED on the patch will turn on. In some arrangements, where no cap is present, and a cuff electrode apparatus 10 is used, the user may verify the stimulus output by touching the exposed contact on the verification bar within the cuff (if present) to a conductive surface used for testing output on the patch itself. In some arrangements, the cuff apparatus 10 may comprise multiple electrodes in a bipolar or multi-polar configuration. Verification of the stimulus output in this arrangement can include observing if the LED or other indicator of the verification bar is activated (e.g., turns on).

In some embodiments, if any or all of the described verification steps above are negative, the user can stop 414 the procedure and remove the patch as the stimulus generator or electrode lead may be defective. If, however, one or more of the tests are positive, the user can continue with the procedure. In one embodiment, for instance, during a surgical procedure with an open incision, the user can additionally verify the output by either using the larger conductive surface of a cap 416 or the conductive lead tip on to touch exposed intact and uninjured nerves or nearby muscles.

In some configurations, if the user is satisfied with the output and the cap is connected, the user can remove the cap 418 and place the lead adjacent (e.g., next to) an injured nerve that is to be treated with neuroregenerative therapy 420. In some embodiments, the user can complete the surgical procedure 422 and suture the wound closed while maintaining the exposed percutaneous lead 424 is exiting the wound appropriately.

According to some arrangements, a patient may then be removed from the operating room and a user, such as a nurse, can connect a second stimulation unit to the patch connector 426. The second stimulation unit can be turned on and initiates neuroregenerative therapy of the injured nerve 428. The user may adjust stimulus amplitudes throughout the course of the therapeutic time 430. If a desired response is achieved 432, and this may be based on patient feedback, muscle contractile response or other metrics, the user can, in some embodiments, leave the stimulation unit to complete the therapy. When the therapy has been completed 434, the stimulation unit is turned off 436, and the electrode lead is removed from the body 438 and the procedure can be completed 440.

In some embodiments, a first stimulation unit can provide both verification stimulus pulses used to test nerves, muscles, and/or verify functionality of the electrode and/or system and also contain necessary hardware to provide neuroregenerative therapy without requirement of a second stimulation unit.

Figure 26:
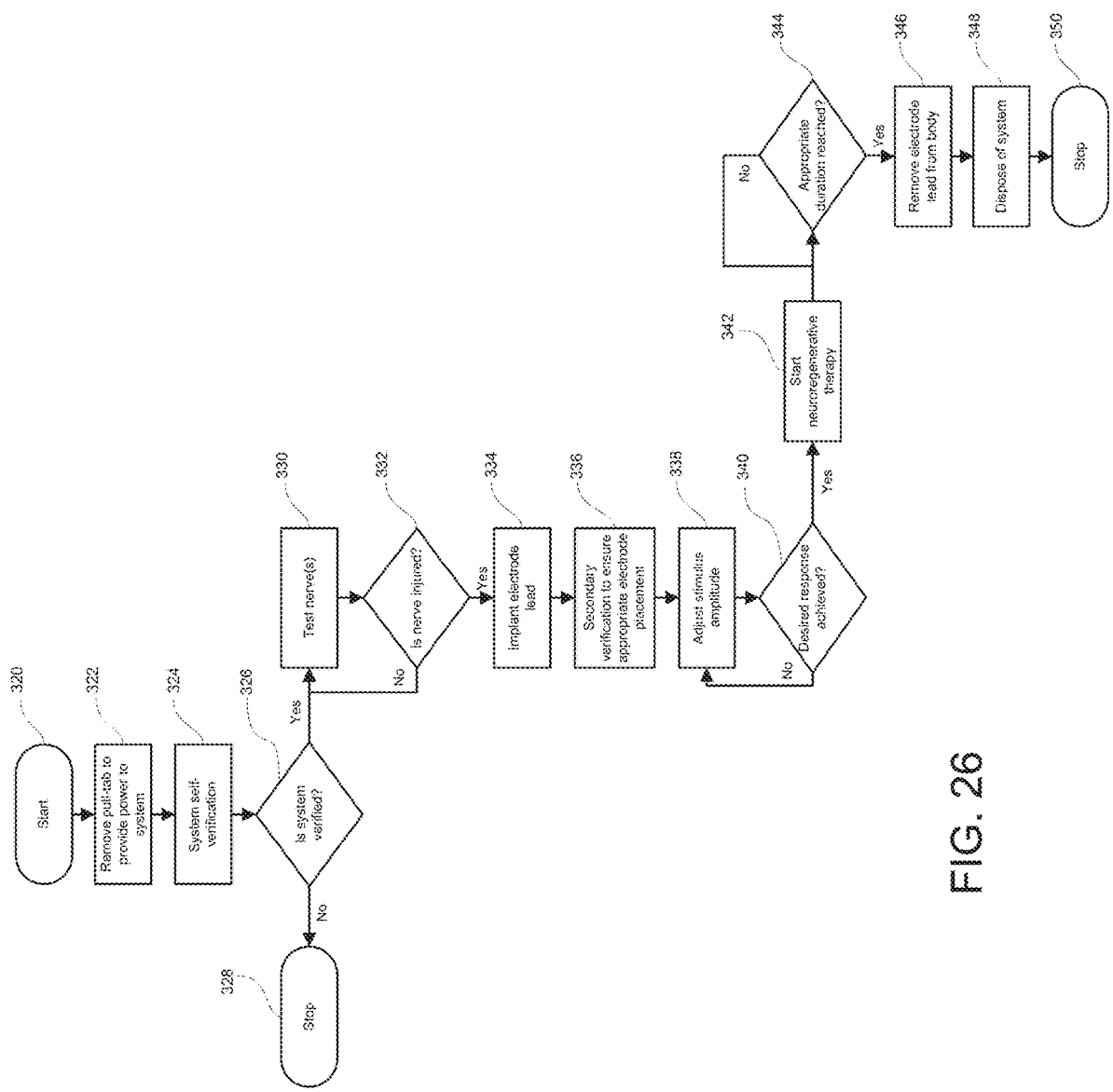
FIG. 26 is a flow diagram illustrating the process of locating and treating an injured nerve using the systems and devices disclosed herein according to another embodiment.

A flow chart of the functionality of such a system is provided in FIG. 26. As illustrated in the example embodiment of FIG. 26, when power is applied to the system, e.g., via removal of a pull-tab 322, the system can be configured to operate in a self-verification state 324. Self-verification can include touching an electrode to an exposed contact on the system housing or placing the lead within the system housing, as described herein. In some embodiments, self-verification comprises placing the electrode on an exposed or recessed contact with a stimulation source providing a characteristic frequency pattern used to "unlock" the system. In some arrangements, when the system has completed self-verification 326, it can be used to locate (e.g., "test") nerves 330. In some arrangements, an accessory or component of the device or system, e.g., such as a cap or hand-held attachment, may be clipped or otherwise attached (e.g., directly or indirectly) to the electrode lead to facilitate grasping and usage as a hand-held nerve locator.

With continued reference to FIG. 26, an injured nerve is located 332, either using the system itself or is determined apriori by a user (e.g., practitioner, medical professional, through some other mechanism or protocol, etc.), the electrode lead may be temporarily implanted 334 using an insertion tool (e.g., in accordance with embodiments disclosed herein). The method of implantation can rely, at least in part, on using tissue (e.g., preferably non-dissect or non-undermined tissue) in the para-incision area to support the anchoring of the lead and reduce or minimize lead movement in the lateral direction (e.g., perpendicular to the longitudinal axis of the lead). Once implanted, the stimulation amplitude and/or stimulation energy delivered can be adjusted, and a secondary verification 336 can take place to ensure adequate electrode placement. This verification step may comprise of measuring current flow between anode and cathode electrodes, measuring action potentials in a nerve, measuring motor or sensory responses and/or any other verification step or method, as desired or required. The stimulus parameters used for this secondary verification step may comprise a repetitive burst sequence with at least two pulses. In some embodiments, the repetitive burst sequence comprises at least three pulses (e.g., 3, 4, 5, more than 5, etc.). When a desired response to the verification has occurred 340, neuroregenerative therapy may commence on the injured nerve 342. The system can be configured to provide neuroregenerative treatment to injured nerves for the appropriate amount of time, as disclosed herein. When such time has elapsed 344, the electrode may be removed from the body 346, and both the electrode and stimulation source may be disposed of 348.

Figure 27C:
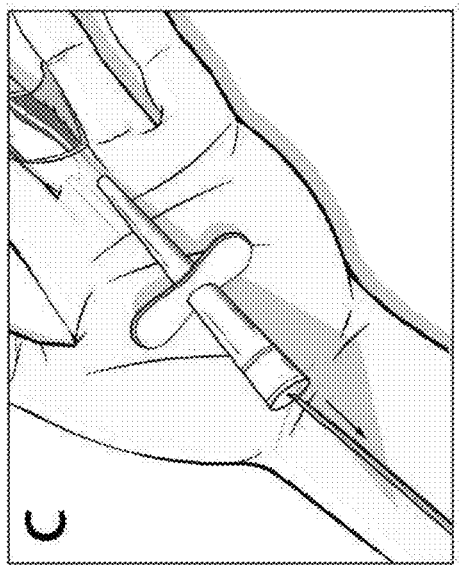
FIGS. 27A to 27E illustrates one embodiment of a procedural diagram depicting a process of inserting an electrode percutaneously using an insertion tool and connection a stimulator to deliver neuroregenerative therapy.
Figure 27B:
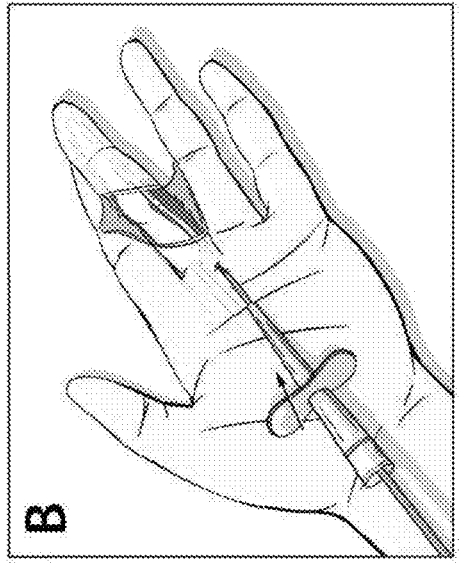
Figure 27E:
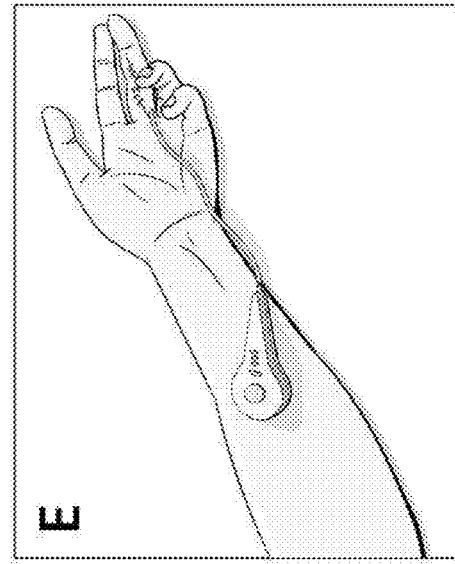
Figure 27A:
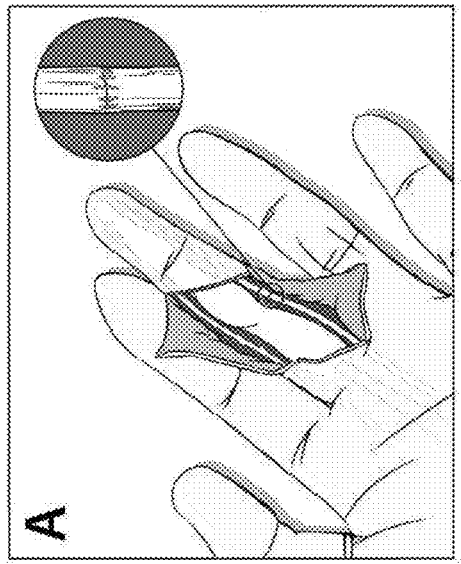

In some embodiments, the insertion tool may comprise an over-the-needle catheter assembly. Such assemblies may be utilized to deploy an electrode in a series of steps as outlined and shown, by way of example, in FIG. 27. According to some embodiments, in order to minimize or otherwise reduce the impact of a surgeon's workflow, an insertion tool is used to place an electrode in the para-incisional area as previously mentioned (FIGS. 27A-27C). In some arrangements, this is advantageous for one or more reasons. For example, such a configuration can prevent a lead wire from protruding (e.g., partially or completely) through an existing incision site. Such protrusions are generally more time-consuming to suture around, and in cases of removal, may damage underlying structures such as a repaired peripheral nerve and the like.

Figure 27D:
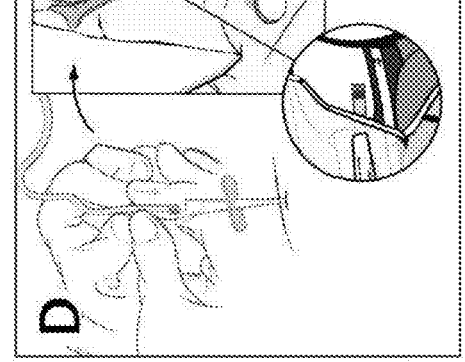

According to some embodiments, once a viable para-incisional pathway has been created using an insertion tool, an electrode lead may be advanced (e.g., fed through using such a pathway) towards an injured nerve (see, e.g., FIG. 27D). In some embodiments, a trocar (e.g., a trocar, another type of hollow tube with or without a sharp end, etc.) may be used to create an access point. Such a trocar is typically used by creating an access point starting from the inside of the body and pushing through tissue towards the skin. In some embodiments, once the trocar has exited the skin, an electrode may be fed through the trocar to the target site. In other embodiments, a robotic surgery unit may be used to percutaneously place an insertion tool or a trocar. In some arrangements, for therapeutic efficacy, it is important to maintain an electric field that is proximal to the nerve injury/repair site.

Electrical stimulation across a nerve gap can be used to slowly increase neurite growth across the gap. These signals can be low level (e.g., sub-threshold) DC currents. In contrast, in some arrangements, AC stimulation that results in an electrical field sufficient to create action potentials on the proximal aspect of an injured nerve that conduct towards the neuron cell body upregulate regeneration associated genes leading to accelerated axonal regeneration.

According to current protocols and treatment techniques, several methodologies can be used to deliver AC stimulation to accelerate nerve regeneration. Such methods include placing two (e.g., separate) wires (e.g., fine-gauge stainless steel wires) on the proximal aspect of the injured and repaired peripheral nerve. Typically, the anode is placed on the most distal aspect of the injured proximal nerve stump, while the cathode is placed further proximally. Such an arrangement of anode/cathode can be used to avoid or reduce the likelihood of potential to induce an anodal block. However, in such embodiments, wires are placed within the surgical incision, requiring a surgeon to carefully suture around these wires when closing the main procedural incision.

In another clinical study, a monopolar cuff electrode is used to deliver AC stimulation to accelerate nerve regeneration. However, in such configurations, the usage of a cuff electrode mandates that the stimulation procedure takes place intraoperatively as percutaneous removal of a cuff electrode is not possible without incurring nerve injury.

In a third clinical example, AC stimulation used to accelerate nerve regeneration employs the usage of a monopolar fine needle electrode. While needle electrodes may be placed in the para-incisional area, the sharp tip used to create a pathway through tissue may also inadvertently puncture the injured nerve that is to be stimulated. Additionally, the rigid nature of needle electrodes allows them to easily be dislodged or moved. In some situations, this creates challenges for the clinician employing AC stimulation for accelerated nerve regeneration in that movement of the active electrode may reduce or eliminate therapeutic effect (e.g., any or a required amount of therapeutic effect) due to a more distant electric field that may not be sufficient to depolarize injured axons.

The methods and systems described in this disclosure help avoid or at least reduce the likelihood of the negative issues described in the current clinical utilization of AC stimulation for accelerating nerve regeneration.

With continued reference to FIG. 27D, a verification or validation step may take place in association with (e.g., during) the placement of the electrode lead. In some embodiments, such a verification or validation step comprises measuring current flow between anode and cathode electrodes, measuring action potentials in a nerve, measuring motor or sensory responses and/or any other verification step or method, as desired or required. In some configurations, once the electrode is positioned and one or more validation steps are completed, a second phase of stimulation may be administered that can include therapeutic stimulation to enhance or otherwise improve nerve regeneration and tissue reinnervation.

Although, in some embodiments, the validation and therapeutic procedure comprises two steps, such steps do not need to be completed as two separate events. In some arrangements, validation and therapy takes place in two separate events. For example, a validation step (e.g., a first stimulation phase) can occur during the event of locating a nerve or measuring a patient response (e.g., sensory, motor, verbal, etc.), while a therapeutic step (e.g., a second stimulation phase to provide neuroregenerative therapy) follows. In some embodiments, these two separate events occur one after another (e.g., in series). In other words, the event of locating a nerve and the event of providing therapy are separate events, but such separate steps still employ a two-phase stimulation approach.

With continued reference to the embodiments where validation and therapeutic stimulation occur as separate steps in series (e.g., one after another), the subsequent therapeutic step can be configured to occur immediately after the validation step ends. In other configurations, a delay exists between the termination of the validation step and the subsequent therapeutic step. In such embodiments, the time delay between the two steps is 0 to 5 seconds (e.g., 0-0.05, 0-0.1, 0.1-0.5, 0-1, 1-2, 2-3, 3-4, 4-5, 0-2 seconds, time ranges between the foregoing values, etc.).

However, in other embodiments, the same devices and systems described herein are adapted to complete the two-step validation and therapeutic procedure in one physical event (e.g., not as separate events). By way of specific example, the stimulation system can be implanted and activated (e.g., turned on) to deliver neuroregenerative therapy. In some embodiments, if a therapeutic stimulus pulse is delivered every 50 ms, for example, sufficient time between consecutive pulses can be provided to deliver validation stimuli as further described below. The responses to the validation stimuli can be used as a decision point to proceed or continue with delivering neuroregenerative therapy. In some embodiments, such a single event (e.g., implant stimulator and activation) still employs two phases of stimulation albeit occurring during one single event.

In some embodiments, the therapeutic pulse itself may satisfy a validation condition if it is of sufficient energy to evoke a biological response (e.g. an action potential).

Figure 28A:
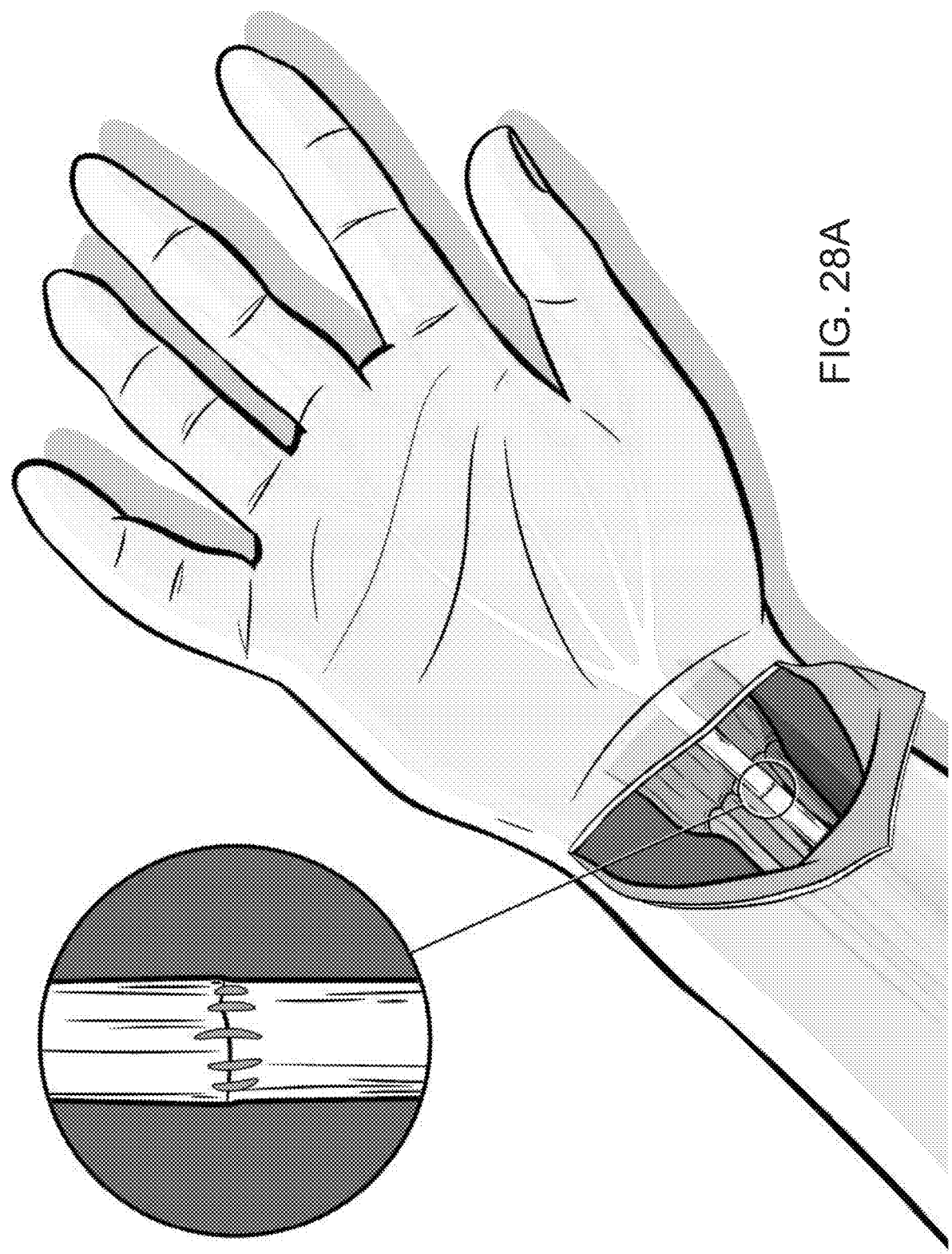
FIGS. 28A to 28D illustrate embodiments of placing an electrode percutaneously in different anatomical locations to deliver neuroregenerative therapy.
Figure 28B:
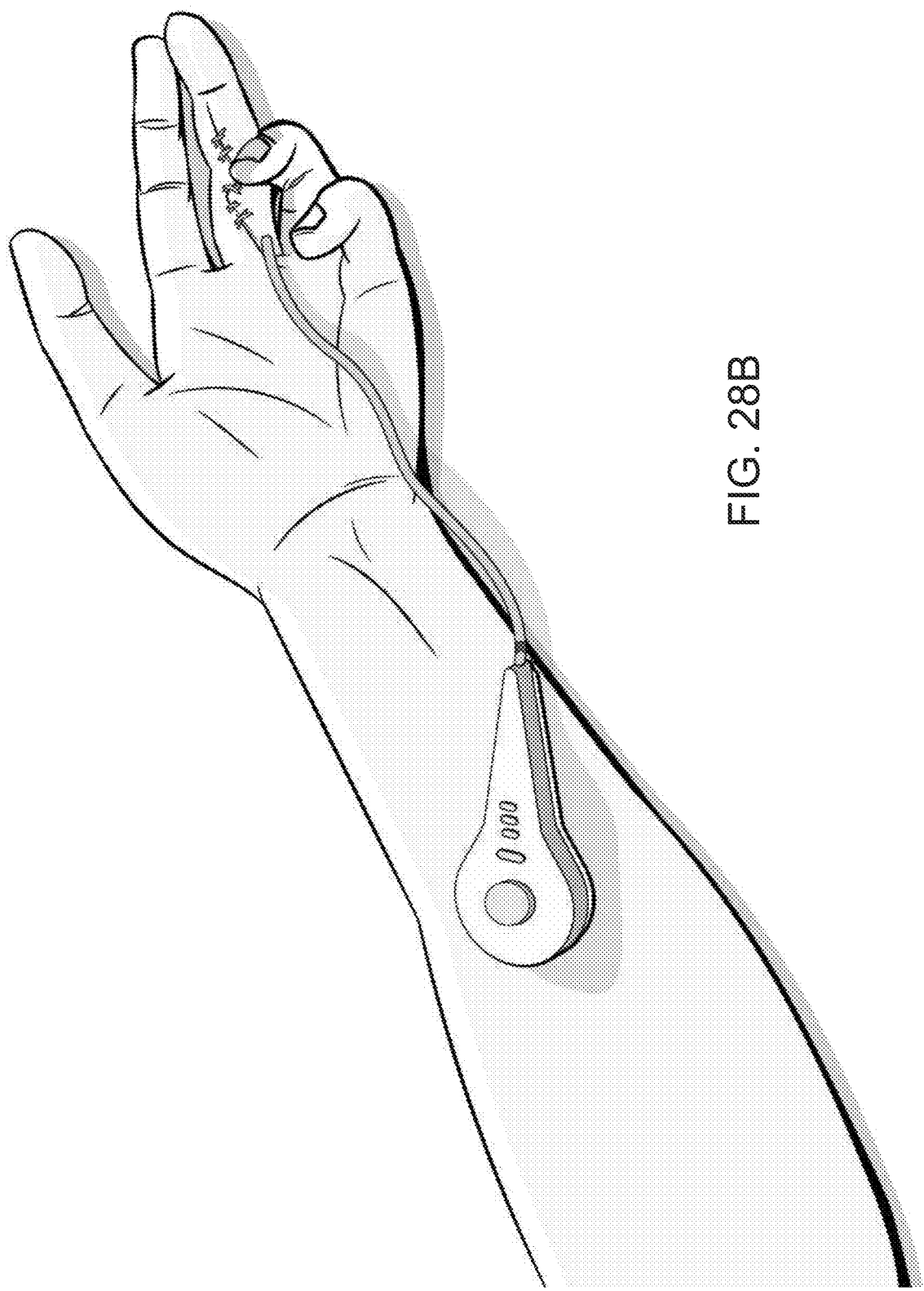
Figure 28C:
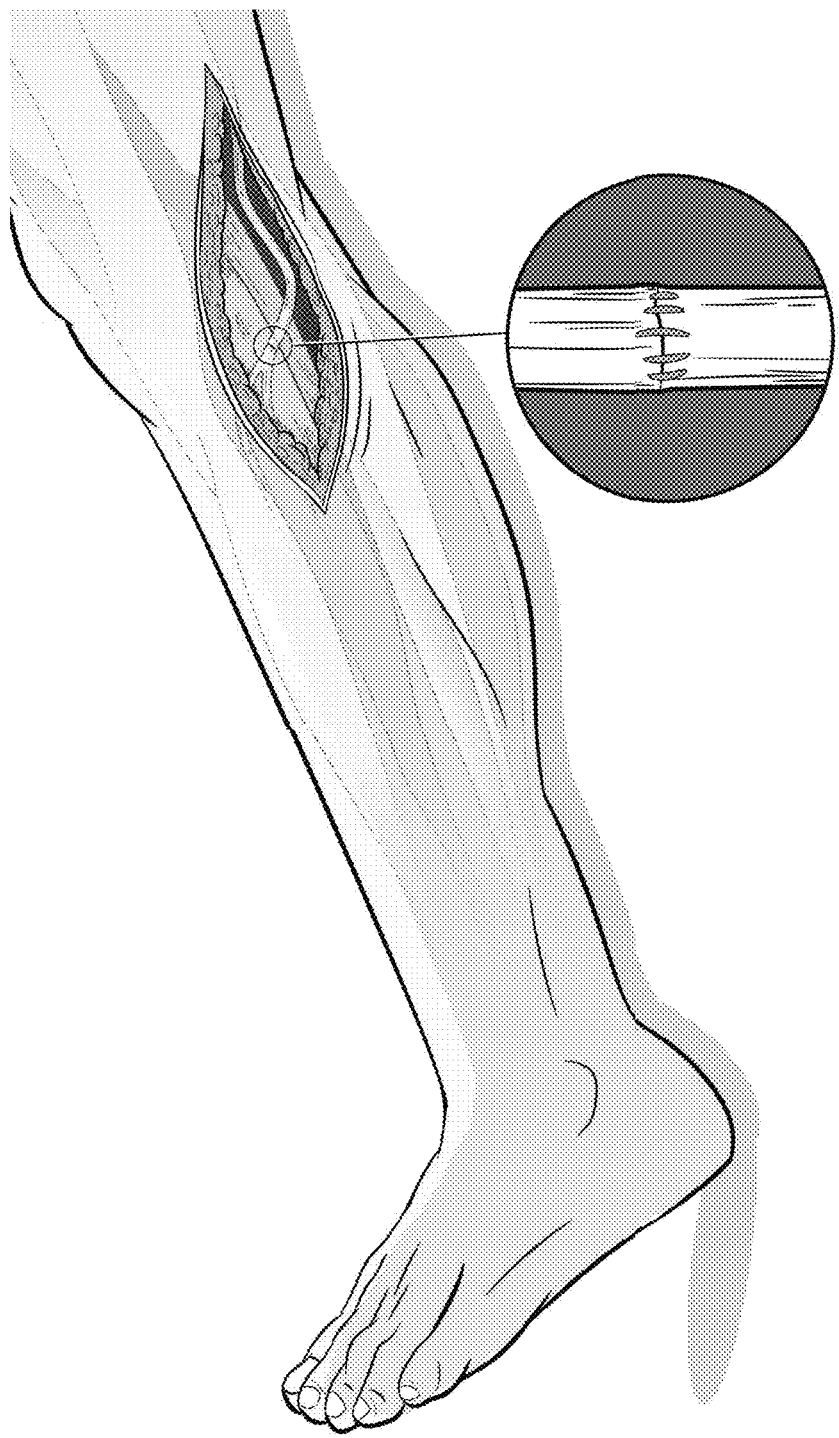
Figure 28D:

FIGS. 27A to 27D provide only one example of utilization of the described technology; however, the technologies described herein can be applied to any injured nerve in the body. For example, as shown in FIGS. 28A and 28B, the devices, systems and methods can be applied in situations where a median nerve was at least partially lacerated (and/or otherwise damaged) and repaired, and a stimulation electrode placed percutaneously connected to a system is used to deliver neuroregenerative therapy. Another example is depicted in FIGS. 28C and 28D, where a peroneal nerve was at least partially lacerated (and/or otherwise damaged) and repaired, and a stimulation electrode placed percutaneously connected to a system is used to deliver neuroregenerative therapy. According to some embodiments, the configurations described above and in other places of the present application are advantageously designed to be anatomy agnostic, that is, amenable to treat any injured nerve anywhere in the body. By way of example, nerves that can targeted for treatment using the devices, systems and methods described herein include, but are not limited to, nerves in the peripheral nervous system (e.g., median, ulnar, radial, peroneal, tibial, sciatic, etc.), the autonomic nervous system (e.g., splanchic, phrenic, vagus, mesenteric, etc.), nerves arising or originating in the brain (e.g., cranial nerves such as facial, trigeminal, spinal accessory, etc.).

In some embodiments, an insertion tool comprises one or more electrically active components that are used to confirm a validation condition. For example, a needle in an over-the-needle catheter assembly may be physically connected to a stimulus source and be used to confirm a validation condition. In other embodiments, the catheter may include one or more (e.g. 2, 3, 4, 5, etc.) conductive elements that are physically connected to a stimulus source used to confirm a validation condition.

In some embodiments, the conductive elements on the catheter may be used to detect a biological signal, such as, for example, an action potential in an injured nerve. Such action potentials may be in the form of individual action potentials (spikes), compound motor action potentials, compound sensory action potentials, or a mix of these.

In some embodiments, the percutaneous electrode lead 250 with multiple conductive elements 258 (e.g., as described herein) may be advantageously used to measure action potentials (FIGS. 29A to 29D). In one example, a multi-element electrode lead is placed near an injured nerve. In some arrangements, the electrode can be positioned parallel or generally parallel to the longitudinal axis of the nerve. Proximal conductive elements 30 can be configured to measure an evoked response in the injured nerve in response to stimulus derived from distal conductive elements. In some arrangements, such an "upstream" measurement is used (either alone or together with some other measurement or metric) to confirm a validation condition. In some arrangements, the recording electrode configuration comprises a monopolar, bipolar, tripolar, or other configuration, as desired or required by a particular design or application. In some embodiments, the distal conductive tip 252 is configured to create a monopolar electric field in conjunction with a distal reference electrode. In some arrangements, the distal reference electrode is a surface patch electrode 80 (or some other type of surface electrode) with integrated electronics. In yet another embodiment, the distal conductive tip 252 with other conductive elements 258 is configured to create a bipolar electric field. In some embodiments, more than 2 conductive elements (e.g. 3, 4, 5, etc.) are used to steer or otherwise direct current more precisely to target an injured nerve, specific fascicles within an injured nerve and/or another targeted anatomical structure.

In some arrangements, a switching mechanism is used to switch electrodes from stimulation to recording. Such a configuration can be applied to any of the electrode embodiments disclosed herein. For example, a distal monopolar stimulation electrode 252 may be used in a first phase of stimulation to deliver a stimulus pulse in conjunction with a distal reference or return electrode, such as a patch 80 with integrated electronics. In some arrangements, once the stimulus pulse has been delivered, the distal stimulation electrode 252 may be switched to be connected to a recording amplifier, and in conjunction with one or more proximal electrodes 30 and a distal reference electrode, such as a patch 80 with integrated electronics, may be used to measure biological signals such as action potentials. A combination of these configurations may also be employed and not limited to what has been described herein.

In some embodiments, the stimulation system includes recording and amplification circuitry to measure biological signals. In some embodiments, amplification circuitry comprises instrumentation amplifiers, filtering circuits, or other analog amplification components. Such amplification circuitry can also be configured to interface with an analog-to-digital converter that converts measured analog signals to a digital format. In some arrangements, such digital signals are further manipulated in order to extract characteristic features. Such features can include, but are not limited to, signal amplitude, area, power, frequency, phase, etc. In some embodiments, such feature extraction occur on a microcontroller or a similar controller or device.

Figure 29A:
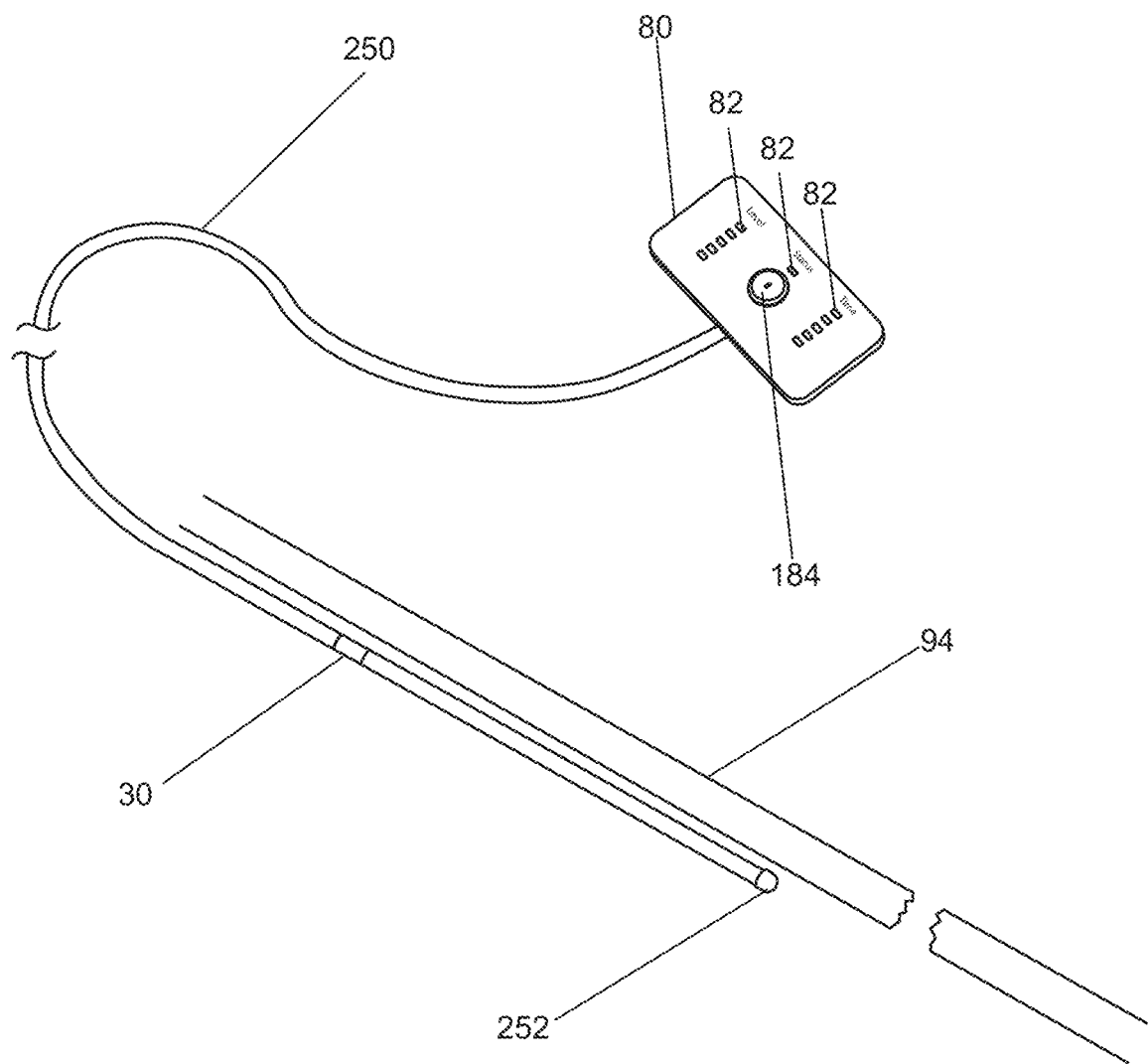
FIGS. 29A to 29D illustrate embodiments of stimulating and measuring one or more biological signals using a percutaneously-placed electrode lead connected to a surface patch with integrated electronics.
Figure 29B:
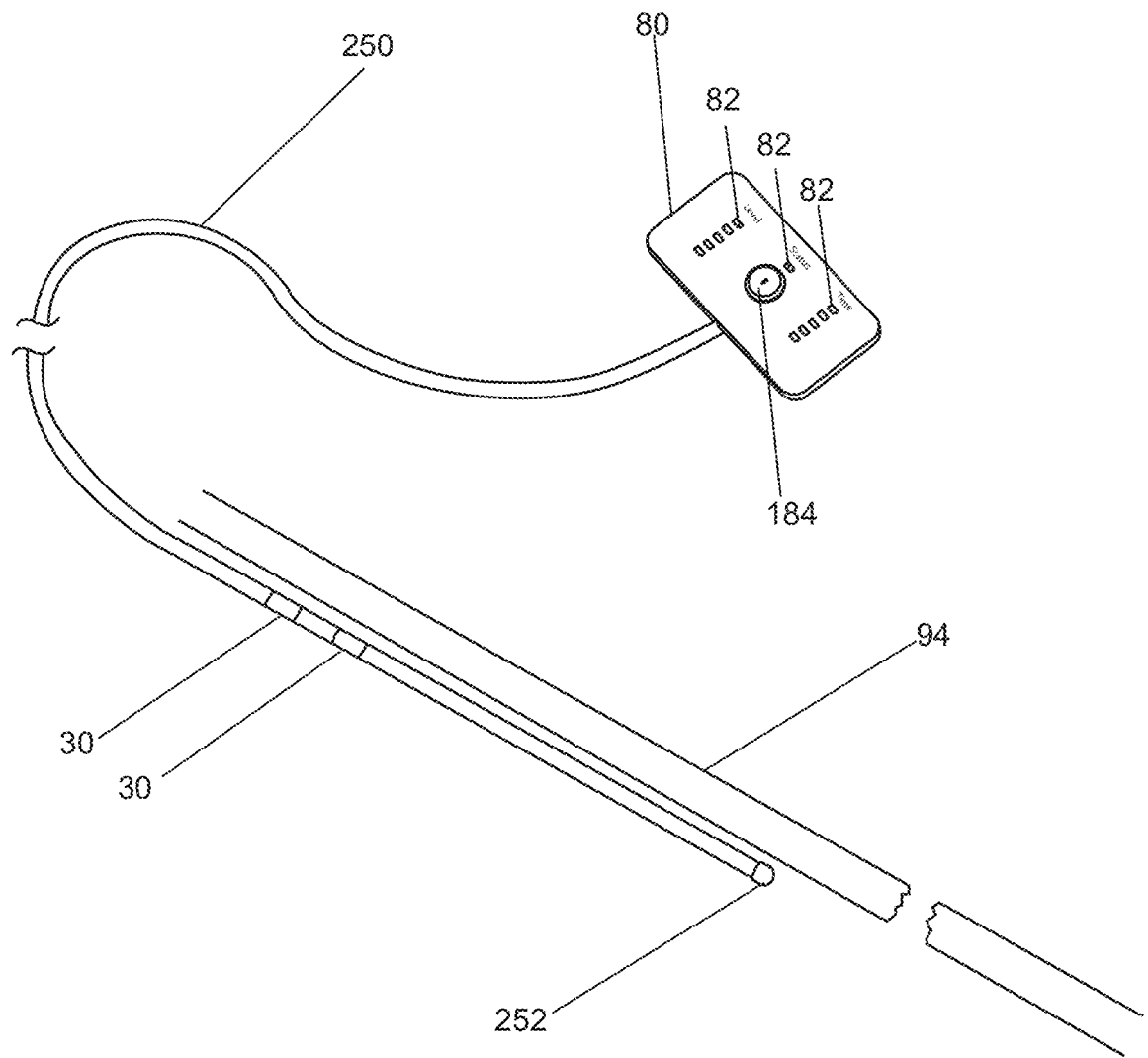
Figure 29C:
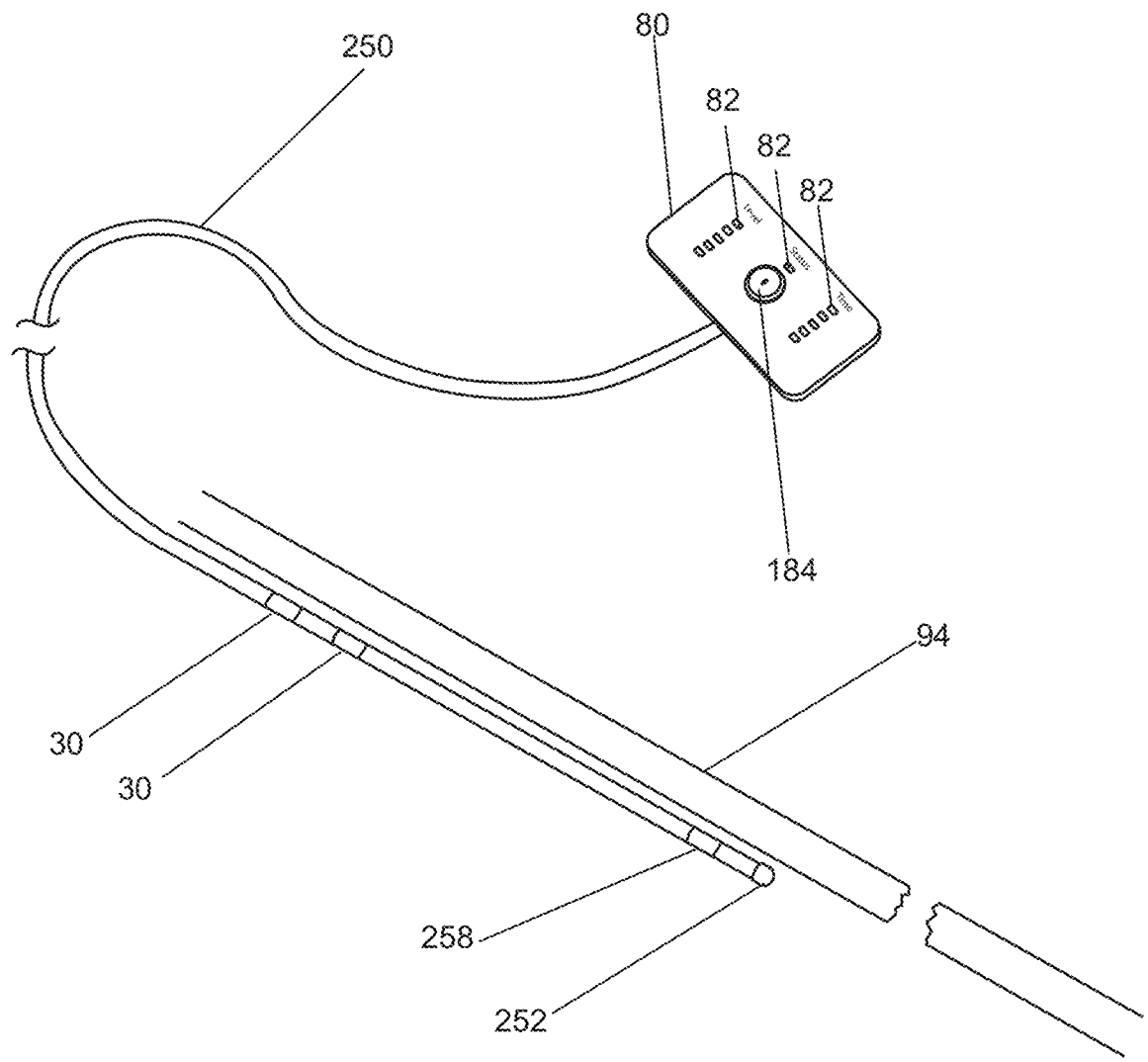
Figure 29D:
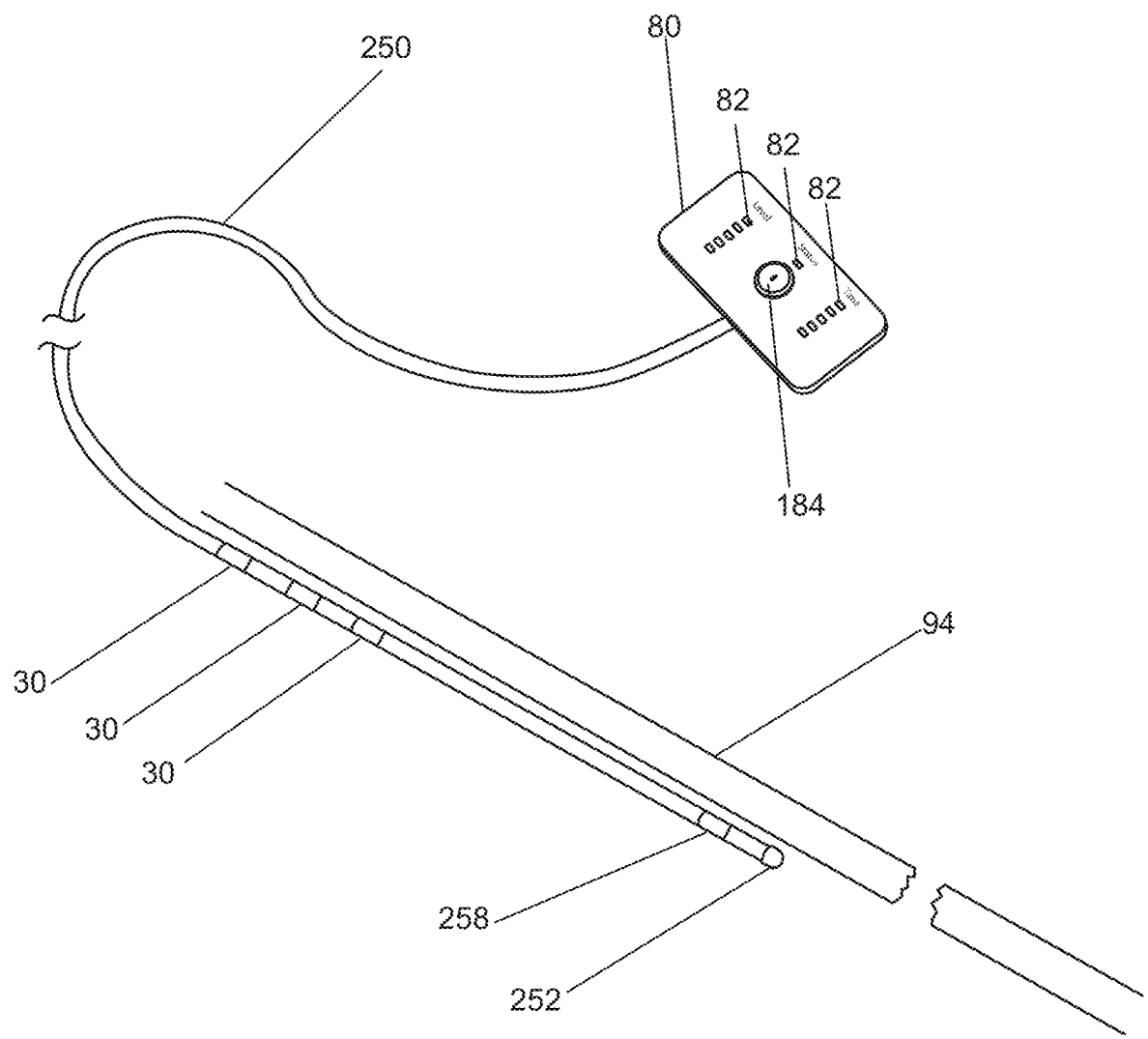
Figure 29E:
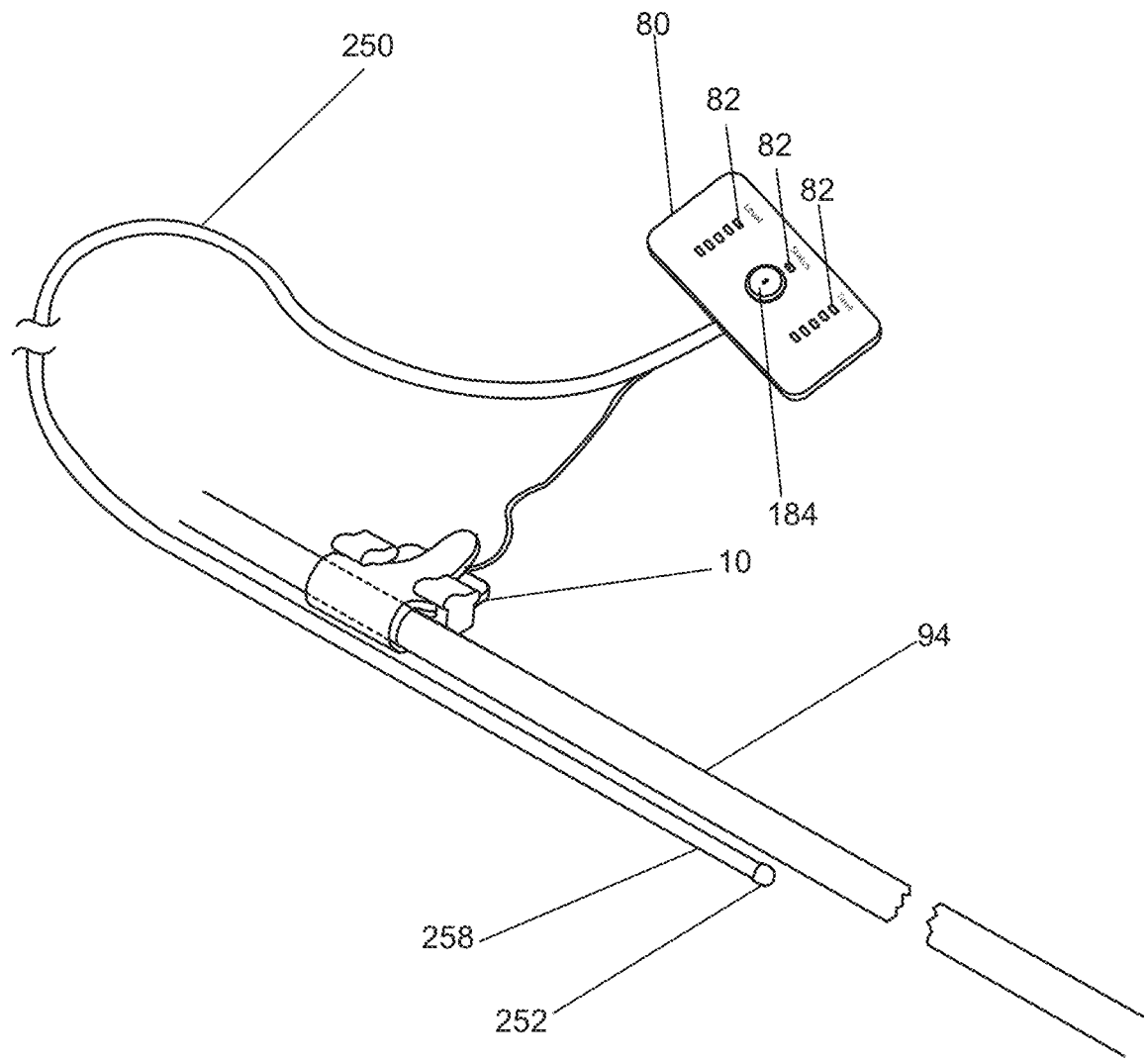
FIG. 29E illustrates one embodiment of stimulating using a percutaneously-placed electrode lead and measuring a biological signal using a cuff electrode around a nerve with both connected to a surface patch with integrated electronics.

In some embodiments, as depicted in FIG. 29E, a cuff electrode assembly 10 may be used to monitor a validation condition. Such a cuff electrode assembly may be connected to a single system that incorporates delivery of stimulation and measurement of action potentials. In some embodiments, such a system can be configured to deliver neuroregenerative therapy.

For any of the embodiments disclosed herein, a measurement system or assembly may be a separate system from a stimulation system or assembly. In some arrangements, a separate measurement system can be configured to communicate wirelessly with a stimulation system (e.g., to confirm a validation condition during a first stimulation phase, to provide information regarding the recorded signal characteristics, or to gate (e.g., provide a go/no-go signal) a second phase of stimulation which may comprise stimulation to enhance nerve regeneration or tissue reinnervation and/or the like). Wireless communication means can include, but are not limited to, radiofrequency protocols (e.g., Bluetooth, Zigbee, Wi-Fi, NFC, etc.), optical communication (e.g., infrared, near infrared, visible light), or magnetic (inductive links). In other arrangements, a wired connection (e.g., via cable) can be used to permit communication between the different systems or assemblies. In some arrangements, the separate system may be used to measure muscle action potentials, nerve action potentials and/or other evoked biological signals, as desired or required. Such potential and other signals can be advantageous or otherwise beneficial in different injury scenarios. For example, in the case of a compressive nerve injury (such as, for instance, carpal tunnel syndrome), a connected muscle action potential measurement system may be used to measure an evoked muscle response from the partially denervated muscle and confirm a validation condition. In another example, a separate system may be employed to measure action potentials from a nerve at a different anatomical location. Such nerve may be physically connected to the injured nerve (e.g., further upstream of the injury site), but not be openly accessible. Under such scenarios, a separate system can be used to confirm a validation condition that may not be possible to confirm using other described means. In some embodiments, the separate system uses surface or percutaneous electrodes to obtain a measurement.

In some arrangements, a stimulation system waits for an external characteristic signature to validate operation (e.g., a validation condition). In some embodiments, such a signature comprises discrete stimulus pulses delivered by a separate stimulation unit. Measured responses to a signature may be used to confirm a validation condition. Such signatures may be elicited not only using electrical stimulation but also using vibratory stimuli, acoustic, or light, or a combination.

In some embodiments, the separate measurement system is adapted and configured to measure, record and/or otherwise consider somatosensory evoked potentials or other electrical activity of the brain that results from the stimulation of touch. By way of example, evoked potentials may be elicited by stimulating an injured nerve on the proximal stump or connected branches. This may elicit a response both in the spinal cord and in the brain that may be recorded using a separate measurement system. In some arrangements, such a separate measurement system is used to confirm a validation condition. In any scenario, such recordings may utilize surface electrodes that reside on the surface of the skin, or on the dura (epidural electrode), or directly (subdural) on the spinal cord or brain.

In some arrangements, a surface patch 80 electrode with integrated electronics is used as a reference electrode for a measurement of a biological signal (e.g., action potential) recorded by proximal conductive elements in the electrode lead. Such a surface patch 80 may include one or more visual indicators 82. In some arrangements, such indicators 82 can be used to advantageously provide data and other information to a user, such as, for example, time, status, stimulus amplitude and/or the like.

In some embodiments, a measurement system is configured to send data wirelessly to a separate device or component, such as, for example, a smart phone, a tablet, another smart portable device, a separate computing device (e.g., a laptop) and/or the like. The separate device or component can include (or can be configured to use) one or more algorithms to analyze data, confirm a validation condition and/or perform any other function. In some arrangements, such a smart or other computing device or component can be configured to communicate with one or more stimulation devices to enable and/or facilitate the execution of neuroregenerative therapy.

Regardless of the configuration utilized, in some embodiments, it is advantageous, while measuring biological signals (e.g., action potentials), to maintain and/or otherwise consider or take into account a running average of measured characteristics (e.g., amplitude, signal area, signal power, frequency spectrum, phase, etc.) to enhance the signal-to-noise ratio or another metric. In some arrangements, such an average comprises at least 2 instances of evoked responses.

In some embodiments, the measurements of biological signals during a validation or verification step may be used to gate (e.g., provide a go/no-go signal) a second or other subsequent phase of stimulation, which may comprise stimulation to enhance nerve regeneration or tissue reinnervation.

To further elaborate on or otherwise supplement or enhance motor/sensory responses during a validation or verification step, in some embodiments, the repetitive burst sequence discussed herein creates a validation signature or other unique identifier. Such a signature may comprise stimulus pulses with various characteristics (e.g., different pulse durations, amplitudes, frequencies, etc.). In some arrangements, the validation signature is configured to synchronize with a display (or other output) and be used for direct patient and/or practitioner feedback (e.g., asking patients if the response they feel from stimulation is similar or dissimilar from what is shown on the display, querying the physician to assess a patient's response, etc.). In some embodiments, it is advantageous to use discrete pulses that may be randomly delivered during this validation phase. Such a configuration can be advantageous because a constant frequency output (e.g., 20 Hz with a fixed pulse width) may provide a "buzzing," other constant sensation and/or another type of sensation to a patient. For example, in the case of a severe nerve injury (e.g., a transection), such a constant sensation from stimulation may be masked or not interpreted as stimulation due to the injured axons randomly firing or being hypersensitive. In some configurations, discrete pulses overcome this limitation and may provide for objective measurement of a validation condition (e.g., a patient response to stimulation). Additionally, it may be advantageous to provide discrete pulses at a frequency below the muscle fusion frequency to prevent any fused muscle contractions. In some embodiments, muscle fusion frequencies vary depending on the muscle. For example, such fusion frequencies may be greater than 100 Hz for fast twitch ocular muscles or between 5 and 20 Hz (5-6, 6-7, 7-8, 8-9, 9-10, 10-11, 11-12, 12-13, 13-14, 14-15, 5-10, 10-15, 15-20, 10-20 Hz, frequencies between the foregoing ranges, etc.) for slow twitch muscles such as the soleus muscle. In some arrangement, such contractions may arise if a transected nerve is stimulated proximal to the injury and proximal to any non-injured nerve branches. These contractions may also arise in nerves injured by compression where some distal conduction is able to take place if said injured nerve is stimulated proximally. Non-tetanic pulse trains are able to be interpreted as discrete events by a patient which may satisfy a validation condition, in some embodiments.

In some embodiments, a validation signature or other unique identifier is used throughout a therapeutic stimulating window (e.g., during 1 hour of neuroregenerative therapy, some other duration of therapy, etc.). This validation signature may advantageously confirm to a user that the system is providing therapeutic efficacy to injured nerves undergoing stimulation. In some arrangements, the validation signature applied throughout the stimulating window may comprise one or more discrete pulses (e.g. 2, 3, 4, 5 pulses, etc.) producing one or more (e.g. 2, 3, 4, 5, etc.) evoked potentials. The timing between subsequent pulses (e.g., pulse frequency) may be uniform or non-uniform (e.g., random), as desired or required. In some arrangements, such evoked potentials can be averaged to create a composite validation response that may confirm to a user if stimulation is applied correctly and the system is providing therapeutic efficacy to injured nerves.

Multiple Nerve Injuries

In cases such as brachial plexus injuries, where multiple nerves are injured, it may be desirable to provide neuroregenerative therapy to all injured nerves at once. In such instances and arrangements, the system can be designed and configured to output to different electrode configurations. See, for example, FIG. 30.

Figure 30:
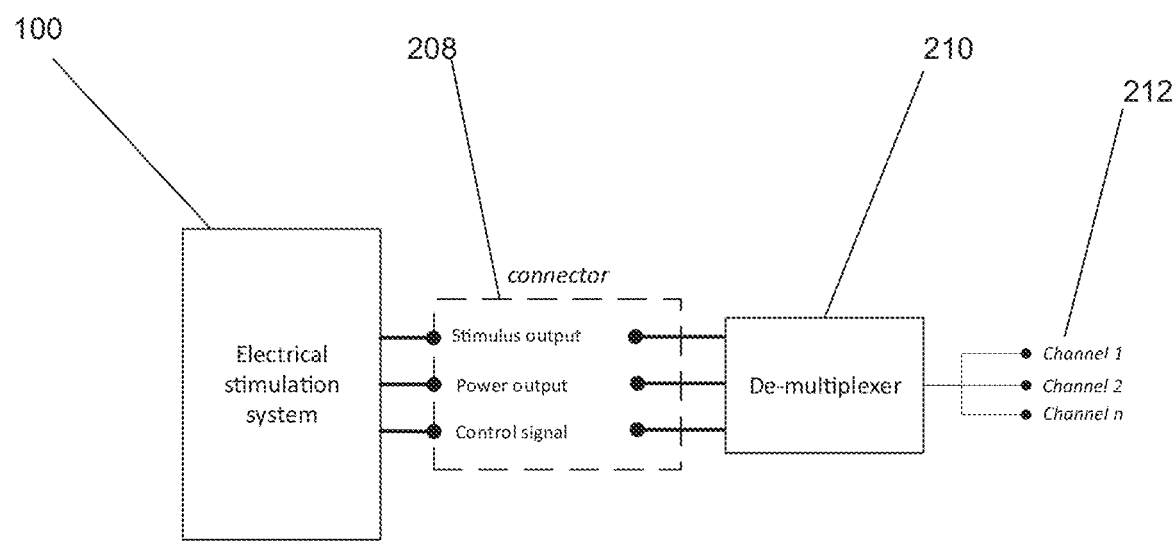
FIG. 30 illustrates a schematic view of how a multi-channel electrode may be interfaced with the system according to one embodiment.

In some embodiments, as illustrated in the example of FIG. 30, an electrode apparatus connector 208 with an analog demultiplexer 210 controlled by the system can be connected to the nerve port. In some arrangements, this permits the system to provide output to one channel at a time by switching between channels 212.

In some embodiments, the nerve port comprises additional conductive signal paths or lines for carrying power and control information to the analog demultiplexer. In some embodiments, the connector may feature connections to control an analog demultiplexer using either a parallel configuration where one control signal line is needed for each electrode connected to the system (e.g. ON Semi MC14067B, Analog Devices ADG5412, Maxim Integrated MAX4623, or equivalent). In other arrangements, the connector can include three control signals for interfacing to an analog demultiplexer using the serial peripheral interface (SPI) (e.g. Analog Devices ADGS1412).

According to some embodiments, a cable containing the multiple electrodes can comprise a connector housing unit that include the demultiplexer circuit and indicators, such as, for example, LEDs displaying the active channel. In yet other arrangements, the connector housing unit can include memory and an energy source (e.g., a relatively small energy source, such as, for example, such as a coin cell battery or the like) to power said memory. In some arrangements, the memory is configured to store information, for example, stimulus settings, other operational parameter and/or the like. In some arrangements, the connector housing unit can include memory, energy source, demultiplexer circuitry and/or any other features or components, as desired or required. Each lead wire connected to an electrode apparatus can include a connector housing unit that comprises one or more of the components described in greater detail with reference to any of the embodiments disclosed herein.

Treatment Method Duration

In terms of therapeutic time duration, studies have demonstrated the optimal duration to be as little as 10 minutes or 30 minutes. However, most studies utilize a treatment duration of or near 1 hour. The duration of a treatment method can therefore be between 10 and 90 minutes (e.g., 10-20, 20-30, 30-40, 40-50, 50-60, 60-70, 70-80, 80-90, 10-30, 30-60, 40-80 minutes, times within the foregoing ranges, etc.), as desired or required. In other embodiments, a treatment procedure can take longer than 90 minutes or less than 10 minutes.

In some embodiments, the treatment of injured nerves comprises the set-up of an appropriate electrode apparatus and stimulus parameters, the initiation of treatment, and the maintenance of a stimulus amplitude sufficient to depolarize axons. Furthermore, the treatment duration need not be applied continuously for the entire treatment duration so long as a total time of treatment is equivalent to the optimal stimulation duration. For example, if the electrode apparatus needs to be moved during a surgical procedure, the end-user has the ability to pause the treatment using a user-operable control as outlined previously. When paused, the system will stop delivering electrical stimulus output and only resume when the pause control is used again. In this specific example, once treatment has been applied for 1 hour, the previously described indicators may notify the user of treatment completion.

In some arrangements, it may be advantageous to deliver multiple bouts of brief electrical stimulation with each bout comprising of the previously described durations (e.g., 10 to 90 minutes) and stimulus parameters. The timing between subsequent bouts of brief electrical stimulation, or rest periods, may vary from multiple bouts per day to a single bout separated by one or more days and delivered on one or more days. In some embodiments, a single bout of brief electrical stimulation of injured axons transiently upregulates regeneration associated genes and neurotrophic factors in the cell bodies of the injured axons. It is the intention, according to some embodiments, that multiple bouts may prolong, transiently increase, or maintain the upregulated expression of these genes and neurotrophic factors.

The number of bouts to be delivered may vary depending on the distance of type of nerve injury. By way of example, a proximal injury in the shoulder may require a minimum of 450 days for injured axons to regenerate from the site of injury to distal muscle in the hand. In a scenario where daily stimulation is provided, delivering multiple bouts of stimulation would require at least 450 bouts in this scenario. Injuries more distal, such a laceration of the digital nerve in the human finger, may require considerably less bouts, for instance 30-60, in the case of daily stimulation. The number of bouts delivered is injury dependent and cannot be determined apriori. In some cases, only a few bouts are needed as repeated bouts may not be beneficial. The primary effect of stimulation is to enhance nerve outgrowth across an injury site and thus after a certain number of days all injured axons have crossed the injury site and may not benefit from further neuroregenerative treatment. Additional benefits of neuroregenerative therapy is the ability to reinnervate more tissue. In some embodiments, not only does this lead to greater function but also a diminished potential for developing chronic pain as regenerating axons are able to reconnect to tissue leaving less free axon ends that could potentially form neuromas or cause pain.

In some embodiments, implementation of multiple bouts of brief electrical stimulation may require modification of the previously described systems and devices. In one example, a second stimulation system that interfaces with the connector 186 on the adhesive patch 80 may be programmed to monitor, track, or verify if appropriate treatment duration and number of treatments have been performed. In some embodiments, the second stimulation system may save patient information, such as a unique identifier, in order to track patient compliance with the treatment.

In another example, the adhesive patch 80 can be configured with an energy source to last for the duration of the delivery of multiple bouts. In such an embodiment, the adhesive patch 80 may comprise of elements allowing it to function as both a validation energy source and stimulation energy source. Additional elements that may be included in the adhesive patch are an indicator or user controls for adjusting stimulus parameters as mentioned herein.

In some embodiments, the adhesive patch includes circuit elements used for wireless communication with an external device or implanted device or a combination thereof. In one example arrangement, such device may include a smart phone or other computing device (e.g., tablet). In such an application, said smart phone may include a software application used to change stimulation parameters and verify appropriate treatment duration and application. In another example, such device may include an implanted electrode lead. In such an application, the electrode lead may include hardware and circuitry to communicate with patch and perform desired functions, like electrical stimulation.

Pain Management

In other embodiments, systems (and methods related thereto) may be modified to not only deliver multiple one or more bouts of neuroregenerative therapy, but also to deliver pain management therapy. Such a pain management therapy may be delivered immediately before and/or after neuroregenerative therapy. Further, the delivery of such pain management therapy can occur before, during and/or after nerve repair surgery, as desired or required. However, the delivery of energy for pain management therapy is not limited to this window and may be provided at a fixed time from delivery of neuroregenerative therapy. Fixed time may represent minutes to hours to days from delivery of neuroregenerative therapy (e.g., 0-10, 0-30, 0-60 minutes, 0-1, 0-2, 0-3, 0-4, 0-5, 0-6, 0-12, 0-12, 0-24 hours, 0-1, 0-2, 0-3, 0-4, 0-5, 0-6, 0-10, 0-20, 0-30 days, more than 30 days, any time period within the foregoing ranges, etc.). The delivery of energy for pain management may also take place when a patient is feeling pain related to the nerve injury without the need for a fixed delivery schedule.

According to some embodiments, pain management therapy comprises stimulation in the 50 to 200 Hz range (e.g., 50-60, 50-55, 55-60, 52-58, 50-100, 50-200, 50-150, 100-150, 100-200, 70-130, 80-120, 60-120, 150-200 Hz, values between the foregoing ranges, etc.). In some arrangements, the frequency of stimulation for reducing pain may be from 20 KHz to 500 KHz (e.g., 20-500, 20-100, 50-100, 100-200, 100-300, 100-400, 100-500, 200-400, 200-500 KHz, frequencies between the foregoing ranges, etc.) or 1 KHz to 10 KHz (e.g., 1-10, 2-8, 4-6, 3-7, 1-5, 5-10 KHz, frequencies between the foregoing ranges, etc.). In some embodiments, the systems can be designed and otherwise configured to (and thus, the corresponding methods involving such systems can be configured to) provide an optimal, efficient and/or comfortable frequency for reducing pain. In some embodiments, the frequency delivered by the system can be configured to modulate the stimulation energy being delivered for reducing pain (e.g., according to a particular patient or other subject, during a procedure for a particular patient or subject, to target specific types of pain, etc.), as desired or required. However, in other embodiments, the stimulation energy being delivered by the system for reducing pain can be fixed.

In some arrangements, a single bout or treatment round of neuroregenerative therapy may be sufficient to enhance tissue reinnervation leading to a reduction of the potential for developing chronic pain or other types of long-term pain. However, short term pain may still exist and persist as nerve tissue is regenerating. Any of the systems described herein may be used to deliver continuous or intermittent pain management therapy after one or more bouts of neuroregenerative therapy.

FIGS. 31, 32, 33 and 34 depict flow diagrams of embodiments of steps for delivering neuroregenerative and pain management therapy to a subject. These flow diagrams illustrate various configurations in time that delivery of neuroregenerative therapy and pain management therapy can be applied. While these flow diagrams present some examples of configurations in time of the delivery of these therapies, practitioners or users of the device may opt to bypass or not perform one or more steps, may substitute alternative steps for depicted steps and/or may include additional steps, as desired or required. For example, a practitioner may opt to perform only one application or neuroregenerative therapy, but multiple applications of pain management therapy. Thus, under such circumstances, a practitioner may omit steps where additional neuroregenerative therapies can be applied.

Figure 31:
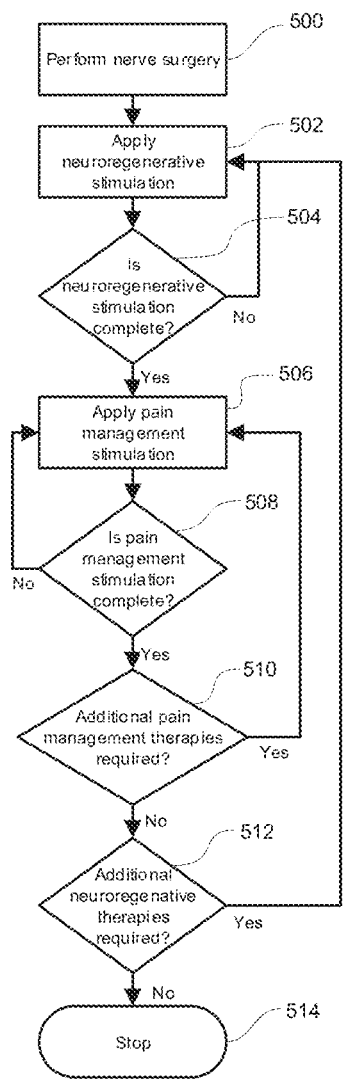
FIG. 31 schematically illustrates a flowchart of a procedure, protocol or method for delivering neuroregenerative and pain management therapy to a subject according to one embodiment.

FIG. 31 schematically summarizes one embodiment of a procedure, protocol or method for delivering neuroregenerative and pain management therapy to a subject. As shown, neuroregenerative stimulation can be applied 502 to the subject in accordance with one or more of the various arrangements disclosed herein or the like. In the illustrated arrangement, neuroregenerative stimulation is applied 502 after nerve surgery is initially performed 500. However, as shown in connection with other embodiments disclosed herein (see, e.g., FIGS. 32 to 34) neuroregenerative stimulation can be initially applied before nerve surgery is performed, as desired or required. Once the delivery of neuroregenerative stimulation is complete 504, pain management stimulation can be applied 506 to the subject. Pain management stimulation can be applied using any of the devices, systems and/or methods disclosed herein.

With continued reference to FIG. 31, once pain management stimulation to the subject is complete, the practitioner can determine if additional pain management therapies are desired or required 510. Likewise, once it has been determined that additional pain management therapies are not desired or required, the practitioner can determine if additional neuroregenerative therapies are desired or required 512. If neither of these additional therapies are desired or required, the protocol, procedure or method can be terminated 514. If, however, additional therapies are desired or required, as shown in FIG. 31, the practitioner can choose to repeat one or more of the steps, as desired or required.

Figure 32:
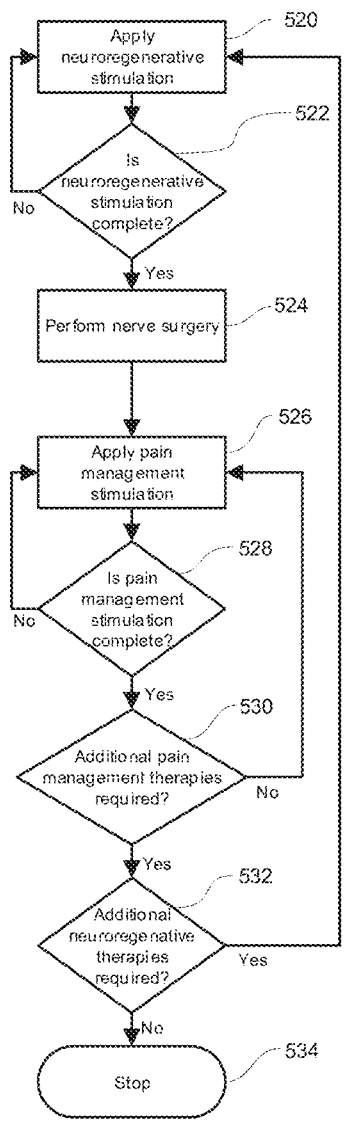
FIG. 32 schematically illustrates a flowchart of a procedure, protocol or method for delivering neuroregenerative and pain management therapy to a subject according to one embodiment.
Figure 33:
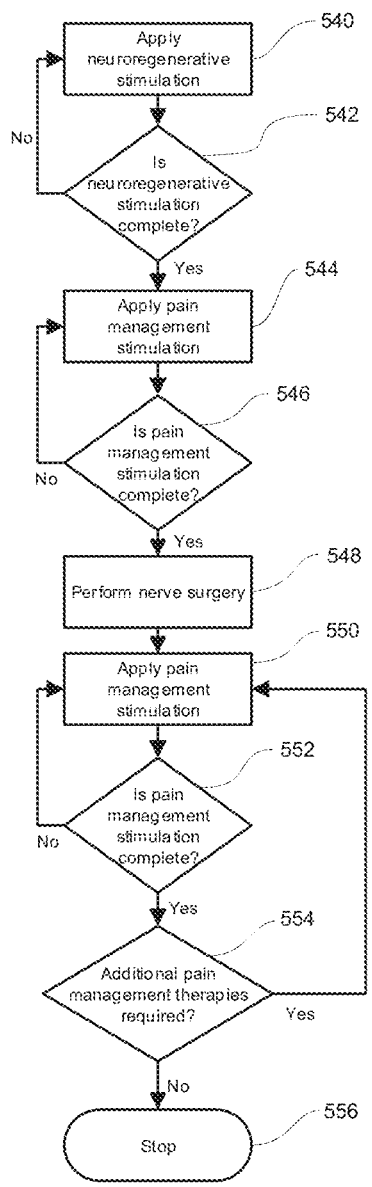
FIG. 33 schematically illustrates a flowchart of a procedure, protocol or method for delivering neuroregenerative and pain management therapy to a subject according to one embodiment.
Figure 34:
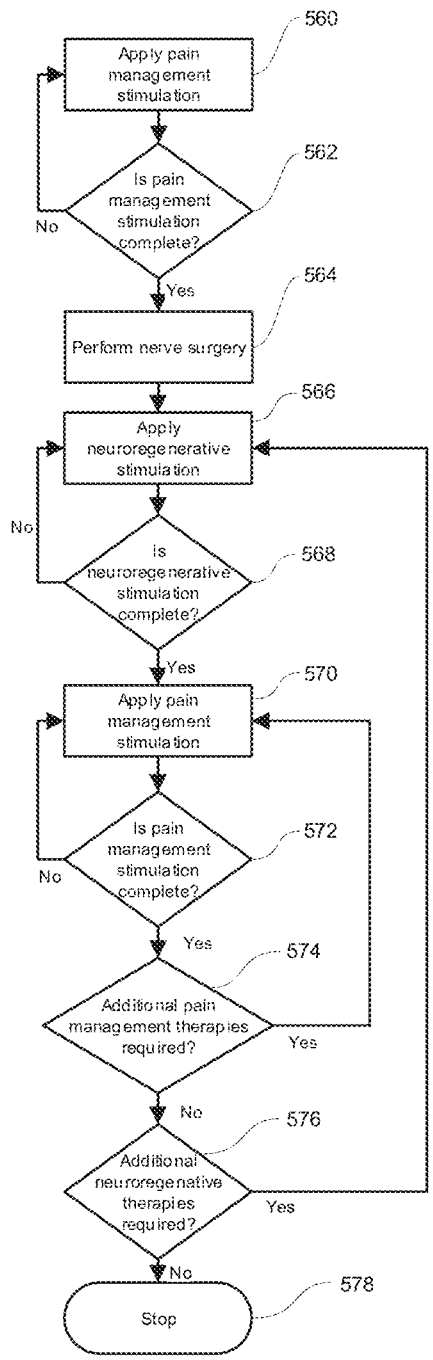
FIG. 34 schematically illustrates a flowchart of a procedure, protocol or method for delivering neuroregenerative and pain management therapy to a subject according to one embodiment.

FIG. 32 schematically summarizes another embodiment of a procedure, protocol or method for delivering neuroregenerative and pain management therapy to a subject that is similar to the one illustrated in FIG. 31. However, in FIG. 32, neuroregenerative stimulation is applied 520 prior to performing nerve surgery 524. In FIG. 32, nerve surgery is performed 524 prior to applying pain management stimulation 526. However, in the procedures schematically illustrated in FIGS. 33 and 34, nerve surgery 548 is performed after the application of both neuroregenerative stimulation 540 and pain management stimulation 544. In FIG. 33, the application of neuroregenerative stimulation 540 occurs prior to the application of pain management stimulation 544. Alternatively, however, in FIG. 34, the application of pain management stimulation 560 occurs prior to the application of neuroregenerative stimulation 566.

Figure 35:
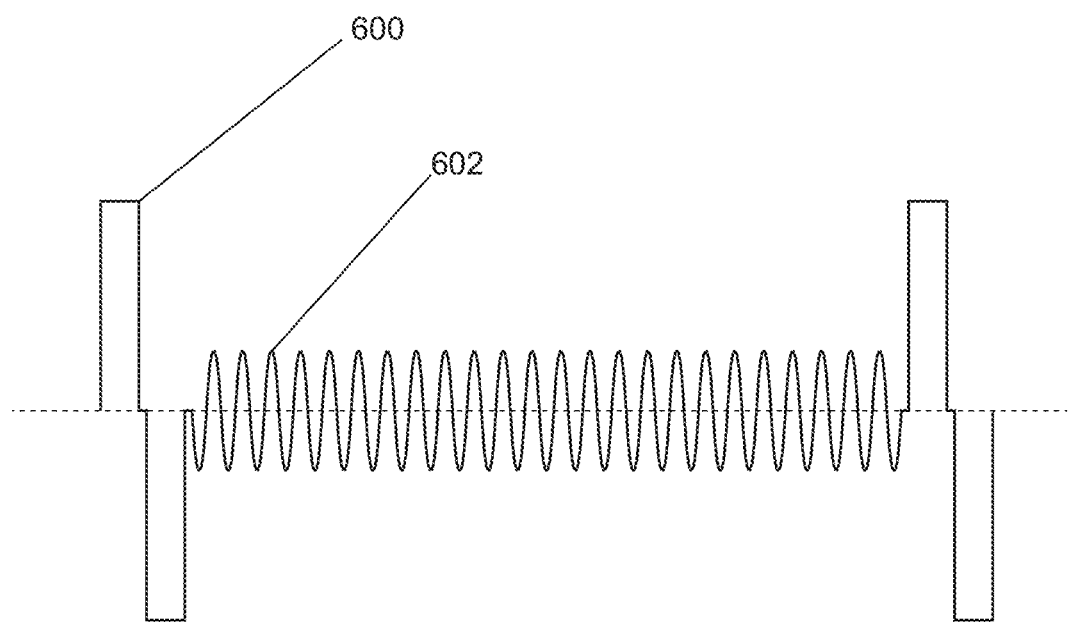
FIG. 35 illustrates one embodiment of a pain reducing waveform applied by a stimulation system.

According to some embodiments, the pain management therapy may be delivered concurrently with neuroregenerative therapy. That is, in between successive pulses in the neuroregenerative paradigm 600, a pain reducing waveform 602 may be delivered. Such waveforms may include sinusoidal, rectangular, ramped and/or any other scheme, pattern or shape. By way of example, FIG. 35 illustrates a 1 KHz sine wave interspersed with biphasic 20 Hz rectangular neuroregenerative pulses. However, any other wave/pattern, frequency and/or other properties can be used with respect to the delivery of stimulation energy, as desired or required.

In some embodiments, the existing of a percutaneously placed lead and electrode already interfaced with an injured nerve provides a unique advantage to providing one or more follow-up stimulation energy for reducing pain. Thus, the requirement for a separate procedure to gain access to nerve tissue (and/or the surrounding anatomical region) for the delivery of stimulation energy for pain management is not necessary. This is important as the site of neuropathic pain would be the site of nerve injury. Other advantages include the ability to validate therapeutic efficacy of the pain management therapy, the ability to titrate stimulus levels to produce optimal or enhanced pain management through recording of biological signals and/or the like.

Figure 36:
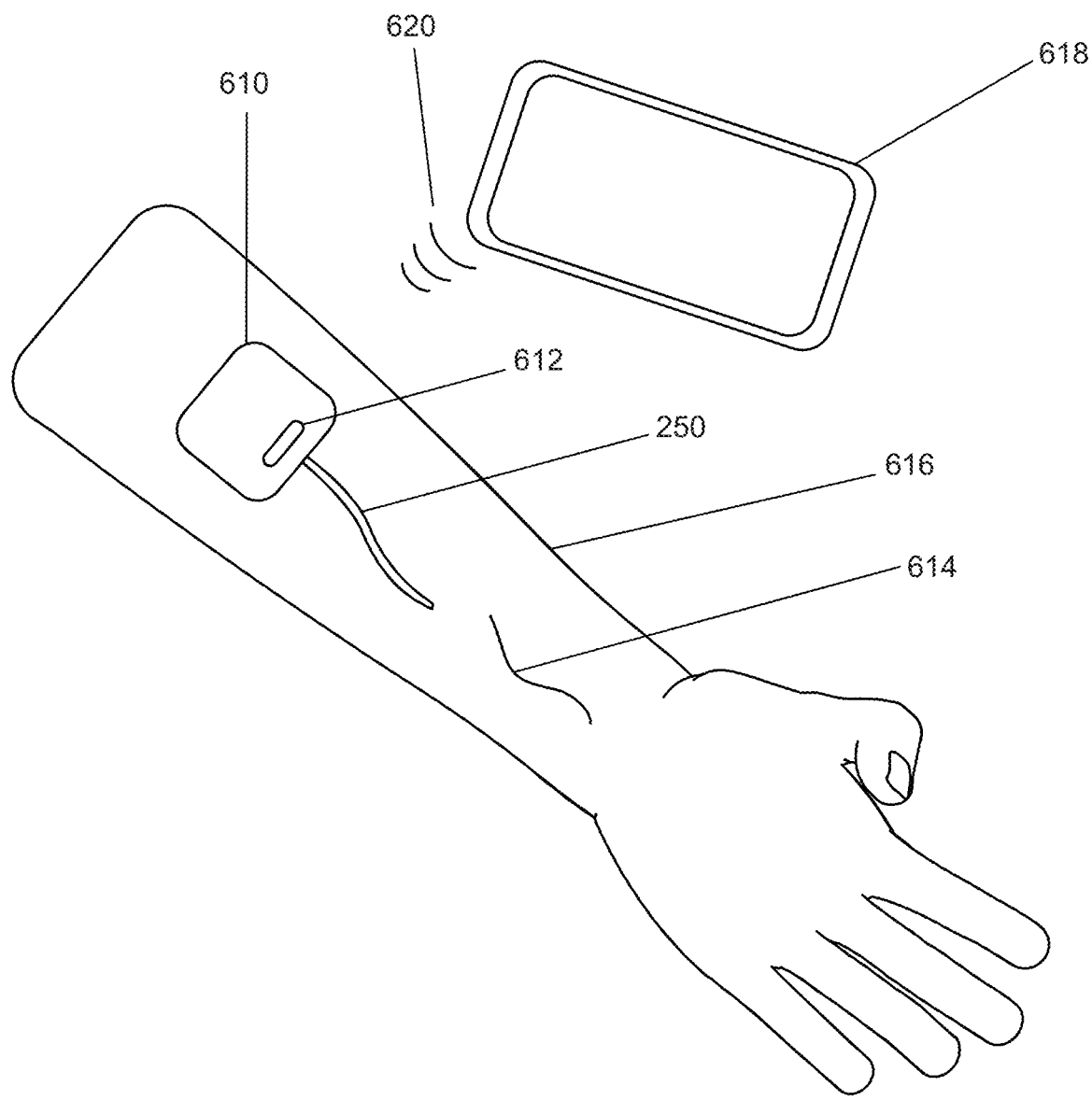
FIG. 36 illustrates one embodiment of a system configured to provide both neuroregenerative therapy and pain management therapy to a subject.

In some embodiments, as illustrated in FIG. 36, a system that delivers neuroregenerative therapy (e.g., in accordance with any of the arrangements disclosed herein or equivalents thereof) comprises a separate actuator, button, control, controller and/or other device, feature or component to help deliver pain management therapy. In some embodiments, such a feature or component can be incorporated into one or more other features, components, devices and/or portions of the system. In other arrangements, a separate system 610 can be used to deliver pain management therapy and can also include a control and indicator 612. In some embodiments, such a separate control is enabled or is otherwise configured to be activated and/or controlled by a patient, caregiver, medical professional and/or the like, as desired or required.

In some embodiments, once neuroregenerative therapy is complete, the system is configured to only deliver pain management therapy. In other embodiments, both neuroregenerative and pain management therapies are available (e.g., intermittently, indefinitely, for a specific time period, until a particular event or threshold is attained, as otherwise determined by the system, directed by the practitioner or other user and/or as dictated by one or more other factors or conditions).

In some embodiments, a separate device or system can be configured to replace a device that delivered neuroregenerative therapy. Neuroregenerative delivery devices, as described herein, can be deployed or otherwise activated at the time or immediately after surgery to repair an injured nerve. For example, pain management therapy, on the other hand, can be performed in home settings or typically performed in settings away from a medical environment (e.g., hospital, clinic, doctor's office, etc.). Therefore, it may be advantageous, under certain embodiments, to change or swap the neuroregenerative device with a pain management device that interfaces the electrode 250 that has already been placed upstream from the incision site 614 and interfaced with the injured nerve.

According to some embodiments, in cases of neuroregenerative therapy and/or pain management therapy, the corresponding system can be a body worn wearable and directly adhere to a limb 616. In some embodiments, the same device or system can be used to deliver both the neuroregenerative therapy and the pain management therapy. In other arrangements, different systems can be used to deliver neuroregenerative therapy and pain management therapy. Regardless if the same or different stimulation energy delivery devices or systems are used for neuroregenerative therapy and pain management therapy, such devices or systems can be body worn (e.g., directly or indirectly attached to a subject) or not body worn, as desired or required by a particular application or use.

In some embodiments, a control (e.g., device, system, component, feature, etc.) to enable, execute or otherwise facilitate pain management is triggered or otherwise initiated using a separate device (e.g., a remote device) 618, such as a smartphone or other radiofrequency (RF), Bluetooth and/or other wireless/wired transmitting enabled remote. In the example of a smartphone or other computing device used to enable pain management therapy, such a smartphone or other device may also be configured to manage or otherwise control management of a desired or required therapy through an application (e.g., a smartphone application or program) and include information such as recording delivery times, amount of energy delivered, compliance with therapy, targeted levels of stimulation, deviations over time from stimulation targets, etc. In some arrangements, no physical controls are found on the pain management system and it is strictly controlled through software found on a computer, tablet, smart phone, etc. Said software may adjust stimulation parameters, time of therapy, delivery times, communication with physicians, etc.

In some embodiments, the system used to deliver pain management therapy or neuroregenerative therapy, may include a battery or similar power source. In other arrangements, the system includes a wireless charge transfer mechanism (e.g., inductive coupling coils or electromagnetic coupling circuitry) that may be used to power the device. In some embodiments, wirelessly transferred power 620 coming from a computing device such as a computer, tablet, smartphone, other computing device and/or the like can be configured to provide power (e.g., to electrically charge) to a charge storage device such as a capacitor (e.g., a super capacitor). In some embodiments, a super capacitor configured to be charged in this manner can be configured to be programmatically charged to deliver set amounts of pain management or neuroregenerative therapy. In some embodiments, a super capacitor in conjunction with a battery may be used to reduce the voltage drop of the battery due to high current consuming events (e.g. transmitting data wirelessly). For example, in some arrangements, set amounts may include preset amount of charge delivered, time durations, stimulus settings, etc. In some arrangements, a near-field communication protocol utilizing an unlicensed frequency band, such as, by way of example, 13.56 MHz, can be used to transfer power and/or data to and/or from the pain management device or system. However, any other configuration can be used to facilitate the transfer of power and/or data to and/or from the pain management device or system, as desired or required.

In some embodiments, the computing device/tablet/smart phone may also pose as a payment system. In such arrangements, the computing device may unlock or enable pain management therapy once a payment has been received.

Shapeable Electrode Lead—Generally

Nerve injuries can occur in various parts of the body and are usually unpredictable. Surgical repair of these injuries typically involves an open incision or open surgical area. Interfacing (e.g., reaching, contacting, accessing, getting close to, etc.) a nerve to deliver neuroregenerative therapy in these scenarios can involve using an electrode (e.g., a cuff style electrode). However, typically, known electrodes (e.g., cuff style electrodes) are not able to be removed percutaneously and are only suitable for the duration of a surgical procedure or they are implanted permanently. Given the general transient nature of neuroregenerative therapy, having a nerve interface that can appropriately contact the nerve in an open surgical scenario, such as for nerve repair, and be subsequently removed (e.g., seamlessly, without the inclusion of additional surgical procedures, etc.) from the body of a subject can be important and helpful for the advancement and/or adaptability of such therapies. Additionally, the use of a shapeable electrode that can be easily withdrawn is advantageous in the delivery of pain management therapy following nerve repair as described herein.

In some embodiments, percutaneously-placed electrodes may be suitable for the delivery of neuroregenerative therapy and/or pain management therapy. In some embodiments, the electrode lead may be shaped to conform to the specific anatomical area in which it will be placed. Advantages and benefits of a shapeable aspect of the electrode lead include, without limitation, the ability for the electrode lead to better conform to a region of the anatomy, allowing placement of the electrode lead along trajectories not parallel to the longitudinal axis of a target nerve, ability to at least partially wrap around and/or otherwise at least partially surround a target structure and maintain position, ability to create a shape used to avoid anatomical structures while still engaging the target nerve, ability to place electrode lead near target nerve without having to rely on surrounding connective tissue for anchoring, ability to withdraw electrode without damaging a repaired target nerve, better localize the treatment to a desired site which may reduce current density needed to elicit treatments (e.g. neuroregenerative and/or pain management therapy), relieve or prevent pain, discomfort, or trauma that might otherwise be caused by inflexible, stiff, or protruding implanted materials, etc.

According to some embodiments, any of the configurations disclosed herein, or equivalents thereof, can include an electrode lead that has one or more portions that are shapeable. In some arrangements, only a portion of the electrode lead is shapeable (e.g., includes a shapeable aspect). However, in other embodiments, the entire electrode lead is shapeable.

Figure 37A:
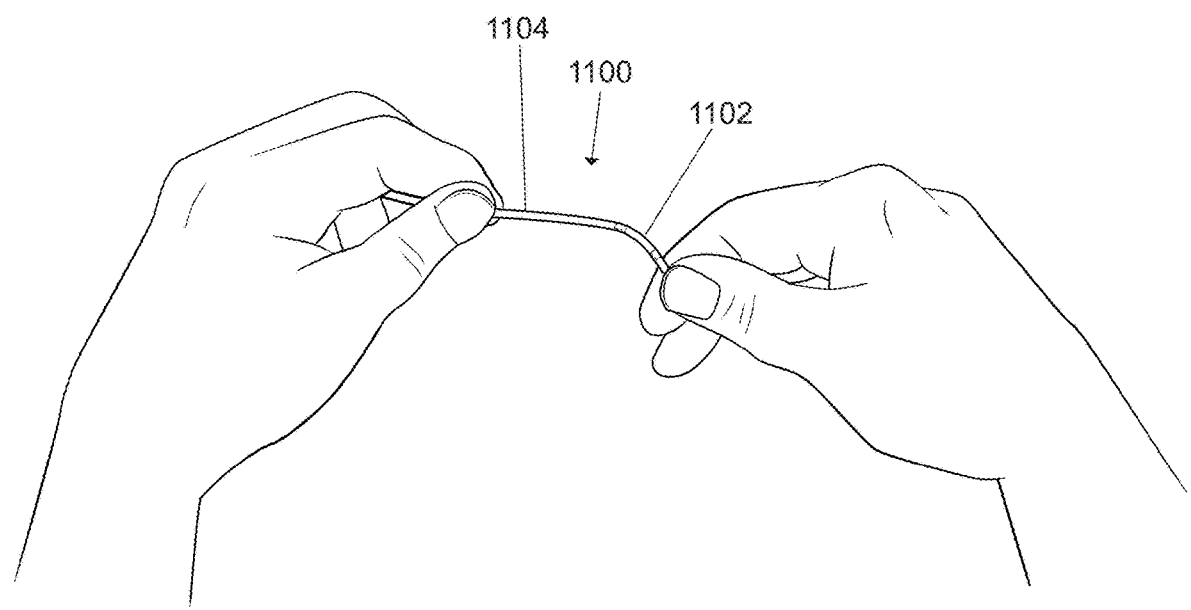
FIG. 37A illustrates a perspective view of an electrode lead being shaped by hand within a surgical field according to one embodiment.
Figure 37B:
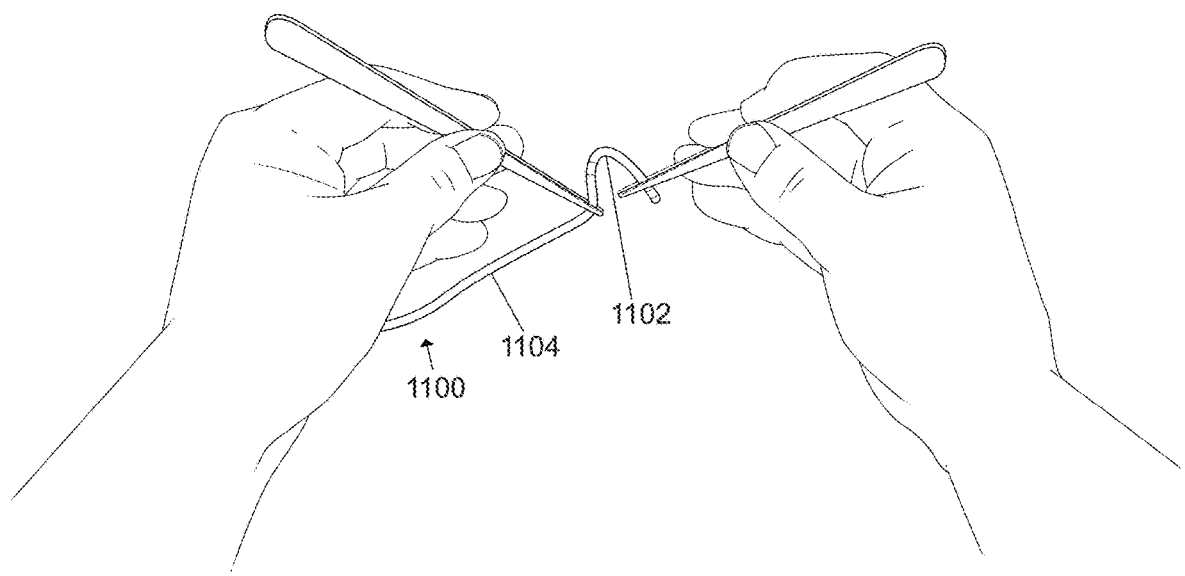
FIG. 37B illustrates a perspective view of an electrode lead being shaped using forceps within a surgical field according to one embodiment.

The surgical area or area that includes and/or surrounds the targeted injured nerve may have undergone sufficient trauma such that it does not resemble standard anatomy (e.g., structural, material changes may have resulted). Moreover, having a shapeable aspect of the electrode lead can be advantageous in cases of open surgery, as the lead may be shaped to conform (e.g., generally, approximately, automatically, manually, etc.) to a particular nerve irrespective of the anatomical landscape. In some arrangements, the shaping of one or more portions of the lead body or assembly 1100 (e.g., the distal aspect 1102 and/or the proximal aspect 1104) may be performed by hand, as depicted in FIG. 37A. In some embodiments, such manual shaping or manipulation can be accomplished using one or more surgical instruments (e.g., forceps), as shown in FIG. 37B, by robotic equipment and/or the like. In other embodiments, no surgical instruments, equipment and/or the like are used. In some embodiments the shaping is performed, at least in part within the surgical area. For example, the electrode lead body 1100 can be shaped either entirely or partially once the lead body 1100 has been positioned within the targeted surgical area, as desired or required. As discussed herein, in some embodiments, the proximal portion or aspect of the lead body or assembly 1100 can be configured to be rigid or substantially rigid to permit the proximal portion or aspect to be inserted into a stimulation device or other device (e.g., directly, without the need for a separate coupler or member, etc.). In some embodiments, the rigidity of the proximal portion is greater than the rigidity of the distal portions of the lead.

For example, the ratio of the rigidity of the proximal portion to the rigidity of one or more portions that are distal to the proximal portion (e.g., the distal end) is at least 5:1, 15:1, 10:1 or 20:1 (e.g., at least 5:1, at least 10:1, at least 20:1, at least 50:1, at least 100:1, at least 150:1, at least 200:1, at least 300:1, at least 400:1, at least 500:1, at least 1000:1, at least 1500:1, at least 2000:1, at least 2500:1, at least 3000:1, at least 4000:1, at least 5000:1, at least 7500:1, at least 10000:1, at least 15000:1, at least 20000:1, at least 25000:1, at least 30000:1, at least 35000:1, at least 40000:1, at least 45000:1, at least 50000:1, 5:1 to 10:1, 10:1 to 15:1, 15:1 to 20:1, 20:1 to 50:1, 10:1 to 50:1, 50:1 to 100:1, 10:1 to 100:1, 100:1 to 500:1, 100:1 to 1000:1, 100:1 to 2000:1, 100:1 to 3000:1, 100:1 to 4000:1, 100:1 to 5000:1, 100:1 to 6000:1, 100:1 to 7000:1, 100:1 to 8000:1, 100:1 to 9000:1, 100:1 to 10000:1, 100:1 to 15000:1, 100:1 to 20000:1, 100:1 to 25000:1, 100:1 to 30000:1, 100:1 to 35000:1, 100:1 to 40000:1, 100:1 to ratios greater than 40000:1, values or ranges within or between the foregoing, etc.), as desired or required.

In some embodiments, the ratios and/or other relative measurements of rigidity discussed herein (e.g., in the preceding paragraph) relate to Young's modulus values or coefficient of stiffness. However, in other embodiments, the above ratios can relate to any other quantitative measure of rigidity or stiffness. In some embodiments, the rigidity or stiffness data provided herein are for the entire relevant portion or section of the lead assembly (e.g., the proximal end, the most distal portion, one or more portions that are distal to the proximal portion, etc.). Thus, such measurements of rigidity or stiffness can include the impact of all components of the lead assembly and the general configuration of the particular lead assembly section (e.g., including outer layer or covering, electrodes, contacts and/or other electrical components or devices, inserts, wires or other electrical conductors, coverings or coatings, etc.). However, in other embodiments, the rigidity of stiffness ratios and/or other data provided herein (e.g., relative data) can pertain only to one or more of the components of the lead assembly along a particular section or portion. For instance, the ratios can apply to the most rigid or stiff component (e.g., the proximal insert, the distal insert, any other insert, etc.) of the assembly along a particular portion or section.

In some non-limiting examples, rigidity along the proximal portion or section of the lead assembly (e.g., the most proximal portion that is configured to directly secure to a stimulation device), as measured by the Young's modulus (e.g., for entire section or portion as a composite that includes all components and/or other member, for only the most rigid or stiff member (e.g., insert), etc.), can be 100 to 250 GPa (e.g., 100, 150, 200, 210, 220, 230, 100 to 200, 200 to 250, 200 to 220, 200 to 230, 210 to 230 GPa, values within and between the foregoing values or ranges, etc.). Further, rigidity along one or more distal portions or sections of the lead assembly (e.g., the most distal section or portion of the assembly, one or more sections or portions that are distal to a more stiff or rigid proximal portion, etc.), as measured by the Young's modulus (e.g., for entire section or portion as a composite that includes all components and/or other member, for only the most rigid or stiff member (e.g., insert), etc.), can be 0.01 to 0.05 GPa (e.g., 0.01, 0.02, 0.03, 0.04, 0.05, 0.01 to 0.05, 0.01 to 0.04, 0.01 to 0.03, 0.01 to 0.02, 0.02 to 0.05, 0.02 to 0.03, 0.03 to 0.05, 0.03 to 0.04, 0.04 to 0.05 GPa, values within or between the foregoing values or ranges, etc.). In such a configuration, the ratio of rigidity (e.g., based on Young's modulus) between proximal and distal sections or portions of the assembly is 2000:1 to 25000:1 (e.g., 2000:1 to 25000, at least 2000:1,). However, in other embodiments, the Young's modulus and/or the relative rigidity ratios can be higher or lower than the values indicated above, as desired or required by a particular use or application.

Shaping can include the application of force to the electrode lead resulting in a change in shape of the lead. Ceasing or changing the force can result in the electrode lead maintaining the shape that was created with the applied force.

For any of the embodiments disclosed herein, a lead can include the necessary structure, components and/or design in order to be able to maintain the shape that is provided to it (e.g., by a surgeon or other practitioner) during use. For example, the lead can be configured to maintain a particular shape provided to it by a surgeon (e.g., using forceps) until another external force is imparted upon it. Such external forces can include, without limitation, a force created by the surgeon, a force created by encountering an anatomical structure (e.g., tissue) while the lead is being manipulated and/or the like.

According to some embodiments, a lead is configured to maintain the shape provided to it with no or relatively minor resilient forces attempting to have the lead otherwise revert to its original shape and/or some other steady-state shape. Such resilient forces can result from the materials used in the lead and their physical properties, the configuration of the lead and/or the like. In certain examples, once shaped in a desired orientation or manner, the lead is configured so the maximum it moves or reshapes (e.g., due to resilient forces associated with its design and configuration) is 0% to 5% (e.g., 0 to 5, 1 to 5, 2 to 5, 3 to 5, 4 to 5, 0 to 4, 1 to 4, 2 to 4, 3 to 4, 0 to 3, 1 to 3, 2 to 3, 0 to 2, 1 to 2, 0 to 1, 0 to 0.10, 0.10 to 0.25, 0.25 to 0.5, 0.5 to 0.75, 0.75 to 1, 0 to 0.25, 0 to 0.5%, values or ranges between the foregoing, etc.). In other arrangements, once shaped in a desired orientation or manner, the lead is configured so the maximum it moves or reshapes (e.g., due to resilient forces associated with its design and configuration) is greater than 5% (e.g., 5 to 10, 10 to 20, 5 to 20%, values or ranges between the foregoing, greater than 20%, etc.).

As noted above, once shaped or reshaped, a lead, according to any of the embodiments disclosed herein, can be configured to maintain or substantially maintain its shape (e.g., until re-shaped). In some embodiments, assuming external forces are imparted (e.g., directly or indirectly) on the lead, the lead can maintain the shape provided to it for a time period that is greater than 0.01, 0.1, 0.2, 0.3, 0.4, 0.5, 0.6, 0.7, 0.8, 0.9, 1, 2, 3, 4 or 5 seconds. In other configurations, such a time period is at least 0.01 to 10, 0.01 to 20, 0.01 to 30 seconds, 0.01 seconds to 1 minute, 0.01 seconds to 2 minutes, greater than 2 minutes, etc.). Accordingly, since a lead is able to maintain its shape (e.g., with no or relatively small movement after shaping) for a minimum time period, the lead can be shaped to strategically surround and/or be adjacent to a desired anatomical structure (e.g., a targeted nerve) and maintain such a shape and orientation (e.g., relative to the anatomical structure) for the duration of a procedure, as desired or required.

In some embodiments, the lead does not include any braids, coils and/or other reinforcement members. For example, many catheters, tubing and other intraluminal devices include braids, coils or other such features or components in order to provide the necessary strength, pushability, flexibility, torquability and/or other desired properties without kinking or other undesirable deformations. In contrast, however, in some embodiments, any of the lead assemblies disclosed herein can be configured to not include any reinforcing members or features (e.g., braids, coils, etc.). This can permit the lead to be shaped or re-shaped in a manner that allows the lead to maintain its shape for a minimum time period (e.g., greater than 1, 5 or 10 seconds, etc.) and/or for a duration of a procedure or step of a procedure.

Further, according to some embodiments, any of the lead assemblies disclosed herein can be manufactured and/or otherwise assembled or configured to be advanced through a portion of the anatomy (e.g., subcutaneously to and/or from an injury site, a surgical incision, etc.) without the need of needle or other rigid member. Therefore, in some arrangements, the lead assembly includes the desired strength, rigidity and/or other physical properties to overcome resistive (e.g., blocking, frictional, etc.) forces encountered when tunneling the lead through anatomical tissue. These embodiments are in contrast to other percutaneous leads commercially available that require a tool (needle assembly, guiding catheter, etc.) paired with the lead assembly to reach the target anatomy. Such lead assemblies are typically extremely flexible and may be prone to fracturing.

Figure 38A:
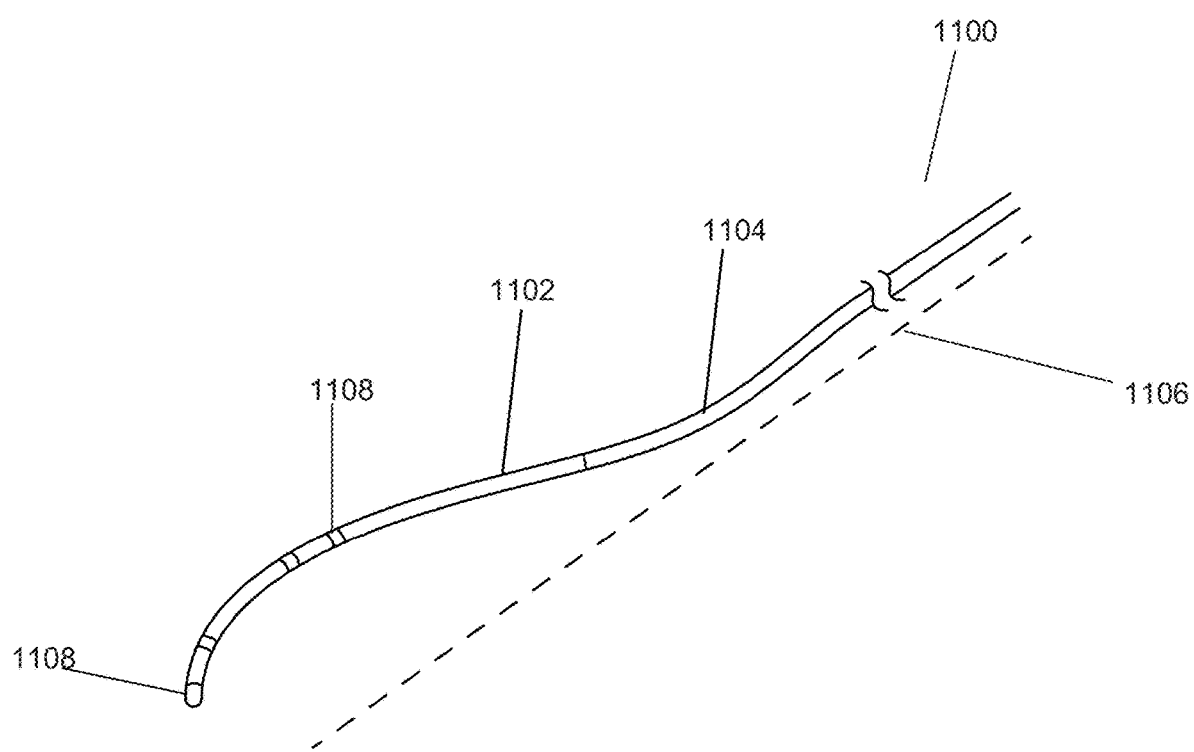
FIG. 38A illustrates a perspective view of an electrode lead that has been shaped with the shape deviating from the general longitudinal axis of the lead body according to one embodiment.
Figure 38B:
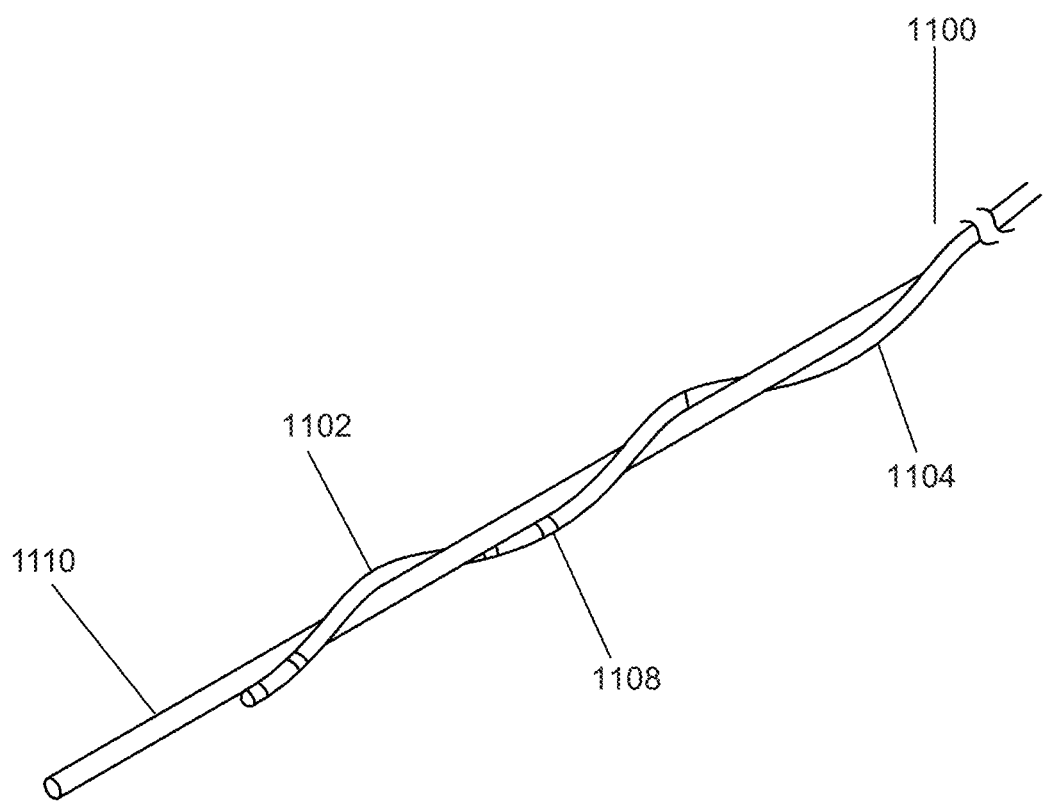
FIG. 38B illustrates a perspective view of an electrode lead that has been shaped to generally surround or wrap around a nerve structure according to one embodiment.

As shown in FIG. 38A, according to some examples, shaping may include creating a curved element of the distal aspect 1102, which may include conductive elements 1108, that deviates from the longitudinal axis 1106 of the electrode lead body 1100. In other examples, shown in FIG. 38B, shaping may be used to give the electrode lead body 1100 a generally helical shape. As illustrated, such a shape can be configured to surround a targeted nerve structure 1110.

For any of the embodiments disclosed herein, the ability for a portion of the electrode lead body 1100 (e.g., the distal aspect 1102) to hold its shape can be advantageous so that the electrode can more predictably and securely contact the nerve structure 1110 and maintain that contact (e.g., similar to a cuff electrode yet with the flexibility to be removed atraumatically).

Figure 38C:
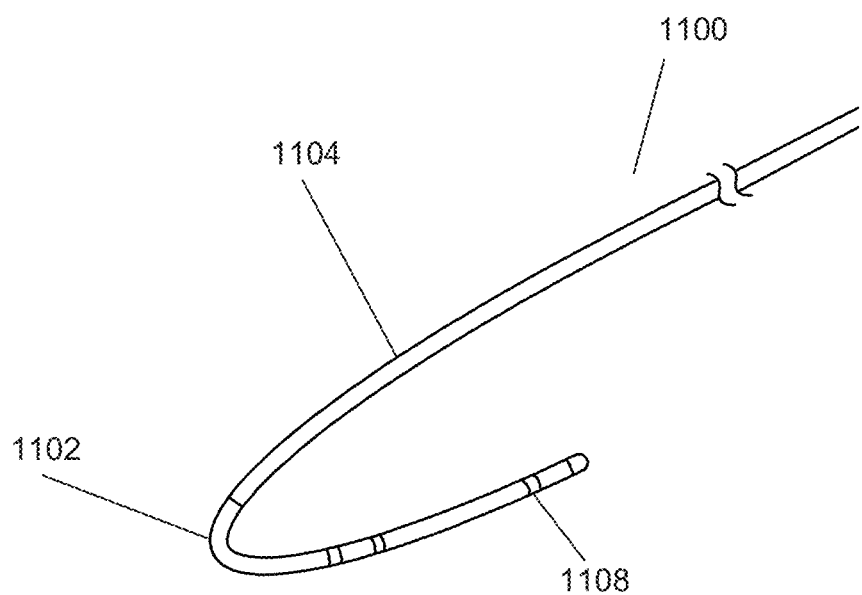
FIG. 38C illustrates a perspective view of an electrode lead that has been shaped to a U-shape according to one embodiment.

In yet another configuration, as depicted in FIG. 38C, shaping of an electrode lead body 1100 may be used to create one or more U-shaped portions. Only a few examples of shaping, the ability to shape the electrode have been illustrated and otherwise disclosed in the present application. It should be understood that selectively shaping of an electrode lead body 1100 may result in a myriad of shapes, including shapes that are not discussed within the present application, to be able to conform to any anatomical scenarios encountered and/or satisfy any other goal or purpose.

Existing devices can include one or more limitations and/or other disadvantages vis-à-vis embodiments disclosed herein. For example, in cardiac applications, catheter type electrode leads are often used to pace the heart (e.g., provide electrical stimulation or other energy to heart tissue), record signals from the heart and/or the like. Any shaping of the distal aspect of these catheter type leads can occur prior to placement within the body. Manufacturers typically produce various models having distal aspects (and/or other portions) that include different shapes. Such varying models can be selected based on one or more factors, such as, for example and without limitation, the insertion method that is used to enter the subject's anatomy (e.g., femoral or radial artery access), one or more characteristics of the subject's anatomy (e.g., whether the subject's aorta is narrow or wide). Furthermore, such prior shaping technologies are not limited to catheters with electrodes, but can also include guidewires, guide catheters or more generally devices that must traverse through a subject's vasculature or other intraluminal anatomical network.

In the neurosurgical field, electrodes used to interface the brain (e.g., deep brain stimulating electrodes) or the spinal cord (e.g., spinal cord stimulation electrodes) are presently placed under image guidance to ensure localization with high precision. These procedures are minimally invasive and do not require open surgery. Under such circumstances, electrodes are not shapeable, but are instead sufficiently flexible to be compliant with the tissue they interface (e.g., brain or spinal cord). A stylet, metal insert or other device is typically used for placement of these leads in order to provide the requisite stiffness, pushability and/or other properties within the tissue. Removal of the stylet can allow for the surrounding tissue to exert forces on the lead to keep it in place. However, without surrounding tissue, the flexibility of the lead may not allow it to be shaped and used in the context of peripheral nerve repair where the repair procedure is typically performed in an open surgical area (e.g., or minimally invasive). The ability to shape the lead to the specific anatomical area (e.g., during a surgical procedure) is not possible with existing technologies.

In some embodiments, the electrode lead may include one or more conductive elements 1108 distributed along one or more portions of the lead (e.g., the distal aspect of the lead). In other arrangements, the conductive elements 1108 are positioned along the length of the lead, either in lieu of or in addition to being at or near the distal end of the lead, as desired or required. The conductive elements can include different shapes, sizes and/or other characteristics, as desired or required. For example, as illustrated in FIG. 38A, the conductive element 1108 at the distal end of the electrode lead body 1100 may be shaped in a manner to cap the electrode lead body 1100 and also provide a larger surface area that may be used to provide stimulus current to tissue such as peripheral nerves. With continued reference to FIG. 38A, a second conductive element 1108, positioned away from the tip element, can be shaped as a ring with said ring varying in width from 0.05 to 5 mm (e.g., 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5 mm, ranges between the foregoing, etc.) and/or can be physically coupled to a conductive insulated wire 1122 (e.g., directly or indirectly). In some arrangements, at least two conductive elements 1108 are used to create a bipolar stimulating field. A plurality of conductive elements can also form an electrical stimulation array allowing to shape or otherwise modify or impact the current field.

According to some embodiments, the orientation of the anode and cathode differ from traditional orientations or configurations. For example and more specifically, in cardiac applications with bipolar electrode configurations, the cathode can be in the distal most electrode. In some arrangements, the shapeable lead with multiple conductive elements comprises a distal anode and a proximally placed cathode (e.g., the opposite of a traditional cardiac pacing electrode). Such a configuration may be advantageous in the delivery of neuroregenerative therapy as one mechanism of action for this therapy is the conduction of action potentials proximally towards the cell body. In some embodiments, when the lead is placed upstream or proximal to the nerve injury site, a resulting electrical field may depolarize the target nerve and cause action potentials to travel proximally towards the cell body. If the electrode configuration is traditional (distal cathode, proximal anode) there is a risk that at higher stimulation amplitudes anodal block may occur resulting in a blocking of conducting action potentials and a potential decrease in therapeutic efficacy. Reversing the configuration (distal anode, proximal cathode) obviates this situation. This holds true only when an electrode lead is inserted into the patient from a proximal to distal trajectory.

In some embodiments, the spacing between the cathode and anode in a bipolar configuration may be large enough to span a site of nerve injury, such distances between anode and cathode may include 3 to 50 mm (e.g., 3 to 10, 10 to 20, 20 to 30, 30 to 40, 40 to 50, 10 to 50, 20 to 50, 30 to 50, 3 to 20, 5 to 20, 10 to 40, 10 to 30, 20 to 50, 20 to 40, 30 to 50 mm, values or ranges between the foregoing ranges, etc.).

According to some embodiments, such configurations include a distal anode and a proximal cathode such that the cathode is situated proximal to the site of injury. This can allow action potentials to travel unimpeded (or substantially unimpeded) towards the cell body for therapeutic efficacy. Another advantage of such a configuration is that the electrical field resulting from the electrodes spanning the injury site can, in some embodiments, further provide a neuroregenerative effect through other mechanisms of action. In some arrangements, this is known that Schwann cells, Macrophages, and other support cells in the vicinity of the nerve injury site are responsive to electrical field gradients and these may in turn further facilitate neuroregeneration.

In some embodiments, the electrode lead body 1100 with multiple conductive elements 1108 (e.g., as described herein) is coupled (e.g., physically, electrically, operatively, directly, indirectly, etc.) to a stimulation source that can include circuitry to test the connectivity and placement of the electrode lead. In some arrangements, the stimulation source can also be configured to provide neuroregenerative therapy (e.g., via the delivery of stimulation energy). In other arrangements, the stimulation source can also be configured to provide pain management therapy (e.g., chronic pain management by electrical stimulation).

In some embodiments, the electrode lead comprises a circular or curved shape (e.g., at least a partial circular or curved shape) and comprises an outer diameter (or other cross-sectional dimension) of 0.1 to 5 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 1-4, 0.5-4, 1-4, 0.1-5, 4-5, 3-5, 2-5 mm, ranges between the foregoing, etc.).

In some embodiments, the electrode lead comprises multiple sections (e.g., 2, 3, 4, 5, more than 5, etc.). Each section can include a different shape. However, in some configurations, two or more of the sections can include a similar or generally similar shape, as desired or required.

Figure 39A:
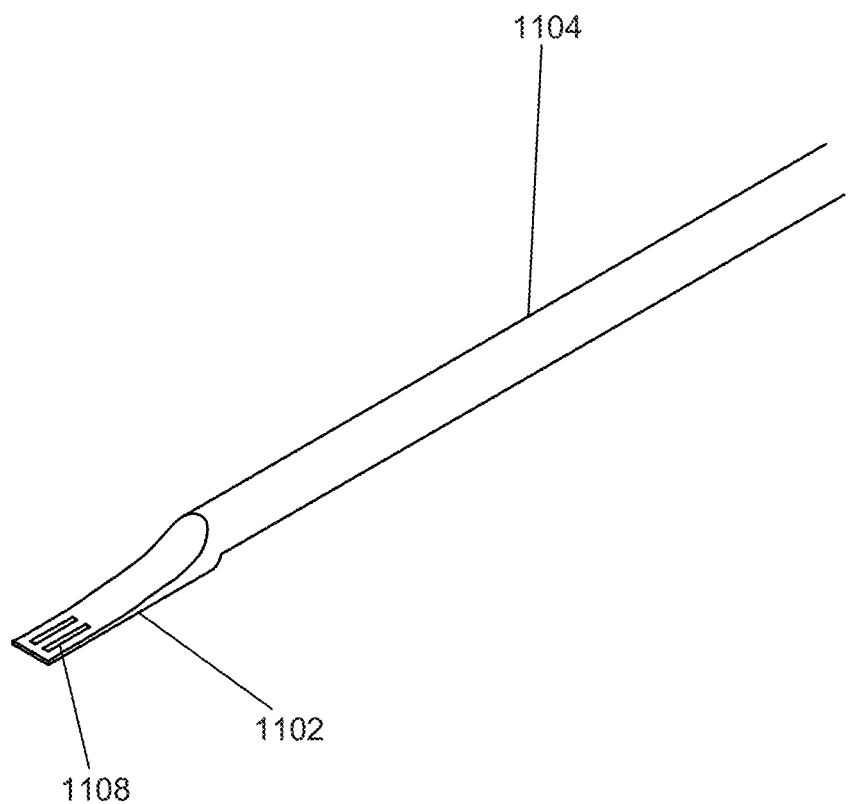
FIG. 39A illustrates a perspective view of an electrode lead with a distal flat portion used to interface a nerve according to one embodiment.

According to some embodiments, as depicted in FIG. 39A, the cross-sectional shape of the proximal aspect of the electrode lead may be at least partially circular, cylindrical and/or otherwise curved, while the cross-sectional shape of the distal aspect may include a thin rectangular shape (or other non-circular or curved shape). In some arrangements, the longitudinal shape may be tapered (e.g., from a larger outer diameter to a smaller outer diameter). In some arrangements, the proximal aspect may be shapeable, allowing the user to have the electrode lead deviate from the longitudinal course of the nerve, while maintaining nerve contact at or along the distal end. However, in other embodiments, the proximal aspect or portion of the electrode lead can remain circular for its entire length. In some configurations, the cross-sectional shape and size of the lead remains constant or substantially constant for the entire or substantially the entire length of the lead (e.g., including the proximal portion that is configured to couple to a stimulation device or other device).

According to some arrangements, the thickness of an electrode lead can vary along its length. For example, the thickness of the lead can be different in one or more sections. The generally flattened rectangular shape, for instance, may be sufficiently thin (e.g., 10 μm to 500 μm) in relation to the cylindrical component. This may be advantageous as the thin rectangular portion may interface the injured nerve atraumatically by being positioned underneath the nerve, while the cylindrical portion facilitates percutaneous placement or delivery and withdrawal of the interface via an insertion tool.

Figure 39B:
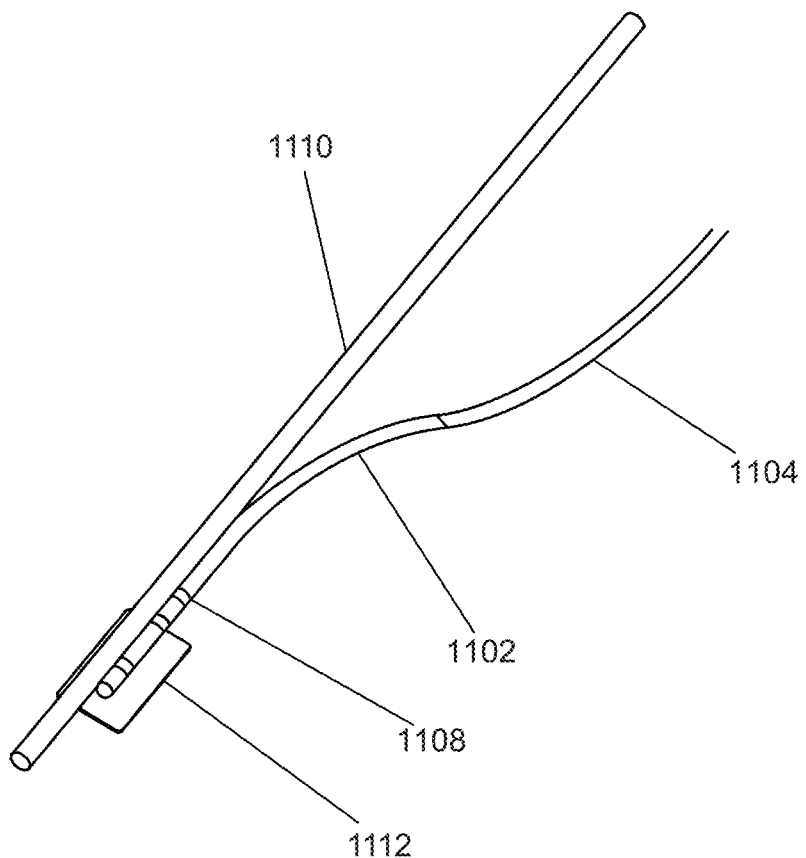
FIG. 39B illustrates a perspective view of an electrode lead interfacing a nerve with a flat rectangular flap used for anchoring according to one embodiment.

In some embodiments, as illustrated, for example, in FIG. 39B, the thin rectangular shape or flap 1112 can be used to anchor or otherwise secure (e.g., temporarily, permanently, etc.) a cylindrical lead through surface tension (e.g., using fluids located in and/or around tissue to provide surface tension with the flap). In some arrangements, the thin rectangular shape comprises one or more flexible (e.g., non-rigid) materials, such as, for example and without limitation, a polymeric material, an elastomeric material and/or the like (e.g., silicone rubber, polyurethane, etc.).

Figure 40A:
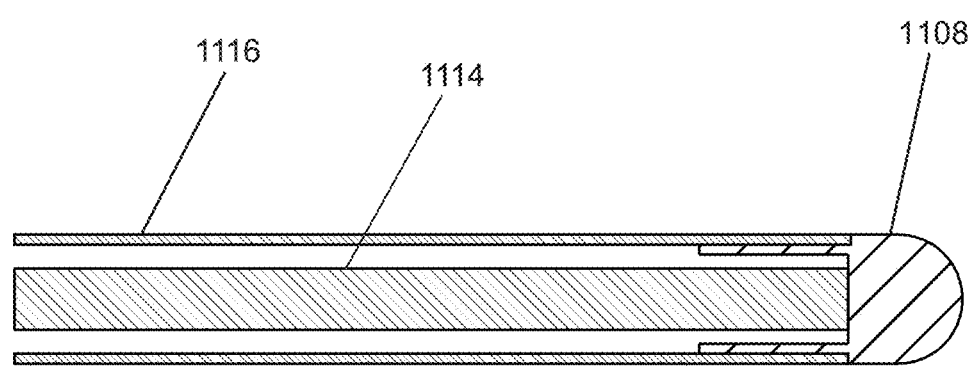
FIG. 40A illustrates a longitudinal cross-sectional view of the distal end of an electrode lead having a shapeable insert visible according to one embodiment.

In some embodiments, the distal aspect of the electrode lead comprises one or more materials that may be shaped. In one example, as illustrated in FIG. 40A, the lead is configured to be shaped as a result of, at least in part, an insert 1114 that may be located within the electrode lead body 1100. Such an insert 1114, in some configurations, may be coupled to a conductive element 1108 placed at the distal end (e.g., tip) of the electrode lead body. Said assembly may then be covered (e.g., using a layer, coating, jacket, other covering, etc. 1116). Such a covering can comprise one or more polymeric and/or elastomeric materials. In one example, the insert 1114 can be conductive (e.g., at least partially) and act as a wire or other conductor carrying signals to and from a conductive element.

Figure 40B:
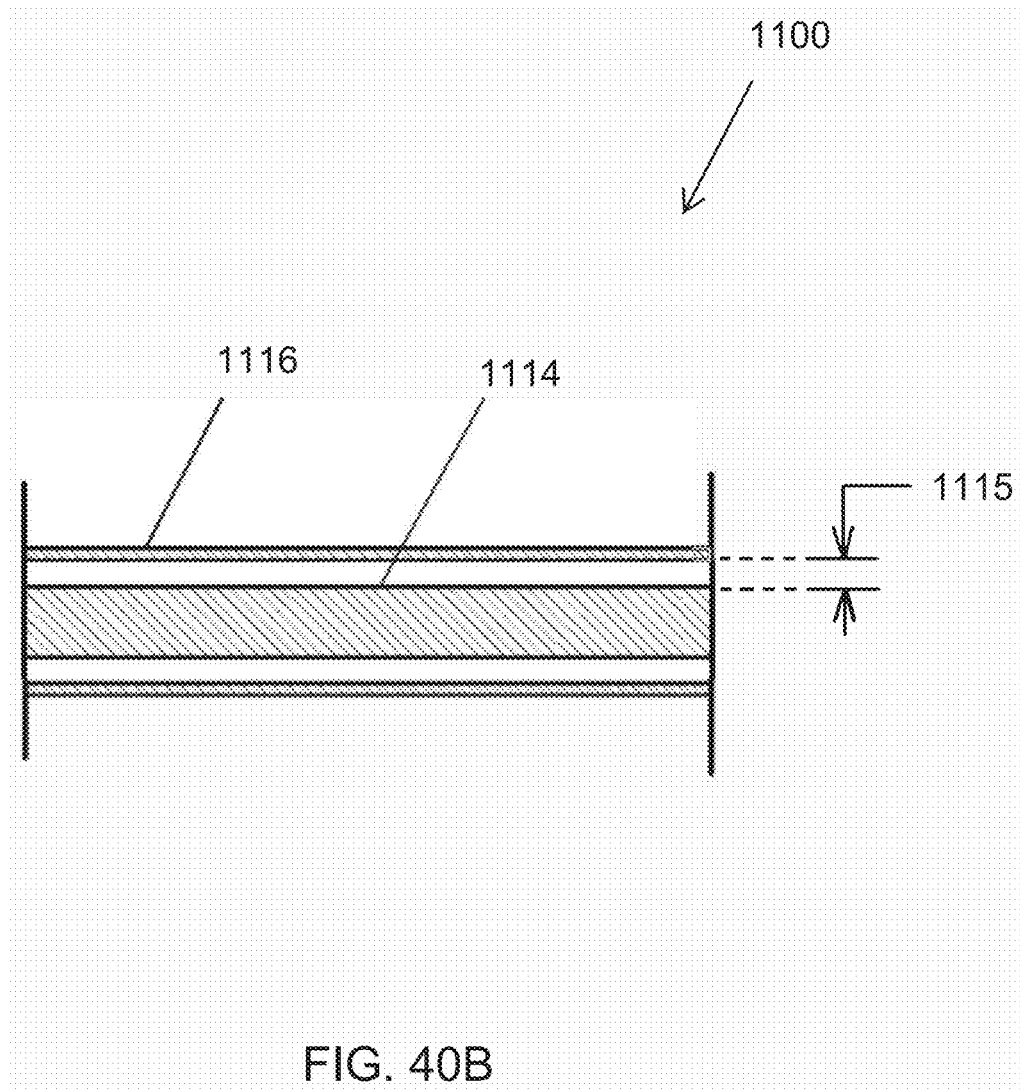
FIG. 40B schematically illustrates a partial longitudinal cross sectional view of a shapeable lead assembly according to one embodiment.

For any of the embodiments disclosed herein, as depicted schematically in the partial longitudinal cross-section of FIG. 40B, an electrode lead assembly 100 can be configured to be shapeable or manipulatable using a combination of: (1) at least one shapeable (e.g., malleable, bendable, etc.) insert or other member 1114, and (2) at least one softer outer jacket and/or other covering 1116. The lead assembly can include additional layers, coatings, members, components, features and/or the like, as desired or required. For instance, the electrode lead can include one or more of the following: electrodes, wires or other electrical conductors, other electrical components, braiding, other structural elements or features, lumens or other passageways and/or the like.

As used herein, electrical wire and electrical conductor are broad terms and can include, but are not limited to, wires, printed circuit boards, conductive tracks, conductive pads, etched conductive features, soldered conductive features, other electrically conductive features and/or any other device, member, component or feature that is configured to have electrically conductive properties.

With continued reference to the schematic of FIG. 40B, for any of the embodiments disclosed herein, the shapeable insert or member 1114 can be configured to maintain its shape after being shaped by a practitioner or other user. Likewise, the electrode lead 1100 that comprises the shapeable insert or member 1114 can be configured to maintain its shape after shaping. Shapeable inserts or members 1114, and thus the corresponding leads or lead assemblies 1100 in which they are included, can be configured to maintain their shape during a procedure. In some embodiments, such leads 1100 can be configured to be re-shaped after the initial shaping during use (e.g., during the execution of a treatment procedure). For instance, a shapeable insert or member 1114 (and as a result, the entire lead) can be reshaped by exerting a force and/or moment on one or more portions of the lead. As discussed herein, such forces can be applied by a practitioner or other user manually (e.g., using the practitioner's hands) and/or using one or more tools (e.g., forceps, other surgical instruments or tools, etc.). In another example, the lead assembly may be shaped and/or re-shaped by the normal forces exerted by the surrounding anatomy. This can be advantageous in at least two scenarios, such as, for example, during long term implantation and/or during a lead removal procedure.

By way of example, during long term implantation (e.g., for pain management therapy), forces (e.g., passive forces) exerted on a shapeable insert or member (e.g., by the surrounding tissue and/or other portions of the anatomy, other sources of force, etc.) can reshape (e.g., continuously reshape) the electrode lead allowing it to conform to the desired location without creating undue tension or stress on the injured nerve. Also for purposes of illustrated non-limiting examples, during lead removal (e.g., pulling the lead out of the anatomy of a subject) forces (e.g., passive forces) exerted on the shapeable insert or member (e.g., by the surrounding tissue and/or other portions of the anatomy, other sources of force, etc.) can cause the lead to deform, at least partially (e.g., to a straight line, generally a straight line, a smooth curve, etc.) such that the lead may be removed without kinking, buckling and/or otherwise undergoing deformation that may induce injury to the surrounding anatomy of the subject.

For any of the embodiments disclosed herein, an insert or other member 1114 of the lead assembly 1100 that is configured to facilitate shaping or re-shaping of the assembly can include plastic deformation properties. In other words, such an insert or other member 1114 can be configured for distortion that occurs when a material is subjected to certain forces or stresses (e.g., tensile, compressive, bending, or torsion forces or stresses) that exceed its yield strength and cause it to elongate, bend, twist and/or the like. Such a distortion can be temporary, such that the insert or other member can maintain its shape when no external forces are exerted on it (e.g., as it sits on a table or other surface, until a user exerts another bending or other re-shaping force or moment, etc.). In some arrangement, when the electrode lead is handled (e.g., in mid-air with the distal shapeable aspect unsupported or otherwise not impacted by other external forces), the force of gravity is not sufficient to shape the lead with the lead being sufficiently rigid to maintain the desired shape.

For any of the embodiments disclosed herein, an outer jacket or other outer covering 1116 of the lead assembly 1100 can include elastic deformation properties. In other words, such an outer jacket or covering can be configured to undergo a temporary change in shape once a force is exerted on the lead assembly, and thus the outer jacket or covering. Such members with elastic deformation properties are configured to reassume their original shape or orientation (e.g., are at least partially self-reversing) once the force or moment is removed or reduced. For example, an extruded polymeric tube used as an outer jacket is typically extruded in a lengthwise manner (e.g., the length of the tube is greater than the diameter or other cross-sectional dimension). In some arrangements, the tube is configured to maintain the extruded conformation when forces are applied (e.g., in a perpendicular direction) to the longitudinal axis of said tube. Such a characteristic can help account for the elastic recoil of the tube back (e.g., completely, substantially completely, partially, etc.) to the original conformation when a force is applied. Plastically deforming of the tube could require stretching the tube beyond its yield strength.

In some embodiments, as illustrated schematically in FIG. 40B, a gap or space 1115 exists between the insert or other member 1114 and the outer jacket or covering 1116. In one arrangement, the gap does not include any materials. However, in some configurations, one or more intermediate layers or members (not shown in FIG. 40B) are located within the gap or space 1115. In other arrangements, the insert or other member 1114 is configured to at least partially contact the outer jacket or covering 1116, as desired or required. Thus, in some embodiments, there is no gap or space between the insert 1114 and the outer jacket 1116.

For any of the embodiments disclosed herein, a shapeable lead assembly 1100 can be configured to not include any lumens or other interior openings. However, for any of the embodiments disclosed herein, a shapeable lead assembly 1100 can be configured to include one or more lumens or other openings. In some embodiments, a shapeable lead assembly 1100 does not include any shapeable tubes and/or other at least partially hollow (e.g., non-solid) members. In some embodiments, the lead assembly 1100 comprises at least one insert or interior member 1114 that at least partially assists with the bending of the assembly and maintaining the shape of the assembly 1100 once it has been shaped or otherwise manipulated.

For any of the embodiments disclosed herein, the lead assembly 1100 can be configured to be shaped and/or reshaped during a treatment procedure (e.g., a neuroregenerative procedure). A practitioner or other user can shape or re-shape an insert once a procedure has commenced. For example, the configuration of any of the lead assemblies 1100 disclosed herein can permit a practitioner to change the shape, direction, orientation and/or the like of the assembly 1100 after it has been inserted within and/or on a subject. In some embodiments, for instance, a practitioner can manipulate the assembly 1100 to shape or re-shape it to conform to the anatomy of the subject (e.g., to contact or be in a desired orientation relative to a nerve, to wrap at least partially around a nerve, to abut, secure to and/or otherwise be located near another anatomical feature of subject, etc.).

Manipulation can be accomplished by selectively applying forces, pressure, moments and/or any other external influence on one or more portions of the lead assembly 1100. In some embodiments, as noted herein, such forces or other external influence can be performed manually (e.g., using the practitioner's hand(s)) using forceps and/or other instrumentation or tools, robotically and/or the like, as desired or required.

According to some arrangements, the insert 1114 may be coupled to a wire or other conductor that is coupled to a conductive element. In other embodiments, the insert 1114 may be coupled to a conductive element on one end and a wire or other conductor on the other end that is coupled to a connector. Such material may include various types of metals and/or alloys, such as, for example and without limitation, copper, silver coated copper, polyimide coated copper, platinum coated tungsten, stainless steel, lead, tin, etc. In some arrangements, the metals may be annealed to soften their structures which may allow them to be shaped with less force than prior to annealing. In some arrangements the metal may be incorporated into the distal aspect of the electrode lead as an insert that may comprise of a rod or cylindrical structure. The length of the insert may not be limited to the distal aspect. For example, in some embodiments, the insert spans the entire length of the electrode lead or a majority of the length of the electrode lead (e.g., 50-60, 60-70, 70-80, 80-90-90-100, 50-75, 5-90, 60-90% of the length of the electrode lead, percentages between the foregoing ranges and values, etc.), as desired or required.

In some embodiments, the insert can be coupled (e.g., directly, indirectly, etc.) to a conductive element. The insert can be coupled to a conductive element using any suitable technology or methods, including, for example, resistance welding, laser welding, soldering, crimping, other technologies/methods used to couple metals to one another and/or like.

In some embodiments, the lead housing or jacket can comprise one or more elastic or semi-elastic materials, such as, for example, silicone rubber (e.g., silicone rubber tube), polyurethane, other polymeric materials, other types of elastomeric or rubber materials, other flexible or semi-flexible materials (PEBAX™, Pellethane™, etc.).

In some embodiments, when force is applied to shape the electrode lead body 1100, the insert 1114 is configured to undergo deformation (e.g., plastic deformation). In some examples, the jacket 1116 may also undergo similar deformation (e.g., plastic deformation) as a result of such an application of force. In some embodiments, the jacket may undergo elastic deformation. In such cases, the elastic recoil force of the jacket may be insufficient to overcome the plastic deformation of the insert resulting in the electrode lead maintaining its shape. In some arrangements, desired shapes are retained until other forces are applied that reshape the lead, for example forces resulting from the manual manipulation or the act of lead removal.

Figure 40C:
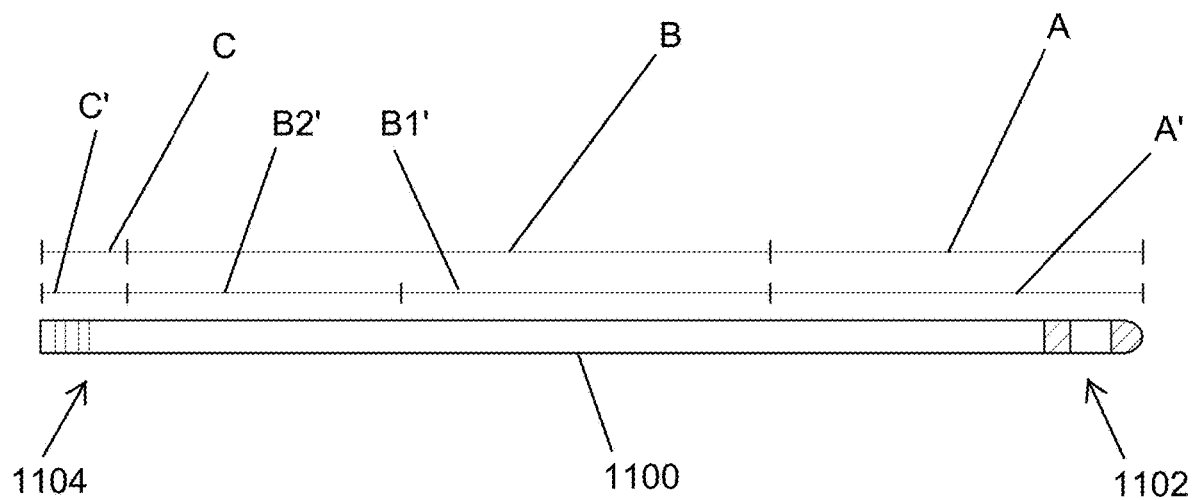
FIG. 40C schematically illustrates one embodiment of a lead assembly.

With reference to the schematic illustrated in FIG. 40C, a lead assembly 1100 can include a proximal portion or aspect 1104 and a distal portion or aspect 1102. As discussed in greater detail herein, the proximal portion 1104 can be configured to be secured (e.g., directly or indirectly) into a corresponding port of a stimulator or other device or component. As shown in FIG. 40C and discussed with reference to other arrangements herein, the lead assembly 1100 can include a constant or substantially constant outer diameter along its length. In some embodiments, the distal end of the assembly includes a rounded or otherwise tapered shape; therefore, in such configurations, the constant or substantially constant outer diameter applies to only to the length of the lead assembly proximal to the beginning of the circular distal end or other tapered configuration of the distal end.

As illustrated in FIG. 40C and discussed in greater detail herein, the distal portion or aspect 1102 of the lead assembly 1100 can include one, two or more electrodes. Further, as also shown, the proximal portion or aspect 1104 of the assembly 1100 can include one, two or more contacts along the exterior surface of the assembly. Such contact can help electrically couple the electrodes to a stimulation unit or other device or component (e.g., once the assembly 1100 has been inserted within a corresponding port or opening of such a device or component).

In some embodiments, as discussed in the present application, the proximal portion or aspect 1104 of the lead assembly 1100 can include a stiffer or more rigid configuration than the distal portion or aspect 1102 of the assembly. In some embodiments, the distal portion or aspect 1102 is further configured to be shaped in a desired configuration. The lead assembly 1100 can be configured such that the distal aspect or portion and/or other sections or portions of the assembly can maintain such a desired shape (e.g., for the duration of a procedure, until re-shaped or removed, for a minimum time period, etc.), as desired or required.

With continued reference to FIG. 40C, the length (e.g., along the longitudinal or axial direction of the lead assembly) of the lead assembly 1100 can include two or more sections or portions with distinct physical characteristics. As discussed, in some embodiments, the proximal portion or aspect 1104 can be rigid or stiff relative to one or more distal portions or aspects 1102. In some arrangements, the section C of the proximal portion or aspect 1104 that includes the relatively rigid or stiff configuration can extend 0% to 10% (e.g., 0 to 2, 2 to 4, 4 to 6, 6 to 8, 8 to 10%, values between the foregoing ranges, etc.) of the total length of the lead assembly 1100. However, in other embodiments, the section C of the proximal portion or aspect 1104 that includes the relatively rigid or stiff configuration can extend more than 10% (e.g., 10 to 15, 15 to 20% more than 20%, etc.) of the lead assembly. By way of example, the length of the section C that includes the relatively rigid or stiff configuration is 30 mm (e.g., for a lead assembly that has a diameter of about 0.05 mm and an overall length of about 440 mm).

The portion of the lead assembly 1100 that is less rigid or less stiff than the proximal section or aspect and that can be configured to maintain a desired shape can be positioned only along the distal portion or aspect 1102 of the assembly 1100. Thus, in such embodiments, such a shapeable portion of the lead assembly can be located along a distal section A of the assembly. In some embodiments, such a shapeable, less rigid portion can extend from the distal end of the assembly to the distal end of the stiffer, more rigid proximal portion. Thus, in the schematic of FIG. 40C, sections of the lead assembly 1100 denoted by lengths A and B can be identical in configuration and design, allowing the entire portion of the assembly 1100 distal to section C to be shaped and reshaped, in accordance with the various embodiments disclosed herein. In other embodiments, however, section B can have a different (e.g., greater) stiffness or rigidity than section A of the lead assembly 1100, as desired or required. Further, a lead assembly can be configured to include one or more additional sections (e.g., Sections A', B1', B2') of varying rigidity, stiffness and/or other physical configuration. In some embodiments, as illustrated schematically in FIG. 40C, the electrode(s) of the lead assembly are located along the less rigid or stiff portion while the contact(s) (e.g., which couple the electrode(s) to a stimulation or other device or component once the lead assembly is coupled to such a device or component) are located along the more rigid or stiff portion.

Figure 40D:
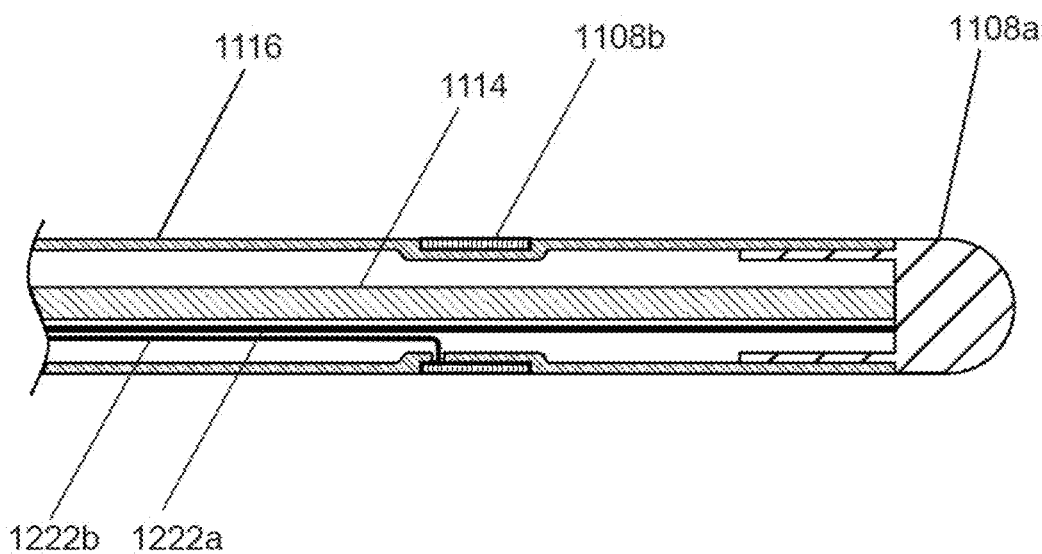
FIG. 40D illustrates a longitudinal cross-sectional view of a distal end of a lead assembly in accordance with one embodiment.
Figure 40E:
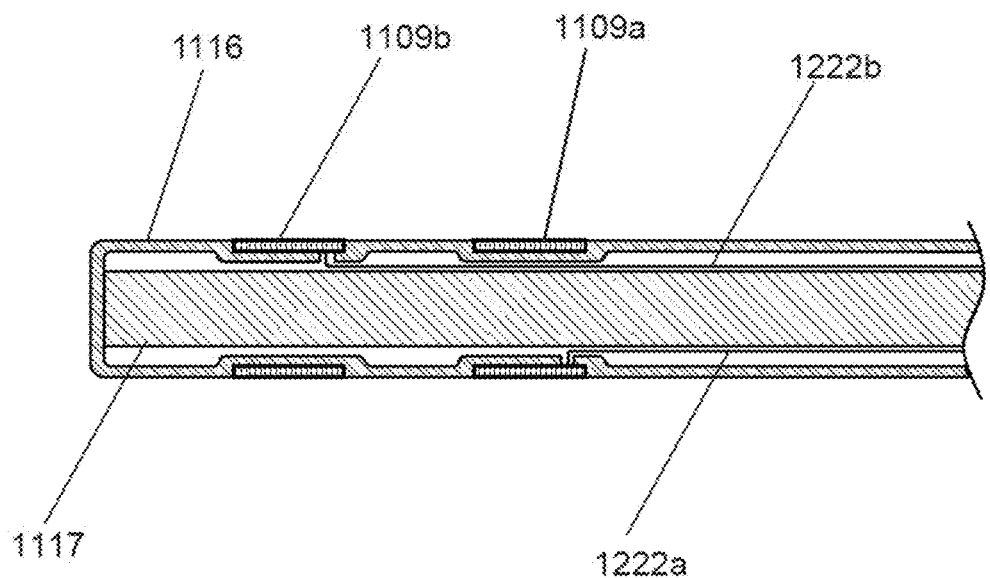
FIG. 40E illustrates a longitudinal cross-sectional view of a proximal end of the lead assembly of FIG. 40D.

FIGS. 40D and 40E illustrate longitudinal cross-sectional views of one embodiment of a lead assembly 1100. As shown, the distal portion includes an insert 1114 positioned along its interior. In some embodiments, the insert 1114 extend to or near the distal end of the lead assembly. The depicted assembly includes two electrodes 1108a, 1108b that are separated by a particular distance from one another. In some embodiments, such a separation distance is 15 mm; however, the separation distance can be greater or lower than 15 mm, as desired or required. Further, in other arrangements, more (e.g., 3, 4, more than 4) or fewer (e.g., 1) electrodes can be included in a particular lead assembly.

With continued reference to FIGS. 40D and 40E, the distal electrode 1108a can include a rounded or tapered distal end. In some arrangements, the distal electrode extends to the distal end of the lead assembly. However, in alternative configurations, the distal electrode 1108a may not extend to the distal end of the assembly. As shown, the electrodes can include any desired shape or configuration (e.g., cylindrical, cylindrical with a domed or cap structure, etc.).

The electrodes 1108a, 1108b can be electrically coupled to corresponding electrical contacts 1109a, 1109b along the proximal portion of the lead assembly (e.g., using one or more wires or other electrical conductors 1222a, 1222b). As discussed herein, the proximal portion of the lead assembly can include a stiffer or more rigid configuration. For example, in some embodiments, the proximal portion or aspect includes its own insert 1117. In some arrangements, the insert 1117 along the proximal portion of the lead assembly is stiffer or more rigid than the insert along the distal portion. A unitary or segmented outer covering 1116 can be positioned along the outside of the assembly. In some embodiments, the inserts 1114, 1117 can include one more metals or alloys (e.g., stainless steel, other steel, copper, brass, etc.). Therefore, for any of the embodiments disclosed herein, the inserts can include an outer jacket, cover, coating, layer and/or the like to electrically insulate the insert from the wires, conductors and/or any other electrical components of the lead assembly. In some embodiments, such a jacket or covering comprises one or more polymeric materials (e.g., polyimide).

Figure 41:
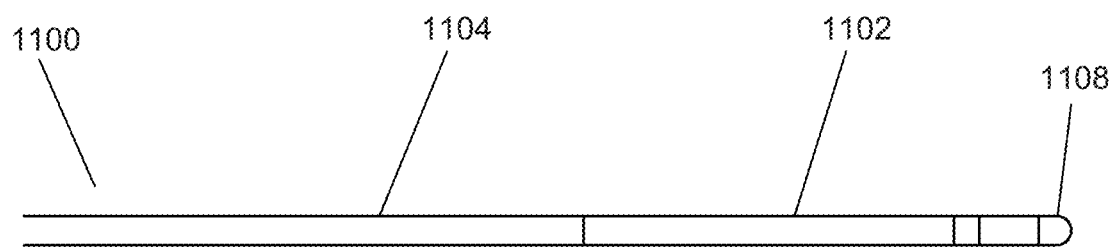
FIG. 41 illustrates a profile view of an electrode lead having two distinct regions according to one embodiment.

In some embodiments, the lead housing or jacket 1116 can comprise a uniform or continuous material thickness throughout the length of the lead body 1100. In some embodiments, the jacket may comprise multiple durometers. For example, as illustrated in FIG. 41, a lower durometer material may be used for the distal shapeable aspect 1102 of the lead while a higher durometer may be used for the proximal aspect 1104 (e.g., that may be advantageous in pushing the lead into and advancing it within tissue). While such an example outlines two sections with two durometers, a lead is not necessarily limited to two durometers, but may include multiple segments with varying durometers within or between segments.

Under certain circumstances, the durometer of the distal aspect of a lead can be 20D to 50D on the shore D scale (e.g., 20D, 25D, 30D, 35D, 40D, 45D, 50D, 20D to 50D, 25D to 45D, 30D to 40D, 20D to 40D, 30D to 50D, values and ranges between the foregoing values and ranges, etc.), while the durometer of the proximal aspect can be 50D to 80D on the shore D scale (e.g., 50D, 55D, 60D, 65D, 70D, 75D, 80D, 50D to 80D, 55D to 75D, 60D to 70D, 50D to 70D, 60D to 80D, values and ranges between the foregoing values and ranges, etc.). Thus, in some embodiments, as noted herein, the hardness, and thus the corresponding durometer, of the proximal aspect of a lead can be greater than that of the distal aspect of the lead, as desired or required.

While the durometer is one parameter that can have an impact (e.g., a significant impact, under certain circumstances) on the shapeability, functionality and/or other aspects of a shapeable lead assembly, one or more other properties, such, for example, wall thicknesses of materials/components, can also be impactful (e.g., can be important).

According to some embodiments, a relatively thick outer jacket and/or other covering may require a relatively large amount of force to shape the lead assembly. For instance, consideration must be given to the fact that such force should be sufficient to also shape the insert positioned within the jacket and/or other covering.

By way of example, under certain embodiments, wall thicknesses for the jacket or other outer covering of a lead assembly between 100 and 400 µm can allow for suitable flexibility of the entire lead assembly (e.g., to permit a practitioner or other user to have the lead assembly assume the desired or require shape). Thus, in some arrangements, the wall thickness of the jacket or other outer covering of the lead assembly should be between 100 and 400 µm (e.g., 100-150, 150-200, 100-200, 100-300, 200-300, 150-300, 100-400, 100-500, 200-400, 200-500, 300-500, 400-500 µm, values between the foregoing ranges, etc.), as desired or required.

In addition, the relation of the wall thickness of the jacket or other outer covering to the diameter (or other cross-section dimension) of the corresponding insert can also impact the shapeablility and/or other aspects of the functionality of the lead assembly. For example, in some embodiments, the diameter of the insert is equal to or greater than the wall thickness of the jacket or other outer covering of the lead assembly. For example, the thickness of the jacket or other outer covering can be 100%-500% (e.g., 100-500, 200-400, 100-400, 200-500, 300-500, 150-200, 100-150, 100-200, 200-300, 400-500%, percentage values between the foregoing ranges, etc.) of the diameter of the insert.

Under certain circumstances, while a thickness of the jacket or other outer covering is greater than the diameter or other cross-sectional diameter of the insert, the lead assembly can still achieve the desired or required shapeability. However, in some embodiments, this can arise only if the material of the jacket is relatively soft and pliable. Thus, under such conditions, this can unfavorably reduce the pushability of the electrode lead and may result in kinking, an undesirable effect.

In some embodiments, a balance can be struck between the combination of the jacket durometer, jacket wall thickness, and insert diameter (assuming a cylindrical structure) to achieve the desired characteristics of a shapeable electrode lead. These desired characteristics may also be chosen to achieve a particular tensile modulus ratio between varying segments in the lead. For example, the ratio of tensile moduli of the proximal aspect to the shapeable distal aspect can be 10 to 20000 or greater (e.g., 10 to 1000, 10 to 100, 100 to 500, 500 to 1000, 250 to 750, 300 to 700, 10 to 200, 10 to 500, 100 to 20000, 10000 to 20000, 10000 to 30000, 20000 to 30000, 20000 to 25000, 20000 to 40000, 30000 to 50000, ratios between the foregoing ranges and values, etc.).

In some embodiments, the shapeable component of an electrode lead may be constructed, at least partially, from and/or with a coiled wire. In some arrangements, the coiled wire spans the length of the lead. In other arrangements, the coiled wire spans only a portion of the length of the lead. For example, the coiled wire can span only a first length or portion (e.g., the first 10 cm or less, such as, for example, 0-10, 2-8, 1-5, 5-10 cm, lengths between the foregoing ranges, etc.) of the lead. However, the extent of the coiled wire need not be limited to these distances (e.g., can be greater than 10 cm, as desired or required). In some embodiments, the coiled wire is physically coupled (e.g., directly or indirectly) to an electrode. In other embodiments, the coiled wire is not electrically coupled to any stimulating electrodes. In some embodiments, the coiled wire serves as an electrical connector to other circuitry located at, along or near the distal end of the lead housing. Depending on the application, required flexibility and memory properties and/or other design considerations, the spacing between adjacent coils is zero (e.g., the coils are touching one another) or is a fixed distance. In some embodiments, the coiled wire is insulated or uninsulated. In some arrangements, the coiled wire is encased, at least partially, in and/or with a flexible jacket or other covering, as discussed above. In some embodiments, the coiled wire may act as an electromagnetic shield, thereby providing at least partial noise immunity to wires or circuitry contained within it.

Figure 42A:
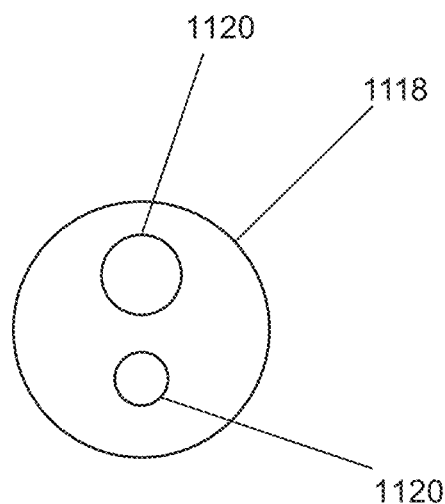
FIG. 42A illustrates an axial view of a multi-lumen lead housing according to one embodiment.
Figure 42B:
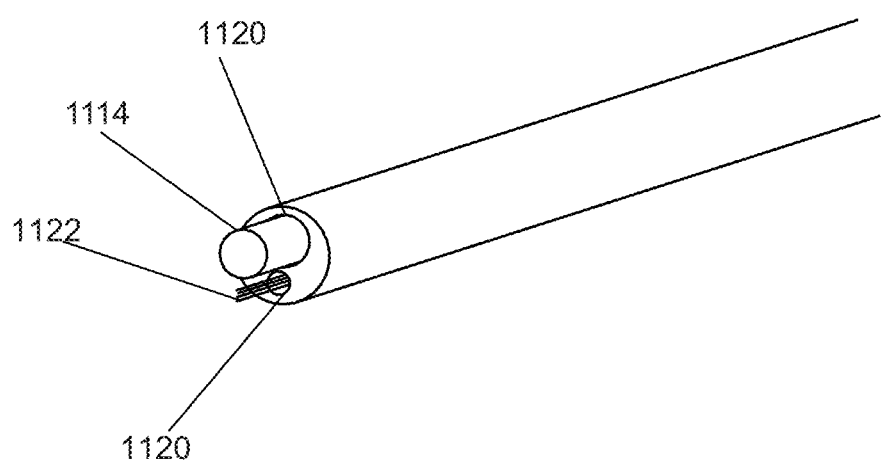
FIG. 42B illustrates a perspective view of a multi-lumen lead housing showing both shapeable insert and wires within the lumens according to one embodiment.

In some embodiments, as shown in FIG. 42A, a multi-lumen extrusion or other design may be used in the lead housing 1118. Thus, in such embodiments, the lead housing can include two or more lumens extending (e.g., partially, completely) through it. In some examples, as shown in FIG. 42B, one lumen 1120 may be used to house or otherwise receive (e.g., slidably, permanently, temporarily, etc.) an insert 1114, while other lumens may house wires or other conductors 1122 that connect to conductive elements. In other arrangements, a lumen may be configured to receive a stylet (e.g., interchangeably) to re-shape or re-position the distal aspect and/or another portion of the lead housing (e.g., in a perioperative setting).

In some embodiments, a proximal (and/or other) aspect of the lead may have properties that enable it to be very flexible. In some embodiments, such flexibility is greater than adjacent or other portions of the lead. In some examples, the flexibility of one or more portions or aspects of a lead are created using silicone tube or other soft polymeric/elastomeric materials. The flexibility of the proximal portion or aspect of the lead assembly may be advantageous or beneficial in the context of external anchoring where the length of electrode lead that is external to the body is coiled loosely (e.g., to provide strain relief). Coiling of a flexible tube can permit for less recoil force. High recoil forces can disadvantageously dislodge the electrode lead.

In some embodiments, the flexibility of the proximal portion or aspect of the lead assembly is advantageous or beneficial. For example, such a design can help prevent or reduce force being transmitted to the distal portion or aspect that contacts, is in proximity to and/or otherwise interfaces with the targeted nerve. In one example, movement of the flexible aspect of the lead does not result in the corresponding displacement of the distal aspect. This can be largely due to the differing properties of the proximal and distal aspects as in the case where the distal aspect contains an insert that is shapeable. In some embodiments, it is advantageous to not have the distal tip deflect (and/or to limit deflection) when forces are applied proximally, as tip deflection may interfere with the efficacy of neuroregenerative therapy since the electrodes may no longer interface with the nerve.

Figure 43:
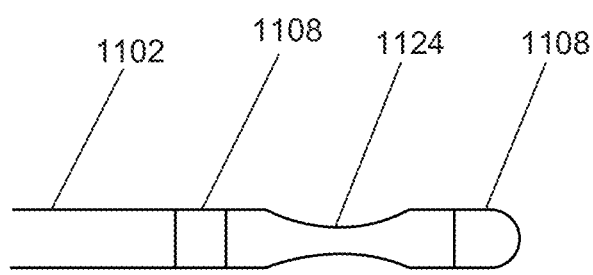
FIG. 43 illustrates a profile view of an electrode lead comprising a groove suitable for handling with forceps according to one embodiment.

In some embodiments, as shown in FIG. 43, the distal aspect may include one or more dimples, grooves, recesses and/or other features 1124 (e.g., to facilitate grasping of the lead using forceps and/or other tools). In some arrangements, the dimple or groove 1124 spans the circumference (or other outer extent) of a cylindrical lead. In other arrangements the dimple or groove 1124 may only partially cover the circumference or other outer extend (e.g., half of the circumference).

In some embodiments, the jacket 1116 of the distal and proximal ends may differ in color. In some arrangements, the distal end may have areas of differing color. Colors may indicate differing segments (e.g., aspects that are shapeable or not) or may indicate a particular length and may be useful in positioning of the lead. In some embodiments, the proximal portion may be colored red with a corresponding matching color on the device to which the proximal end would connect (e.g., stimulation device). In some embodiments, the distal portion can be colored in a different color such as blue, purple and/or any other color to clearly distinguish between proximal and distal ends. This allows the user to quickly, predictably and safely match the lead color to the device color to minimize confusion about how to connect the lead assembly. In some embodiments, marker bands or arrows may be screen printed or laser etched onto the jacket of the lead assembly. These marker or indicators may aid a user in understanding what end of the assembly to connect with a device or how far to plug in the proximal portion of the lead into the device (e.g., the lead should not be inserted past the marker band or the marker band communicates the extent that the lead inserts into a device). In some embodiments, line segments corresponding to unit measures can be printed on the lead to aid as a ruler.

In some embodiments, the proximal portion or aspect 1104 of the electrode lead assembly may terminate with a connector. Such a connector may be a standard medical connector (e.g., manufactured by Redel, Lemu, ODU, etc.). However, the connector can be non-standard (e.g., customized), as desired or required. The connector can be configured to be inserted into a stimulation device and/or controller in order to selectively energize the electrodes included in the lead assembly and/or otherwise electrically couple the electrodes to the stimulation device and/or controller (e.g., to provide electrical power to the lead, to send and/or receive electrical signals to and/or from electrodes, etc.). As discussed in greater detail herein, in some arrangements, the lead incorporates a seamless or substantially seamless outer surface (e.g., from the perspective of the outer shape of the lead) from the proximal end to the distal end. In some embodiments, the proximal end or aspect of the lead is configured to be inserted directly into a stimulation device or other component to selectively energize one or more electrodes and/or otherwise electrically couple the electrodes to the stimulation device or other component. By way of example, in some arrangements, the outer diameter of the lead from the proximal end to the distal end changes a maximum of 0% to 5% (e.g., 0 to 5, 0 to 4, 0 to 3, 0 to 2, 0 to 1, 0 to 0.5%, values between the foregoing values and ranges, etc.). In other embodiments, the outer diameter of the lead from the proximal end to the distal end changes a maximum of 5% to 10%. Standard medical connectors, e.g., as outlined herein, are typically at least 2 times larger than the outer diameter of the described lead assembly. While the greater size of said connectors is advantageous for handling and connecting to peripherals, it limits the usability of traditional insertion tools. In contrast to having a larger connector on the proximal end, incorporating a smaller deviation in outer diameter along the length of the lead assembly advantageously permits a user to withdraw seamlessly insertion tools or other elements used to facilitate entry towards the anatomical target of interest. However, if large connectors are desirable, insertion tools of other elements may need to be designed to be separable or peelable to facilitate removal of said tools.

In other arrangements, the lead incorporates a seamless or substantially seamless (e.g., from the perspective of the outer shape of the lead) from the proximal end to just proximal to the distal end. For example, as illustrated in FIG. 40A, the distal end of the lead assembly comprises a conductive element 1108 that has a rounded shape (e.g., along the distal end). Thus, in such configurations, the outer diameter or other cross-sectional shape of the lead assembly is constant or substantially constant from the proximal end to or near the distal end. As discussed above, according to some embodiments, the outer diameter of the lead from the proximal end to the distal end changes a maximum of 0% to 5% or 5% to 10%.

Figure 44A:
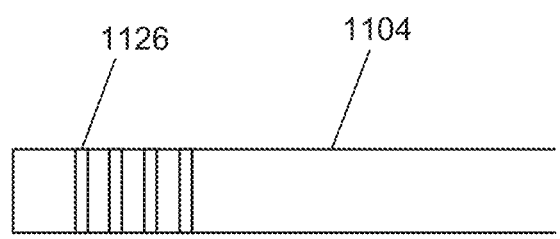
FIG. 44A illustrates a profile view of the proximal end of an electrode lead having concentric ring contacts according to one embodiment.
Figure 44B:
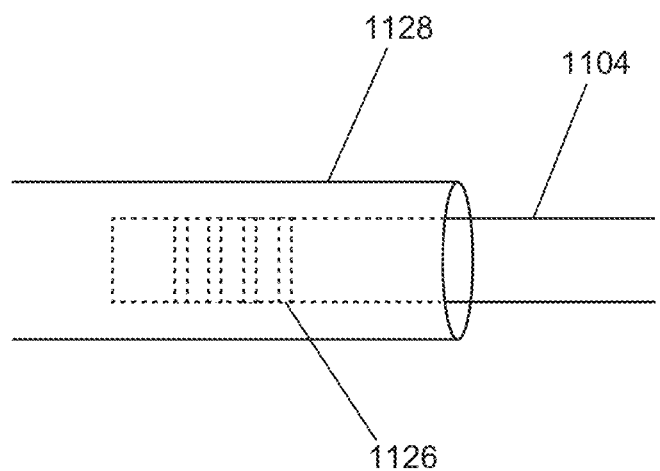
FIG. 44B illustrates a profile view of an insertion tool being drawn over the proximal end of an electrode lead having concentric ring contacts according to one embodiment.

In other arrangements, shown in FIG. 44A, the connector may comprise one or more concentric rings 1126 that are conductive. Said rings can be configured to fully or partially encompass or otherwise surround the circumference of the lead. In some embodiments, ring contacts are more advantageous compared to standard medical connectors. The advantages of using such contacts can be highlighted when employing an insertion tool (e.g., over the needle catheter) to place the electrode lead within the subject percutaneously. Ring contacts can permit direct removal of the insertion tool by sliding the lumen of the insertion tool 1128 over the length of the lead body and removing it over the proximal aspect of the lead 1104, as shown in FIG. 44B. In the case of a standard medical connector, the tool may not be removed (e.g., may need to remain with the lead assembly). In such an embodiment, the use of a peelable (or otherwise separable) catheter can overcome this obstacle, thereby adding to overall complexity, expense, etc.

In some embodiments (including any of the embodiments disclosed herein or variations thereof), the lead comprises a stiffened proximal section (e.g., at least relative to distal sections or portions) that may be used to aid with insertion of the connector end of the lead into a mating connector, port or other receptacle. The stiffened section can facilitate a practitioner with handling the lead and/or inserting it into a mating connector, port or receptacle in an enclosure or housing of a device that prevents the lead from falling out or otherwise disengaging such lead assembly from such a separate device. In some arrangements, without the increased stiffness of the proximal portion, the lead may bend, kink and/or otherwise be damaged or undermined while aiming to insert the lead into a mating connector. For example, the resulting deformities can increase the likelihood that the lead fractures, breaks, gets stuck, etc. or that the conductive wires within the lead break or fracture resulting in a failed lead. The addition of a stiffened section or portion along the proximal end of the lead assembly can be helpful from a durability, strength and the other physical properties, especially in light of the relatively small outer diameter or other cross-sectional dimension of the lead (e.g., circular lead). For instance, in some embodiments, the diameter or other cross-sectional dimension of the lead is 0.1 to 5 mm (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 1-4, 0.5-4, 1-4, 0.1-5, 4-5, 3-5, 2-5 mm, ranges between the foregoing, etc.).

In some embodiments, the length of the stiffened proximal section is 0.5 to 5 cm (e.g., 0.5-0.6, 0.6-0.7, 0.7-0.8, 0.8-0.9, 0.9-1, 1-2, 2-3, 3-4, 4-5, 1-4, 0.5-4, 1-4, 0.1-5, 4-5, 3-5, 2-5 cm, ranges between the foregoing, etc.). In some arrangements, the length of the stiffened proximal section is at least as long as the distal aspect. In other arrangements, the length of the stiffened proximal section is 10-100% the length of the distal aspect.

In some embodiments, the stiffened proximal section may comprise one or more inserts that helps improve the assembly's resistance to fracturing and/or other damage. In some arrangements, such an insert or other member comprises a relatively high tensile modulus. In some arrangements, such materials include plastics, metals, alloys and/or the like with tensile moduli greater than 10 GPa. In some arrangements, such inserts or other members have a melting temperature greater than the melting temperature of the outer jacket. In some embodiments, this can be helpful as assembly of the lead may require the jacket to reflow (e.g., melt or shrink) over the insert. For example, the distal section may comprise a polymer jacket with a melting temperature of 130 to 160° C. and with overall Young's modulus between 0.01 to 0.05 GPa; the proximal section may comprise of a polymer jacket with a melting temperature of 160 to 175° C. and with overall Young's modulus of 100 to 250 GPa which includes the stiffening insert.

In some embodiments, the lead comprises of two sections, a relatively rigid proximal section and a less rigid and shapeable distal section. The rigid proximal section may be inserted directly into a peripheral or stimulation device while the distal shapeable section may be percutaneously inserted through tissue to interface a target nerve. For example, the distal section may comprise a polymer jacket with a melting temperature of 130 to 160° C. and with overall Young's modulus of 0.01 to 0.05 GPa; the proximal section may comprise of a polymer jacket with a melting temperature of 160 to 175° C. and with overall Young's modulus of 100 to 250 GPa which includes the stiffening insert.

In some embodiments, the lead comprises three or more (e.g., 3, 4, 5, more than 5) distinct sections with each successive section having ratios of tensile moduli greater than the previous section. For example, in some embodiments, in a lead with three sections: a distal aspect, a body aspect and a proximal aspect, the ratio of tensile moduli is greater in the body than the distal aspect, and greater in the proximal aspect to the body or distal aspect. More specifically, in some configurations, the body aspect has a tensile modulus ratio of 1.5 to 5 times (e.g., 1.5 to 5, 1.5 to 4, 1.5 to 3, 1.5 to 2, 2 to 5, 2 to 4, 2 to 3, 3 to 5, 3 to 4, ratios between the foregoing, etc.) the distal aspect. In some embodiments, the proximal aspect has a tensile modulus ratio of 10 to 1000-20000 times (e.g., 10 to 1000, 10 to 100, 100 to 500, 500 to 1000, 250 to 750, 300 to 700, 10 to 200, 10 to 500, 100 to 20000, 10000 to 20000, 10000 to 30000, 20000 to 30000, 20000 to 25000, 20000 to 40000, 30000 to 50000, etc.) greater than the body or distal aspect.

In some embodiments, the insert or other member spans the entire length of the proximal aspect and a part of the body aspect. In other embodiments, the insert or other member spans only partially the length of the proximal aspect (e.g., 10 to 90, 20 to 70, 30 to 60, 40 to 50%, percentages between the foregoing, etc.). In some arrangements, the insert may span only the length or a portion of the proximal aspect but not any part of the body or distal aspect.

In some embodiments, each of the distinct sections may comprise of a jacket color different from one or more other sections of the lead to distinguish the sections from one another. In some examples, the color of the proximal jacket may match the color of the mating connector or housing or enclosure where the lead is to be inserted.

Figure 44C:
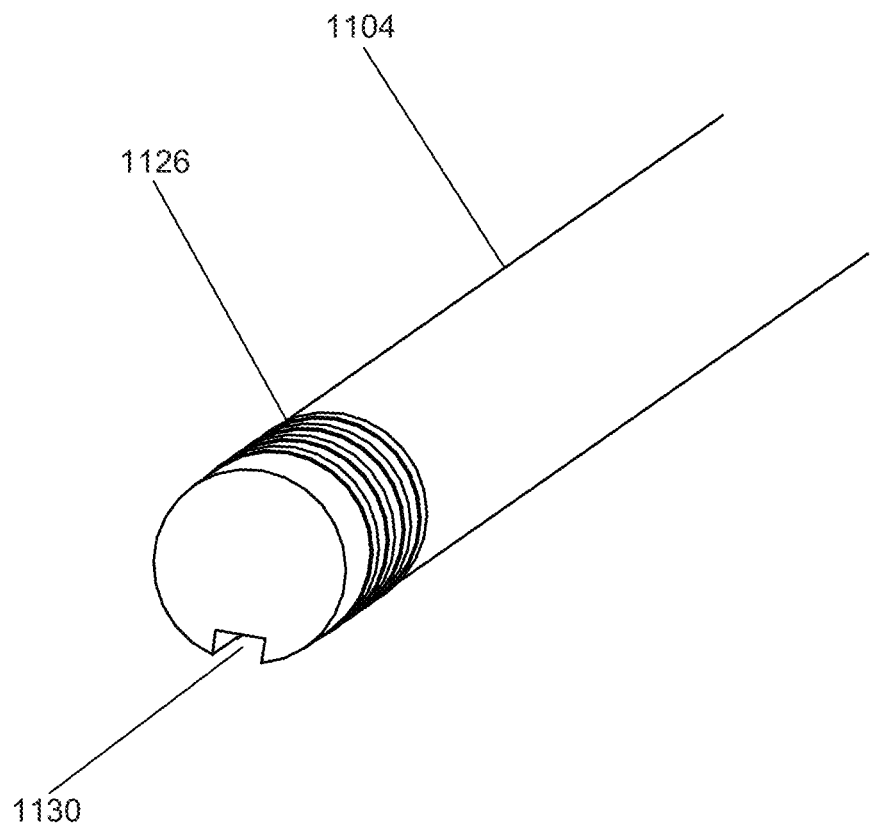
FIG. 44C illustrates a perspective view of the proximal end of an electrode lead having concentric ring contacts and a keyed groove according to one embodiment.

In some embodiments, as shown in FIG. 44C, the space between proximal concentric ring contacts that do not span the full circumference of the cylindrical lead may contain a groove or other recess or feature 1130. Such groove 1130 may be used as a key to insert the lead into a stimulus generator unit.

In some embodiments, the electrode lead body 1100 with multiple conductive elements 1108 (e.g., as described herein) may be advantageously used to measure action potentials. In one example, a multi-element electrode lead is placed near an injured nerve. In some arrangements, the electrode can be shaped to track the anatomical course of the nerve. Proximal conductive elements can be configured to measure an evoked response in the injured nerve in response to stimulus derived from distal conductive elements. In some arrangements, such an "upstream" measurement is used (either alone or together with some other measurement or metric) to confirm a validation condition. In some arrangements, the recording electrode configuration comprises a monopolar, bipolar, tripolar, or other configuration, as desired or required by a particular design or application. In some embodiments, the distal conductive tip is configured to create a monopolar electric field in conjunction with a distal reference electrode. In some arrangements, the distal reference electrode is a surface patch electrode (or some other type of surface electrode) with integrated electronics. In yet another embodiment, the distal conductive tip with other conductive elements 1108 is configured to create a bipolar electric field. In some embodiments, more than 2 conductive elements (e.g., 3, 4, 5, more than 5, etc.) are used to steer or otherwise direct current more precisely to target an injured nerve, specific fascicles within an injured nerve and/or another targeted anatomical structure. Said element may be arranged in as circumferential elements (e.g., ring electrodes), segmented elements (e.g., partial ring electrodes), or other shapes. In some embodiments, a plurality of conductive elements is used to deliver electrical stimulus to a target nerve and/or measure bioelectrical signals from the target at various positions along the length of the target nerve.

Figure 45:
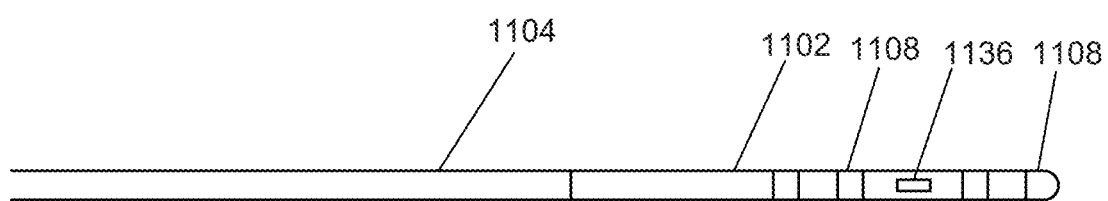
FIG. 45 illustrates a profile view of an electrode lead having an indicator for a validation condition according to one embodiment.

In some embodiments, as shown in FIG. 45, the distal end of the electrode lead may include an indicator. Such an indicator can be positioned along any other portion of the lead, either in addition to or in lieu of the distal end. In some arrangements, the indicator can comprise a LED 1136. In one example, the LED may be used to indicate a validation condition (e.g., successful action potential capture with proximal electrode conductive elements). It may be advantageous to incorporate an indicator within the surgical field as a surgeon's visual attention is directed to the site of nerve repair or electrode interface area, whereas the stimulus generator may be placed immediately outside this field of view. Without diverting a surgeon's attention, the surgeon may manipulate (e.g., move and/or shape) the lead and be informed by the indicator that a validation condition has been confirmed.

While neuroregenerative therapy has not been shown to be a chronic therapy, it may be advantageous to maintain an electrode near an injured nerve to deliver therapy other than neuroregenerative therapy. Such therapies may include, for example, pain management therapy which traditionally has been a chronic therapy. Percutaneous electrical stimulation can be employed to deliver pain management therapy. Typically, such chronic stimulation paradigms require more sufficient anchoring of a nerve interface. In the case of the embodiments disclosed in the present application, the shapeable aspect(s) (e.g., distal aspect) may be utilized to surround, at least partially, a nerve for long-term nerve interfacing as in the context of pain management therapy.

Long-Term Implantation

In some embodiments, the ability to apply a bioadhesive for long term or chronic implantation may be advantageous. Long term or chronic implantation may be defined as greater than 30 days, for which, typically beyond this time frame, a chronic inflammatory and foreign body response occurs and as defined by ISO 10993-1. The adhesive material may act as an interface to secure or anchor the electrode lead body and/or conductive elements to the nerve, while maintaining a shaped conformation to the surrounding anatomical tissue via the electrode lead's ability to be shaped as previously described herein.

In some embodiments, the tissue adhesive comprises a biomaterial with some, any, or all of the following properties: at least partially biodegradable, at least partially bioerodible, at least partially bioresorbable, at least partially biocompatible, at least partially bioinert and/or the like. The biomaterial can include a single material or can include two or more materials, such as, for example and without limitation, a polymer, an elastomer, a composite material, particles, molecules, layered materials, gels and/or the like. In some embodiments, the polymers are synthetic, natural, hybrids, chemically-modified versions of any of these and/or the like, as desired or required. Synthetic polymers can include, but are not limited to, polyethylene glycol (PEG), poly(N-isopropylacrylamide) (poly(NIPAAm)), poly(lactic-co-glycolic acid) (PLGA), polyurethane (PU) and/or the like. Natural polymers include, but are not limited to, fibrin, collagen, gelatin, derivatives thereof and/or the like. Chemical modifications to polymers may include, but are not limited to, attachment, inclusion, or presence of bioadhesive functional groups, such as catecholamines. For example, a bioinspired bioadhesive component is L-3,4-dihydroxyphenylalanine (DOPA), which achieves its superior adhesive properties mainly due to the presence of a catechol functional group.

In some embodiments, the bioadhesive may be tunable or otherwise modifiable and may be present in the body and function as an adhesive for a controlled or pre-defined time period. Tuning of the bioadhesive to achieve desired characteristics or responses may be a function of the chemical, material, and/or physical properties, or as a function of an externally-applied stimulus. Tunability or modifiability of a bioadhesive as used herein refers to the design and/or control of any one or more of the aforementioned factors to achieve desired characteristics or responses, such as, for example, and without limitation: the biodegradation rate, the release profile of bioactive molecules or agents, the adhesion strength, the mechanical properties (e.g., shear, compressive, and/or tensile moduli), or the responsiveness to external stimuli.

In some embodiments, the bioadhesive may degrade within an acute or relatively short time period (e.g., less than 30 minutes, 30 minutes to 1 hour, 1 to 6 hours, 6 to 12 hours, 12 to 24 hours, 1 to 30 days, values between the foregoing values or ranges, etc.). Such an acute time period as used herein is based on what is typically acceptable for acute human implants as defined by ISO 10993-1.

According to some arrangements, degradation of the bioadhesive within an acute time period may be advantageous for application of neuroregenerative therapy since, for example, the bioadhesive would secure the lead to the nerve at the beginning of the treatment. This can help prevent mobility of the lead assembly and ensure optimal or more advantageous contact during stimulation. Further, degradation of the bioadhesive during the treatment can allow for easy removal of the lead post-therapy with little or no resistance from the bioadhesive.

In some embodiments, the bioadhesive may be tuned or otherwise configured to degrade over a longer time period (e.g., 30 to 40 days, 40 to 50 days, 50 to 60 days, 60 to 70 days, 70 to 80 days, 80 to 90 days, 90 to 100 days, 100 to 120 days, greater than 120 days, time periods between the foregoing ranges, etc.). This may be advantageous in scenarios that require long term implantation of the lead for neuroregenerative therapy and/or pain management purposes. In such scenarios, it may be advantageous or desired to design the implanted materials so as to modulate this host response. Such design considerations may include, but are not limited to, biocompatibility, bioresorbability, use of bioinert materials, delivery of anti-inflammatory or immunosuppressive agents and/or the like.

Anchoring Using Glues or Other Adhesives

In some embodiments, the bioadhesive is in the form of a bulk gel or other gel or gel-like material (e.g., hydrogel, glue, other adhesive, other polymeric material, etc.). The gel can be pre-formed (e.g., prior to implantation), can be configured to be formed in situ, or a combination of both. In some arrangements, a pre-formed gel may be applied directly to the anatomical site of interest and/or surface of the electrode lead prior to or during lead implantation (e.g., to achieve adhesion between the lead and tissue surfaces). In some embodiments, pre-formed bulk gels require no mixing prior to application. Such arrangements can function (e.g., immediately, promptly, etc.) as an adhesive upon contact to the surfaces of interest. Such pre-formed bulk gels may include, but are not limited to, pre-existing commercial materials (e.g., Dermabond™, Indermil®, Liquidband®, etc.), custom-made materials, or a hybrid of these.

In some embodiments, the bioadhesive is formed and/or mixed at the time of application. As used herein, in situ formation refers to chemical and/or physical reactions that occur to result in the formation of the final bioadhesive. The chemical or physical mechanisms by which this occurs can include, but are not limited to, interfacial bonding, covalent or ionic bonding, crosslinking (e.g., chemical, physical, enzymatic, photochemical), photopolymerization, thermal curing (e.g., thermosetting), oxidation and/or the like. In some embodiments, such reactions may be initiated by physical mixing of multiple components and/or application of an external stimulus. Additional initiation mechanisms can be used, either in lieu of or in addition to those indicated in the preceding sentence. In some embodiments, in situ formed bioadhesives may be pre-existing commercial tissue glues or adhesives (e.g., fibrin-based gels like Tisseel™, PEG-based gels like Coseal™, etc.), custom-made materials, or a hybrid of these.

In other embodiments, the bioadhesive comprises (e.g., is in the form of) a coating or film on the surface of the electrode lead. The coating/film can incorporate or otherwise include physical characteristics (e.g., rough surface topography, micropatterning, etc.) to facilitate adhesion of the bioadhesive (e.g., as the primary mechanism, as a supplemental mechanism, etc.). In some embodiments, the adhesive functionality of the coating/film may be activated prior to, during and/or after device implantation. In some embodiments, the bioadhesive is already functional. In some embodiments, activation requires removal of a protective layer that prevents adhesion prior to application. In some embodiments, the coating/film is adhesive due to uniquely-designed chemical and/or physical properties. Such properties may include, but are not limited to, topographical patterns or indents, surface charge (anionic, cationic, etc.), etc. In some embodiments, the bioadhesive coating can become functional or active (e.g., immediately, after the passage of a certain time period, etc.) upon contact to the surfaces of interest by the adhesive. In other arrangements, the adhesive functionality is activated by application of an external stimulus. Stimuli can include, but are not limited to, one or more of the following: electricity or other electrical stimulus, thermal energy, light energy, chemical, pressure, acoustic energy, other types of energy, etc.

In some embodiments, anchoring of the electrode lead body 1100 may employ or use a form of bioadhesive or other adhesive tape 1300. In some arrangements, the tape is included with the electrode lead assembly. In arrangements such as this, it may be advantageous to use a separate device and/or actuator to release or deploy the bioadhesive tape anchor. The bioadhesive tape can include one or more wings/flaps that are attached to the tip of the lead and configured to unfurl or otherwise release in response to a designated control. For example, once a lead assembly is positioned at a desired anatomical position (e.g., on or adjacent to a peripheral nerve, proximal to the injury and/or repair site), a designated button or other controller on a control system may be activated (e.g., pushed) to deploy or otherwise release the bioadhesive tape at the distal tip of the lead. In some embodiments, prior to deployment, the bioadhesive tape can be configured to be moved (e.g., furled inwards toward the lead and flush with the edges of the lead to prevent catching on any tissue during lead placement). After deployment, the bioadhesive tape may release (e.g., unfurl) and conform (e.g., instantaneous, generally instantaneously) to and adhere the lead to the surrounding anatomy. In other arrangements, the tape is a separate device that is applied prior to, during and/or after device implantation.

Figure 46A:
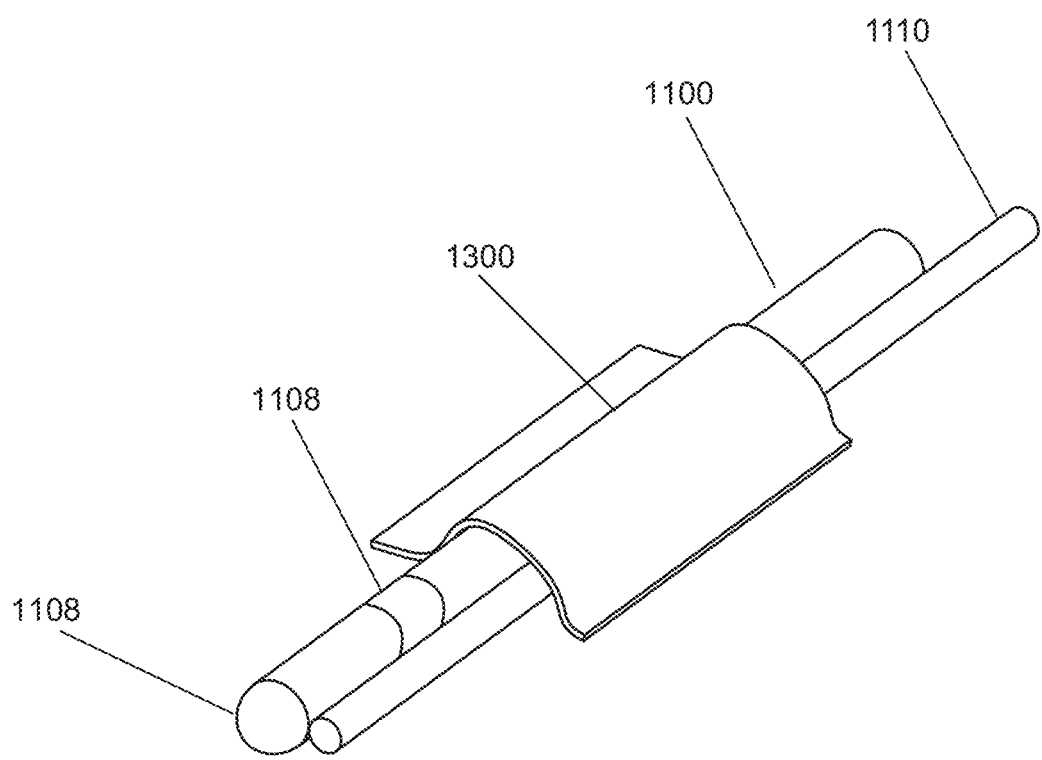
FIG. 46A illustrates a perspective view of an electrode lead with a bioadhesive tape used for anchoring proximal to conductive elements according to one embodiment.
Figure 46B:
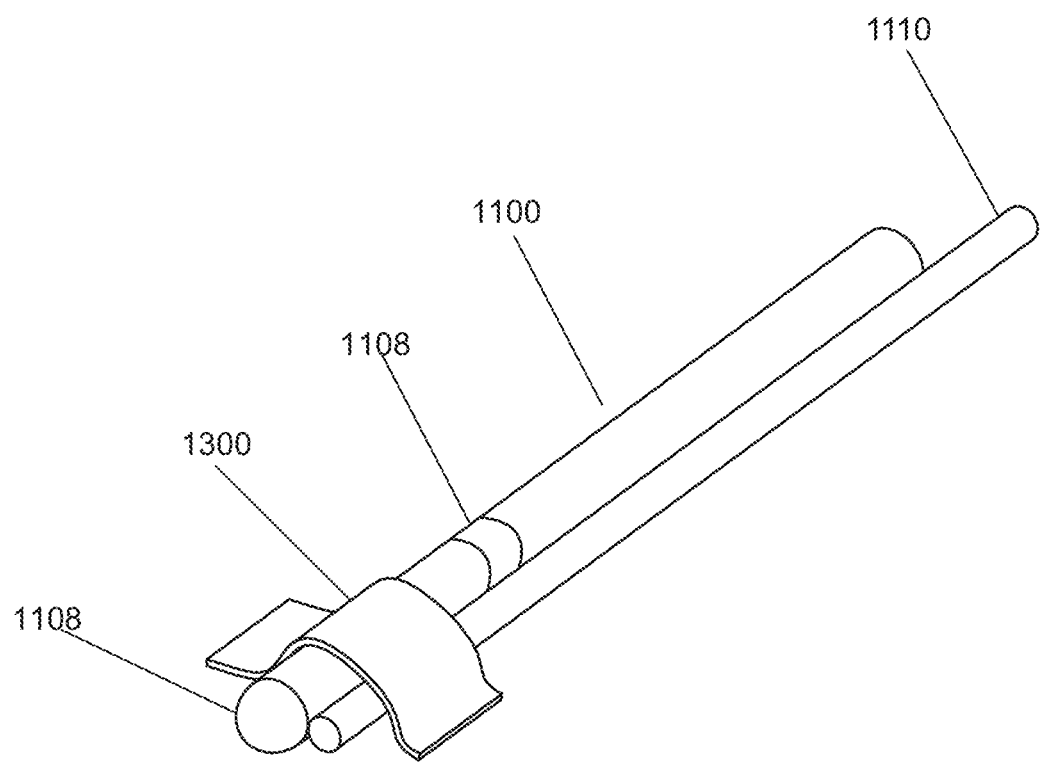
FIG. 46B illustrates a perspective view of an electrode lead with a bioadhesive tape used for anchoring between conductive element according to one embodiment.

In some arrangements, the tape 1300 is applied semi-circumferentially or circumferentially, either partially or completely wrapping around a circular or cylindrical anatomical site, or interfacing the electrode lead to an anatomical site with adhesive functionality on both faces of the tape. In one example, the tape may be used to anchor an electrode lead body 1100 to a nerve structure 1110 by placing the tape 1300 proximal to conductive elements 1108, as shown in FIG. 46A. In yet another example, shown in FIG. 46B, the tape 1300 may be placed between conductive elements 1108.

In some arrangements, securing the lead to the anatomical site is achieved with one or more (two, three, etc.) bioadhesive tapes. In some embodiments, the tape is rectangular, circular, cylindrical, elliptical, or of any other geometry.

In some embodiments, the tape is relatively thin (e.g., 1 to 10 µm, 10 to 50 µm, 50 to 100 µm, less than 1 mm, 1 to 9 mm, any values between the foregoing ranges or values, etc.) or relatively thick (e.g., 9 to 10 mm, 10 to 15 mm, greater than 15 mm, etc.).

In some embodiments the tape may have a controlled and tunable biodegradation profile, such that it degrades within a desired timeframe to facilitate easy removal of the lead from an anatomical site.

In other embodiments, the lead anchor tape may be disabled instantaneously by a control on the device. In embodiments such as this, the tape may stay attached to the lead during removal, but have material or physical properties that permit smooth removal of the lead and bioadhesive through the para-incisional site. In other embodiments, the control may induce ejection of the tape from the lead prior to lead removal. In this case, the tape would remain at the anatomical site during and following lead removal, but it would be advantageous for it to be biocompatible and rapidly biodegradable (e.g., less than 1 hour, 1 to 2 hours, 2 to 4 hours, 4 to 6 hours, 6 to 12 hours, 12 to 24 hours, 1 to 30 days, any value between the foregoing values or ranges, etc.) such as to not induce a negative immune response as it degrades.

Adhesive Delivery and Curing Methods

In some embodiments, the bioadhesive includes a pre-mixed and pre-formed fluid solution that is delivered to a desired anatomical site via injection and is configured to function as an adhesive instantaneously. One example may include the pre-formed bioadhesive being dispensed from a built-in or attached reservoir in the neuroregenerative stimulation system and flowed (or otherwise delivered) through a cannula or other opening (e.g., lumen) that is built into or otherwise included within the corresponding lead. In other scenarios, such as those in which the pre-formed bioadhesive is a pre-existing commercial product, the bioadhesive solution can be applied to the desired anatomical site prior to and/or immediately after adhering or otherwise at least partially securing at least a portion of the lead to and/or near the same site.

In other embodiments, the bioadhesive is formed and/or functionally activated in situ. In some arrangements, in situ formation occurs via physical and/or chemical crosslinking by mixing (e.g., at least partially in situ) two or more compatible polymer precursor solutions. In some arrangements, a multi-barrel syringe or extrusion device is either built-in (or otherwise included with) or external to (or otherwise not include with) the stimulation system. Such a syringe or other delivery device can be configured to house (e.g., at least partially, completely, etc.) the precursors (or other materials to be combined) separately such that crosslinking does not occur prior to use. In some arrangements, mixing and crosslinking occurs proximal to the site of application. In other arrangements, mixing and crosslinking occurs directly at the site of application. Two or more (e.g., 3, 4, 5, more than 5, etc.) materials can be configured to be mixed or combined at least partially in situ.

In some arrangements, for any of the embodiments disclosed herein, a lead assembly includes a single lumen or other opening to facilitate flow of materials and/or other substances (e.g., a single fluid or other solution, two or more fluids or solutions, etc.) to or near the distal tip and delivery site. In other arrangements, multiple lumens, cannulas and/or other openings are included in the lead assembly to permit delivery of separate solutions, fluids and/or other materials to or near the distal tip and to or near a targeted delivery site.

In some embodiments, the materials or other substances (e.g., precursors) are mixed to form crosslinks, and the mixed material is extruded and applied directly to or near the desired site, using a separate device or devices. The mixed material may be in its completely crosslinked form or partially crosslinked at the point of extrusion. In some embodiments, complete crosslinking may be desired to achieve fast gelation or otherwise activate the bioadhesive quickly. In other embodiments, it may be advantageous to extrude a partially crosslinked material to allow for slower gelation time and active the bioadhesive at a slower rate.

In some embodiments, bioadhesive solutions are applied to a cuff-like device that may act as a localized chamber mechanism to at least partially contain the bioadhesive along, adjacent and/or near the nerve. Said cuff-like devices may be configured to act as a mold that permits only a thin layer of bioadhesive to be extruded onto a nerve or enveloped structure. Such an application is advantageous as bulk hydrogel delivery may compress a nerve and cause nerve injury. Such an application can also be advantageous as the use of a cuff-like device may help isolate (e.g., fully, partially, etc.) adhesive from the surrounding tissue.

In some arrangements, it may be advantageous to extrude pre-loaded precursor solutions from a double-barrel syringe or other delivery device having a mixing tip directly onto an anatomical site, then adhered the lead to that site. For example, Tisseel™, a commonly-used commercial surgical tissue adhesive that could be used to anchor the lead to a nerve during application of long-term neuroregenerative therapy, as Tisseel™ remains active as an adhesive and biodegrades within 14 days. It is composed of fibrinogen and thrombin precursor solutions that crosslink to form fibrin (the bioadhesive) when mixed. It is packaged in a double-barrel syringe system that houses the two precursors separately. Upon extrusion of the syringe, the precursors enter the mixing chamber at the tip of the syringe, whereby, upon contact, the precursors undergo a chemical reaction to form crosslinks, resulting in the formation of fibrin, the bioadhesive. In some scenarios, Tisseel™ may be extruded through a cannula in the body of the lead using an adaptor. In other scenarios, Tisseel™ may be applied to a surface on the lead tip and/or anatomical site prior to lead positioning and to anchor the lead to the nerve for treatment.

In an embodiment, the bioadhesive is photocurable and configured to be activated (e.g., photo-activated) by applying light (e.g., of a specific wavelength and/or other property). The inactivated bioadhesive may be applied to a site of interest (e.g., on tissue, the electrode lead surface, combination thereof, etc.). In some embodiments, once the lead assembly is positioned in a desired location, light can be applied (e.g., for a desired or required time period) to cure and activate the bioadhesive, and thereby ensure sufficient, at least partial, anchoring of the electrode lead in a desired place. In some embodiments, the bioadhesive is also photodegradable and degradation of the material is controlled by application of light of a wavelength (e.g., a different wavelength than that required to cure the adhesive).

In some scenarios, it may be advantageous for the bioadhesive to contain both photocurable and photodegradable moieties that cure or degrade instantaneously in response to application of a unique wavelength. For example, the bioadhesive may comprise an ortho-nitrobenzyl protecting functional group that is reactive to light in the visible spectrum (wavelengths between 400 to 700 nm) and cured within seconds of light exposure. This could be applied to adhere (e.g., instantaneously, rapidly, within a particular time duration, etc.) an electrode lead to a proximal nerve segment prior to electrical stimulation therapy. The bioadhesive could also include a diortho-nitrobenzaldehyde moiety that is reactive to UV light (10 to 400 nm) and configured to degrade (e.g., instantaneously, rapidly, within a particular time duration, etc.) upon exposure to detach the lead from the nerve and allow for easy removal of the lead following treatment.

Figure 47:
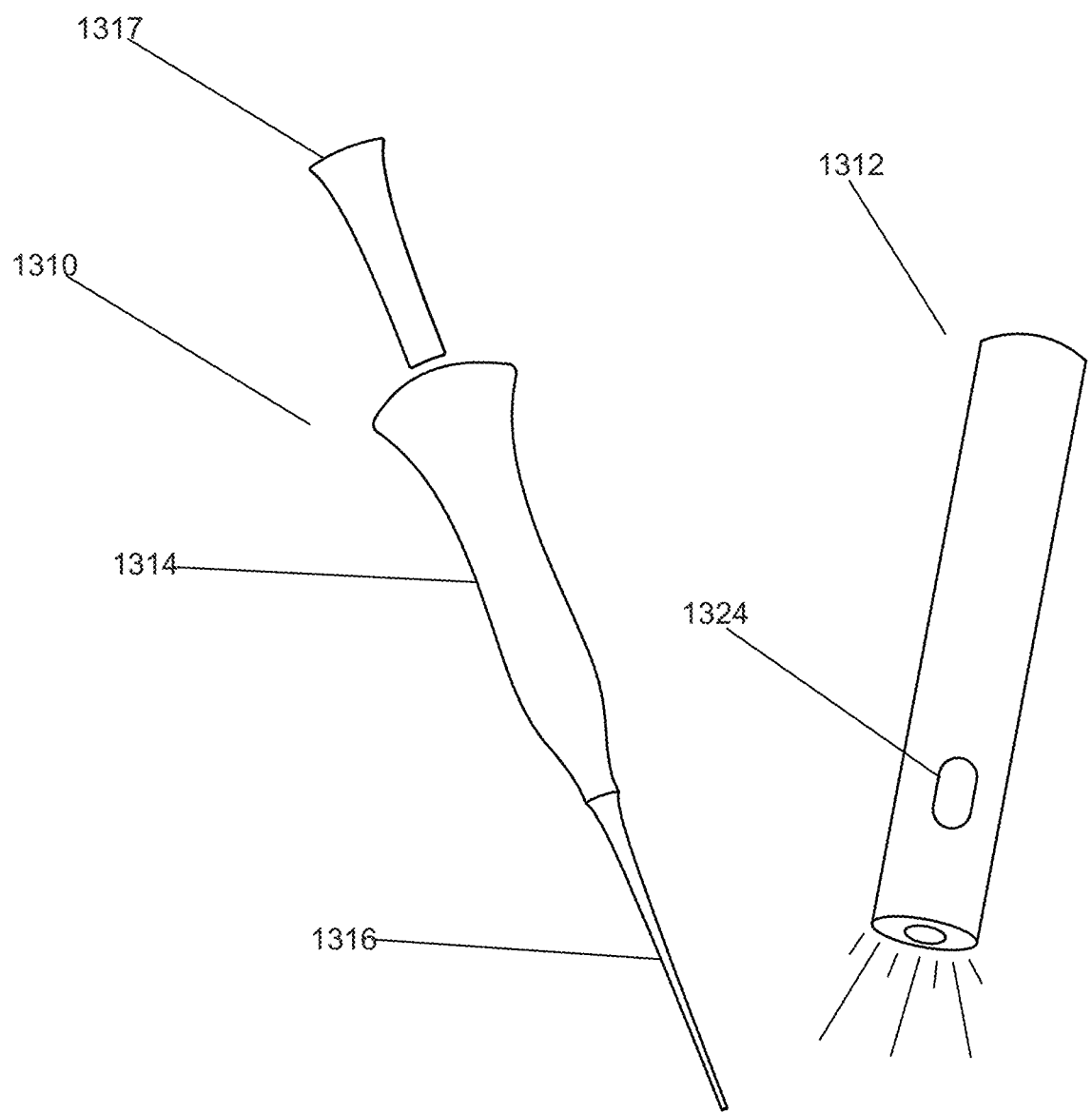
FIG. 47 illustrates a perspective view of a bioadhesive dispensing device and a light-based curing device according to one embodiment.

According to some embodiments, as shown in FIG. 47, a bioadhesive dispensing device 1310 and light source 1312 are individual devices, e.g., separate from the stimulation system and may be included as part of a kit. The bioadhesive dispensing device can comprise a reservoir, opening, other chamber and/or the like 1314 with a pre-loaded amount of bioadhesive that is extruded through a nozzle 1316 at a controlled flow rate (e.g., syringe dispenser) or using a plunger 1317. The light source may comprise a power supply, light source, transmission mechanisms (e.g., bulbs, optical fiber cables, etc.), controls 1318 to turn on/off or change the light type (e.g., buttons or switches) and/or any other components or features, as desired or required.

In some embodiments, the light source is included in a handheld device or wand 1312, in which the tip and/or other portion is configured to emit light. In some arrangements, it may be advantageous to transmit light through the device tip to concentrate the photoenergy to one location, for localized small-area illumination of the bioadhesive.

In other scenarios, it may be advantageous for at least part of the device (e.g., a portion of the device, the entire device, etc.) to be configured to transmit light as it is held horizontally (or in some other orientation relative to a reference point or plane), especially in cases where a larger surface area of bioadhesive needs to be illuminated at one time.

In another embodiment, the photoresponsive bioadhesive applicator and light source make up (or are included in) one device, separate from the stimulation system. In one arrangement, the device is a handheld tool that comprises a bioadhesive reservoir, a power supply, a light source and transmission mechanisms, and is configured to control or otherwise regulate at least one aspect of the dispensing of bioadhesive (e.g., automated button dispenser, manual plunger, etc.) and is configured to control or otherwise regulate light transmission.

Figure 48A:
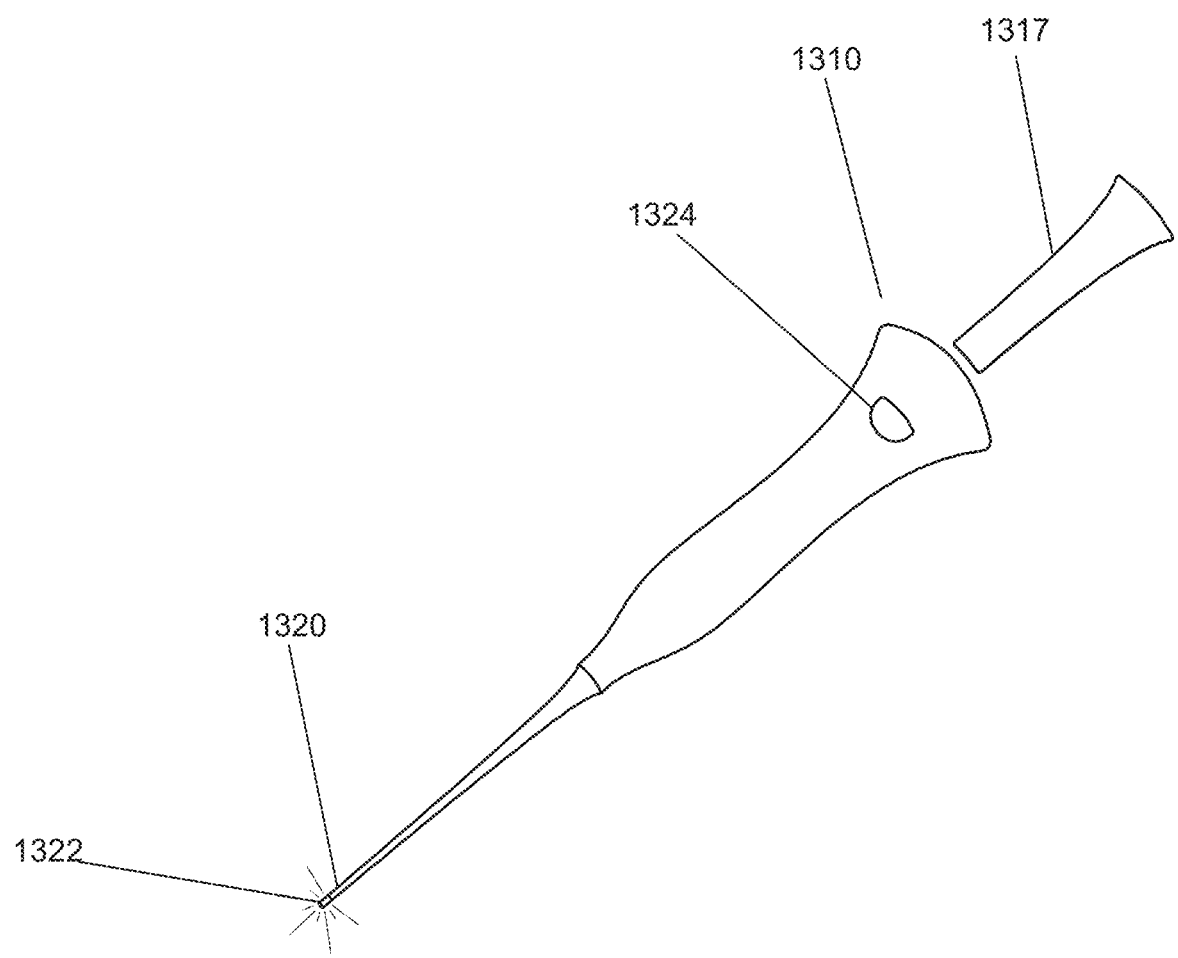
FIG. 48A illustrates a perspective view of a bioadhesive dispensing device comprising a light source and a smaller illumination area at the distal end of the dispensing device according to one embodiment.

According to some arrangements, as depicted in FIG. 48A, the bioadhesive dispensing nozzle tip 1320 contains one or more light sources 1322 (e.g., LEDs). Such light sources 1322 can be configured to be controlled by one or more controllers (e.g., buttons, switches, dials, etc.) on the body of the device and can be configured to transmit or otherwise provide light of a desired type (e.g., UV or visible light).

Figure 48B:
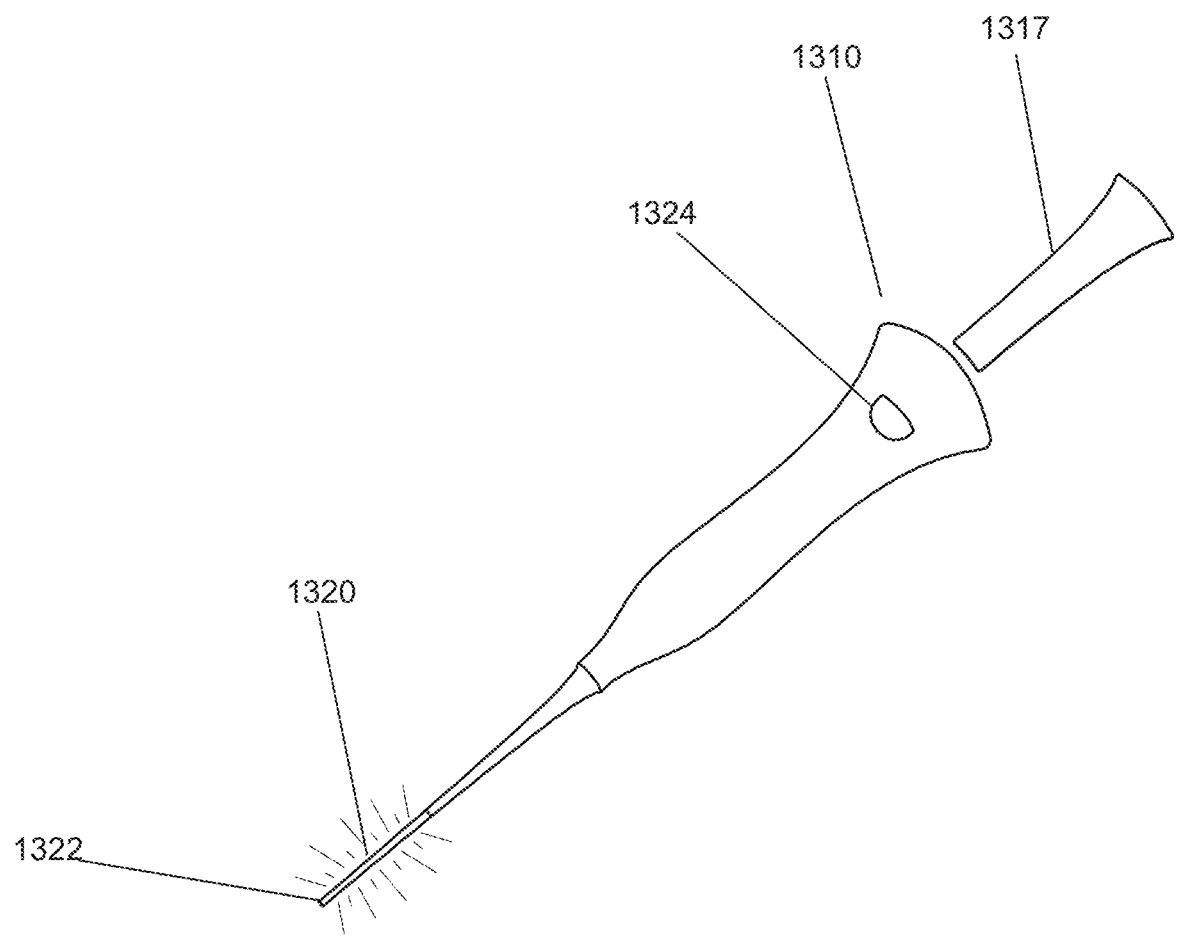
FIG. 48B illustrates a perspective view of a bioadhesive dispensing device comprising a light source and a larger illumination area at the distal end of the dispensing device according to one embodiment.

In some arrangements, as shown in FIG. 48B, it may be advantageous for at least part of the device shaft to transmit or otherwise provide light as it is held in a particular orientation (e.g., horizontally). In some embodiments, such a configuration can be desirable in instances where a larger surface area of bioadhesive must be illuminated at one time. The bioadhesive dispensing control may allow the user to dispense an amount (e.g., preset amount, customizable amount, etc.) of the adhesive (e.g., up to the maximum reservoir limit).

Figure 48C:
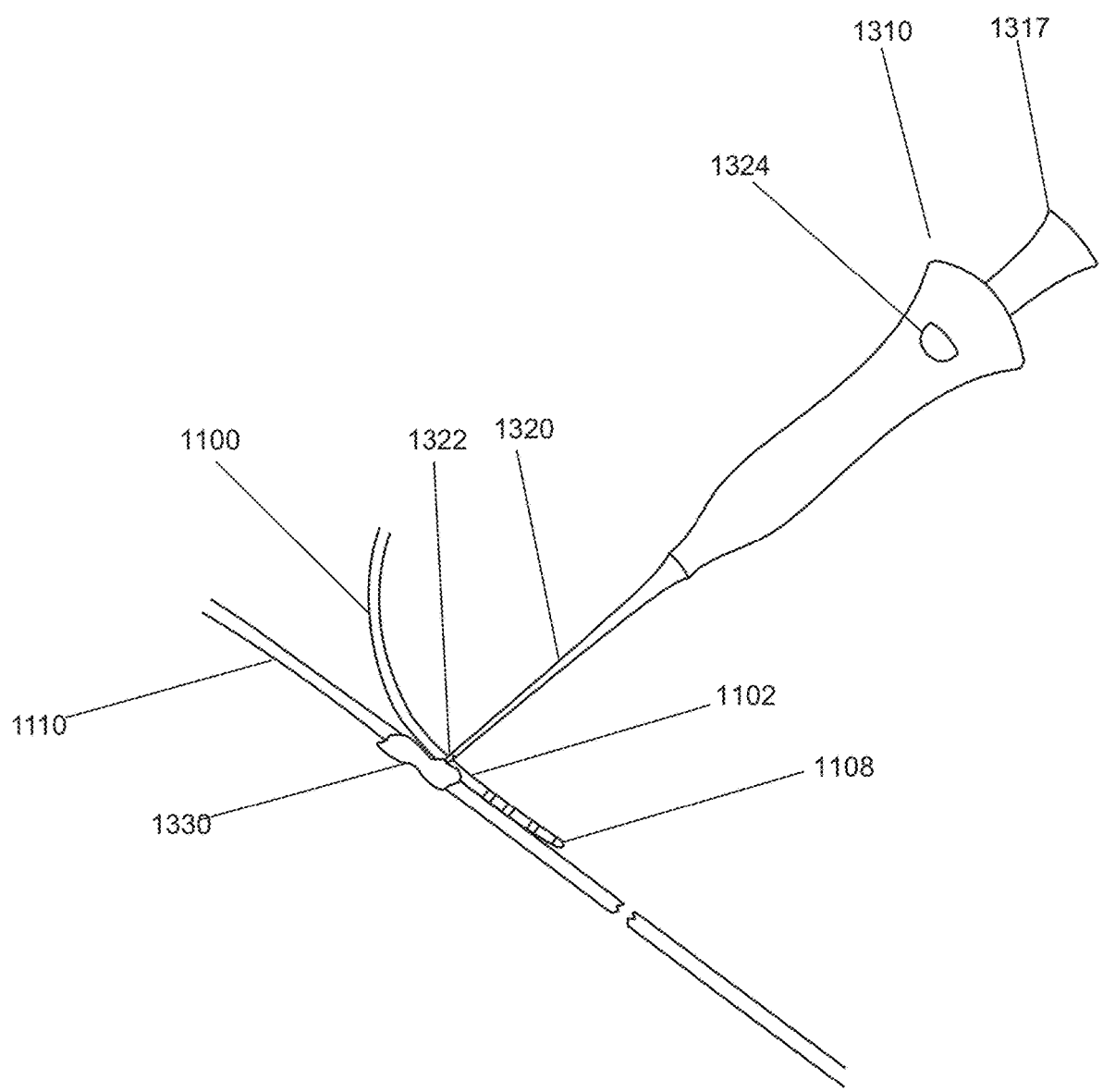
FIG. 48C illustrates a perspective view of a bioadhesive dispensing device comprising a light source dispensing bioadhesive to anchor an electrode lead to a nerve according to one embodiment.

In some embodiments, as shown in FIG. 48C, the dispenser may be configured to dispense a curable bioadhesive 1330 that may be used to anchor an electrode lead body 1100 or distal aspect of an electrode 1102 to a nerve structure 1110. The dispenser can be configured to also cure such a bioadhesive. The device can include an indicator (e.g., a visual indicator, another type of indicator, etc.), such as, for example, but not limited to, sensor output to a display (e.g., LCD screen, other display, other output, etc.). Such a display can be configured to display various information, including but not limited to the selected or preset volume of bioadhesive to be dispensed, the volume of bioadhesive remaining in the reservoir and/or the like, as desired or required. The visual indicator can also be configured to provide additional information, such as, for example, information regarding the light source (e.g., if the light source is on or off), regarding the wavelength of light being transmitted or to be transmitted, regarding the time of illumination (e.g., elapsed, remaining time, etc.) and/or the like. In some embodiments, the bioadhesive itself is configured to change color (e.g., in real-time, after another condition is satisfied, etc.) to indicate appropriate curing.

In some embodiments, bioadhesive solutions are applied to a cuff-like device that may act as a localized chamber mechanism to contain the bioadhesive strategically near or along the nerve (or another location relative to the nerve). Said cuff-like devices may be configured to act as a mold that permits only a thin layer, a patterned layer, or multi-patterned layer of bioadhesive to be extruded onto a nerve or enveloped structure. Said device may also comprise a light source and/or light diffusing elements directed internally at the enveloped structure and may be utilized for curing a polymer.

In some arrangements, it may be advantageous to pre-program the photoresponsive bioadhesive applicator and light source system. For example, the system may be operated in the following manner with one or more preset controls (e.g., built-in or incorporated controls) to secure a lead tip to a nerve: (1) operate a button or other controller configured to be pressed or otherwise controllable to apply a volume of bioadhesive (e.g., a controlled volume, at a constant flow rate, directly, indirectly, uniformly, non-uniformly, etc.) on or near the surface of a nerve, (2) position or otherwise locate a lead on the surface of the nerve, where the bioadhesive is an interface between the two surfaces, and (3) press or otherwise activate another button or other controller to activate one or more light sources (e.g., for a preset, predetermined or fixed time duration (e.g., e.g., 30 seconds, 1 minute, 2 minutes, 3 minutes, 4 minutes, 5 minutes, 5 to 10 minutes, values between the foregoing ranges, greater than 10 minutes, etc.)). Such a time period can be selected based on, at least in part, the required time for photocuration and activation of the bioadhesive. In some embodiments, the bioadhesive passively biodegrades over a controlled period of time to allow for easy lead detachment and removal at the end of the biodegradation period. In other embodiments, the bioadhesive degrades instantaneously or rapidly upon application of light of a wavelength different than the requirement for curing.

In some embodiments, the bioadhesive application system and light source are built or otherwise incorporated into the stimulation system and/or lead. In one arrangement, the bioadhesive solution reservoir may be housed in the stimulation unit. In other arrangements, the reservoir may be an external component (e.g., not incorporated into or a part of the stimulation and/or lead assembly), as desired or required. In one arrangement, the bioadhesive is a solution that is extruded or otherwise positioned through (e.g., at least partially) the body of the lead assembly in one or more contained channels, reservoirs and/or other portions. In some embodiments, the bioadhesive is configured to exit at or near the tip or distal end of the lead assembly.

Figure 49A:
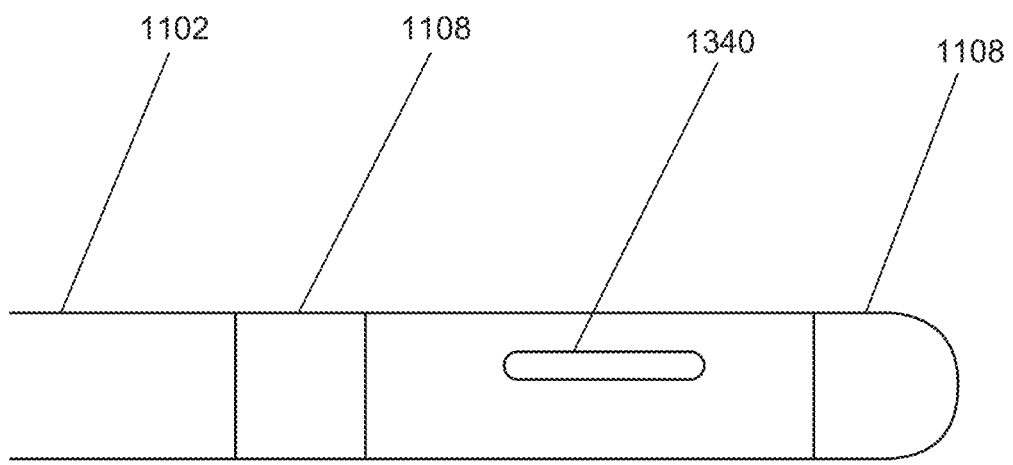
FIG. 49A illustrates a longitudinal view of an electrode lead with a perfusion aperture used for dispensing bioadhesive according to one embodiment.

In one example, as illustrated in FIG. 49A, the bioadhesive solution is configured to exit near or at a distal portion of the electrode lead body 1102 (e.g., through one or more dedicated perfusion ports, holes, pores, apertures and/or other openings 1340). Such openings can be located at or near the distal end of the electrode lead body between conductive elements 1108. In some embodiments, the bioadhesive may also exit through one or more ports, holes, pores, apertures and/or other openings that may be located along the distal aspect or portion, proximal aspect or portion, location between the proximal and distal portions, combinations thereof, etc. of the electrode lead body or assembly.

Figure 49B:
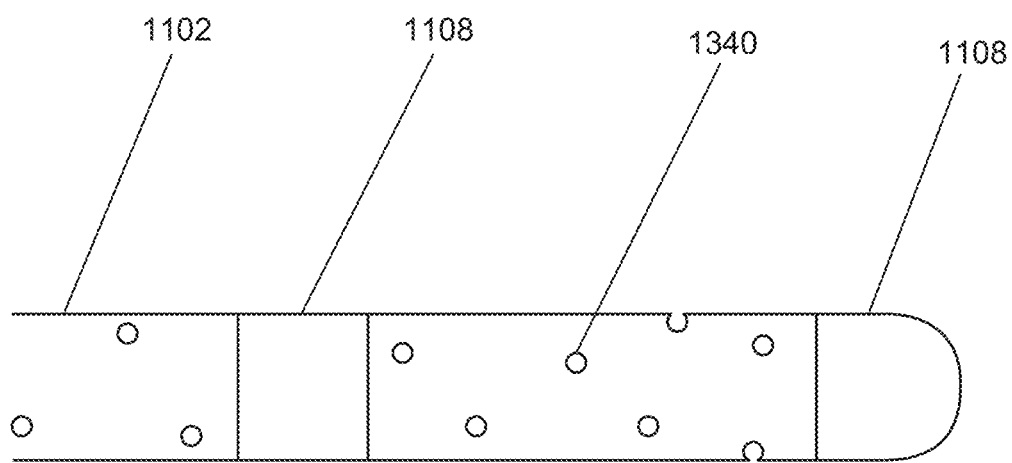
FIG. 49B illustrates a longitudinal view of an electrode lead with multiple perfusion apertures used for dispensing bioadhesive according to one embodiment.

According to some arrangements, as shown in FIG. 49B, it may be advantageous for the bioadhesive to be configured to exit through numerous (e.g., two or more) apertures 1340 located along or near the distal and/or proximal lead body to achieve uniform extrusion around the circumferential surface area of the lead tip for optimal adherence to an anatomical site. A lead assembly can include any arrangement of openings 1340 to permit the bioadhesive to be delivered to specific areas of the lead assembly and/or the anatomy of the subject.

In another arrangement, the bioadhesive comprises a coating or film located on the surface of the lead assembly. In some embodiments, such a coating or film extends from the tip to a preset length (e.g., the entire length of the lead, up to half the length of the lead, the distal quarter length of the lead, any other portion of the lead, etc.), and can be activated/deactivated by application of light (e.g., light of unique wavelengths) and/or any activation source.

In some arrangements, the light source is located, at least in part, at and/or near the tip of the lead assembly and may be controlled by one or more controls (e.g., buttons or other controls located on a stimulation unit, another device, etc.).

According to some embodiments, the activating light source includes one or more sets of light generators (e.g., one or more LEDs, one or more other light sources, etc.). In other arrangements, the light source is encased (e.g., partially or completely) within a housing of the stimulation unit and/or transmitted through the body of the lead assembly (e.g., through mechanisms like, for example, optical fibers, other transmitters, etc.). In some arrangements, at least a portion of the lead assembly is at least partially translucent or transparent to permit the transmission of light through a dedicated portion of the lead body or in its entirety.

In some embodiments, the activation and/or deactivation of the bioadhesive is controlled by other external stimuli, which may include, for example, but are not limited to, thermal energy, electrical energy, photoacoustic energy, chemical and/or biochemical stimuli. In some embodiments, the bioadhesive is thermoresponsive or thermosensitive. In such an arrangement, the bioadhesive may be inactive at temperature ranges above/below normal physiological temperature (e.g., ambient hospital storage temperature), but configured to become active once exposed to temperatures within the normal physiological range.

In other embodiments, the bioadhesive is responsive to electrical energy stimuli. In some scenarios, the bioadhesive may be activated or deactivated in response to electrical stimulus of given parameters or within a specified range of parameters. These parameters may include, but are not limited to, differences in stimulation current, voltage, amplitude, pulse frequency, alternating or direct current and/or the like. In some arrangements, activation of the bioadhesive can be configured to occur in response to electrical stimulus parameters that are the same (or substantially the same) or different than that of neuroregenerative therapy. For example, after an electrode lead assembly has been positioned on or near an anatomical site with the bioadhesive as an interface between the two surfaces. Controls on the stimulation unit can be used to apply a desired dose (e.g., predetermined, fixed or variable, etc.) of electrical stimulation, such that the bioadhesive is cured and activated to attach the lead to the anatomy.

In some embodiments, the electrical stimulation dose that is delivered with respect to the bioadhesive is the same or generally the same as the dose for neuroregenerative therapy. In some embodiments, such a stimulation dose is activated upon start of the treatment. In other embodiments, the curing dose may be different than that of neuroregenerative therapy, such as, for example, stimulation at the same current output, but lower pulse frequency (e.g., less than 1 Hz, 1 Hz, 1 to 2 Hz, 2 to 3 Hz, 3 to 4 Hz, 4 to 5 Hz, 1 to 5 Hz, 5 Hz, 10 Hz, 15 Hz, 25 Hz, 5 to 10 Hz, 10 to 15 Hz, 15 to 20 Hz, 20 to 25 Hz, frequencies within the foregoing ranges and/or between the foregoing values, greater than 25 Hz, etc.). Such a frequency can be equal to, less than or greater than the frequency used for neuroregenerative therapy).

According to some arrangements, the bioadhesive is activated upon electrical stimulation. Such activation can occur instantaneously or at some point following activation of electrical stimulation. In some arrangements, the various embodiments disclosed herein can have two stimulation phases: (1) the bioadhesive curing stimulation phase, and (2) the neuroregenerative therapy stimulation phase. In some embodiments, the curing dose of electrical stimulation is applied for a relatively short time, such as, for example, less than 5 minutes (e.g., less than 30 seconds, 30 seconds, 1 minute, 2 minutes, 30 seconds to 1 minute, 1 to 2 minutes, 2 to 3 minutes, 3 to 5 minutes, values between the foregoing ranges or values, etc.) in order to activate the bioadhesive. In other arrangements, the curing dose is required to be applied for longer lengths of time (e.g., 5 minutes, 10 minutes, 5 to 10 minutes, greater than 10 minutes, values between the foregoing ranges or values, etc.). In some scenarios, it may be advantageous for the bioadhesive to be activated instantaneously or within a short time period following electrical stimulation, such that the total surgical operating time is minimized or otherwise reduced.

In some arrangements, the bioadhesive is activated via electrical stimulation and deactivated through passive biodegradation to allow for easy removal of the lead assembly (e.g., following a biodegradation time period). It may be advantageous, under certain circumstances, to design the biodegradation period such that it is within the time period required for neuroregenerative therapy. Thus, the biodegradation period can be equal to or greater than the time period for neuroregenerative therapy.

According to some arrangements, the bioadhesive is both activated and deactivated via electrical stimulation. In such an arrangement, application of the electrical stimulus for deactivation of the bioadhesive may be the same or different than that required for activation and/or neuroregenerative therapy. In one aspect, the bioadhesive may be activated with a specified curing dose of electrical stimulation, but deactivated when exposed to neuroregenerative therapy electrical stimulation. In another aspect, the bioadhesive may be activated with a specified curing dose of electrical stimulation, remain active during neuroregenerative therapy, and then deactivated by applying electrical stimulation of different parameters than the curing dose and neuroregenerative therapy.

In some arrangements, deactivation of the bioadhesive via electrical stimulation occurs instantaneously or over short or long time periods. For example, it may be advantageous to apply an electrical stimulus to deactivate the bioadhesive instantaneously following neuroregenerative therapy in the acute setting to minimize the total lead removal time.

In some embodiments, the bioadhesive is responsive to photoacoustic and/or other acoustic energy. For example, an ultrasound system may be used intraoperatively and/or or perioperatively in a multifunctional manner. In such arrangements, an ultrasound or other acoustic system can be configured to (1) guide the user during lead placement, (2) allow the user to visualize a lead assembly within, at least partially, in the subject's anatomy, (3) activate the bioadhesive, (4) deactivate the bioadhesive and/or perform any other tasks. In some arrangements, activation/deactivation of the bioadhesive may require the same or different photoacoustic energy parameters.

In some embodiments, the bioadhesive is responsive to chemical and/or biochemical stimuli. In one aspect, the bioadhesive is pH responsive and activated via exposure to physiological pH (pH 7.4). In some aspects, the bioadhesive is pH-responsive and activated/deactivated in response to application of a solution with a pH above or below physiological conditions. For example, the bioadhesive may be positioned as an interface between an anatomical site and an electrode lead, but only activated when an acidic or basic solution (pH<7.4 or pH>7.4) is applied to the area. The bioadhesive may also be deactivated via passive biodegradation or in response to chemical changes, for example, application of a solution with a different pH than that of normal physiological conditions.

In some embodiments, the bioadhesive is multifunctional and responsive to chemical and/or biochemical stimuli (and/or other stimuli) to deliver a therapeutic or non-therapeutic agent in addition to securing a lead to an anatomical site. For example, following securing of the lead to a nerve, the bioadhesive may be configured to react when exposed to physiological pH values and/or other physiological biochemical factors. In such circumstances, a neuroregenerative agent (e.g., nerve growth factor, glial derived growth factor, Tacrolimus, etc.) can be released or delivered at a rate (e.g., a controlled rate) to synergistically boost the regeneration rate and enhance regeneration of an injured peripheral nerve in combination with neuroregenerative electrical stimulation. Additionally, or alternatively, the bioadhesive may be configured to release or provide a pain modulation agent (e.g., nonsteroidal anti-inflammatory drugs like aspirin and ibuprofen, other agents, etc.) in combination with neuroregenerative electrical stimulation. Examples of pH-responsive bioadhesives include, but are not limited to, oligo (methyl methacrylate)-grafted poly(acrylic acid), modified poly(ethylene glycol), modified poly(amino ester), including derivatives thereof.

Combination Systems

In some embodiments, the bioadhesive is configured to be multifunctional and is configured to deliver bioactive and/or therapeutic molecules (e.g., in addition to maintaining certain adhesive properties and characteristics). Bioactive and/or therapeutic molecules that may be delivered by the bioadhesive include, but are not limited to, anti-inflammatory agents (e.g., ibuprofen, celecoxib, diclofenac, etc.), anesthetics (e.g., lidocaine), immunosuppressive agents (e.g., Tacrolimus, cyclosporin A, rapamycin, etc.), antimicrobial agents (e.g., ciprofloxacin), steroidal or hormonal agents (e.g., erthropoetin, melatonin, testosterone, estrogen, etc.), neurological agents (e.g., lithium, gapapentin, etc.), proteins and neurotrophins (e.g., brain derived neurotrophic factor, glial derived neurotrophic factor, nerve growth factor, etc.), cells (e.g., stem cells, Schwann cells, macrophages, etc.), vitamins (e.g., vitamin B12, etc.), delivery vehicles (e.g., nano/microparticles, liposomes, micelles, precipitates, etc.) and/or the like.

In some arrangements, the bioadhesive is tuned to deliver the bioactive and/or therapeutic molecule within an optimal or desired timeframe. In some arrangements, such a timeframe depends on, at least in part, the molecule(s), site of delivery, clearance rate, etc. Delivery can occur according to regular or irregular frequency (e.g., a constant or a non-constant rate), according to the design of the biomaterial and properties of the molecule or agent and/or one or more other factors or considerations, as desired or required.

In one example, the bioadhesive is used to at least partially anchor the electrode lead to a nerve that was surgically repaired for up to or greater than 60 days (e.g., more than 60, 70, 80, 90, 100, 110, 120, 150, 200, 250, 300 days, day values in between the preceding values, more than 1 year, etc.). Under such circumstances, the bioadhesive can be multifunctional and can be configured to release an immunosuppressant (e.g., Cyclosporin A or Tacrolimus) at a constant rate for the duration the lead is anchored to prevent or reduce the likelihood of a major inflammatory or host immune rejection response to the implanted lead, that might otherwise result in premature removal of the lead, ineffective treatment, and pain or other negative or potentially problematic physiological effects for the patient or other subject.

In some arrangements, it may be advantageous to deliver an agent or multiple agents that enact or otherwise create certain desired effects. In some embodiments, more than one desired effect is created. For example, Tacrolimus (e.g., also known as FK506) is a commercially available immunosuppression agent that has also been proven to enhance peripheral nerve regeneration in acute and chronic animal nerve injury models. Therefore, under certain circumstances, since the biological neuroregenerative mechanism of Tacrolimus is different than that of neuroregenerative electrical stimulation therapy, the delivery of both Tacrolimus and electrical stimulation may act synergistically to optimize or otherwise improve peripheral nerve regeneration beyond what is achievable with application of either individual methods on their own. Therefore, it may be advantageous to design the electrode lead bioadhesive such that it is also a therapeutic delivery device that delivers one or more therapeutics (e.g., Tacrolimus) in a desired manner (e.g., in a controlled manner) to synergistically boost or otherwise enhance the neuroregenerative capacity of an injured peripheral nerve. This can be in addition to application of electrical stimulation treatment. Furthermore, with the Tacrolimus example in mind, since Tacrolimus is an immunosuppressant, delivery of this drug may also assist with mitigating the chronic immune or foreign body response to any of the implanted components.

In other aspects, the combination of neuroregenerative electrical stimulation and delivery of pro-regenerative agents may be desired (e.g., to create an optimal or enhanced effect) under certain circumstances (e.g., for severe nerve injury models (e.g., chronic axotomy, nerve plexus injuries, gap nerve injuries, etc.)). Current treatment strategies for gap nerve injuries requiring surgical implementation of nerve grafts (e.g., autograft, xenograft, allograft, etc.) or nerve conduits, remain largely insufficient for meaningful regeneration and functional recovery post-injury.

Furthermore, some nerve graft types that are often selected due to their availability and lack of requirement for a secondary surgical site have also been reported to induce acute and/or chronic host inflammatory or immunogenic responses. In such cases, it may be advantageous or otherwise desirable to apply a multifactorial treatment strategy, in which surgical nerve gap repair using a graft or conduit, neuroregenerative electrical stimulation, local delivery of anti-inflammatory and/or immunosuppresive agents and/or other materials/treatments are applied to enhance regeneration and prevent or reduce the likelihood of graft-rejection following nerve gap injury.

In some arrangements, following surgical repair of a nerve gap, the neuroregenerative stimulation system may be implemented. The lead may be inserted using a para-incisional approach and anchored into place with a multifunctional bioadhesive (e.g., according to any of the technologies and methods described herein). In some aspects, the bioadhesive may contain an immunosuppressant, such as, for example, Tacrolimus (FK506) or other immunosuppressive agents (e.g., cyclosporin A, rapamycin, etc.).

According to some embodiments, the bioadhesive may secure, at least partially, the lead to and/or near a site on the nerve (e.g., proximal to the repair site) and may also cover (e.g., completely, partially, etc.) the surface area of the corresponding nerve graft. The bioadhesive may function to anchor or otherwise secure the stimulation lead for the duration and course of neuroregenerative electrical stimulation therapy. In some embodiments, it can be configured to remain for the therapy and to remain at the site for longer (e.g., 2 hours, 4 hours, 1 to 4 hours, less than 1 hour, 4 to 6 hours, 6 to 8 hours, 8 to 12 hours, 4 to 16 hours, 12 to 18 hours, 12 to 24 hours, 18 to 24 hours, 1 to 30 days, 30 to 60 days, 60 to 90 days, time values within the foregoing ranges, greater than 90 days, etc.), as desired or required for a particular application or use.

Regardless of the exact time frame, for the corresponding duration, the bioadhesive can be configured to biodegrade and to deliver a therapeutic (e.g., Tacrolimus (FK506)) at a desired (e.g., controlled) rate. In some embodiments, such an embodiment can be configured to provide local immunosuppression during the course of axon regeneration and graft remodeling. As previously discussed, in addition to being an immunosuppressant, Tacrolimus (FK506), for example, can be a neurotrophic agent. Therefore, under certain circumstances, controlled and local delivery of a substance (e.g., Tacrolimus) in combination with neuroregenerative electrical stimulation therapy may not only prevent host rejection of any nerve grafts and/or conduits, but may also synergistically encourage axonal regrowth and enhance nerve regeneration in a gap nerve injury model (and/or create some other beneficial effect or result), beyond what is achievable with surgical treatments alone.

In another example, the bioadhesive is multifunctional and is also a drug delivery system for acute and/or chronic pain modulation purposes. In some aspects, the bioadhesive may act as a local delivery vehicle for pain-suppressing or pain-inhibiting agents (e.g., anti-inflammatory agents, steroidal agents, local anesthetics, etc.). This drug delivery system may act synergistically or separately from pain modulation electrical stimulation. The bioadhesive drug delivery system may be tuned to release the drug payload depending on the optimal therapeutic window. In some aspects, it may be advantageous for the bioadhesive drug delivery system to rapidly dispense the agent, whilst retaining its adhesive and shapeability properties over the course of which the lead is to be implanted.

In some embodiments, it may be advantageous for the bioadhesive drug delivery system to dispense the agent over a slower time course.

In some embodiments, the drug release profile may be continuous, non-continuous or occur at designed intervals (e.g., pulsed drug delivery). For example, a peripheral nerve injury patient may receive an electrical stimulation phase for neuroregenerative therapy and a second electrical stimulation phase for pain management therapy. A bioadhesive may be used to interface and secure the electrode lead proximal to the nerve injury site during the neuroregenerative therapy phase and throughout the course of pain modulation therapy phase. Furthermore, the bioadhesive may be designed to release a local dose of an anti-inflammatory and pain modulation agents, such as, but not limited to, ibuprofen, pregabalin, gabapentin, topiramate, carbamazepine, etc. The release profile of the pain modulation agent from the drug delivery system may be linear, in which a constant dose and rate of the pain modulation agent is released over time to provide pain relief for the patient over the course of their recovery, in addition to the pain modulation therapy phase delivered by electrical stimulation. The bioadhesive may passively degrade over either or both of the neuroregenerative or pain modulation therapy time frames, such that when it is time the remove the lead, it is no longer adhered to the anatomical site and permits easy removal.

In some embodiments, the bioadhesive is multifunctional and composed of or contains radiopaque elements to allow for image-guided visualization, placement, and/or removal of it or the lead. Furthermore, the radiopaque elements may be an additional safety feature, especially in the case of long-term lead implantation, to monitor the location and position of the lead. In some arrangements, the bioadhesive may comprise entirely, partially, or a hybrid of radiopaque elements and/or imaging contrast agents. Such radiopaque elements may include, but are not limited to, radiopaque polymer agents, radiopaque agents (e.g., acrylic derivatives, inorganic salts, and high atomic number elements like bismuth, iodine, barium, etc.), contrast agent-eluting nano/microparticles, etc.

In some embodiments, the bioadhesive is electroconductive and/or piezoelectric. In some aspects, the bioadhesive may comprise electroconductive or piezoelectric materials (e.g., polypyrrole, polyaniline, polythiophene, etc.). In other aspects, the bioadhesive may be a composite material containing electroconductive or piezoelectric elements, such as, but not limited to, carbon nanotubes, graphene particles, gold nanoparticles, silver nanoparticles, etc. Electroconductive or piezoelectric material properties can be advantageous and otherwise beneficial. For example, to act synergistically with electrical stimulation applied to a nerve for neuroregenerative and/or pain modulation therapy, but permitting more localized charge concentration to the anatomical region of interest.

In other embodiments, various therapeutic substances can be delivered via the electrode lead body to various locations along a trajectory near or on the target injured nerve. Such substances can act synergistically with neuroregenerative therapy, acting by alternative mechanisms, and/or can act to minimize pain, local inflammation, among others.

Kits

In some embodiments, a nerve treatment kit comprises two or more of the following: a bioadhesive, an electrode lead having at least one electrode, a stimulation system, an insertion tool, and a user manual. In one arrangement, a kit may be deployed intraoperatively during or prior to the treatment of a nerve injury.

Although several embodiments and examples are disclosed herein, the present application extends beyond the specifically disclosed embodiments to other alternative embodiments and/or uses of the various inventions and modifications, and/or equivalents thereof. It is also contemplated that various combinations or subcombinations of the specific features and aspects of the embodiments may be made and still fall within the scope of the inventions. Accordingly, various features and aspects of the disclosed embodiments can be combined with or substituted for one another in order to form varying modes of the disclosed inventions. Thus, the scope of the various inventions disclosed herein should not be limited by any particular embodiments described above. While the embodiments disclosed herein are susceptible to various modifications, and alternative forms, specific examples thereof have been shown in the drawings and are described in detail herein. However, the inventions of the present application are not limited to the particular forms or methods disclosed, but, to the contrary, cover all modifications, equivalents, and alternatives falling within the spirit and scope of the various embodiments described and the appended claims. Further, the disclosure herein of any particular feature, aspect, method, property, characteristic, quality, attribute, element and/or the like in connection with an implementation or embodiment can be used in all other implementations or embodiments set forth herein.

In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, any structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages.

The methods disclosed herein include certain actions taken by a practitioner; however, they can also include any third-party instruction of those actions, either expressly or by implication. For example, actions such as "locating" a nerve, "coupling" an electrode to a nerve, "initiating" a stimulation procedure include "instructing locating," "instructing coupling," and "instructing initiating" etc., respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 mm" includes "1 mm." Phrases preceded by a term such as "substantially" include the recited phrase and should be interpreted based on the circumstances (e.g., as much as reasonably possible under the circumstances). For example, "substantially rigid" includes "rigid," and "substantially parallel" includes "parallel."

The invention claimed is:

1. A method of managing pain related to a peripheral nerve injury of a subject, the method comprising:
   delivering stimulation energy of a first frequency to the target nerve via at least one electrode assembly during a regenerative phase, wherein delivering said stimulation energy of the first frequency creates a neuroregenerative effect to the target nerve resulting in enhanced tissue reinnervation;
   wherein the enhanced tissue reinnervation is configured to result in a reduced potential for developing long-term pain; and
   delivering stimulation energy of a second frequency via the at least one electrode assembly during at least one neuropathic pain management phase, wherein delivering stimulation energy during the at least one neuropathic pain management phase is configured to occur following a delivery of at least one bout of stimulation energy during the regenerative phase to reduce neuropathic pain of the subject caused by the peripheral nerve injury;
   wherein the second frequency is greater than the first frequency;
   wherein stimulation energy is delivered to the target nerve during both the regenerative and the at least one neuropathic pain management phases while the at least one electrode assembly is positioned adjacent the target nerve and while the at least one electrode is operatively coupled to a non-implantable stimulator, the at least one electrode assembly configured to be positioned adjacent the target nerve via a percutaneous pathway; and
   wherein the at least one electrode is configured to be removed from the subject via the percutaneous pathway following a termination of the regenerative and the at least one neuropathic pain management phases.

2. The method of claim 1, further comprising accessing the target nerve using a para-incisional approach, wherein the target nerve is a peripheral nerve that has sustained injury.

3. The method of claim 1, wherein the second frequency is 20 KHz to 500 KHz.

4. The method of claim 1, wherein the second frequency is 1 KHz to 10 KHz.

5. The method of claim 1, wherein the second frequency is 50 Hz to 200 Hz.

6. The method of claim 1, wherein delivering stimulation energy during the regenerative phase is sufficient to elicit a response.

7. The method of claim 6, wherein the response relates to an action potential or an evoked response in the subject.

8. The method of claim 6, wherein the elicited response during the regenerative phase is configured to, at least in part, confirm validation of therapeutic efficacy of neuroregenerative therapy in the subject.

9. The method of claim 1, wherein delivering stimulation energy during the neuropathic pain management phase is sufficient to elicit a response.

10. The method of claim 9, wherein the elicited response during the neuropathic pain management phase is configured to, at least in part, confirm relief from neuropathic pain in the subject.

11. The method of claim 1, wherein delivering at least one bout of stimulation energy of the second frequency to the target nerve via at least one electrode assembly during the at least one neuropathic pain management phase precedes at least one bout of delivering stimulation energy of the first frequency to the target.

12. A method of managing pain related to a peripheral nerve injury of a subject, the method comprising:
   delivering stimulation energy of a first frequency to the target nerve via at least one electrode assembly during at least one neuroregenerative phase; and
   delivering stimulation energy of a second frequency via the at least one electrode assembly during at least one neuropathic pain management phase;
   wherein delivering the stimulation energy during the at least one neuroregenerative phase is configured to create a neuroregenerative effect to the target nerve resulting in enhanced tissue reinnervation, wherein enhanced tissue reinnervation is configured to reduce a potential for developing long-term pain; and
   wherein delivering stimulation energy during the at least one neuropathic pain management phase is configured to reduce neuropathic pain of the subject caused by the peripheral nerve injury, wherein the second frequency is different than the first frequency;
   wherein stimulation energy is delivered to the target nerve during both the at least one neuroregenerative phase and the at least one neuropathic pain management phases while the at least one electrode assembly is positioned adjacent the target nerve and while the at least one electrode is operatively coupled to a non-implantable stimulator, the at least one electrode assembly configured to be positioned adjacent the target nerve via a percutaneous pathway; and
   wherein the at least one electrode is configured to be removed from the subject via the percutaneous pathway following a termination of the at least one neuroregenerative phase and the at least one neuropathic pain management phase.

13. The method of claim 12, wherein the second frequency is 20 KHz to 500 KHz.

14. The method of claim 12, wherein the second frequency is 1 KHz to 10 KHz.

15. The method of claim 12, wherein the second frequency is 50 Hz to 200 Hz.

16. The method of claim 12, wherein the at least one electrode assembly is configured to be placed upstream or proximal to an injury site of the target nerve, wherein delivering stimulation energy results in action potentials traveling proximally towards a cell body of the target nerve.

17. The method of claim 12, the second frequency can be varied by a user.

18. The method of claim 12, the second frequency is fixed.

19. The method of claim 12, wherein delivering stimulation energy during the at least one neuropathic pain management phase is continuous or intermittent.

20. The method of claim 12, wherein delivering at least one bout of stimulation energy during the at least one neuropathic pain management phase after delivering stimulation energy during at least one neuroregenerative phase.

21. The method of claim 12, wherein delivering at least one bout of stimulation energy during the at least one neuropathic pain management phase occurs before or during delivering stimulation energy during at least one neuroregenerative phase.

* * * * *